US010877037B2

(12) United States Patent
Ibrahim et al.

(10) Patent No.: US 10,877,037 B2
(45) Date of Patent: Dec. 29, 2020

(54) FUNGAL TOXINS AND METHODS RELATED TO THE SAME

(71) Applicant: LOS ANGELES BIOMEDICAL RESEARCH INSTITUTE AT HARBOR-UCLA MEDICAL CENTER, Torrance, CA (US)

(72) Inventors: Ashraf S. Ibrahim, Torrance, CA (US); Sameh Soliman, Torrance, CA (US); John Edwards, Jr., Torrance, CA (US)

(73) Assignee: LOS ANGELES BIOMEDICAL RESEARCH INSTITUTE AT HARBOR-UCLA MEDICAL CENTER, Torrance, CA (US)

( * ) Notice: Subject to any disclaimer, the term of this patent is extended or adjusted under 35 U.S.C. 154(b) by 0 days.

(21) Appl. No.: 16/462,511

(22) PCT Filed: Nov. 20, 2017

(86) PCT No.: PCT/US2017/062537
§ 371 (c)(1),
(2) Date: May 20, 2019

(87) PCT Pub. No.: WO2018/094322
PCT Pub. Date: May 24, 2018

(65) Prior Publication Data

US 2019/0265238 A1 Aug. 29, 2019

Related U.S. Application Data

(60) Provisional application No. 62/424,882, filed on Nov. 21, 2016.

(51) Int. Cl.

| | |
|---|---|
| ***A61P 31/10*** | (2006.01) |
| ***A61P 35/00*** | (2006.01) |
| ***A61K 39/00*** | (2006.01) |
| ***A61K 39/39*** | (2006.01) |
| ***C07K 16/14*** | (2006.01) |
| ***C12Q 1/6895*** | (2018.01) |
| ***C07K 14/37*** | (2006.01) |
| ***A61P 31/00*** | (2006.01) |
| ***G01N 33/569*** | (2006.01) |

(52) U.S. Cl.
CPC ... *G01N 33/56961* (2013.01); *A61K 39/0002* (2013.01); *A61K 39/0011* (2013.01); *A61K 39/39* (2013.01); *A61P 31/00* (2018.01); *A61P 31/10* (2018.01); *A61P 35/00* (2018.01); *C07K 14/37* (2013.01); *C07K 16/14* (2013.01); *C12Q 1/6895* (2013.01); *A61K 2039/505* (2013.01); *A61K 2039/55505* (2013.01); *A61K 2039/585* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 2006/0269477 | A1 | 11/2006 | Waldman |
| 2009/0110699 | A1 | 4/2009 | Cigarini et al. |
| 2013/0108642 | A1 | 5/2013 | Ibrahim et al. |
| 2016/0130330 | A1 | 5/2016 | Ibrahim et al. |
| 2016/0159887 | A1 | 6/2016 | Ibrahim et al. |
| 2016/0319294 | A1 | 11/2016 | Kovalic et al. |

FOREIGN PATENT DOCUMENTS

| | | | |
|---|---|---|---|
| EP | 2404928 | A1 | 1/2012 |

OTHER PUBLICATIONS

Patent Cooperation Treaty, International Search Report for PCT/US2017/062537, dated Mar. 20, 2018, pp. 1-3.

*Primary Examiner* — Padmavathi Baskar
(74) *Attorney, Agent, or Firm* — Pillsbury Winthrop Shaw Pittman, LLP

(57) ABSTRACT

Presented herein, in certain aspects, are compositions that comprise novel toxin proteins, the nucleic acids that encode them, and/or portions thereof, which toxins are expressed by fungi of the Mucorales order and are thought to contribute to the pathogenesis of Mucormycosis. Also presented herein, in certain aspects, are methods of detecting the presence or absence of novel fungal toxins and/or the nucleic acids that encode them in a sample, which methods can be used to identify the presence of Mucorales in a subject. Methods and/or compositions presented herein can be used to prevent and/or treat a Mucorales infection.

13 Claims, 27 Drawing Sheets

Specification includes a Sequence Listing.

| Membrane Barrier | - | + | - | + |
|---|---|---|---|---|
| Fungal Living/Growth | + | + | - | - |
| Secreted Toxin | + | + | - | - |
| Hyphae-Associate Toxin | + | - | + | - |

Sequence Aligment of H-toxins of Mucorales

```
R._delemar_ricin    MYFEEGRLFFIKSQFNGRVLDVEDGSTEEDANIIVYTQKY    40
R._microsporus_r    MSYLAGRTFYIKSQFNGRVLDVEGASTEEDAPVIVYTQKY    40
M._circinelloide    ...MTGTMEFIKSQMNGRVLDVSEGSTEEEAPIIVYSQKG    37
Lichtheimia_cory    .................MVLDVAWDSLKANAKIIVNPRKK    23
Consensus                             vldv  s    a  iv   k

R._delemar_ricin    FDCINQLWRYENGYFINAKSAKVLDIRGGEMQFESQIIQY    80
R._microsporus_r    DDNINQLWRYENGYFVNVNSAKVLDIRGGQNDFESEIIQY    80
M._circinelloide    FDCINQLWRYEDGYFINAKSAKVLDISGGEMQFESPIIQY    77
Lichtheimia_cory    QDYDNQLWMYEHGYLINKNSGIVLDVAGGILETDKQIIQY    63
Consensus            d  nqlw y  gy  n  s  vld  gg        iqy

R._delemar_ricin    AQKNVEEAANQRWAILEEGYIFCEARPDLVLDIQGAEEED    120
R._microsporus_r    SQKVYEEAVNQRWNILEEGYIYIEARPDLVLDIQGAEEED    120
M._circinelloide    AQKMSEEAANQRWEILEEGYIFCSARPDLVLDIQGREEED    117
Lichtheimia_cory    FRKMLEIAHNQRWYYREEGKIYPQVDENLVLDIRGNWTKP    103
Consensus             k  e a nq w   e g i     p lvldi g

R._delemar_ricin    CVPVILYEPREGEVSANQRWELVPFEG.............    147
R._microsporus_r    CVPVILYNPREGEVSSNQRWVLEPVD..............    146
M._circinelloide    CAVVILYEKRDGEIASNQRWFLEEYSG.............    144
Lichtheimia_cory    CTVVILYEKKYSDNE.NQLWDLIPDTSDDESSASILLREE    142
Consensus              v ly         nq w l

R._delemar_ricin    ...............                             147
R._microsporus_r    ...............                             146
M._circinelloide    ...............                             144
Lichtheimia_cory    EDGDDDYSFSTSSYA                             157
Consensus
```

FIG. 15

```
M_circinelloides         ------------------------------------------------ATGACTGGTACC
M_ambiguus               ------------------------------------------------ATGACTGGTACC
R_O                      ---------------------------------------ATGTATTTCGAAGAAGGCCGC
R_microsporus            ---------------------------------------ATGAGTTACTTAGCAGGACGT
L_corymbifera            ------------------------------------------------------------
Mortierella_verticillata ATGGCAGGCTCCCCTTCAACTTCTGCCCGATCCAGTCGTGTGCTGTCCTTCCCCAAGGGC

M_circinelloides         ATGTTCTTTATCAAAAGCCAAATGAACGGCC-----------------------------
M_ambiguus               ATGTATTTTATCAAAAGCCAAATGAACGGCC-----------------------------
R_O                      TTATTTTTTATCAAAAGTCAATTTAACGGACGTGTCCTTGATGTTGAGGATGGTTCTACT
R_microsporus            ACATTCTATATCAAGAGTCAATTCAATGGACGCGTGCTCGATG-----------------
L_corymbifera            ------------------------------------------------------------
Mortierella_verticillata CAGTTCTACATCCAGTCGCCCATTGCTGACCTGGTTCTCGACATTGAGTCCGGGTTCCTG

M_circinelloides         ------------------------------------------------------------
M_ambiguus               ------------------------------------------------------------
R_O                      ------------------------------------------------------------
R_microsporus            ------------------------------------------------------------
L_corymbifera            ------------------------------------------------------------
Mortierella_verticillata AAGGACCCCCTCAAGGCCAACGCGCGTGTCGAGCTCGTACACAAGAAGTCACCCAAACAC

M_circinelloides         ------------------------------------------------------------
M_ambiguus               ------------------------------------------------------------
R_O                      ------------------------------------------------------------
R_microsporus            ------------------------------------------------------------
L_corymbifera            ------------------------------------------------------------
Mortierella_verticillata AACGCCGAGTCCTCGCTGATCCAGCAGGAGCAGCAGCAGTGGCGCGAGGAGGAGGGTTAC

M_circinelloides         ------------------------------------------------------------
M_ambiguus               ------------------------------------------------------------
R_O                      ------------------------------------------------------------
R_microsporus            ------------------------------------------------------------
L_corymbifera            ------------------------------------------------------------
Mortierella_verticillata ATCATCAACACTCGTACTGGCCACGTCTTGGATATCCAAGGAGGGGCCCCATTGGACAAC

M_circinelloides         --------------------------------------------GTGTTCTCGATG----
M_ambiguus               --------------------------------------------GTGTTCTTGATG----
R_O                      ----------------------GAGGTAAGAATTATTGGGTTGTTTATGCTTGCT-----
R_microsporus            ------------------------------------------------------------
L_corymbifera            ------------------------------------------------------------
Mortierella_verticillata GGGCATTGGTATTGGGCAGTGGGCGGCATCCATGGTATCATTGCCATCAATATGACTAAC

M_circinelloides         ------------------------------------------------------------
M_ambiguus               ------------------------------------------------------------
R_O                      ------------------------------------------------------------
R_microsporus            ------------------------------------------------------------
L_corymbifera            ------------------------------------------------------------
Mortierella_verticillata CGTCCATCTCTCCACATCACCTTTCTTCACACACACACAGGTGTCATCCGTTCCGGTACT
```

FIG. 17

```
M_circinelloides          ------------------------------------------------------------
M_ambiguus                ------------------------------------------------------------
R_O                       ------------------------------------------------------------
R_microsporus             ------------------------------------------------------------
L_corymbifera             ------------------------------------------------------------
Mortierella_verticillata  CGCGTTATCCAAAACGTGCGCAAGACTGGAAAGGATGCTGCTGGCCAGCACTGGTTGAAC

M_circinelloides          --------------------------------------------------TGAGCGAAGGC
M_ambiguus                --------------------------------------------------TGAGTGAAGGC
R_O                       --------------------------------------------------AAATCTAACTT
R_microsporus             --------------------------------------------------TTGAAGGCGCT
L_corymbifera             ------------------------------------------------------------
Mortierella_verticillata  GATGACGGTGTCCTGACCTTGGCCAGCAACCCCAAGTTCGTCGTCACCATCGATGGAGAT

M_circinelloides          TCTACTGAGGATGAAGCCCCTATCATTGTC------------------------------
M_ambiguus                TCTACCGAGGACGAGGCCCCTATCATTGTC------------------------------
R_O                       TGTATAAAGGATGATGCCAATATCATTGTT------------------------------
R_microsporus             TCCACCGAAGATGATGCCCCCGTGATTGTT------------------------------
L_corymbifera             ------------------------------------------------------------
Mortierella_verticillata  GCCACCAAAGATGGAACCCGCATCACTATCCAAGAAAAGAAGCCATACTACGAGAAGCAA

M_circinelloides          ------------------------------------------------------------
M_ambiguus                ------------------------------------------------------------
R_O                       ------------------------------------------------------------
R_microsporus             ------------------------------------------------------------
L_corymbifera             ------------------------------------------------------------
Mortierella_verticillata  AAATGGTTGTATCTGAACGGCTTCGATGCTCGCCCTGTGTCGCCTTCTCCTTCCAGAGCA

M_circinelloides          ------------------------------------------------------------
M_ambiguus                ------------------------------------------------------------
R_O                       ------------------------------------------------------------
R_microsporus             ------------------------------------------------------------
L_corymbifera             ------------------------------------------------------------
Mortierella_verticillata  GAGTCACTCTCCATCCGCCCTGACAACTTCCCCACCAGCTGGTTCTACATCAAGTCCGCT

M_circinelloides          ------------------------------------------------------------
M_ambiguus                ------------------------------------------------------------
R_O                       ------------------------------------------------------------
R_microsporus             ------------------------------------------------------------
L_corymbifera             ------------------------------------------------------------
Mortierella_verticillata  GCCTCGGGCTTGGTCGTCGACATTGAGCACGGCTACTTCACAGACCCCATGAAGGCCGGT

M_circinelloides          ---------------TACTCTCAAAAGG---------------GCGAAGATTGC-------
M_ambiguus                ---------------TACTCTCAAAAGG---------------GCGAACATTGC-------
R_O                       ---------------TACACACAAAAGT--------------ATGAAGATTGC-------
R_microsporus             ---------------TATACCCAAAAAT--------------ATGATGACAAC-------
L_corymbifera             ------------------------------------------------------------
Mortierella_verticillata  GCCCGCGCCGAAATGAACCACCAAAAGATCGACAACGGTGACGGCCGCCACTCCTTGCTT

M_circinelloides          TTGAACCAATTGTGGCGCTACGAAGACGGTTATTTCATCAATGCCAAGTCTGCCAAGGTT
M_ambiguus                TTGAACCAATTGTGGCGTTATGAAGATGGATACCTCATCAATGCTAACTCTGCCAAGGTG
R_O                       TTGAACCAACTCTGGCGTTACGAAAATGGTTATTTCATCAACGCAAAGTCTGCCAAGGTC
R_microsporus             TTGAATCAACTCTGGCGTTATGAAAATGGTTACTTTGTCAACGTCAACTCTGCCAAGGTT
L_corymbifera             ------------------------------------------------------------
Mortierella_verticillata  GAGCTCCAGCTTTGGCGCTACGAGGCTGGTTTCCTTATCAACCGTCGCACCGGTTTCGTT
```

FIG. 17 (Cont.)

```
M_circinelloides           CTCGATATTAGCGGTGGTGAAATGCAACCCGAGTCTCCTATCATTCAATATGCTCAAAAG
M_ambiguus                 CTCGATATCAGTGGTGGAGAAATGCAACCCGAATCTGCTATCATTCAATATGCTCAAAAG
R_O                        TTGGATATCCGTGGAGGTGAAATGCAACCTGAGTCTCAAATCATTCAATATGCTCAAAAG
R_microsporus              TTGGATATCCGCGGTGGCCAAATGGACCCTGAATCTGAAATTATTCAATACTCTCAAAAG
L_corymbifera              ---------------------------------------ATGATCCAATATCGTCGAAAG
Mortierella_verticillata   CTGGACATTCAAGGAGGCACTCTCAAACTCGCCGCCAGAGTCGTCCAGTGGCAGCGCAAG
                                                                  *   *  ** *      *   ***

M_circinelloides           ATGTCTGAGGAAGCTGCTAATCAAAAGTGGGAAATCGATGAAGATGGTTATATCTTCTGT
M_ambiguus                 ATGTCTGAGGAGGCCGCTAATCAGAAATGGGAAATCGATGGTGAAGGCTATATCTGTTGT
R_O                        ATGGTCGAAGAAGCTGCCAACCAAAGATGGGCTATAGATGAGGATGGCTATATCTTTTGT
R_microsporus              GTATACGAAGAAGCTGTGAACCAAAGATGGAACATTGATGGGGAAGGCTATATCTATATT
L_corymbifera              ATGCTCGAAGATGCGCACAATCAACGCTGGTATTATCGTGAGGATGGTTTCATTTACCCT
Mortierella_verticillata   TCTGGAAAGGAGGCCCAGAACCAGCACTGGTTC---TACGAGAACGGCTTCATTGCCAAC
                                   *  **  **     ** **     ***         *    *  **  *   **

M_circinelloides           TCTGCTCGCCCTGATTTAGTCTTGGACATTCAAGGTCGTGAAGACGAGGATGGCGCTGTT
M_ambiguus                 TCTGCTCGCCCTGATTTAGTCTTGGACATTGCAGAGCGCAATGACGAGGATGGTGCTGCT
R_O                        GAAGCCCGTCCTGATTTAGTTTTAGATATCCAAGGCGCTGAAGATGAAGACTGTGTACCT
R_microsporus              GAAGCTCGTCCTGACTTAGTCTTGGACATTCAAGGTGCCGAGGATGAGGATGGTGTTCCC
L_corymbifera              CAAGTCGATCCTAATTTGGTTCTTGATATTCGCGGCAATTGGACCAAGCCTGGAACGGTG
Mortierella_verticillata   GTCTACAACTCGAGGCTGGTTCTGGACATTGATGGCGATGGTTCCAAGGACGGAGCCAAG
                                      *     * **    * **  **      *               *      *

M_circinelloides           GTCATTTTGTACGAAAAGCGTGATGGTGAAATTGCTTCTAACCAACGCTGGTTCTTGGAA
M_ambiguus                 GTCATCTTGTATGAGAAGCGCGAGGGTGAGATTGCCTCTAACCAACGTTGGTTCTTGGAA
R_O                        GTGATTTTATACGAAAGACGTGAAGGTGAAGTTTCAGCCAACCAACGCTGGGAATTAGTG
R_microsporus              GTCATCTTGTACAATAGACGTGAGGGTGAAGTCTCTTCTAACCAACGTTGGGTGTTGGAA
L_corymbifera              GTACTTC---TTTACGAGCGAAAATACAGCGATAACGAGAATCA-------GCTA-----
Mortierella_verticillata   ATCGCCA---TCGGTGAGCGCAAGGCTGTCAGCAACGCTGATCAGAAGTGGCTGTTGGAG

M_circinelloides           GAGTACTCTGGTTAA---------------------------------------------
M_ambiguus                 GAGTTCTCTGGTTAA---------------------------------------------
R_O                        CCATTTGAAGGATAA---------------------------------------------
R_microsporus              CCAGTTGATTAA------------------------------------------------
L_corymbifera              ------------------------------------------------------------
Mortierella_verticillata   GAGGTTCGCTTCCAATGGTTGGCTGCTCCTACCTCAGCCTCGGCCTCCATCTCCTCCAAT

M_circinelloides           ------------------------------------------------------------
M_ambiguus                 ------------------------------------------------------------
R_O                        ------------------------------------------------------------
R_microsporus              ------------------------------------------------------------
L_corymbifera              ------------------------------------------------------------
Mortierella_verticillata   GTCACCGAGGAGATTACCGTCGTCGAGAGAGGCATCTCGTCCCCCAAGGTCGCCACTCCC

M_circinelloides           ------------------------------------------------------------
M_ambiguus                 ------------------------------------------------------------
R_O                        ------------------------------------------------------------
R_microsporus              ------------------------------------------------------------
L_corymbifera              ------------------------------------------------------------
Mortierella_verticillata   CCCACCACCGTCACCGCTCTGCCCACCAGCGGCTGGTTCTACATCAAGTCCCAGTCCTCT

M_circinelloides           ------------------------------------------------------------
M_ambiguus                 ------------------------------------------------------------
R_O                        ------------------------------------------------------------
```

FIG. 17 (Cont.)

```
R_microsporus           ------------------------------------------------------------
L_ corymbifera          ------------------------------------------------------------
Mortierella_verticillata GGTCTCGTTGTCGACGTTGAGCAGGATGCCGATCCTTTGGCCCCTAACGTCCTCGTCAGC

M_circinelloides        ------------------------------------------------------------
M_ambiguus              ------------------------------------------------------------
R_O                     ------------------------------------------------------------
R_microsporus           ------------------------------------------------------------
L_corymbifera           ------------------------------------------------------------
Mortierella_verticillata ATGAACACCCAGATCACCTCTGTCACTGAGGAGAACCAGGCCAAGGTCGAGTCACAGCTC

M_circinelloides        ------------------------------------------------------------
M_ambiguus              ------------------------------------------------------------
R_O                     ------------------------------------------------------------
R_microsporus           ------------------------------------------------------------
L_corymbifera           ---------------------------------------TGGGATCTTAT----------
Mortierella_verticillata TGGACATACCAGAATGGTCAGATCATCAACAGGAGAGATCTCAGCTCGTCCTCGACTGCAAA

M_circinelloides        ------------------------------------------------------------
M_ambiguus              ------------------------------------------------------------
R_O                     ------------------------------------------------------------
R_microsporus           ------------------------------------------------------------
L_corymbifera           ------------------------------------------------------------
Mortierella_verticillata CAGGGTGTCGTCCGCTATGGCGCCAGACTGATGCAGGGAATTCCCAAGGAGGGCAAAGAG

M_circinelloides        ------------------------------------------------------------
M_ambiguus              ------------------------------------------------------------
R_O                     ------------------------------------------------------------
R_microsporus           ------------------------------------------------------------
L_corymbifera           ------------------------------------------------------------
Mortierella_verticillata AGCCACCACCAGCGTTGGGAGTCATCCAACGGCACCCTCGTCGTCCAGGGCAAGCCTCTC

M_circinelloides        ------------------------------------------------------------
M_ambiguus              ------------------------------------------------------------
R_O                     ------------------------------------------------------------
R_microsporus           ------------------------------------------------------------
L_corymbifera           ------------------------------------------------------------
Mortierella_verticillata TACGCTATCGACATTGAGGGTGATGGCACCAAGTCCGGTTCCCGCCTCTCGCTCCAGCGC

M_circinelloides        ------------------------------------------------------------
M_ambiguus              ------------------------------------------------------------
R_O                     ------------------------------------------------------------
R_microsporus           ------------------------------------------------------------
L_corymbifera           ------------------------------------------------------------
Mortierella_verticillata CCCAAGGTCCAGAACAACTCGGATCAGCAGTGGTCCTTCCAGATCGCCACTTACGAGTGG

M_circinelloides        ------------------------------------------------------------
M_ambiguus              ------------------------------------------------------------
R_O                     ------------------------------------------------------------
R_microsporus           ------------------------------------------------------------
L_corymbifera           ------------------------------------------------------------
Mortierella_verticillata CTCAAGGTCCAGCGTTCTGTCACCCGCACCTTCACCGAGACCACCACCTCTTCGTCTAAG
```

FIG. 17 (Cont.)

```
M_circinelloides          ------------------------------------------------------------
M_ambiguus                ------------------------------------------------------------
R_O                       ------------------------------------------------------------
R_microsporus             ------------------------------------------------------------
L_corymbifera             ----------------------------------T-------------------------
Mortierella_verticillata  GTTGTTAACATCGAGAAGAACGACTGGTTCTTCATCAAGTCCGGAGCCACCGGCTTGGTC

M_circinelloides          ------------------------------------------------------------
M_ambiguus                ------------------------------------------------------------
R_O                       ------------------------------------------------------------
R_microsporus             ------------------------------------------------------------
L_corymbifera             ------------------------------------------------------------
Mortierella_verticillata  ATGGATCTCGAGGCTGGCTGGATTACTCAGCCCACCGATGTTGGTGCCTACATTTCCATG

M_circinelloides          ------------------------------------------------------------
M_ambiguus                ------------------------------------------------------------
R_O                       ------------------------------------------------------------
R_microsporus             ------------------------------------------------------------
L_corymbifera             ------------------------------------------------------------
Mortierella_verticillata  AAGAAGCAGCGCTCGCTCGAGGAGTCTGATCGTGCCCTTTTGGAGAGACAGTTGTGGCGC

M_circinelloides          ------------------------------------------------------------
M_ambiguus                ------------------------------------------------------------
R_O                       ------------------------------------------------------------
R_microsporus             ------------------------------------------------------------
L_corymbifera             ------------------------------------------------------------
Mortierella_verticillata  TATGAGGACGGCTACCTCATCAACCGCAGAACCAACTACGTCGTTGACATCTATGGTCGC

M_circinelloides          ------------------------------------------------------------
M_ambiguus                ------------------------------------------------------------
R_O                       ------------------------------------------------------------
R_microsporus             ------------------------------------------------------------
L_corymbifera             ------------------------------------------------------------
Mortierella_verticillata  TCCGCCGTTGTTGGCGTCAAGTTGATCCAGCAGTACAAGGCTACCACCGAGGTCTATGAT

M_circinelloides          ------------------------------------------------------------
M_ambiguus                ------------------------------------------------------------
R_O                       ------------------------------------------------------------
R_microsporus             ------------------------------------------------------------
L_corymbifera             ------------------------------------------------------------
Mortierella_verticillata  GCTGTCCTCACCGAGAAGCACACTGGTGTTACCTACGTGACCCAGCTGTTGTTCGACACC

M_circinelloides          ------------------------------------------------------------
M_ambiguus                ------------------------------------------------------------
R_O                       ------------------------------------------------------------
R_microsporus             ------------------------------------------------------------
L_corymbifera             ------------------------------------------------------------
Mortierella_verticillata  CAGACCAATGCCTACTACGTCTACGTCCGCTGGGGCGAGACCGAGTACAGATTGGATGGG

M_circinelloides          ------------------------------------------------------------
M_ambiguus                ------------------------------------------------------------
R_O                       ------------------------------------------------------------
R_microsporus             ------------------------------------------------------------
L_corymbifera             ------------------------------------------------------------
```

FIG. 17 (Cont.)

```
Mortierella_verticillata  CCCCACGAGACCATTGAGTCCGCCAAGGCCGCTTTCTTGATCACCTACCACGATCAGTTT

M_circinelloides          ------------------------------------------------------------
M_ambiguus                ------------------------------------------------------------
R_O                       ------------------------------------------------------------
R_microsporus             ------------------------------------------------------------
L_corymbifera             ------------------CCAGATACCAGCGACGACGAGTC-------------------
Mortierella_verticillata  GGTGTTGAATGGCAAACTCGCGAGACCACCGTCAGCGAACAATGGACCTACGAAGTCAAG

M_circinelloides          ------------------------------------------------------------
M_ambiguus                ------------------------------------------------------------
R_O                       ------------------------------------------------------------
R_microsporus             ------------------------------------------------------------
L_corymbifera             ------------------------------------------------------------
Mortierella_verticillata  ACCTATGAGACTTTCGAGGAGATCGAGTACGTTGAGGAGGTCGTTGAGGAGACTGAGGCA

M_circinelloides          ------------------------------------------------------------
M_ambiguus                ------------------------------------------------------------
R_O                       ------------------------------------------------------------
R_microsporus             ------------------------------------------------------------
L_corymbifera             -------------ATCAGCATC----GATATTATTACGAGAAGA----------------
Mortierella_verticillata  GTCACCATCATTGAGCAGCAGCGCGAGATCGTTGTCCAGGAACAGTCCGAGCATGTTGAA

M_circinelloides          ------------------------------------------------------------
M_ambiguus                ------------------------------------------------------------
R_O                       ------------------------------------------------------------
R_microsporus             ------------------------------------------------------------
L_corymbifera             --------------------------------------------GGAGGATGGTGATGAT
Mortierella_verticillata  GTTACCGAGGGCGAGGAGATCATCAAGGTTGTCACCACCGTCAAGGAGACTGGTGTCGTT

M_circinelloides          ------------------------------------------------------------
M_ambiguus                ------------------------------------------------------------
R_O                       ------------------------------------------------------------
R_microsporus             ------------------------------------------------------------
L_corymbifera             GATTACT---------CCTTCAGCACTTCAAGCTAT------------------------
Mortierella_verticillata  GCCGAGCCCGCCGTGTCCAAGGGCACTTCCTGGTTCCGCCGCCTGGCCTCCGGAGCTGGC

M_circinelloides          ------------------------------------------------------------
M_ambiguus                ------------------------------------------------------------
R_O                       ------------------------------------------------------------
R_microsporus             ------------------------------------------------------------
L_corymbifera             ------------------------------------------------------------
Mortierella_verticillata  GCCGTCGCATCGGGCGCTTTGACTGAGGTCGATGGCGTCTGGAAGCGCACTGTCCAGGTC

M_circinelloides          ------------------------------------------------------------
M_ambiguus                ------------------------------------------------------------
R_O                       ------------------------------------------------------------
R_microsporus             ------------------------------------------------------------
L_corymbifera             ------------------------------------------------------------
Mortierella_verticillata  CTCACCACCCGCAAGGCTCACGTCGACAAGGTTGCCCCTATTGCCGAGACCTCGTATGTG

M_circinelloides          ------------------------------------------------------------
M_ambiguus                ------------------------------------------------------------
```

FIG. 17 (Cont.)

```
R_O                        ------------------------------------------------------------
R_microsporus              ------------------------------------------------------------
L_corymbifera              ------------------------------------------------------------
Mortierella_verticillata   TACTATGATGAGGAGGTCTACGATTCCGTCCTTGTTGAGAAGTCGACTGGCATCACCTAT

M_circinelloides           ------------------------------------------------------------
M_ambiguus                 ------------------------------------------------------------
R_O                        ------------------------------------------------------------
R_microsporus              ------------------------------------------------------------
L_corymbifera              ------------------------------------------------------------
Mortierella_verticillata   GTCACCCAGCTTCTGTTCGACACCAAGGTCCAGAAGTACTACGTCTACGTCCGCTGGGGC

M_circinelloides           ------------------------------------------------------------
M_ambiguus                 ------------------------------------------------------------
R_O                        ------------------------------------------------------------
R_microsporus              ------------------------------------------------------------
L_corymbifera              ------------------------------------------------------------
Mortierella_verticillata   GAGACTGACTACAAGTTGGATGGACCCCACGACACTATCGAGGCTGCCAAGGCCGCTTTC

M_circinelloides           ------------------------------------------------------------
M_ambiguus                 ------------------------------------------------------------
R_O                        ------------------------------------------------------------
R_microsporus              ------------------------------------------------------------
L_corymbifera              ------------------------------------------------------------
Mortierella_verticillata   CAGATCACCTACAAGGAGAGATTCGGTTTGGAGTGGGCTACCCGCGAGACCACCGTCAGC

M_circinelloides           ------------------------------------------------------------
M_ambiguus                 ------------------------------------------------------------
R_O                        ------------------------------------------------------------
R_microsporus              ------------------------------------------------------------
L_corymbifera              ------------------------------------------------------------
Mortierella_verticillata   GAACGCTGGACCTATGAGGTTCGCACCTACGAGACCTTCGAGGAGACTGAGGAGATCGAG

M_circinelloides           ------------------------------------------------------------
M_ambiguus                 ------------------------------------------------------------
R_O                        ------------------------------------------------------------
R_microsporus              ------------------------------------------------------------
L_corymbifera              ------------------------------------------------------------
Mortierella_verticillata   GAGATCGTGGAGGATTACGAGGTCAAGGAGATTGTTGCCCGTGAGCAGCAGGTCATTGTC

M_circinelloides           ------------------------------------------------------------
M_ambiguus                 ------------------------------------------------------------
R_O                        ------------------------------------------------------------
R_microsporus              ------------------------------------------------------------
L_corymbifera              ------------------------------------------------------------
Mortierella_verticillata   GAGGGCAAGGTCATTTCGACCGAGCAGTCCGTGTCGTCGTCCCATGACGACACTGTTGTC

M_circinelloides           ------------------------------------------------------------
M_ambiguus                 ------------------------------------------------------------
R_O                        ------------------------------------------------------------
R_microsporus              ------------------------------------------------------------
L_corymbifera              ------------------------------------------------------------
Mortierella_verticillata   CGCACCGTGAGCGAGCAGGTTGTGTCCAAGGATGGCTCTGCCTCTGGATCTTCGTCCAGC
```

FIG. 17 (Cont.)

```
M_circinelloides          ------------------------------------------------------------
M_ambiguus                ------------------------------------------------------------
R_O                       ------------------------------------------------------------
R_microsporus             ------------------------------------------------------------
L_corymbifera             ------------------------------------------------------------
Mortierella_verticillata  CGCGGTGGCGCCTTTGGCTTTGGTGGCTCGTCGTCTTACGAGTACACCCAGACCCAGTCT

M_circinelloides          ------------------------------------------------------------
M_ambiguus                ------------------------------------------------------------
R_O                       ------------------------------------------------------------
R_microsporus             ------------------------------------------------------------
L_corymbifera             --------------------------------------------GCACTCTAG-------
Mortierella_verticillata  GAGGAGAGCAAGAAGTCCACTTTCTTGGCCAACCTCCCCACCTTGAACGCTGGCATCAAC

M_circinelloides          ------------------------------------------------------------
M_ambiguus                ------------------------------------------------------------
R_O                       ------------------------------------------------------------
R_microsporus             ------------------------------------------------------------
L_corymbifera             ------------------------------------------------------------
Mortierella_verticillata  GCCGATACCGGTGCCGCCATTGGCGTGATCGATCTGACCTCTGGCACCGCCGAGAACCTT

M_circinelloides          ------------------------------------------------------------
M_ambiguus                ------------------------------------------------------------
R_O                       ------------------------------------------------------------
R_microsporus             ------------------------------------------------------------
L_corymbifera             ------------------------------------------------------------
Mortierella_verticillata  CGCGAGTTGCCCGCCCACTTGCGCCCCCGTGCCTGGGTCTCGCTCCACGTTGGAGGCTGG

M_circinelloides          ------------------------------------------------------------
M_ambiguus                ------------------------------------------------------------
R_O                       ------------------------------------------------------------
R_microsporus             ------------------------------------------------------------
L_corymbifera             ------------------------------------------------------------
Mortierella_verticillata  CAGAACGCCCCCCACGAGCTTGAAGGATTTATGCGCCTCGATGACCAGTCGGGCCAGCGT

M_circinelloides          ------------------------------------------------------------
M_ambiguus                ------------------------------------------------------------
R_O                       ------------------------------------------------------------
R_microsporus             ------------------------------------------------------------
L_corymbifera             ------------------------------------------------------------
Mortierella_verticillata  CTGATGGAGACTGCCCGCGATGAGTCCCTTGGCAAGGCCCAGGAGTCGACCCCTATTGAC

M_circinelloides          ------------------------------------------------------------
M_ambiguus                ------------------------------------------------------------
R_O                       ------------------------------------------------------------
R_microsporus             ------------------------------------------------------------
L_corymbifera             ------------------------------------------------------------
Mortierella_verticillata  AACCTGAGCTTGCCCGAGATTGTGGGATTGTTTGCCCAGAAGTTGTACGGACACTTTGGC

M_circinelloides          ------------------------------------------------------------
M_ambiguus                ------------------------------------------------------------
R_O                       ------------------------------------------------------------
R_microsporus             ------------------------------------------------------------
```

FIG. 17 (Cont.)

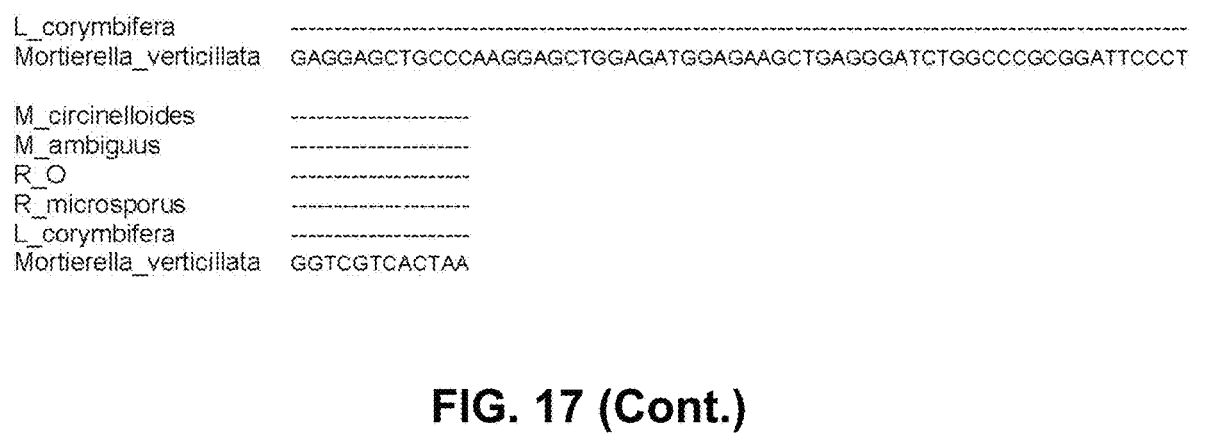

```
L_corymbifera            ------------------------------------------------------------------------------------------
Mortierella_verticillata GAGGAGCTGCCCAAGGAGCTGGAGATGGAGAAGCTGAGGGATCTGGCCCGCGGATTCCCT

M_circinelloides         ------------
M_ambiguus               ------------
R_O                      ------------
R_microsporus            ------------
L_corymbifera            ------------
Mortierella_verticillata GGTCGTCACTAA
```

FIG. 17 (Cont.)

Combined data with n= 20 mice per group from two independent experiments with similar results.

**P* =0.00004 by Log Rank test.

SEQUENCE LISTING

<160> NUMBER OF SEQ ID NOS: 47

<210> SEQ ID NO 1
<211> LENGTH: 494
<212> TYPE: DNA
<213> ORGANISM: Rhizopus oryzae

<400> SEQUENCE: 1
atgtatttcg aagaaggccg cttatttttt atcaaaagtc aatttaacgg acgtgtcctt 60
gatgttgagg atggttctac tgaggtaaga attattgggt tgtttatgct tgctaaatct 120
aactttgtat aaaggatgat gccaatatca ttgtttacac acaaaagtat gaagattgct 180
tgaaccaact ctggcgttac gaaaatggtt atttcatcaa cgcaaagtct gccaaggtct 240
tggatatccg tggaggtgaa atgcaacctg agtctcaaat cattcaatat gctcaaaaga 300
tggtcgaaga agctgccaac caaagatggg ctatagatga ggatggctat atcttttgtg 360
aagcccgtcc tgatttagtt ttagatatcc aaggcgctga agatgaagac tgtgtacctg 420
tgattttata cgaaagacgt gaaggtgaag tttcagccaa ccaacgctgg gaattagtgc 480
catttgaagg ataa 494

<210> SEQ ID NO 2
<211> LENGTH: 444
<212> TYPE: DNA
<213> ORGANISM: Rhizopus oryzae

<400> SEQUENCE: 2
atgtatttcg aagaaggccg cttatttttt atcaaaagtc aatttaacgg acgtgtcctt 60
gatgttgagg atggttctac tgaggatgat gccaatatca ttgtttacac acaaaagtat 120
gaagattgct tgaaccaact ctggcgttac gaaaatggtt atttcatcaa cgcaaagtct 180
gccaaggtct tggatatccg tggaggtgaa atgcaacctg agtctcaaat cattcaatat 240
gctcaaaaga tggtcgaaga agctgccaac caaagatggg ctatagatga ggatggctat 300
atcttttgtg aagcccgtcc tgatttagtt ttagatatcc aaggcgctga agatgaagac 360
tgtgtacctg tgattttata cgaaagacgt gaaggtgaag tttcagccaa ccaacgctgg 420
gaattagtgc catttgaagg ataa 444

<210> SEQ ID NO 3
<211> LENGTH: 147
<212> TYPE: PRT
<213> ORGANISM: Rhizopus oryzae

<400> SEQUENCE: 3

```
Met Tyr Phe Glu Glu Gly Arg Leu Phe Phe Ile Lys Ser Gln Phe Asn
1               5                   10                  15

Gly Arg Val Leu Asp Val Glu Asp Gly Ser Thr Glu Asp Asp Ala Asn
            20                  25                  30

Ile Ile Val Tyr Thr Gln Lys Tyr Glu Asp Cys Leu Asn Gln Leu Trp
        35                  40                  45

Arg Tyr Glu Asn Gly Tyr Phe Ile Asn Ala Lys Ser Ala Lys Val Leu
    50                  55                  60

Asp Ile Arg Gly Gly Glu Met Gln Pro Glu Ser Gln Ile Ile Gln Tyr
65                  70                  75                  80

Ala Gln Lys Met Val Glu Glu Ala Ala Asn Gln Arg Trp Ala Ile Asp
```

```
                85                  90                  95

Glu Asp Gly Tyr Ile Phe Cys Glu Ala Arg Pro Asp Leu Val Leu Asp
            100                 105                 110

Ile Gln Gly Ala Glu Asp Glu Asp Cys Val Pro Val Ile Leu Tyr Glu
        115                 120                 125

Arg Arg Glu Gly Glu Val Ser Ala Asn Gln Arg Trp Glu Leu Val Pro
    130                 135                 140

Phe Glu Gly
145


<210> SEQ ID NO 4
<211> LENGTH: 146
<212> TYPE: PRT
<213> ORGANISM: Rhizopus microspores

<400> SEQUENCE: 4

Met Ser Tyr Leu Ala Gly Arg Thr Phe Tyr Ile Lys Ser Gln Phe Asn
1               5                   10                  15

Gly Arg Val Leu Asp Val Glu Gly Ala Ser Thr Glu Asp Asp Ala Pro
            20                  25                  30

Val Ile Val Tyr Thr Gln Lys Tyr Asp Asp Asn Leu Asn Gln Leu Trp
        35                  40                  45

Arg Tyr Glu Asn Gly Tyr Phe Val Asn Val Asn Ser Ala Lys Val Leu
    50                  55                  60

Asp Ile Arg Gly Gly Gln Met Asp Pro Glu Ser Glu Ile Ile Gln Tyr
65                  70                  75                  80

Ser Gln Lys Val Tyr Glu Glu Ala Val Asn Gln Arg Trp Asn Ile Asp
                85                  90                  95

Glu Glu Gly Tyr Ile Tyr Ile Glu Ala Arg Pro Asp Leu Val Leu Asp
            100                 105                 110

Ile Gln Gly Ala Glu Asp Glu Asp Gly Val Pro Val Ile Leu Tyr Asn
        115                 120                 125

Arg Arg Glu Gly Glu Val Ser Ser Asn Gln Arg Trp Val Leu Glu Pro
    130                 135                 140

Val Asp
145


<210> SEQ ID NO 5
<211> LENGTH: 144
<212> TYPE: PRT
<213> ORGANISM: Mucor circinelloides

<400> SEQUENCE: 5

Met Thr Gly Thr Met Phe Phe Ile Lys Ser Gln Met Asn Gly Arg Val
1               5                   10                  15

Leu Asp Val Ser Glu Gly Ser Thr Glu Asp Glu Ala Pro Ile Ile Val
            20                  25                  30

Tyr Ser Gln Lys Gly Glu Asp Cys Leu Asn Gln Leu Trp Arg Tyr Glu
        35                  40                  45

Asp Gly Tyr Phe Ile Asn Ala Lys Ser Ala Lys Val Leu Asp Ile Ser
    50                  55                  60

Gly Gly Glu Met Gln Pro Glu Ser Pro Ile Ile Gln Tyr Ala Gln Lys
65                  70                  75                  80

Met Ser Glu Glu Ala Ala Asn Gln Lys Trp Glu Ile Asp Glu Asp Gly
                85                  90                  95

Tyr Ile Phe Cys Ser Ala Arg Pro Asp Leu Val Leu Asp Ile Gln Gly
```

```
            100                 105                 110

Arg Glu Asp Glu Asp Gly Ala Val Val Ile Leu Tyr Glu Lys Arg Asp
        115                 120                 125

Gly Glu Ile Ala Ser Asn Gln Arg Trp Phe Leu Glu Glu Tyr Ser Gly
    130                 135                 140


<210> SEQ ID NO 6
<211> LENGTH: 144
<212> TYPE: PRT
<213> ORGANISM: Mucor ambiguous

<400> SEQUENCE: 6

Met Thr Gly Thr Met Tyr Phe Ile Lys Ser Gln Met Asn Gly Arg Val
1               5                   10                  15

Leu Asp Val Ser Glu Gly Ser Thr Glu Asp Glu Ala Pro Ile Ile Val
            20                  25                  30

Tyr Ser Gln Lys Gly Glu His Cys Leu Asn Gln Leu Trp Arg Tyr Glu
        35                  40                  45

Asp Gly Tyr Leu Ile Asn Ala Asn Ser Ala Lys Val Leu Asp Ile Ser
    50                  55                  60

Gly Gly Glu Met Gln Pro Glu Ser Ala Ile Ile Gln Tyr Ala Gln Lys
65                  70                  75                  80

Met Ser Glu Glu Ala Ala Asn Gln Lys Trp Glu Ile Asp Gly Glu Gly
                85                  90                  95

Tyr Ile Cys Cys Ser Ala Arg Pro Asp Leu Val Leu Asp Ile Ala Glu
            100                 105                 110

Arg Asn Asp Glu Asp Gly Ala Ala Val Ile Leu Tyr Glu Lys Arg Glu
        115                 120                 125

Gly Glu Ile Ala Ser Asn Gln Arg Trp Phe Leu Glu Glu Phe Ser Gly
    130                 135                 140


<210> SEQ ID NO 7
<211> LENGTH: 174
<212> TYPE: PRT
<213> ORGANISM: Absidia idahoensis

<400> SEQUENCE: 7

Met Ser Asn Phe Pro Ser Gly Trp Phe Phe Ile Gln Ser Lys Cys Pro
1               5                   10                  15

His Lys Met Val Leu Asp Val Ala Met Asp Ser His Lys Asp Thr Ala
            20                  25                  30

Lys Ile Val Val Trp Pro Arg Lys Glu Gln Asp Phe Asp Asn Gln Leu
        35                  40                  45

Trp Met Tyr Asp Asn Gly Tyr Ile Ile Asn Lys Ser Ser Gly Leu Val
    50                  55                  60

Leu Asp Val Ile Gly Gly Val Leu Glu Asn Asp Lys Gln Ile Ile Gln
65                  70                  75                  80

Tyr Arg Arg Lys Met Val Glu Asp Ala Gln Asn Gln Arg Trp Tyr Tyr
                85                  90                  95

Arg Glu Asp Gly Phe Ile Tyr Pro Gln Val Asn Pro Asn Leu Val Leu
            100                 105                 110

Asp Ile Arg Gly Asn Trp Thr Lys Pro Gly Thr Val Val Leu Leu Tyr
        115                 120                 125

Asp Arg Lys Phe Ser Asp Asn Glu Asn Gln Leu Trp Asp Leu Ile Pro
    130                 135                 140

His Asp Pro Gln Gly Ser Asn Thr Pro Lys Asp Asp Asp Ala Ser Asp
```

145 150 155 160

Ile Asp Lys Asp Tyr Ser Phe Ser Thr Ala Ser Tyr Ala Leu
165 170

<210> SEQ ID NO 8
<211> LENGTH: 158
<212> TYPE: PRT
<213> ORGANISM: Lichtheimia corymbifera

<400> SEQUENCE: 8

Met Val Leu Asp Val Ala Trp Asp Ser Leu Lys Ala Asn Ala Lys Ile
1 5 10 15

Ile Val Trp Pro Arg Lys Lys Gln Asp Tyr Asp Asn Gln Leu Trp Met
20 25 30

Tyr Asp His Gly Tyr Leu Ile Asn Lys Asn Ser Gly Leu Val Leu Asp
35 40 45

Val Ala Gly Gly Ile Leu Glu Thr Asp Lys Gln Met Ile Gln Tyr Arg
50 55 60

Arg Lys Met Leu Glu Asp Ala His Asn Gln Arg Trp Tyr Tyr Arg Glu
65 70 75 80

Asp Gly Phe Ile Tyr Pro Gln Val Asp Pro Asn Leu Val Leu Asp Ile
85 90 95

Arg Gly Asn Trp Thr Lys Pro Gly Thr Val Val Leu Leu Tyr Glu Arg
100 105 110

Lys Tyr Ser Asp Asn Glu Asn Gln Leu Trp Asp Leu Ile Pro Asp Thr
115 120 125

Ser Asp Asp Glu Ser Ser Ala Ser Ile Leu Leu Arg Glu Glu Glu Asp
130 135 140

Gly Asp Asp Asp Tyr Ser Phe Ser Thr Ser Ser Tyr Ala Leu
145 150 155

<210> SEQ ID NO 9
<211> LENGTH: 660
<212> TYPE: PRT
<213> ORGANISM: Mortierella verticillata

<400> SEQUENCE: 9

Met Ala Gly Ser Pro Ser Thr Ser Ala Arg Ser Ser Arg Val Leu Ser
1 5 10 15

Phe Pro Lys Gly Gln Phe Tyr Ile Gln Ser Pro Ile Ala Asp Leu Val
20 25 30

Leu Asp Ile Glu Ser Gly Phe Leu Lys Asp Pro Leu Lys Ala Asn Ala
35 40 45

Arg Val Glu Leu Val His Lys Lys Ser Pro Lys His Asn Ala Glu Ser
50 55 60

Ser Leu Ile Gln Gln Glu Gln Gln Gln Trp Arg Glu Glu Glu Gly Tyr
65 70 75 80

Ile Ile Asn Thr Arg Thr Gly His Val Leu Asp Ile Gln Gly Gly Val
85 90 95

Ile Arg Ser Gly Thr Arg Val Ile Gln Asn Val Arg Lys Thr Gly Lys
100 105 110

Asp Ala Ala Gly Gln His Trp Leu Asn Asp Asp Gly Val Leu Thr Leu
115 120 125

Ala Ser Asn Pro Lys Phe Val Val Thr Ile Asp Gly Asp Ala Thr Lys
130 135 140

Asp Gly Thr Arg Ile Thr Ile Gln Glu Lys Lys Pro Tyr Tyr Glu Lys

-continued

```
145                 150                 155                 160

Gln Lys Trp Leu Tyr Leu Asn Gly Phe Asp Ala Arg Pro Val Ser Pro
                165                 170                 175

Ser Pro Ser Arg Ala Glu Ser Leu Ser Ile Arg Pro Asp Asn Phe Pro
            180                 185                 190

Thr Ser Trp Phe Tyr Ile Lys Ser Ala Ala Ser Gly Leu Val Val Asp
        195                 200                 205

Ile Glu His Gly Tyr Phe Thr Asp Pro Met Lys Ala Gly Ala Arg Ala
    210                 215                 220

Glu Met Asn His Gln Lys Ile Asp Asn Gly Asp Gly Arg His Ser Leu
225                 230                 235                 240

Leu Glu Leu Gln Leu Trp Arg Tyr Glu Ala Gly Phe Leu Ile Asn Arg
                245                 250                 255

Arg Thr Gly Phe Val Leu Asp Ile Gln Gly Gly Thr Leu Lys Leu Ala
            260                 265                 270

Ala Arg Val Val Gln Trp Gln Arg Lys Ser Gly Lys Glu Ala Gln Asn
        275                 280                 285

Gln His Trp Phe Tyr Glu Asn Gly Phe Ile Ala Asn Val Tyr Asn Ser
    290                 295                 300

Arg Leu Val Leu Asp Ile Asp Gly Asp Gly Ser Lys Asp Gly Ala Lys
305                 310                 315                 320

Ile Ala Ile Gly Glu Arg Lys Ala Val Ser Asn Ala Asp Gln Lys Trp
                325                 330                 335

Leu Leu Glu Glu Val Arg Phe Gln Trp Leu Ala Ala Pro Thr Ser Ala
            340                 345                 350

Ser Ala Ser Ile Ser Ser Asn Val Thr Glu Glu Ile Thr Val Val Glu
        355                 360                 365

Arg Gly Ile Ser Ser Pro Lys Val Ala Thr Pro Pro Thr Thr Val Thr
    370                 375                 380

Ala Leu Pro Thr Ser Gly Trp Phe Tyr Ile Lys Ser Gln Ser Ser Gly
385                 390                 395                 400

Leu Val Val Asp Val Glu Gln Asp Ala Asp Pro Leu Ala Pro Asn Val
                405                 410                 415

Leu Val Ser Met Asn Thr Gln Ile Thr Ser Val Thr Glu Glu Asn Gln
            420                 425                 430

Ala Lys Val Glu Ser Gln Leu Trp Thr Tyr Gln Asn Gly Gln Ile Ile
        435                 440                 445

Asn Arg Arg Ser Gln Leu Val Leu Asp Cys Lys Gln Gly Val Val Arg
    450                 455                 460

Tyr Gly Ala Arg Leu Met Gln Gly Ile Pro Lys Glu Gly Lys Glu Ser
465                 470                 475                 480

His His Gln Arg Trp Glu Ser Ser Asn Gly Thr Leu Val Val Gln Gly
                485                 490                 495

Lys Pro Leu Tyr Ala Ile Asp Ile Glu Gly Asp Gly Thr Lys Ser Gly
            500                 505                 510

Ser Arg Leu Ser Leu Gln Arg Pro Lys Val Gln Asn Asn Ser Asp Gln
        515                 520                 525

Gln Trp Ser Phe Gln Ile Ala Thr Tyr Glu Trp Leu Lys Val Gln Arg
    530                 535                 540

Ser Val Thr Arg Thr Phe Thr Glu Thr Thr Thr Ser Ser Ser Lys Val
545                 550                 555                 560

Val Asn Ile Glu Lys Asn Asp Trp Phe Phe Ile Lys Ser Gly Ala Thr
                565                 570                 575
```

```
Gly Leu Val Met Asp Leu Glu Ala Gly Trp Ile Thr Gln Pro Thr Asp
            580                 585                 590

Val Gly Ala Tyr Ile Ser Met Lys Lys Gln Arg Ser Leu Glu Glu Ser
        595                 600                 605

Asp Arg Ala Leu Leu Glu Arg Gln Leu Trp Arg Tyr Glu Asp Gly Tyr
    610                 615                 620

Leu Ile Asn Arg Arg Thr Asn Tyr Val Val Asp Ile Tyr Gly Arg Ser
625                 630                 635                 640

Ala Val Val Gly Val Lys Leu Ile Gln Gln Tyr Lys Ala Thr Thr Glu
                645                 650                 655

Val Cys Gly Lys
            660


<210> SEQ ID NO 10
<211> LENGTH: 20
<212> TYPE: DNA
<213> ORGANISM: Artificial Sequence
<220> FEATURE:
<223> OTHER INFORMATION: H-Toxin Forward Primer

<400> SEQUENCE: 10

ctggcgttac gaaaatggtt                                                  20


<210> SEQ ID NO 11
<211> LENGTH: 20
<212> TYPE: DNA
<213> ORGANISM: Artificial Sequence
<220> FEATURE:
<223> OTHER INFORMATION: H-Toxin Forward Primer

<400> SEQUENCE: 11

acggacgtgt ccttgatgtt                                                  20


<210> SEQ ID NO 12
<211> LENGTH: 20
<212> TYPE: DNA
<213> ORGANISM: Artificial Sequence
<220> FEATURE:
<223> OTHER INFORMATION: H-Toxin Forward Primer

<400> SEQUENCE: 12

aacggacgtg tccttgatgt                                                  20


<210> SEQ ID NO 13
<211> LENGTH: 20
<212> TYPE: DNA
<213> ORGANISM: Artificial Sequence
<220> FEATURE:
<223> OTHER INFORMATION: H-Toxin Forward Primer

<400> SEQUENCE: 13

taacggacgt gtccttgatg                                                  20


<210> SEQ ID NO 14
<211> LENGTH: 20
<212> TYPE: DNA
<213> ORGANISM: Artificial Sequence
<220> FEATURE:
<223> OTHER INFORMATION: H-Toxin Reverse Primer

<400> SEQUENCE: 14

taaatcagga cgggcttcac                                                  20
```

```
<210> SEQ ID NO 15
<211> LENGTH: 20
<212> TYPE: DNA
<213> ORGANISM: Artificial Sequence
<220> FEATURE:
<223> OTHER INFORMATION: H-Toxin Reverse Primer

<400> SEQUENCE: 15

ctaaatcagg acgggcttca                                                   20


<210> SEQ ID NO 16
<211> LENGTH: 20
<212> TYPE: DNA
<213> ORGANISM: Artificial Sequence
<220> FEATURE:
<223> OTHER INFORMATION: H-Toxin Reverse Primer

<400> SEQUENCE: 16

aggttgcatt tcacctccac                                                   20


<210> SEQ ID NO 17
<211> LENGTH: 142
<212> TYPE: PRT
<213> ORGANISM: Rhizopus oryzae

<400> SEQUENCE: 17

Met Ile Met Asn His His Asn Lys Arg Lys Ala Phe Ser Leu Leu Ser
1               5                   10                  15

Leu Asn Ser Asn Ser Arg Phe Lys Val Ser Asn Pro Thr Ser Gln Lys
            20                  25                  30

His Leu Ile Arg Tyr Ile Arg Ser Lys Ser Pro Thr Phe Val Ala Leu
        35                  40                  45

Gln Glu Ile Asp Asn Ser Gly Gly Thr Gly Ile His Leu Gln Thr Leu
    50                  55                  60

His Gln Gln Phe Cys Ser Gln Gln Ser Leu Trp Ala Gln Tyr Cys Gly
65                  70                  75                  80

Leu Leu Cys Phe Asp Pro Gln Tyr Ser Leu Gln Arg Ile Pro Leu Pro
                85                  90                  95

Glu Asp Ser Arg Cys Ile Leu Ala Lys Val Thr His Val Asn Glu Gln
            100                 105                 110

Met Ala Pro Phe His Ile Leu Trp Pro His Phe His Gln Tyr Arg Phe
        115                 120                 125

Gln Asn Val Met Thr Asp Leu Phe Leu Arg Asn His His Leu
    130                 135                 140


<210> SEQ ID NO 18
<211> LENGTH: 235
<212> TYPE: PRT
<213> ORGANISM: Rhizopus microspores

<400> SEQUENCE: 18

Met Phe Val Thr Leu Gln Glu Val Asp Asn Ser Asp Asn Ser Ser Ser
1               5                   10                  15

His Phe Asp Leu Trp His Gln Gln Phe Val Cys His Gln Ser Leu Trp
            20                  25                  30

Ile Gln Tyr Cys Gly Leu Ala Cys Phe Asp Pro Ser Phe Ser Thr Thr
        35                  40                  45

Cys Ile Pro Ile Pro Glu Asp Ala Arg Cys Leu Leu Ala Gln Val Thr
    50                  55                  60
```

-continued

His Ile Asn Asp Phe Ile Glu Pro Phe Phe Ile Leu Val Ile Tyr Val
65 70 75 80

Ser Ala Asn Val Thr Arg Glu Arg Arg Glu Phe Phe Glu Gln Leu Leu
85 90 95

Gln Phe His Gln Leu Asp Pro Tyr Asp Asp Arg Ser Cys Ala Asp Arg
100 105 110

Leu Ile Ile Ala Gly Asp Cys Asn Phe Thr Ile Gln Ser Ser Gln Ala
115 120 125

Ser Ser Ser Tyr Arg Asn Trp Ile Gln Leu Leu Asn Ser His Phe His
130 135 140

Asn Leu Met Ser Glu Leu Arg Asp Leu Cys Ile Leu Thr Phe Arg Arg
145 150 155 160

Ser Ala Val Thr Arg Ser Thr Ile Asn Tyr Leu Phe Leu Ser Thr Ile
165 170 175

Leu Ser Ala Asn His Ile Asp Ala Thr Val Asp Phe Ala Asp Pro Glu
180 185 190

Trp Ser Asp His Ala Ile Ile Ser Val Glu Leu Lys Leu Asp Leu Ala
195 200 205

Asp Ser His Gly Pro Gly Ala Trp Arg Ala Asn Pro Val Tyr Leu Asp
210 215 220

His Arg Asp Phe Leu Asp Val Leu Leu Thr Cys
225 230 235

<210> SEQ ID NO 19
<211> LENGTH: 304
<212> TYPE: PRT
<213> ORGANISM: Mucor circinelloides

<400> SEQUENCE: 19

Met Ser Leu Leu Asp Pro Ile Ile Ser Asn Ile Glu Ile Ile Asp Ser
1 5 10 15

Ser Tyr Ser Thr Val Asn Tyr Ser Gln Thr Ser Leu Asn Pro Pro Asp
20 25 30

Thr Ser Phe Val Lys Leu Asn Ile Gly Ser Leu Asn Cys Arg Gly Pro
35 40 45

Thr Lys Ile Ala Ala Thr Ser Thr Arg Ser Gln Phe Ile Arg Tyr Leu
50 55 60

Arg Thr Arg Ser Leu Asp Leu Leu Ala Leu Gln Glu Thr His Ala Ser
65 70 75 80

Ser Thr Ser Leu Gln Asp Met Phe His Ser Gln Phe Gln Ala Lys Ser
85 90 95

Ser Ile Trp Ser Pro His Cys Gly Leu Val Ser Phe Ser Ser Asp Ile
100 105 110

Ser Phe Ser Asn Ser Ile Val Ser Ile Cys Gly Arg Ile Ile Ser Thr
115 120 125

Thr Ile Ser His Ser Ser Asp Ala Phe Glu Pro Phe Ser Ile Thr Val
130 135 140

Val Tyr Leu Pro Ala Phe Arg Ser Glu Arg Phe His Phe Leu Ser Ser
145 150 155 160

Ile Leu Thr Asp Phe Arg Ser Val Phe Ser Ser Ser Pro Ser Arg Ser
165 170 175

Thr Phe Leu Gly Asp Phe Asn Tyr Thr Tyr Ser Asn Ala Ser Ser Ser
180 185 190

Arg Asn Arg Gln Ala Pro Arg Ser Trp Leu Gln Tyr Tyr Ile Asp Asp
195 200 205

```
Tyr Phe Leu Asp Gly Val Thr Pro Thr Gly Lys Ala Ser Ser Val Thr
    210                 215                 220

Phe Gln Arg Gly Ile Ser His Ser Cys Ile Asp Tyr Ile Met Phe Ser
225                 230                 235                 240

Asn Asp Leu Ala Ser Ser Val Ala Phe Phe Asp His Cys Asn Thr Ser
                245                 250                 255

Tyr Ile Gln Pro Ala Trp Trp Ser Asp His Leu Leu Ile Ser Ser Ser
            260                 265                 270

Lys Leu Arg Leu His Pro Ala Pro Asp Ala Ser Val Glu Tyr Ile His
        275                 280                 285

Cys Asp Leu Tyr Ser Val His Ser Ser Ser Ser Tyr His Ile Leu Ile
    290                 295                 300


<210> SEQ ID NO 20
<211> LENGTH: 1189
<212> TYPE: PRT
<213> ORGANISM: Lichtheimia corymbifera

<400> SEQUENCE: 20

Met Ile Ser Arg Asn Asn His Ile Thr Phe Leu Ser Leu Asn Cys Asn
1               5                   10                  15

Gly Leu Ala Lys Leu Arg Arg Pro Ser Ala Arg Ser Ser Leu Ile Arg
            20                  25                  30

Phe Leu Arg Gln Gln Ser Ala His Ile Ile Thr Leu Gln Glu Thr His
        35                  40                  45

Ala Ser Thr Pro Thr Leu Lys Asp Thr Phe His Lys Gln Phe Cys Ala
    50                  55                  60

His Gln Ser Phe Trp Thr Pro His Cys Gly Ile Val Leu Leu Ser Ser
65                  70                  75                  80

Asp Leu His Met Asn Glu Ile Ser Leu Asp Phe Thr Thr Arg Ala Gln
                85                  90                  95

Leu Val His Val Gln His Asn Asp Gln Ala Phe His Asp Phe Tyr Val
            100                 105                 110

Leu Asn Ile Tyr Ala Pro Ala His Ser Thr Arg Glu Arg Phe Gln Phe
        115                 120                 125

Phe Asn Ser Leu Tyr Gln His Leu Ala Pro Leu Leu Asp Asn Gln Ile
    130                 135                 140

Asn Ile Asp Arg Leu Phe Ile Met Gly Asp Phe Asn Tyr Asp Leu Gln
145                 150                 155                 160

Arg Ser Gly Leu His Leu Asn Ala Pro Ser Thr Trp Leu Thr Trp Leu
                165                 170                 175

Asp Ser His Phe Val Asn Cys Thr Arg Asp Asp Val His Phe Ala Gly
            180                 185                 190

Ile Pro Thr Tyr Arg His Ser Asn Tyr Leu Ser Thr Ile Asp Tyr Ile
        195                 200                 205

Tyr Ala Pro Ser His Phe Ser Ser Ser Ile His Asn Lys Asp Ile Ser
    210                 215                 220

Phe Val Asn Asn Asp Trp Thr Asp His Ala Leu Leu Ser Ala Thr Phe
225                 230                 235                 240

Ile Met Gly Pro Pro Lys Leu Gly Lys Gly Leu Trp Arg Gly Asn Pro
                245                 250                 255

Leu Leu Phe Lys Gln Pro Ser Phe Arg Arg Gln Leu Asn Asp Ala Leu
            260                 265                 270

Thr Gln His Tyr Gln Gln Leu His Asp Met Pro Ser Pro Gln Ser Gln
```

```
        275                 280                 285

Trp Glu Ser Ile Lys Gly Ile Ile Thr Gln His Leu Lys Thr Tyr Ser
    290                 295                 300

Arg Gln Gln Ala Glu Trp Arg Lys Lys Gln Leu Ser Ala Leu Gln Ser
305                 310                 315                 320

Lys Arg Asn Arg Phe Leu Arg Ser Lys Pro Pro Ala Ala Ile Arg Ala
                325                 330                 335

Trp Arg Leu Pro Ile Met Glu Arg Gln Ile Ala Thr Leu Gln Gln Glu
            340                 345                 350

Leu Val Asp Ile Gln Ala Leu Arg Ala Gly Gln Arg Trp Arg Glu Arg
        355                 360                 365

Gly Glu Thr Ser Ala Gly Tyr Leu Lys Arg Thr Ile His Asp Arg Gln
    370                 375                 380

Val Lys Arg Ser Ile Ala Thr Leu Gln His Pro His Thr Gly Ala Met
385                 390                 395                 400

Cys Ser Thr Thr Asp Asp Met His Ser Ala Val Gln Cys Phe Tyr Gln
                405                 410                 415

Asp Leu Tyr Ser Pro Asp Pro Ile Ser Thr Thr Asp Met Asn Thr Leu
            420                 425                 430

Leu Asp Gln Leu Pro Ser His Leu Arg Leu Asp His Thr Asp Gln Glu
        435                 440                 445

His Leu Val Arg Ala Phe Ser Ile Asp Asp Leu Gln Ser Ala Ala Ser
    450                 455                 460

Arg Thr Pro His His Ser Ser Pro Gly Pro Asp Gly Leu Pro Tyr Gln
465                 470                 475                 480

Ala Trp Arg Leu Val Phe Thr His Pro Leu Tyr Thr Thr Leu Val Met
                485                 490                 495

Arg Val Tyr Glu Asp Ala Leu Gln His Gly Ile Phe Pro Ser Ser Trp
            500                 505                 510

Asn Asp Thr Cys Met Cys Leu Leu Pro Lys Lys Gly Asp Leu Ser Asn
        515                 520                 525

Leu Ala Asn Trp Arg Pro Ile Ser Leu Ile Asn Cys Asp Ala Lys Ile
    530                 535                 540

Phe Thr Arg Leu Leu Asn Ala Arg Ile Ile Asp Ala Ala Thr Ser Leu
545                 550                 555                 560

Val Thr Pro Tyr Gln Arg Gly Phe Met Pro Gly Arg Phe Ile Gly Val
                565                 570                 575

Asn Gly Leu Leu Thr Arg Ile Thr Met Glu Gln Ala Ser Glu Gln Ala
            580                 585                 590

Ser Thr Glu Ile Gly Leu Leu Leu Asp Gln Glu Lys Ala Tyr Asp Arg
        595                 600                 605

Val His Pro Asn Tyr Leu Ser Ala Val Leu His Arg Phe Gly Phe Pro
    610                 615                 620

Ser Ser Ile Ile Gln Ala Ile Cys Thr Leu Phe Phe Ser Thr Ser Ile
625                 630                 635                 640

Arg Ile Asn Val Asn Gly His Ile Ser Gln Pro Ile Gln Gln Leu Arg
                645                 650                 655

Gly Leu Arg Gln Gly Asp Pro Leu Ser Pro Ile Leu Phe Asn Leu Ala
            660                 665                 670

Leu Glu Pro Phe Leu Arg Ser Ile Ile Asp Asp Ala Asn Phe Gln Gly
        675                 680                 685

Phe Gln Pro Trp His Ser Gly Ala Thr Ser Pro Leu Pro Pro Ile Lys
    690                 695                 700
```

```
Val Leu Ala Tyr Ala Asp Asp Val Met Val Phe Leu Lys Asp Pro Met
705                 710                 715                 720

Asp Phe Glu Arg Leu Leu Ala His Val Ala Cys Tyr Gln Lys Ala Ser
                725                 730                 735

Asn Ala Arg Phe Asn Arg Gln Lys Thr Gln Ala Ile Ser Leu Ser Gly
            740                 745                 750

Ala Thr His Asp Thr Trp Cys Gln Val Leu Leu Ser Asn Ala Met Ser
        755                 760                 765

Thr Pro His Asp Arg Arg Cys Pro Thr Ala Val Thr Tyr Leu Gly Tyr
    770                 775                 780

Pro Leu Thr Ser Ser Lys His Gln Leu Glu Leu Phe Leu Asp Gln Leu
785                 790                 795                 800

Leu Gln Asp Leu Thr Ser Ala Cys Asn Gln His Ser Gln Arg Thr Leu
                805                 810                 815

Ser Ile Arg Gly Arg Ala Thr Val Ala Asn Ser Leu Ile Leu Ser Arg
            820                 825                 830

Ile Trp His Val Leu Arg Leu Thr Pro Thr Thr Thr Val Phe Leu Asn
        835                 840                 845

Gln Leu Lys Ser Val Ile Gly Lys Phe Leu Met Arg Asn Ile Phe Pro
    850                 855                 860

Arg Val Ala Phe Thr Thr Leu Cys Arg Ser Arg Ser His Gly Gly Ile
865                 870                 875                 880

Gly Ile Leu Asp Pro Val Thr Gln Gln Ser Ala Leu Gln Thr Arg Trp
                885                 890                 895

Ile Gln Glu Leu Leu Ser Phe Ser Thr Asp Glu Trp Ser Pro His Thr
            900                 905                 910

His Val Leu Tyr His His Leu Leu Arg Asp Cys Arg Phe Ala Ser Gly
        915                 920                 925

Thr Ile His Thr Leu Leu Arg Cys Pro Gly Ala Arg Lys Pro Arg Thr
    930                 935                 940

Asn Glu Val Ser Ile Ser Thr Leu Ile Tyr Arg Thr Met Asp Leu Ile
945                 950                 955                 960

Pro Thr Ser Trp Asp Thr Ile Gln Pro Ser Pro Ala Thr Cys Leu Ile
                965                 970                 975

Leu Pro Leu Asn Ala Ile Trp Tyr Ala Ser Ala Glu Ser Thr Ser Phe
            980                 985                 990

Arg Gln Pro Gly Phe Lys Asn Leu  Leu Val Gly Asp Leu  Phe Val Leu
        995                 1000                1005

Glu Glu  Asn Glu Asn Tyr Ser  Leu Arg Leu Arg Thr  Ser Ala Asp
    1010                1015                1020

Gly Cys  His Tyr Pro Ile Leu  Leu Ser Arg Phe Arg  Ser Tyr Leu
    1025                1030                1035

Ala Gln  Asn Gln Leu Gln Leu  His Pro Tyr Phe Ala  Arg Leu Cys
    1040                1045                1050

Asp His  Thr His Val Thr His  Ile His Thr His Thr  Ser Pro Arg
    1055                1060                1065

Leu Gln  Asp Thr Ser Pro Leu  Leu Ser Ser Phe Val  Gln Val Met
    1070                1075                1080

Asp Gly  Lys Met Trp Arg Ser  Lys Ala Tyr Arg Lys  Phe Ile Ala
    1085                1090                1095

Pro Asp  Thr Pro Ser Asp Asn  Ser Ser Val Ser Trp  Thr Thr Phe
    1100                1105                1110
```

-continued

Trp His Thr Pro Met His His Thr Ala Arg Asn Val Trp Phe Arg
1115 1120 1125

Leu Leu His Gly Arg Ile Pro Thr Ser Ser Arg Val His His Tyr
1130 1135 1140

Ala Pro Asp Phe Val Thr Ser Pro Leu Cys Arg Ile Cys Ser Thr
1145 1150 1155

Thr Ser Asp Asp Asp Phe His Phe Leu Met Gly Cys Pro Lys Lys
1160 1165 1170

Arg Arg Ser Leu Asp Ser Ser Leu Glu Thr His Ser Phe Cys Gly
1175 1180 1185

Ser

<210> SEQ ID NO 21
<211> LENGTH: 701
<212> TYPE: PRT
<213> ORGANISM: Mucor ambiguous

<400> SEQUENCE: 21

Met Arg Asn Asn Ile Lys Asn Lys Ile Thr Asp Leu Gln Ile Gly Ser
1 5 10 15

Ile Asn Cys Arg Ser Leu Ser Lys Ser Ser Asn Ile Pro Arg Ser Gln
20 25 30

Ser Phe Ser Arg His Leu Thr Thr Gln His Leu Asp Ile Ile Cys Leu
35 40 45

Gln Glu Thr Gln Glu Ala His Ser Asp Thr Ile Gln Gln Arg Leu Asp
50 55 60

Met Gln Leu Lys Ala Gln Gln Ser Ile Trp Ser Ser His Cys Gly Ile
65 70 75 80

Val Ser Leu Asn Pro Gln Val His Ile Thr Ser Leu Tyr Val Ser Ser
85 90 95

Asp Asp Arg Val Ile Leu Cys Lys Val Ser His Pro Asn Asn Val Phe
100 105 110

Pro Ser Phe Thr Ile Met Asn Ile Tyr Ala Ser Ala Thr Asn Phe Gln
115 120 125

Arg Tyr Ala Phe Tyr Ala Thr Leu Leu Gln Leu Val Tyr Phe Gln Ser
130 135 140

Ile Leu Thr Asn Met Asn Thr Gly Asn Pro Leu Pro Ser Gln His Pro
145 150 155 160

Asp Ile Val Val Gly Asp Phe Asn Tyr Asn Phe Thr Gln Phe Pro Ala
165 170 175

His Ser Ile Thr Asp Tyr Ser Pro Pro Ala Leu Glu Phe Leu Ser Ser
180 185 190

Ser Tyr Ala Ser Gln Val Leu Thr Glu Thr Ser Leu Asp Pro Asp Ser
195 200 205

His Phe Val Met Pro Gln Leu Asp Gln His Thr Thr Pro Pro Val Cys
210 215 220

Ser Gln Trp Ile Trp His Gly Leu Leu Leu His His Tyr Ser Glu Val
225 230 235 240

Ser His Lys Leu Asn Thr Asp Pro Thr Thr Pro Thr Phe Arg Arg Glu
245 250 255

Phe Thr Ser Thr Thr Ile Asp Tyr Ile Phe Ile Ser Pro Asp Leu Ala
260 265 270

Pro Phe Val Thr Lys Ser Asp Ile Gln Phe Ile Ser Ser Thr Trp Thr
275 280 285

-continued

```
Asp His Ala Leu Leu Arg Phe Asp Leu Arg Phe Thr Ser Thr Thr His
    290                 295                 300

Gly Thr Gly Ile Trp Lys Ala Asn Leu Tyr Leu Val Gln Asn Glu Tyr
305                 310                 315                 320

Phe Ile Thr Gln Leu His Thr Ala Leu Asp Glu Phe His Ser Asn Leu
                325                 330                 335

Ala Ser Phe Thr Val Pro Pro Pro Val Gln Ile Ser Trp Asp Glu Ile
            340                 345                 350

Lys Ile Leu Thr Ile Asn Ile Val Lys Lys Ile Ser Arg His Lys Ala
        355                 360                 365

Cys Trp Cys Thr Arg His Leu Ile Leu Leu Gln Lys Lys Arg Asn Lys
    370                 375                 380

Leu Ile Lys Ser Tyr Gln Gly Gln Ala Tyr Ile Ala Thr Gln Ile Leu
385                 390                 395                 400

Lys Val Glu Arg Leu Ile Asn Asn Leu Gln Glu Glu Leu Val Glu Val
                405                 410                 415

Ala Thr Leu Arg Ser Gly Leu Arg Trp Arg Glu Lys Gly Glu Lys Ser
            420                 425                 430

Ala Gly Leu Met Lys Arg Leu Ile Thr Gln Arg Thr Ile Arg Arg Ser
        435                 440                 445

Ile Glu Thr Leu Gln His Thr Asp Thr Asn Val Ile Cys Thr Gln Pro
    450                 455                 460

Ser Asp Leu Gln Ser Ala Ala Arg Arg Tyr Tyr Glu Ile Leu Tyr Thr
465                 470                 475                 480

Pro Thr Pro Val Asp Pro Ser Asn Val Thr Tyr Phe Thr Asn Gln Thr
                485                 490                 495

Pro Gln Ser Asp Arg Leu Ser Asp Ser Ser His Gly Pro Leu Cys Ala
            500                 505                 510

Pro Phe Ser Pro Glu Asp Leu Ile Asp Gly Ala Ser Arg Ser Pro Asn
        515                 520                 525

Lys Asn Ser Pro Gly Met Asp Ser Leu Pro Tyr Glu Val Leu Ala Leu
    530                 535                 540

Leu Phe Gln His Pro Ala Ser Leu Lys Leu Ala Leu Gln Val Phe Asp
545                 550                 555                 560

Lys Ala Leu Ser Thr Gly Ala Phe Pro Ala Thr Trp Gln Glu Thr Cys
                565                 570                 575

Leu Ile Leu Leu Pro Lys Lys Gly Asp Leu Ser Gln Leu Lys Asn Trp
            580                 585                 590

Arg Pro Ile Ser Val Ile Asn Thr Asp Ala Lys Ile Phe Thr Arg Val
        595                 600                 605

Ile Asn His Arg Leu Met Ile Gln Leu Gly Thr Lys Leu Cys Thr Asn
    610                 615                 620

Gln Met Gly Phe Met Pro Gln Arg Phe Ile Gly Glu Gln Gly Met Ile
625                 630                 635                 640

Val Gln Cys Met Gln Glu Ile Ala Thr Lys Thr Gly Ser Pro Ala Ile
                645                 650                 655

Ala Leu Leu Leu Asp Gln Glu Lys Ala Tyr Asp Gln Val His Leu Asp
            660                 665                 670

Tyr Leu Arg Ala Cys Met Ala Ala Phe Asn Ile Pro Ser Thr Leu Ile
        675                 680                 685

Thr Ala Val Thr Pro Tyr Ser His Pro Gln Leu Val Gln
    690                 695                 700
```

<210> SEQ ID NO 22
<211> LENGTH: 611
<212> TYPE: PRT
<213> ORGANISM: Rhizopus oryzae

<400> SEQUENCE: 22

```
Ala Thr Gly Ala Thr Thr Ala Thr Gly Ala Ala Thr Cys Ala Thr Cys
1               5                   10                  15

Ala Thr Ala Ala Cys Ala Ala Ala Cys Gly Ala Ala Ala Gly Gly Cys
            20                  25                  30

Ala Thr Thr Thr Thr Cys Thr Thr Thr Ala Cys Thr Thr Thr Cys Cys
        35                  40                  45

Thr Thr Gly Ala Ala Thr Ala Gly Cys Ala Ala Cys Ala Gly Thr Cys
    50                  55                  60

Gly Cys Thr Thr Cys Ala Ala Gly Gly Thr Thr Ala Gly Thr Ala Ala
65                  70                  75                  80

Thr Cys Cys Ala Ala Cys Thr Thr Cys Ala Cys Ala Ala Ala Ala Ala
                85                  90                  95

Cys Ala Thr Thr Thr Ala Ala Thr Cys Cys Gly Gly Thr Ala Cys Ala
            100                 105                 110

Thr Thr Cys Gly Cys Thr Cys Cys Ala Ala Ala Thr Cys Thr Cys Cys
        115                 120                 125

Cys Ala Cys Thr Thr Thr Thr Gly Thr Cys Gly Cys Thr Cys Thr Thr
    130                 135                 140

Cys Ala Ala Gly Ala Ala Ala Thr Thr Gly Ala Thr Ala Ala Thr Ala
145                 150                 155                 160

Gly Thr Gly Gly Thr Gly Gly Thr Ala Cys Thr Gly Gly Thr Ala Thr
                165                 170                 175

Thr Cys Ala Thr Thr Thr Ala Cys Ala Gly Ala Cys Thr Thr Thr Ala
            180                 185                 190

Cys Ala Thr Cys Ala Ala Cys Ala Gly Thr Thr Thr Thr Gly Thr Ala
        195                 200                 205

Gly Thr Cys Ala Ala Cys Ala Ala Thr Cys Cys Cys Thr Gly Thr Gly
    210                 215                 220

Gly Gly Cys Thr Cys Ala Ala Thr Ala Cys Thr Gly Thr Gly Gly Thr
225                 230                 235                 240

Cys Thr Thr Cys Thr Cys Thr Gly Thr Thr Thr Thr Gly Ala Thr Cys
                245                 250                 255

Cys Thr Cys Ala Ala Thr Ala Cys Thr Cys Thr Thr Thr Ala Cys Ala
            260                 265                 270

Gly Cys Gly Thr Ala Thr Thr Cys Cys Thr Cys Thr Thr Cys Cys Ala
        275                 280                 285

Gly Ala Ala Gly Ala Thr Thr Cys Ala Cys Gly Thr Thr Gly Thr Ala
    290                 295                 300

Thr Thr Thr Thr Ala Gly Cys Cys Ala Ala Ala Gly Thr Thr Ala Cys
305                 310                 315                 320

Gly Cys Ala Thr Gly Thr Cys Ala Ala Thr Gly Ala Gly Cys Ala Ala
                325                 330                 335

Ala Thr Gly Gly Cys Thr Cys Cys Thr Thr Thr Cys Cys Ala Thr Ala
            340                 345                 350

Thr Thr Thr Thr Gly Gly Thr Ala Ala Thr Cys Thr Ala Thr Gly Cys
        355                 360                 365

Cys Cys Gly Gly Cys Thr Thr Cys Ala Thr Cys Ala Ala Ala Thr Thr
    370                 375                 380
```

Gly Ala Gly Cys Thr Cys Gly Thr Cys Ala Thr Gly Ala Ala Thr Thr
385 390 395 400

Thr Thr Thr Thr Ala Ala Cys Cys Cys Ala Thr Thr Gly Thr Thr Gly
405 410 415

Ala Cys Thr Thr Thr Cys Cys Gly Thr Cys Ala Ala Thr Thr Ala Thr
420 425 430

Cys Ala Cys Cys Gly Thr Ala Cys Cys Ala Thr Cys Cys Thr Ala Thr
435 440 445

Cys Thr Cys Thr Thr Gly Thr Gly Thr Gly Gly Ala Thr Cys Gly Cys
450 455 460

Ala Thr Gly Gly Thr Thr Ala Thr Thr Gly Cys Cys Gly Gly Ala Gly
465 470 475 480

Ala Thr Thr Thr Thr Ala Ala Thr Thr Ala Cys Thr Cys Ala Cys Thr
485 490 495

Gly Cys Ala Ala Thr Cys Cys Thr Cys Thr Thr Cys Ala Ala Thr Gly
500 505 510

Gly Cys Gly Cys Ala Thr Cys Gly Ala Thr Cys Thr Ala Thr Thr Cys
515 520 525

Cys Ala Thr Ala Thr Cys Cys Thr Cys Ala Gly Thr Gly Gly Cys Cys
530 535 540

Ala Cys Ala Thr Thr Thr Thr Cys Ala Cys Cys Ala Ala Thr Ala Thr
545 550 555 560

Cys Gly Cys Thr Thr Cys Cys Ala Ala Ala Ala Cys Gly Thr Gly Ala
565 570 575

Thr Gly Ala Cys Cys Gly Ala Cys Cys Thr Gly Thr Thr Cys Cys Thr
580 585 590

Thr Ala Gly Ala Ala Ala Cys Cys Ala Cys Cys Ala Cys Cys Thr Thr
595 600 605

Thr Ala Gly
610

<210> SEQ ID NO 23
<211> LENGTH: 429
<212> TYPE: PRT
<213> ORGANISM: Rhizopus oryzae

<400> SEQUENCE: 23

Ala Thr Gly Ala Thr Thr Ala Thr Gly Ala Ala Thr Cys Ala Thr Cys
1 5 10 15

Ala Thr Ala Ala Cys Ala Ala Ala Cys Gly Ala Ala Ala Gly Gly Cys
20 25 30

Ala Thr Thr Thr Thr Cys Thr Thr Thr Ala Cys Thr Thr Thr Cys Cys
35 40 45

Thr Thr Gly Ala Ala Thr Ala Gly Cys Ala Ala Cys Ala Gly Thr Cys
50 55 60

Gly Cys Thr Thr Cys Ala Ala Gly Gly Thr Thr Ala Gly Thr Ala Ala
65 70 75 80

Thr Cys Cys Ala Ala Cys Thr Thr Cys Ala Cys Ala Ala Ala Ala Ala
85 90 95

Cys Ala Thr Thr Thr Ala Ala Thr Cys Cys Gly Gly Thr Ala Cys Ala
100 105 110

Thr Thr Cys Gly Cys Thr Cys Cys Ala Ala Ala Thr Cys Thr Cys Cys
115 120 125

Cys Ala Cys Thr Thr Thr Thr Gly Thr Cys Gly Cys Thr Cys Thr Thr
130 135 140

```
Cys Ala Ala Gly Ala Ala Ala Thr Thr Gly Ala Thr Ala Ala Thr Ala
145                 150                 155                 160

Gly Thr Gly Gly Thr Gly Gly Thr Ala Cys Thr Gly Gly Thr Ala Thr
                165                 170                 175

Thr Cys Ala Thr Thr Thr Ala Cys Ala Gly Ala Cys Thr Thr Thr Ala
            180                 185                 190

Cys Ala Thr Cys Ala Ala Cys Ala Gly Thr Thr Thr Thr Gly Thr Ala
        195                 200                 205

Gly Thr Cys Ala Ala Cys Ala Ala Thr Cys Cys Cys Thr Gly Thr Gly
    210                 215                 220

Gly Gly Cys Thr Cys Ala Ala Thr Ala Cys Thr Gly Thr Gly Gly Thr
225                 230                 235                 240

Cys Thr Thr Cys Thr Cys Thr Gly Thr Thr Thr Thr Gly Ala Thr Cys
                245                 250                 255

Cys Thr Cys Ala Ala Thr Ala Cys Thr Cys Thr Thr Thr Ala Cys Ala
            260                 265                 270

Gly Cys Gly Thr Ala Thr Thr Cys Cys Thr Cys Thr Thr Cys Cys Ala
        275                 280                 285

Gly Ala Ala Gly Ala Thr Thr Cys Ala Cys Gly Thr Thr Gly Thr Ala
    290                 295                 300

Thr Thr Thr Thr Ala Gly Cys Cys Ala Ala Ala Gly Thr Thr Ala Cys
305                 310                 315                 320

Gly Cys Ala Thr Gly Thr Cys Ala Ala Thr Gly Ala Gly Cys Ala Ala
                325                 330                 335

Ala Thr Gly Gly Cys Thr Cys Cys Thr Thr Thr Cys Cys Ala Thr Ala
            340                 345                 350

Thr Thr Thr Thr Gly Thr Gly Gly Cys Cys Ala Cys Ala Thr Thr Thr
        355                 360                 365

Thr Cys Ala Cys Cys Ala Ala Thr Ala Thr Cys Gly Cys Thr Thr Cys
    370                 375                 380

Cys Ala Ala Ala Ala Cys Gly Thr Gly Ala Thr Gly Ala Cys Cys Gly
385                 390                 395                 400

Ala Cys Cys Thr Gly Thr Thr Cys Cys Thr Thr Ala Gly Ala Ala Ala
                405                 410                 415

Cys Cys Ala Cys Cys Ala Cys Cys Thr Thr Thr Ala Gly
            420                 425
```

<210> SEQ ID NO 24
<211> LENGTH: 20
<212> TYPE: DNA
<213> ORGANISM: Artificial Sequence
<220> FEATURE:
<223> OTHER INFORMATION: S-Toxin Forward Primer

<400> SEQUENCE: 24
gcaaatggct cctttccata 20

<210> SEQ ID NO 25
<211> LENGTH: 20
<212> TYPE: DNA
<213> ORGANISM: Artificial Sequence
<220> FEATURE:
<223> OTHER INFORMATION: S-Toxin Forward Primer

<400> SEQUENCE: 25
ccctgtgggc tcaatactgt 20

-continued

<210> SEQ ID NO 26
<211> LENGTH: 20
<212> TYPE: DNA
<213> ORGANISM: Artificial Sequence
<220> FEATURE:
<223> OTHER INFORMATION: S-Toxin Forward Primer

<400> SEQUENCE: 26
gtaatctatg cccggcttca 20

<210> SEQ ID NO 27
<211> LENGTH: 20
<212> TYPE: DNA
<213> ORGANISM: Artificial Sequence
<220> FEATURE:
<223> OTHER INFORMATION: S-Toxin Forward Primer

<400> SEQUENCE: 27
tctcccactt ttgtcgctct 20

<210> SEQ ID NO 28
<211> LENGTH: 20
<212> TYPE: DNA
<213> ORGANISM: Artificial Sequence
<220> FEATURE:
<223> OTHER INFORMATION: S-Toxin Forward Primer

<400> SEQUENCE: 28
ccctgtgggc tcaatactgt 20

<210> SEQ ID NO 29
<211> LENGTH: 20
<212> TYPE: DNA
<213> ORGANISM: Artificial Sequence
<220> FEATURE:
<223> OTHER INFORMATION: S-Toxin Reverse Primer

<400> SEQUENCE: 29
gaatagatcg atgcgccatt 20

<210> SEQ ID NO 30
<211> LENGTH: 20
<212> TYPE: DNA
<213> ORGANISM: Artificial Sequence
<220> FEATURE:
<223> OTHER INFORMATION: S-Toxin Reverse Primer

<400> SEQUENCE: 30
tgaagccggg catagattac 20

<210> SEQ ID NO 31
<211> LENGTH: 20
<212> TYPE: DNA
<213> ORGANISM: Artificial Sequence
<220> FEATURE:
<223> OTHER INFORMATION: S-Toxin Reverse Primer

<400> SEQUENCE: 31
ccatttgctc attgacatgc 20

<210> SEQ ID NO 32
<211> LENGTH: 20
<212> TYPE: DNA
<213> ORGANISM: Artificial Sequence
<220> FEATURE:
<223> OTHER INFORMATION: S-Toxin Reverse Primer

<400> SEQUENCE: 32
ccgggcatag attaccaaaa 20

<210> SEQ ID NO 33
<211> LENGTH: 1440
<212> TYPE: PRT
<213> ORGANISM: Artificial Sequence
<220> FEATURE:
<223> OTHER INFORMATION: ADP-rhibosylation

<400> SEQUENCE: 33

```
Val Leu Ala Val Pro Arg Asn Glu Ser Thr Met Thr Ala Glu Glu Leu
1               5                   10                  15

Ala Glu Arg Glu Gln Glu Ala Lys Met Thr Lys Leu Glu Asn Ser Glu
            20                  25                  30

Leu Met Met Gln Gln His Asp Val Thr Glu Asp Thr Asn Lys Asn Asp
        35                  40                  45

Thr Phe Ala Asn Gln Leu Val Thr Arg Ile Leu Asn Asn Leu Gln Phe
    50                  55                  60

Ser Ile Gln Thr Ile His Ile Arg Tyr Glu Asp Asn Val Ser Thr Glu
65                  70                  75                  80

His Arg Phe Ala Ala Gly Ile Thr Leu Asn Glu Leu Ser Ala Ile Thr
                85                  90                  95

Thr Asp Glu Glu Trp Thr Pro Asn Thr Leu Gly Glu Ala Ala Asn Thr
            100                 105                 110

Ile Tyr Lys Leu Ala Thr Leu Glu Ser Leu Ser Ile Tyr Trp Asp Thr
        115                 120                 125

Asn Ile Gln Ser Ile Ala Asp Glu Asp Asn Glu His Glu Ala Phe Lys
    130                 135                 140

Ala Leu Ile Ala Thr Lys Gln His Val Pro Lys Glu His Gln Tyr Ile
145                 150                 155                 160

Leu Lys Pro Val Ser Gly Ser Gly Arg Val Lys Phe Asn Lys His Phe
                165                 170                 175

Gly Asp Lys Val Pro Lys Phe Glu Ala Ser Leu Leu Phe Asp Glu Leu
            180                 185                 190

Ser Phe Thr Val Asp Asn Glu Gln Tyr Arg Asp Thr Ile Leu Met Ile
        195                 200                 205

Asp Leu Phe His Ser Tyr Leu Lys Lys Gln Lys Tyr Arg Glu Cys His
    210                 215                 220

Pro Pro Ser His Met Thr Pro Lys Ser His Pro Leu Glu Tyr Phe Arg
225                 230                 235                 240

Phe Ala Gly Gln Ala Ile Leu Ser Glu Ile His Glu Arg Asn Gln Arg
                245                 250                 255

Trp Thr Trp Asp Arg Leu Lys Lys Arg Arg Asp Asp Arg Lys Ala Tyr
            260                 265                 270

Ile His Cys Tyr Val Asn Tyr Lys Leu Asp Arg Ala Thr Pro Glu Glu
        275                 280                 285

Leu Glu Gln Leu Glu Gly Leu Glu Arg Ala Leu Ser Phe Glu Asp Leu
    290                 295                 300

Arg Phe Tyr Arg Ser Leu Ala Lys Pro Lys Leu Arg Ser Glu Lys Ala
305                 310                 315                 320

Arg Leu Ala Ala Ile Glu Lys Arg Arg Lys Glu Glu Glu Thr Ala Lys
                325                 330                 335

Lys Ala Lys Gln Gly Trp Gly Ile Ser Ser Trp Trp Tyr Gly Ser Gly
```

```
            340                 345                 350

Lys Leu Ser Glu Asp Ser Glu Asn Glu Ala Glu Glu Ile Val Ile Thr
        355                 360                 365

Glu Glu Gln Lys Gln Glu Phe Tyr Asp Val Ile Asp Tyr Asp Ala Asp
    370                 375                 380

Lys Ala Ala Ile Ala Ala Ser Ile Asp Leu Pro Lys Asp Thr Thr Leu
385                 390                 395                 400

Leu Ser Leu Asn Met Thr Leu Asn Arg Gly Ser Phe Asn Val Arg Lys
                405                 410                 415

Asn Pro His Lys Gln Pro Val Asp Leu Leu Ser Leu Val Phe Asp Asn
            420                 425                 430

Phe Ser Met Ser Leu Thr Lys Tyr Val Glu Ser Phe Thr Ala Thr Ala
        435                 440                 445

Ala Leu Gly Asp Met Ser Leu Tyr Asp Gly Gln Arg Pro Glu Ser Pro
    450                 455                 460

Tyr Tyr Lys Leu Met Gly Ala Lys Gly Lys Asp Val Ser His Arg Lys
465                 470                 475                 480

Ser Ile Thr Leu Asp Ser Gln Leu Lys Asn Phe Ser Asn Pro Met Lys
                485                 490                 495

Asp Pro Phe Phe Thr Ala Thr Phe Glu Tyr Lys Pro Leu Asp Glu Arg
            500                 505                 510

Ala Asp Asn Ala Ala Ala Leu Tyr Met Arg Asn Ile Asp Ile Val Tyr
        515                 520                 525

Asn Pro Gln Val Ile Tyr Glu Ile Val Glu Phe Phe Thr Pro Ser Glu
    530                 535                 540

Thr Ser Ala Asp Ser Ile Asn Ala Leu Ile Glu Val Ala Gly Asp Thr
545                 550                 555                 560

Leu Glu Gly Phe Lys Lys Gln Thr Arg Ala Ser Leu Lys Tyr Ala Leu
                565                 570                 575

Glu Gln His Thr Thr Leu Asp Leu Lys Val Asp Met Asp Ala Pro Val
            580                 585                 590

Ile Ile Ile Pro Glu Asn Ala Ile Val Ile Asp Ala Gly His Ile Asn
        595                 600                 605

Val Glu Ser Asn Leu Leu Pro Pro Glu Thr Arg Ala Gln Leu Lys Ser
    610                 615                 620

Arg Ser Gly Ala Glu Met Thr Ala Glu Asp Asp Thr Asn Leu His Ser
625                 630                 635                 640

Leu Met Phe Asp Arg Phe Thr Val Gln Leu Thr Gln Thr Lys Ile Leu
                645                 650                 655

Val Gly Asp Ser Leu Asp Thr Cys Leu Val Gln Val Arg Arg Pro Arg
            660                 665                 670

Pro Glu Leu Asp Tyr Leu His Leu Val Asp Arg Ile Asp Met Thr Phe
        675                 680                 685

Leu Leu Glu Leu Cys Ile Ile Arg Lys Ser Phe Asp Met Pro Arg Leu
    690                 695                 700

Lys Val Ser Gly His Leu Pro Leu Leu Lys Val Asn Phe Ser Asp Thr
705                 710                 715                 720

Lys Tyr Lys Ala Ile Met Gln Leu Pro His Leu Ile Glu Ala Ser Gly
                725                 730                 735

Leu Leu Gly Asp Lys Lys Thr Glu Val Asp Leu Asn Glu Tyr Pro Val
            740                 745                 750

Gln Asn Gln Ala Asp Gln Ser Trp Phe Asn Leu Met Gly Asn Pro Leu
        755                 760                 765
```

-continued

```
Trp Asn Lys Pro Glu Glu Glu Asp Asp Met Phe Leu Leu Ser Asp Ser
    770                 775                 780

Glu Ser Ser Asp Leu Tyr Thr Asp Ser Leu Ala Asp Thr Val Asp Thr
785                 790                 795                 800

Glu Val Thr Lys Ala Thr Thr Val Lys Ser Val Lys Ser Ser Lys Glu
                805                 810                 815

Thr Val Asn Val Glu Glu Arg Leu Phe Glu Leu Asp Phe Lys Val Asp
            820                 825                 830

Arg Val Leu Ala Asn Ile Leu Arg Ala Gln Lys Gly His Arg Ser Asp
        835                 840                 845

Ser Asp Gly Leu Ser Pro Glu His Leu Leu Cys Glu Val Asp Leu Lys
    850                 855                 860

Ser Leu Lys Leu Asn Tyr Asn Met Arg Pro Met Asp Met Thr Val Gly
865                 870                 875                 880

Leu Ser Leu Lys Ser Leu Asp Val Thr Asp Arg Met Lys His Gly Asn
                885                 890                 895

Glu Phe Lys Tyr Leu Val Thr Ser Asp Gln His Ile Leu Gln Pro Asp
            900                 905                 910

Ala Ser Asn Asp Ser Gly Leu Lys Glu Leu Val Asn Val Glu Tyr Val
        915                 920                 925

Gln Cys Asp Lys Gln Asn Pro Glu Tyr Met Thr Arg Tyr Lys Gly Val
    930                 935                 940

Gly Gln Thr Val His Val Thr Leu Ser Thr Leu Asn Phe Ile Val Thr
945                 950                 955                 960

Arg Ser Ser Val Leu Thr Leu His Ser Phe Val Met Asp Thr Phe Val
                965                 970                 975

Asp Ser Glu Ile Asn Ser Asn Gln Lys Thr Ala Ala Ile Thr Pro Ser
            980                 985                 990

Leu Ala His Thr Ile Pro Ala Thr  Gln Ala Ser Lys Pro  Ser Ser Asn
        995                 1000                1005

Thr Thr  Asp Asn Asn Ile Tyr  Val Arg Leu Leu Leu  Asp Ser Val
    1010                1015                1020

Asn Phe  Val Leu Asn Asn Asp  Gly Val Arg Leu Ala  Thr Gly Glu
    1025                1030                1035

Leu Ser  Leu Gly Asp Leu Ser  Thr Val Val Ser Asp  Gly Gln Val
    1040                1045                1050

Asn Val  Ala Ala Lys Phe Ala  Asn Phe Thr Leu Thr  Asp Asp Leu
    1055                1060                1065

Ser Pro  Arg Lys Ala Ala Asp  Thr Gln Thr Trp Pro  His Gln Leu
    1070                1075                1080

Leu Thr  Ile Gln Gly Glu Glu  Leu Ile Asp Leu Lys  Tyr Thr Ser
    1085                1090                1095

Phe Val  Asp Asp Gly Arg Gln  Asp Tyr Pro Gly Tyr  Asp His Ala
    1100                1105                1110

Val Tyr  Leu Arg Met Gly Ser  Ala Gln Phe Arg Phe  Leu Glu Glu
    1115                1120                1125

Pro Val  His Gln Leu Leu Gln  Phe Leu Ser Lys Phe  Ala Glu Met
    1130                1135                1140

Lys Leu  Ala Tyr Asp Met Ala  Arg Ala Ala Ala Leu  Glu Ser Ala
    1145                1150                1155

Gln Gln  Leu Ser Gln Ala Ala  Thr Lys Met His Phe  Asp Val Val
    1160                1165                1170
```

```
Ile Lys  Thr Pro Val Val Leu  Phe Pro Glu Phe His  Gln His Pro
    1175                 1180                 1185

Ser Asp  Cys Val Val Ala His  Leu Gly Glu Ile Trp  Ala Ser Asn
    1190                 1195                 1200

Thr Phe  Val Thr Asp Glu Asp  Gly Cys Ile Asn Thr  Ile Gln Ala
    1205                 1210                 1215

Gly Leu  Arg Ala Ile Asn Leu  Thr Ser Lys Phe His  Phe Ala Arg
    1220                 1225                 1230

Pro Glu  Ile Leu Leu Gln Thr  Leu Pro Ile Val Asp  Asp Ile Asp
    1235                 1240                 1245

Val Thr  Phe Ala Ile Asp Ile  Pro Glu Gln Gly Ser  Ser Glu Arg
    1250                 1255                 1260

Pro Met  Val Asp Ile Lys Gly  Lys Val Ser Asp Ile  Ser Met Arg
    1265                 1270                 1275

Leu Thr  Glu Arg Gln Tyr Ile  Phe Leu Met Glu Ala  Ile His Met
    1280                 1285                 1290

Phe Ser  Arg Ile Phe Thr Asp  Thr Asp Glu Asp Glu  Ala Asn Leu
    1295                 1300                 1305

Gln Ala  Leu Ser Asn Lys Arg  Ser Ser Thr Val Gln  His Arg Ser
    1310                 1315                 1320

Ser Gln  Ala Ser Ile Gln Pro  Ala Ala Ala Thr Glu  Lys Thr Arg
    1325                 1330                 1335

Ser Pro  Gln Ile Gln Met Ala  Ile Asp Ala Lys Met  Ile Lys Leu
    1340                 1345                 1350

Glu Ile  Tyr Met Gly Thr Gly  Pro Asp Leu Gln Ser  Pro Pro Ser
    1355                 1360                 1365

Leu Ala  Ser Phe Ala Leu His  Asn Ser Gln Val Asn  Phe Arg Met
    1370                 1375                 1380

Gln Arg  Asp Asn Thr Met Asp  Val Phe Leu Val Ile  Pro Ser Leu
    1385                 1390                 1395

Thr Val  Asp Asp Thr Arg Pro  Gly Ile Asn Ser Gly  Phe Lys Asn
    1400                 1405                 1410

Ile Met  Pro Val Val Lys Asp  Lys Asn Gln Phe Glu  Leu Gln Leu
    1415                 1420                 1425

Asp Leu  Lys Ala Pro Asn Pro  Ile Arg Ser Gly Ile
    1430                 1435                 1440
```

<210> SEQ ID NO 34
<211> LENGTH: 10
<212> TYPE: PRT
<213> ORGANISM: H-toxin Common Epitope 1
<220> FEATURE:
<221> NAME/KEY: SITE
<222> LOCATION: (7)..(7)
<223> OTHER INFORMATION: Xaa is Asp or Glu

<400> SEQUENCE: 34

```
Asn Gln Leu Trp Arg Tyr Xaa Asx Gly Tyr
1               5                   10
```

<210> SEQ ID NO 35
<211> LENGTH: 441
<212> TYPE: DNA
<213> ORGANISM: Rhizopus microspores

<400> SEQUENCE: 35

```
atgagttact tagcaggacg tacattctat atcaagagtc aattcaatgg acgcgtgctc     60
```

-continued

```
gatgttgaag gcgcttccac cgaagatgat gcccccgtga ttgtttatac ccaaaaatat    120

gatgacaact tgaatcaact ctggcgttat gaaaatggtt actttgtcaa cgtcaactct    180

gccaaggttt tggatatccg cggtggccaa atggaccctg aatctgaaat tattcaatac    240

tctcaaaagg tatacgaaga agctgtgaac caaagatgga acattgatgg ggaaggctat    300

atctatattg aagctcgtcc tgacttagtc ttggacattc aaggtgccga ggatgaggat    360

ggtgttcccg tcatcttgta caatagacgt gagggtgaag tctcttctaa ccaacgttgg    420

gtgttggaac cagttgatta a                                              441
```

```
<210> SEQ ID NO 36
<211> LENGTH: 435
<212> TYPE: DNA
<213> ORGANISM: Mucor circinelloides

<400> SEQUENCE: 36

atgactggta ccatgttctt tatcaaaagc caaatgaacg gccgtgttct cgatgtgagc     60

gaaggctcta ctgaggatga agcccctatc attgtctact ctcaaaaggg cgaagattgc    120

ttgaaccaat tgtggcgcta cgaagacggt tatttcatca atgccaagtc tgccaaggtt    180

ctcgatatta gcggtggtga aatgcaaccc gagtctccta tcattcaata tgctcaaaag    240

atgtctgagg aagctgctaa tcaaaagtgg gaaatcgatg aagatggtta tatcttctgt    300

tctgctcgcc ctgatttagt cttggacatt caaggtcgtg aagacgagga tggcgctgtt    360

gtcattttgt acgaaaagcg tgatggtgaa attgcttcta accaacgctg gttcttggaa    420

gagtactctg gttaa                                                     435
```

```
<210> SEQ ID NO 37
<211> LENGTH: 435
<212> TYPE: DNA
<213> ORGANISM: Mucor ambiguous

<400> SEQUENCE: 37

atgactggta ccatgtattt tatcaaaagc caaatgaacg gccgtgttct tgatgtgagt     60

gaaggctcta ccgaggacga ggcccctatc attgtctact ctcaaaaggg cgaacattgc    120

ttgaaccaat tgtggcgtta tgaagatgga tacctcatca atgctaactc tgccaaggtg    180

ctcgatatca gtggtggaga aatgcaaccc gaatctgcta tcattcaata tgctcaaaag    240

atgtctgagg aggccgctaa tcagaaatgg gaaatcgatg gtgaaggcta tatctgttgt    300

tctgctcgcc ctgatttagt cttggacatt gcagagcgca atgacgagga tggtgctgct    360

gtcatcttgt atgagaagcg cgagggtgag attgcctcta accaacgttg gttcttggaa    420

gagttctctg gttaa                                                     435
```

```
<210> SEQ ID NO 38
<211> LENGTH: 300
<212> TYPE: DNA
<213> ORGANISM: Lichtheimia corymbifera

<400> SEQUENCE: 38

atgatccaat atcgtcgaaa gatgctcgaa gatgcgcaca atcaacgctg gtattatcgt     60

gaggatggtt tcatttaccc tcaagtcgat cctaatttgg ttcttgatat tcgcggcaat    120

tggaccaagc ctggaacggt ggtacttctt tacgagcgaa aatacagcga taacgagaat    180

cagctatggg atcttattcc agataccagc gacgacgagt catcagcatc gatattatta    240

cgagaagagg aggatggtga tgatgattac tccttcagca cttcaagcta tgcactctag    300
```

<210> SEQ ID NO 39
<211> LENGTH: 3666
<212> TYPE: DNA
<213> ORGANISM: Mortierella verticillata

<400> SEQUENCE: 39
atggcaggct ccccttcaac ttctgcccga tccagtcgtg tgctgtcctt ccccaagggc 60
cagttctaca tccagtcgcc cattgctgac ctggttctcg acattgagtc cgggttcctg 120
aaggaccccc tcaaggccaa cgcgcgtgtc gagctcgtac acaagaagtc acccaaacac 180
aacgccgagt cctcgctgat ccagcaggag cagcagcagt ggcgcgagga ggagggttac 240
atcatcaaca ctcgtactgg ccacgtcttg gatatccaag gaggggcccc attggacaac 300
gggcattggt attgggcagt gggcggcatc catggtatca ttgccatcaa tatgactaac 360
cgtccatctc tccacatcac ctttcttcac acacacacag gtgtcatccg ttccggtact 420
cgcgttatcc aaaacgtgcg caagactgga aaggatgctg ctggccagca ctggttgaac 480
gatgacggtg tcctgacctt ggccagcaac cccaagttcg tcgtcaccat cgatggagat 540
gccaccaaag atggaacccg catcactatc caagaaaaga agccatacta cgagaagcaa 600
aaatggttgt atctgaacgg cttcgatgct cgccctgtgt cgccttctcc ttccagagca 660
gagtcactct ccatccgccc tgacaacttc cccaccagct ggttctacat caagtccgct 720
gcctcgggct tggtcgtcga cattgagcac ggctacttca cagaccccat gaaggccggt 780
gcccgcgccg aaatgaacca ccaaaagatc gacaacggtg acggccgcca ctccttgctt 840
gagctccagc tttggcgcta cgaggctggt ttccttatca accgtcgcac cggtttcgtt 900
ctggacattc aaggaggcac tctcaaactc gccgccagag tcgtccagtg gcagcgcaag 960
tctggaaagg aggcccagaa ccagcactgg ttctacgaga acggcttcat tgccaacgtc 1020
tacaactcga ggctggttct ggacattgat ggcgatggtt ccaaggacgg agccaagatc 1080
gccatcggtg agcgcaaggc tgtcagcaac gctgatcaga agtggctgtt ggaggaggtt 1140
cgcttccaat ggttggctgc tcctacctca gcctcggcct ccatctcctc caatgtcacc 1200
gaggagatta ccgtcgtcga gagaggcatc tcgtcccccca aggtcgccac tccccccacc 1260
accgtcaccg ctctgcccac cagcggctgg ttctacatca agtcccagtc ctctggtctc 1320
gttgtcgacg ttgagcagga tgccgatcct ttggccccta acgtcctcgt cagcatgaac 1380
acccagatca cctctgtcac tgaggagaac caggccaagg tcgagtcaca gctctggaca 1440
taccagaatg gtcagatcat caacaggaga tctcagctcg tcctcgactg caaacagggt 1500
gtcgtccgct atggcgccag actgatgcag ggaattccca aggagggcaa agagagccac 1560
caccagcgtt gggagtcatc caacggcacc ctcgtcgtcc agggcaagcc tctctacgct 1620
atcgacattg agggtgatgg caccaagtcc ggttcccgcc tctcgctcca gcgccccaag 1680
gtccagaaca actcggatca gcagtggtcc ttccagatcg ccacttacga gtggctcaag 1740
gtccagcgtt ctgtcacccg caccttcacc gagaccacca cctcttcgtc taaggttgtt 1800
aacatcgaga agaacgactg gttcttcatc aagtccggag ccaccggctt ggtcatggat 1860
ctcgaggctg gctggattac tcagcccacc gatgttggtg cctacatttc catgaagaag 1920
cagcgctcgc tcgaggagtc tgatcgtgcc cttttggaga gacagttgtg gcgctatgag 1980
gacggctacc tcatcaaccg cagaaccaac tacgtcgttg acatctatgg tcgctccgcc 2040
gttgttggcg tcaagttgat ccagcagtac aaggctacca ccgaggtcta tgatgctgtc 2100

-continued

```
ctcaccgaga agcacactgg tgttacctac gtgacccagc tgttgttcga cacccagacc   2160

aatgcctact acgtctacgt ccgctggggc gagaccgagt acagattgga tgggccccac   2220

gagaccattg agtccgccaa ggccgctttc ttgatcacct accacgatca gtttggtgtt   2280

gaatggcaaa ctcgcgagac caccgtcagc gaacaatgga cctacgaagt caagacctat   2340

gagactttcg aggagatcga gtacgttgag gaggtcgttg aggagactga ggcagtcacc   2400

atcattgagc agcagcgcga gatcgttgtc caggaacagt ccgagcatgt tgaagttacc   2460

gagggcgagg agatcatcaa ggttgtcacc accgtcaagg agactggtgt cgttgccgag   2520

cccgccgtgt ccaagggcac ttcctggttc cgccgcctgg cctccggagc tggcgccgtc   2580

gcatcgggcg ctttgactga ggtcgatggc gtctggaagc gcactgtcca ggtcctcacc   2640

acccgcaagg ctcacgtcga caaggttgcc cctattgccg agacctcgta tgtgtactat   2700

gatgaggagg tctacgattc cgtccttgtt gagaagtcga ctggcatcac ctatgtcacc   2760

cagcttctgt tcgacaccaa ggtccagaag tactacgtct acgtccgctg gggcgagact   2820

gactacaagt tggatggacc ccacgacact atcgaggctg ccaaggccgc tttccagatc   2880

acctacaagg agagattcgg tttggagtgg gctacccgcg agaccaccgt cagcgaacgc   2940

tggacctatg aggttcgcac ctacgagacc ttcgaggaga ctgaggagat cgaggagatc   3000

gtggaggatt acgaggtcaa ggagattgtt gcccgtgagc agcaggtcat tgtcgagggc   3060

aaggtcattt cgaccgagca gtccgtgtcg tcgtcccatg acgacactgt tgtccgcacc   3120

gtgagcgagc aggttgtgtc caaggatggc tctgcctctg gatcttcgtc cagccgcggt   3180

ggcgcctttg gctttggtgg ctcgtcgtct tacgagtaca cccagaccca gtctgaggag   3240

agcaagaagt ccactttctt ggccaacctc cccaccttga acgctggcat caacgccgat   3300

accggtgccg ccattggcgt gatcgatctg acctctggca ccgccgagaa ccttcgcgag   3360

ttgcccgccc acttgcgccc ccgtgcctgg gtctcgctcc acgttggagg ctggcagaac   3420

gccccccacg agcttgaagg atttatgcgc ctcgatgacc agtcgggcca gcgtctgatg   3480

gagactgccc gcgatgagtc ccttggcaag gcccaggagt cgacccctat tgacaacctg   3540

agcttgcccg agattgtggg attgtttgcc cagaagttgt acggacactt tggcgaggag   3600

ctgcccaagg agctggagat ggagaagctg agggatctgg cccgcggatt ccctggtcgt   3660

cactaa                                                               3666
```

<210> SEQ ID NO 40
<211> LENGTH: 21
<212> TYPE: DNA
<213> ORGANISM: Artificial Sequence
<220> FEATURE:
<223> OTHER INFORMATION: H-Toxin Forward Primer

<400> SEQUENCE: 40
atcattcaat atgctcaaaa g 21

<210> SEQ ID NO 41
<211> LENGTH: 27
<212> TYPE: DNA
<213> ORGANISM: Artificial Sequence
<220> FEATURE:
<223> OTHER INFORMATION: H-Toxin Forward Primer

<400> SEQUENCE: 41
gaagaagctg ccaaccaaag atgggct 27

<210> SEQ ID NO 42
<211> LENGTH: 31
<212> TYPE: DNA
<213> ORGANISM: Artificial Sequence
<220> FEATURE:
<223> OTHER INFORMATION: H-Toxin Reverse Primer

<400> SEQUENCE: 42
tcagcgcctt ggatatctaa aactaaatca g 31

<210> SEQ ID NO 43
<211> LENGTH: 27
<212> TYPE: DNA
<213> ORGANISM: Artificial Sequence
<220> FEATURE:
<223> OTHER INFORMATION: H-Toxin Reverse Primer

<400> SEQUENCE: 43
tggttggctg aaacttcacc ttcacgt 27

<210> SEQ ID NO 44
<211> LENGTH: 20
<212> TYPE: DNA
<213> ORGANISM: Artificial Sequence
<220> FEATURE:
<223> OTHER INFORMATION: H-Toxin Forward Primer

<400> SEQUENCE: 44
tctggcgtta cgaaaatggt 20

<210> SEQ ID NO 45
<211> LENGTH: 20
<212> TYPE: DNA
<213> ORGANISM: Artificial Sequence
<220> FEATURE:
<223> OTHER INFORMATION: H-Toxin Reverse Primer

<400> SEQUENCE: 45
tccaagacct tggcagactt 20

<210> SEQ ID NO 46
<211> LENGTH: 20
<212> TYPE: DNA
<213> ORGANISM: Artificial Sequence
<220> FEATURE:
<223> OTHER INFORMATION: H-Toxin Forward Primer

<400> SEQUENCE: 46
ggacgtgtcc ttgatgttga 20

<210> SEQ ID NO 47
<211> LENGTH: 600
<212> TYPE: DNA
<213> ORGANISM: Puccinia graminis f. sp. tritici

<400> SEQUENCE: 47
atggccgact tccctaccgc ttggttttac atcaagtcgg tttgctcaaa gaaagtcatc 60
caaccactcg gtggaagttt cgaaccaacc cgactagtcg ttgtcgatca aaaattcggt 120
caggaatcag cagcccaact ctggaaacat gagaacggtt acttggtcaa caagctgact 180
aacctctgtc tggattacga acatggcaac tataagcgct taggtgatat tcacgtttgc 240
cagtggcatc aaaaagtcgg caaggatgct cataaccaaa aatggctata caggacaagc 300
aacttgattg catcgaatga cgacatcaac cgagtattag acatcaaggg aggatcgatt 360

-continued

```
catccggggg cagaagtttt actcaagaaa ctcgagacga tcaaaggcgc ccatccggcc    420

caccaacgat ggctgctaga agtgattgac caggacggct taccagactc attatcaacc    480

taccaggaag accaaatcgc tggcagctat gctgcccccg tggaacacgt caatccttgg    540

gctactctcg agccttcgac ggatgatgaa ccaggcgaag ctcaaaccac atattactaa    600
```

FUNGAL TOXINS AND METHODS RELATED TO THE SAME

RELATED PATENT APPLICATIONS

This patent application is a national phase entry of, and claims priority to, International Patent Application No. PCT/US2017/062537, filed Nov. 20, 2017, entitled "NOVEL FUNGAL TOXINS AND METHODS RELATED TO THE SAME", naming Ashraf S. Ibrahim, Sameh Soliman and John Edwards Jr. as an inventor, which designated the U.S. and was published under PCT Article 21(2) in English, which claims the benefit of U.S. Provisional Patent Application No. 62/424,882 filed on Nov. 21, 2016, entitled "NOVEL FUNGAL TOXINS AND METHODS RELATED TO THE SAME" naming Ashraf S. Ibrahim, Sameh Soliman and John Edwards as an inventor. The entire content of the foregoing patent applications are incorporated herein by reference, including all text, tables, sequence listing and drawings.

GOVERNMENT FUNDING

This invention was made with government support under grant numbers A1063503 and A1082414. The government has certain rights in the invention.

FIELD

This technology relates in part to novel fungal toxins, uses thereof, and method of detection and treating fungal infections.

BACKGROUND

The present invention relates generally to compositions and methods for detecting, treating and preventing infectious diseases in a patient, and more specifically to compositions and methods that target specific proteins or nucleic acids unique to fungi that cause mucormycosis.

About 180 of the 250,000 known fungal species are recognized to cause disease (mycosis) in man and animal. Fungi of the class Zygomycetes, order Mucorales, can cause mucormycosis, a potentially deadly fungal infection in human. Fungi belonging to the order Mucorales are distributed into at least six families, all of which can cause mucormycosis. However, fungi belonging to the family Mucoraceae, and specifically the genus *Rhizopus*, are by far the most common cause of infection in mammals. Increasing cases of mucormycosis have also been reported due to infection with *Cunninghamella* spp. (family: Cunninghamellaceae).

Mucormycosis often affects immunocompromised hosts. Some of the major risk factors for mucormycosis include uncontrolled diabetes mellitus in ketoacidosis known as diabetes ketoacidosis (DKA), other forms of metabolic acidosis, treatment with corticosteroids, organ or bone marrow transplantation, neutropenia, trauma and burns, malignant hematological disorders, and deferoxamine chelation-therapy in subjects receiving hemodialysis.

Recent reports have demonstrated a striking increase in the number of reported cases of mucormycosis over the last two decades. There has also been an alarming rise in the incidence of mucormycosis at major transplant centers. Given the increasing prevalence of diabetes, cancer, and organ transplantation in the aging United States population, the incidence of mucormycosis may continue to rise unabated for the foreseeable future unless effective methods of prevention, diagnosis and treatment are developed.

SUMMARY

Provided herein in certain embodiments is a method of detecting the presence of Mucorales in a sample, the method comprising, a) contacting a sample comprising nucleic acids obtained from a mammal with an oligonucleotide primer pair thereby providing a mixture, wherein the oligonucleotide primer pair is configured to specifically hybridize to and amplify one or more nucleic acids having at least 80% identity to SEQ ID NO:1, SEQ ID NO: 2, SEQ ID NOs: 35-39, SEQ ID NO: 47, SEQ ID NO: 22, and/or SEQ ID NO: 23, or a portion thereof, b) performing an amplification reaction with the mixture, thereby providing an amplification product; and, c) analyzing the amplification product for the presence of an amplicon of a predetermined length, wherein the presence of the amplicon indicates the presence of Mucorales in the sample. In certain aspects, a method of detecting the presence of Mucorales in a sample comprises, a) contacting a sample comprising nucleic acids obtained from a mammal with an oligonucleotide primer pair thereby providing a mixture, wherein the oligonucleotide primer pair is configured to produce an amplicon under amplification conditions, wherein the amplicon comprises at least 80% identity to SEQ ID NO:1, SEQ ID NO: 2, SEQ ID NOs: 35-39, SEQ ID NO: 47, SEQ ID NO: 22, and/or SEQ ID NO: 23, or a portion thereof, b) performing an amplification reaction with the mixture, thereby providing an amplification product; and, c) analyzing the amplification product for the presence of the amplicon, wherein the presence of the amplicon indicates the presence of a Mucorales species in the sample.

Also provided here is a composition comprising nucleic acids obtained from a mammal, an oligonucleotide primer pair configured to specifically hybridize to and amplify a nucleic acid having at least 80% identity to one or more of SEQ ID NOs: 1, 2, 35, 36, 37, 38, 39, 47, 22, and/or 23, or a portion thereof; and a recombinant polymerase. In certain embodiments, a composition comprises nucleic acids obtained from a mammal, an oligonucleotide primer pair configured to produce an amplicon under amplification conditions, wherein the amplicon comprises at least 80% identity to one or more of SEQ ID NOs: 1, 2, 35, 36, 37, 38, 39, 47, 22, and/or 23, or a portion thereof, and a recombinant polymerase.

In some embodiments, provided herein is an antibody binding agent that specifically binds to a polypeptide comprising an amino acid sequence having at least 80% identity to any one of SEQ ID NOs: 3-9 or SEQ ID NOs: 17-21.

In certain aspects, provided herein is method comprising a) providing an antibody binding agent that specifically binds to a polypeptide comprising an amino acid sequence having at least 80% identity to any one of SEQ ID NOs: 3-9 or SEQ ID NOs: 17-21 and b) contacting the antibody binding agent with the polypeptide, wherein the antibody binding agent specifically binds to the polypeptide. In certain embodiments a method comprises a) providing an antibody binding agent that specifically binds to a polypeptide comprising 16 or more consecutive amino acids having 80% or more identity to SEQ ID NOs: 3-9, SEQ ID NOs: 17-21, or a portion thereof; and b) contacting the antibody binding agent with the polypeptide, wherein the antibody binding agent specifically binds to the polypeptide. In some embodiments a method comprises, a) providing an antibody binding agent that specifically binds to a polypeptide comprising 16 or more consecutive amino acids of any one of SEQ ID NOs: 3-9 or SEQ ID NOs: 17-21 and b) contacting the antibody binding agent with the polypeptide, wherein the antibody binding agent specifically binds to the polypeptide.

In some embodiments, provided herein is a method of detecting the presence of Mucorales in a sample comprising, a) contacting an antibody binding agent with a sample suspected of comprising a Mucorales species, or portion thereof, wherein the antibody binding agent is configured to specifically bind to a polypeptide comprising an amino acid sequence having at least 80% identity to any one of SEQ ID NOs: 3-9 or SEQ ID NOs: 17-21, or a portion thereof and b) detecting the presence or absence of a bound complex in the sample, wherein the bound complex comprises the antibody binding agent and the polypeptide, and the presence of the bound complex indicates the presence of a Mucorales species, or portion thereof, in the sample. In certain embodiments a method herein comprises a) contacting an antibody binding agent with a sample suspected of comprising a Mucorales species, or portion thereof, wherein the antibody binding agent is configured to specifically bind to a polypeptide comprising 16 or more consecutive amino acids having 80% or more identity to SEQ ID NOs: 3-9, SEQ ID NOs: 17-21, or a portion thereof, and b) detecting the presence or absence of a bound complex in the sample, wherein the bound complex comprises the antibody binding agent and the polypeptide, and the presence of the bound complex indicates the presence of a Mucorales species, or portion thereof, in the sample. In certain aspects, the 16 or more consecutive amino acids have 80% or more identity to a portion of any one of SEQ ID NOs: 3-9 or SEQ ID NOs: 17-21, and wherein the 16 or more consecutive amino acids and the portion consists of the same number of consecutive amino acids.

In some embodiments, provided herein is method of detecting the presence of Mucorales in a sample comprising a) contacting an antibody binding agent with a sample suspected of comprising a Mucorales species, or portion thereof, wherein the antibody binding agent is configured to specifically bind to a polypeptide comprising 16 or more consecutive amino acids of any one of SEQ ID NOs: 3-9 or SEQ ID NOs: 17-21 and b) detecting the presence or absence of a bound complex in the sample, wherein the bound complex comprises the antibody binding agent and the polypeptide, and the presence of the bound complex indicates the presence of a Mucorales species, or portion thereof, in the sample. In certain embodiments, a composition comprises a polypeptide comprising an amino acid sequence having at least 80% identity to any one of SEQ ID NOs: 3-9 or SEQ ID NOs: 17-21, or a portion thereof, and an adjuvant. In certain aspects, a composition comprises a polypeptide comprising 16 or more consecutive amino acids having 80% or more identity to SEQ ID NOs: 3-9, SEQ ID NOs: 17-21, or a portion thereof, and an adjuvant. In some embodiments, a polypeptide comprises 16 or more consecutive amino acids of any one of SEQ ID NOs: 3-9 or SEQ ID NOs: 17-21, and an adjuvant. In certain aspects the polypeptide is immunogenic. In certain aspects the composition comprises a pharmaceutically acceptable carrier. In some embodiments the adjuvant comprises an aluminum salt.

In certain aspects, provided herein is method comprising a) providing a polypeptide comprising at least 90% identity to an amino acid sequence selected from SEQ ID NOs: 3-9, SEQ ID NOs: 17-21, or a portion thereof, wherein the polypeptide comprises a toxin activity and b) administering the polypeptide to a mammal having or suspected of having a cancer, wherein the polypeptide contacts a cancer cell in the mammal. In some embodiments, upon contacting the cancer cell in (b), the polypeptide induces cell-damage to the cancer cell. In some embodiments, the polypeptide comprises a cancer cell binding molecule.

Certain embodiments are described further in the following description, examples, claims and drawings.

BRIEF DESCRIPTION OF THE DRAWINGS

The drawings illustrate embodiments of the technology and are not limiting. For clarity and ease of illustration, the drawings are not made to scale and, in some instances, various aspects may be shown exaggerated or enlarged to facilitate an understanding of particular embodiments.

FIG. 4B indicates that only Fraction 3 (S3) retained toxin activity.

FIG. 12A shows amplification products produced using genomic DNA isolated from $10^4$ (Lane 1), 100 (Lane 2), 10 (Lane 3), 1 (Lane 4), and zero (Lane 5) fungal spores of *R. oryzae*. Specificity to Mucorales was demonstrated by production of H-toxin specific amplicons in *R. oryzae* (lane 8) and *Mucor circinelloides* (lane 6) but not *Aspergillus fumigatus* (lane 7). FIG. 12B shows detection of H-toxin specific amplicons in serum samples obtained from human subjects (lanes 1, 2 & 3) and mice (lanes 4, 5 & 6) infected with Mucorales. Negative serum controls are shown in FIG. 12B, lanes 7 and 8.

FIG. 13A shows detection of H-toxin specific amplicons in serum samples (lanes 3, 5 and 7) and bronchoalveolar lavage samples (lanes 4, 6 and 8) obtained from mice infected with Mucorales (i.e., *Rhizopus oryzae*). FIG. 13A, lane 1 shows a positive PCR control using genomic DNA obtained from *R. oryzae* spores and lane 2 shows a positive PCR control of normal mouse serum (i.e., not infected) spiked with genomic DNA obtained from *R. oryzae* spores. FIG. 13B shows detection of H-toxin specific amplicons in serum samples obtained from human subjects infected with Mucorales (lanes 2-8)(i.e., human subjects having mucormycosis). FIG. 13B, lane 1 shows a positive control.

FIG. 14A shows detection of H-toxin specific amplicons in serum samples obtained from mice infected with Mucorales of the genus species *Cunninghamella bertholletiae* (lanes 2 & 3), *Lichtheimia corymbigera* (lanes 4 & 5) and *Mucor circinelloides* (lanes 6, 7, & 8). Similar results were obtained from urine samples obtained from Mucorales infected mice (data not shown). FIGS. 14A and 14B, lane 1 shows a positive control (i.e., genomic DNA of *R. oryzae*). FIG. 14B, lanes 2-8 shows the absence of H-toxin specific amplicons in serum samples obtained from mice infected with *Aspergillus fumigatus* (lanes 2-5) and in uninfected mice (lanes 6-8).

FIG. 15 shows an alignment of H-toxins protein sequences of Mucorales species.

FIG. 17 shows an alignment of nucleic acids that encode H-Toxin polypeptides of six Mucorales species. The nucleic acid sequence alignment of FIG. 17 is shown in nine parts and each sequence shown is contiguous starting in part 1 and continuing to part 9. A "-" symbol indicates the absence of a nucleotide or a gap in a nucleic acid sequence.

DETAILED DESCRIPTION

Figure 1:
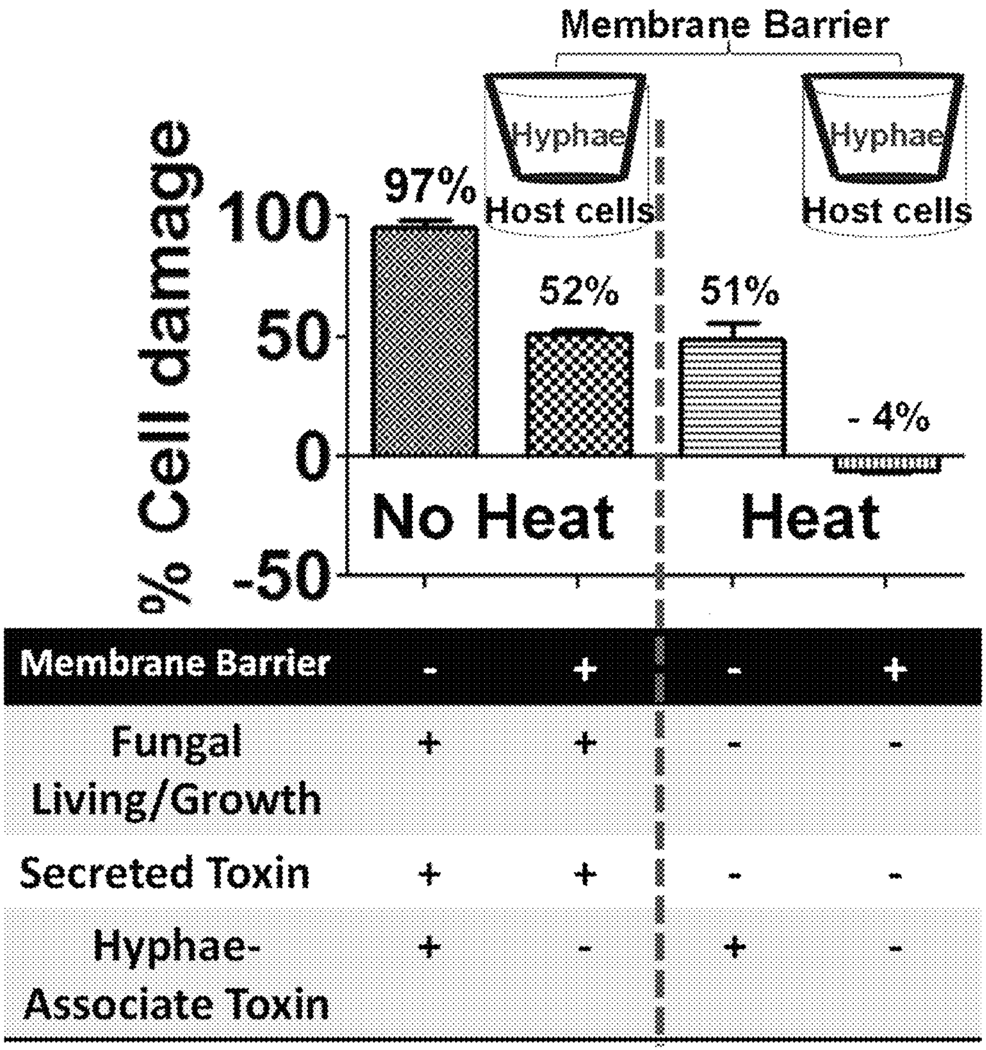
FIG. 1 shows damage to alveolar epithelial cells by *R. oryzae* produced toxins. *R. oryzae* hyphae were heat-killed ("Heat", right panel) or were viable ("No Heat", left panel) and added to alveolar epithelial cell cultures directly or separated by a 0.45 μm semi-permeable membrane barrier to measure the contribution of secreted and hyphae associated toxins to endothelial cell damage.

The compositions and methods disclosed herein are based, at least in part, on the identification and characterization of novel toxin proteins that are uniquely expressed by fungi of the Mucorales order which contribute to the pathogenesis of Mucormycosis.

Subjects

The term "subject" refers to animals, typically mammalian animals. Any suitable mammal can be treated by a method or composition described herein. Non-limiting examples of mammals include humans, non-human primates (e.g., apes, gibbons, chimpanzees, orangutans, monkeys, macaques, and the like), domestic animas (e.g., dogs and cats), farm animals (e.g., horses, cows, goats, sheep, pigs) and experimental animals (e.g., mouse, rat, rabbit, guinea pig). In some embodiments a mammal is a human. A mammal can be any age or at any stage of development (e.g., an adult, teen, child, infant, or a mammal in utero). A mammal can be male or female. A mammal can be a pregnant female. In certain embodiments a mammal can be an animal disease model, for example, animal models used for the study of fungal infections.

In some embodiments a subject has a Mucorales infection or is suspected of having a Mucorales infection. In some embodiments a subject suspected of having a Mucorales infection shows physiologic signs and/or symptoms associated with a Mucorales infection. In some embodiments a medical professional (e.g., a physician) determines that a subject is a subject suspected of having a Mucorales infection. In some embodiments a subject or mammal is "at risk" of acquiring a Mucorales infection. A mammal that is at risk may have increased risk factors for acquiring a fungal infection, non-limiting examples of which include immunocompromised individuals or immune deficient subjects (e.g., bone marrow transplant recipients, irradiated individuals, subjects having certain types of cancers, particularly those of the bone marrow and blood cells (e.g., leukemia, lymphoma, multiple myeloma), subjects with certain types of chronic infections (e.g., HIV, e.g., AIDS), subjects treated with immunosuppressive agents, subjects suffering from malnutrition and aging, subjects taking certain medications (e.g. disease-modifying anti-rheumatic drugs, immunosuppressive drugs, glucocorticoids), subjects undergoing chemotherapy, the like or combinations thereof). In some embodiments a subject at risk is, will be, or has been in a location or environment suspected of containing a Mucorales species (e.g.; a Mucorales pathogen, e.g., spores of a Mucorales pathogen). For example, a subject at risk can be a medical professional that is providing care to another who is suspected of being infected with, or known to be infected with Mucorales. In certain embodiments, a subject at risk is any subject that has been exposed to Mucorales. In certain embodiments, a subject at risk is any patient who is, will be, or has been in a hospital or medical care facility suspected of containing Mucorales. In certain embodiments, a subject at risk is any patient who is, will be, or has recently been (e.g., within 1 day to 1 year, or within 3 months to 6 months), in an intensive care unit, long term acute care hospital, rehabilitation hospital or facility, or skilled nursing facility. In certain embodiments, a subject at risk is on mechanical ventilation. In certain embodiments, a subject at risk is any patient who has, will have, or has had a central venous catheter, including a peripherally inserted central catheter. In certain embodiments, a subject at risk is on mechanical ventilation. In certain embodiments, a subject at risk is any patient who has undergone an invasive medical treatment or procedure.

In some embodiments a subject in need of a treatment or composition described herein is a subject at risk of a Mucorales infection and/or a subject that has a Mucorales infection. In some embodiments a subject in need of a treatment or composition described herein is infected with, or is suspected of being infected with Mucorales. In certain embodiments an antibody binding agent (e.g., an antibody or the like) or composition described herein is used to treat or prevent a Mucorales infection in a subject or a subject at risk of acquiring a Mucorales infection.

In some embodiments a subject in need of a treatment or composition described herein is a donor. In some embodiments a donor is healthy subject or a moderately healthy subject. In some embodiments a donor is free of a Mucorales infection. A donor may or may not be at risk of acquiring a Mucorales infection. In some embodiments a donor is an organ donor. In some embodiments a donor is preselected or predetermined to donate an organ, blood, bone marrow, serum, or the like to a subject who is at risk, or will become at risk of acquiring a Mucorales infection. Thus a donor is sometimes a subject in need of a treatment or a composition described herein.

Samples

Provided herein, in some embodiments, are methods and compositions for analyzing samples. In some embodiments, the presence or absence of Mucorales in a subject is determined by analyzing a sample obtained from the subject. In some embodiments, the presence or absence of a Mucorales infection in a subject is determined by analyzing a sample obtained from a subject. In some embodiments, a sample is analyzed for the presence or absence of Mucorales. In certain embodiments, an amount of Mucorales in a sample is determined by a method herein.

A sample can be any specimen that is isolated or obtained from a subject or part thereof (e.g., a human subject). A sample is often obtained from a subject. In some embodiments, a sample (e.g., a sample obtained from a subject) is comprises or is suspected of comprising a Mucorales species, or portion thereof (e.g., nucleic acid or polypeptides derived from, and/or unique to a Mucorales species. Non-limiting examples of samples include fluid or tissue from a subject, including, without limitation, blood or a blood product (e.g., serum, plasma, or the like), umbilical cord blood, chorionic villi, amniotic fluid, cerebrospinal fluid, spinal fluid, lavage fluid (e.g., broncho alveolar, gastric, peritoneal, ductal, ear, arthroscopic), a biopsy sample, urine, feces, sputum, saliva, nasal mucous, prostate fluid, lavage, semen, lymphatic fluid, bile, tears, sweat, breast milk, breast fluid, any secretion or discharge (e.g., from a wound, surgical lesion, abscess, cysts, or the like), the like or combinations thereof. A sample can comprise molecules derived from one or more different organisms. For example a sample can comprise molecules derived from a subject and molecules derived from one or more pathogens.

Collection of a sample is often performed in accordance with a standard protocol that medical practitioners, hospitals and/or clinics generally follow. An appropriate amount of a sample can be between about 1 μl and 200 ml, between about 100 μl and 50 ml or between about 0.5 ml and 10 ml. A sample can be collected and may be stored according to standard procedure prior to further preparation. Blood samples may be collected, stored or transported in a manner that minimizes degradation or the quality of proteins and/or nucleic acids present in the sample.

In certain embodiments a sample is prepared and/or processed prior to, or during analysis of a sample. For example, a sample may be centrifuged and/or washed to isolate or concentrate micro-organisms (e.g., Mucorales) that may be present in a sample. In some embodiments, a sample is subjected to a lysis procedure. In certain embodiments, certain materials of a sample (e.g., whole fungi, hyphae, proteins, nucleic acids, membranes, mitochondria, membrane-bound proteins) are isolated or concentrated using a suitable method, non-limiting examples of which include immunoprecipitation, column chromatography (e.g., affinity chromatography), centrifugation, lysis, extraction, precipitation, heat denaturation, detergent treatment, filtering, sonication, the like or combinations thereof. In some embodiments, micro-organisms of a sample, or portions thereof, are resuspended in a buffer suitable for analysis.

In some embodiments a sample obtained from a subject comprises nucleic acids. Nucleic acids obtained from a sample can comprise nucleic acids derived from one or more organisms. In some embodiments, a sample obtained from a subject comprises nucleic acids derived from a mammal and nucleic acids derived from one or more pathogens. Nucleic acids may be derived from one or more samples or sources (non-limiting examples of which include spores, cells, or parts thereof (e.g., nuclei, hyphae, extracts, etc.), serum, plasma, buffy coat, lymphatic fluid, skin, urine, soil, and the like) by methods known in the art. Cell lysis procedures and reagents are known in the art and cell lysis may generally be performed by chemical (e.g., detergent, hypotonic solutions, enzymatic procedures, and the like, or combination thereof), physical (e.g., French press, sonication, and the like), or electrolytic lysis methods. Any suitable lysis procedure can be utilized. For example, chemical methods generally employ lysing agents to disrupt cells and extract the nucleic acids from the cells. Physical methods such as freeze/thaw followed by grinding, the use of cell presses and the like also are useful. High salt lysis procedures are also commonly used. For example, an alkaline lysis procedure may be utilized. The latter procedure traditionally incorporates the use of phenol-chloroform solutions, and an alternative phenol-chloroform-free procedure involving three solutions can be utilized. In the latter procedures, one solution can contain 15 mM Iris, pH 8.0; 10 mM EDTA and 100 μg/ml Rnase A; a second solution can contain 0.2 N NaOH and 1% SDS; and a third solution can contain 3M KOAc, pH 5.5. Methods of lysing cells, and method of extracting polypeptides and nucleic acids from samples, are described in Current Protocols in Molecular Biology, John Wiley & Sons, N.Y., 6.3.1-6.3.6 (1989), which is incorporated by reference herein in its entirety.

Mucorales

In some embodiments method are described herein for detecting, diagnosing, and/or treating Mucorales (e.g., the presence or absence of a Mucorales species) or a Mucorales infection (e.g., Mucormycosis). In some embodiments Mucorales refers to any pathogenic or potentially pathogenic strain, species or isolate of Mucorales capable of causing an infection in a subject. A Mucorales infection refers to the presence of any pathogenic or potentially pathogenic strain, species or isolate of Mucorales in a subject (e.g., a mammalian subject, e.g., a human). In some embodiments Mucorales refers to a strain or isolate of Mucorales that displays resistance to one or more drugs (e.g., anti-fungal drugs) or anti-fungal treatments. In certain embodiments Mucorales is a Mucorales species, strain or isolate that is resistant to multiple drugs (e.g., a multi-drug resistant strain).

A Mucorales infection can be detected, prevented or treated by a method or use of a composition herein. Mucorales infections can be systemic and/or local. Non-limiting examples of local Mucorales infections include infections of the skin (epidermis, dermis, hypodermis, subcutaneous tissue), epithelial membranes, sinus membranes, ears, eyes, nose, throat, mouth, scalp, feet, nails, vagina, endometrium, urinary tract (e.g., bladder, urethra), the like, portions thereof or combinations thereof. Non-limiting examples systemic Mucorales infections include infection of one or more tissues or organs, non-limiting examples of which include liver, kidney, heart, muscle, lung, stomach, large intestine, small intestine, testis, ovaries, brain, nervous tissue, blood, lymph, lymph nodes, salivary glands, the like or combinations thereof.

Non-limiting examples of Mucorales species include *A. idahoensis, A. corymbifera, Apophysomyces elegans, Actinomucor elegans, A. rouxii, B. circina, B. multispora, C. breteldii, C. angarensis, C. recurvatus, D. fulva, E. anomalus, H. elegans, H. assamensis, K. cordensis, Lichtheimia corymbifera, Lichtheimia ramosa, M. ambiguus, Mucor amphibiorum, Mucor circinelloides, M. verticillata, P. parasitica, P. agaricine, P. anomala, P. circinans, S. umbellata, S. megalocarpus, T. elegans, T. indicae-seudaticae, Z. californiensis, Rhizomucor endophyticus, Rhizopus javensis, R. azygosporus, Rhizopus caespitosus, Rhizopus homothallicus, Rhizopus oryzae* (i.e., *Rhizopus delemari, Rhizopus delemar* (*R. delemar* 99-880)), *Rhizopus stolonifer, Rhizopus retlexus, Rhizopus microsporus, Rhizopus microsporus* (e.g., var. *rhizopodiformis*), and *Rhizopus schipperae.*

Nucleic Acids

The term "nucleic acid" may refer to one or more nucleic acids or a plurality of nucleic acids. The term refers to nucleic acids of any composition form, such as deoxyribonucleic acid (DNA, e.g., complementary DNA (cDNA), genomic DNA (gDNA), cDNA and the like), ribonucleic acid (ANA, e.g., message RNA (mRNA), short inhibitory RNA (siRNA), ribosomal RNA (rRNA), transfer RNA (tRNA), microRNA, the like or combinations thereof), and/or nucleic acids comprising DNA or RNA analogs (e.g., containing base analogs, sugar analogs and/or a non-native backbone and the like), RNA/DNA hybrids and polyamide nucleic acids (PNAs), all of which can be in single- or double-stranded form. Unless otherwise limited, a nucleic acid can comprise known analogs of natural nucleotides, some of which can function in a similar manner as naturally occurring nucleotides. A nucleic acid can be in any form useful for conducting processes herein (e.g., linear, circular, supercoiled, single-stranded, double-stranded and the like). A nucleic acid can be naturally occurring, isolated, purified and or synthetic (e.g., produced by chemical synthesis). A nucleic acid may be, or may be from, a plasmid, phage, autonomously replicating sequence (ARS), centromere, artificial chromosome, chromosome, or other nucleic acid able to replicate or be replicated in vitro, in vivo, or in a host cell, a cell, a cell nucleus or cytoplasm of a cell in certain embodiments. In certain embodiments nucleic acids comprise nucleosomes, fragments or parts of nucleosomes or nucleosome-like structures. Nucleic acids sometimes comprise protein (e.g., histones, DNA binding proteins, and the like). Nucleic acids analyzed by processes described herein sometimes are substantially isolated and/or purified and are not substantially associated with protein, carbohydrate, lipids or other molecules. Nucleic acids can also include derivatives, variants and analogs of RNA or DNA synthesized, replicated or amplified from single-stranded ("sense" or "antisense", "plus" strand or "minus" strand, "forward" reading frame or "reverse" reading frame) and double-stranded polynucleotides. Non-limiting examples of deoxyribonucleotides include deoxyadenosine, deoxycytidine, deoxyguanosine and deoxythymidine. For RNA, the base cytosine is replaced with uracil and the sugar 2' position includes a hydroxyl moiety. A nucleic acid may be prepared using a nucleic acid obtained from a subject as a template (e.g., by use of a recombinant polymerase). The terms nucleic acid template and target nucleic acid are used synonymously herein and refer to a nucleic acid of known sequence that can be detected and/or amplified by a method described herein. In some embodiments a target nucleic acid is a nucleic acid that encodes an H-toxin or S-toxin of a Mucorales species as described herein. In some embodiments a target nucleic acid comprises an entire H-toxin or S-toxin gene, a portion of an H-toxin or S-toxin gene, a portion of one or both flanking regions (e.g., up to 20, 50, 100, 200, 400, 800 or 1000 nucleotides 5' or 3' of a coding region), one or more exons, one or more introns, or a portion of an H-toxin or S-toxin gene (e.g., any portion of an H-toxin or S-toxin gene of at least 30, at least 50 or at least 150 nucleotides in length). A target nucleic acid can refer to a double stranded target nucleic acid or a single stranded nucleic acid. In some embodiments a target nucleic acid comprises an mRNA or cDNA derived therefrom. In some embodiments a target nucleic acid comprises an mRNA that encodes an H-toxin, S-toxin or a portion thereof. In some embodiments a target nucleic acid comprises a cDNA comprising a coding region that encodes an H-toxin, S-toxin or a portion thereof.

Nucleic acid may be isolated at a different time point as compared to another nucleic acid, where each of the samples is from the same or a different source. A nucleic acid may be from a nucleic acid library, such as a cDNA or RNA library, for example. A nucleic acid may be a result of nucleic acid purification or isolation and/or amplification of nucleic acid species from a plurality of nucleic acids in a sample. Nucleic acid provided for processes described herein may contain nucleic acid from one sample or from two or more samples (e.g., from 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 or more samples).

Nucleic acids can include extracellular nucleic acid in certain embodiments. The term "extracellular nucleic acid" as used herein can refer to nucleic acid isolated from a sample or source having substantially no cells and also is referred to as "cell-free" nucleic acid. For example, cell-free nucleic acid can be obtained from bodily fluids (e.g., urine and serum). Cell-free nucleic acid can comprise nucleic acid derived from a host and/or from a pathogen. Extracellular nucleic acid can be present in and obtained from blood. Non-limiting examples of acellular sources for extracellular nucleic acid are blood, blood plasma, blood serum and urine. As used herein, the term "obtain" includes obtaining a sample directly (act, collecting a sample directly from a subject) or obtaining a sample from another who has collected a sample directly from a subject.

Nucleic acid may be provided for conducting methods described herein without processing of the sample(s) containing the nucleic acid, in certain embodiments. In some embodiments, nucleic acid is provided for conducting methods described herein after processing of the sample(s) containing the nucleic acid. For example, a nucleic acid can be extracted, isolated, purified, partially purified or amplified from a sample. The term "isolated" as used herein refers to nucleic acid removed from its original environment (e.g., the natural environment if it is naturally occurring, e.g., a cell), and thus is altered by human intervention (e.g., "by the hand of man") from its original environment. The term "isolated nucleic acid" as used herein can refer to a nucleic acid removed from a subject. An isolated nucleic acid can be provided with fewer non-nucleic acid components (e.g., protein, lipid, carbohydrate, and the like) than the amount of components present in a source sample. A composition comprising isolated nucleic acid can be about 50% to greater than 99% free of non-nucleic acid components. A composition comprising isolated nucleic acid can be about 90%, 91%, 92%, 93%, 94%, 95%, 96%, 97%, 98%, 99% or greater than 99% free of non-nucleic acid components. The term "purified" as used herein can refer to a nucleic acid provided that contains fewer non-nucleic acid components (e.g., protein, lipid, carbohydrate) than the amount of non-nucleic acid components present prior to subjecting the nucleic acid to a purification procedure. A composition comprising purified nucleic acid may be about 80%, 81%, 82%, 83%, 84%, 85%, 86%, 87%, 88%, 89%, 90%, 91%, 92%, 93%, 94%, 95%, 96%, 97%, 98%, 99% or greater than 99% free of other non-nucleic acid components. The term "purified" as used herein can refer to a nucleic acid provided that contains fewer nucleic acid species than in the sample source from which the nucleic acid is derived. A composition comprising purified nucleic acid may be about 90%, 91%, 92%, 93%, 94%, 95%, 96%, 97%, 98%, 99% or greater than 99% free of other nucleic acid species. For example, fungal nucleic acid species can be purified from a mixture comprising mammalian and fungal nucleic acid.

Nucleic acid may be single or double stranded. Single stranded DNA, for example, can be generated by denaturing double stranded DNA by heating or by treatment with alkali, for example.

Two or more nucleic acids and proteins can be compared, described and/or defined by their sequence identity. Techniques for determining nucleic acid and amino acid "sequence identity" or "sequence homology" are known in the art. In some embodiments such techniques include comparing a first nucleic acid to a second, or another nucleic acid sequence. In some embodiments such techniques include comparing a first amino acid sequence of a polypeptide to an amino acid sequence of a second, or another, polypeptide. In some embodiments such techniques include determining the nucleotide sequence of an mRNA for a gene and/or determining an amino acid sequence encoded thereby, and comparing these sequences to a second nucleotide or amino acid sequence. In general, "identity" refers to an exact nucleotide-to-nucleotide or amino acid-to-amino acid correspondence of two nucleic acids or polypeptide sequences, respectively. Two or more sequences (nucleic acid or amino acid) can be compared by determining their "percent identity." In some embodiments the percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, Advances in Applied Mathematics 2:482-489 (1981). This algorithm can be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). A preferred method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using default parameters: for example genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the following internet address: http://www.ncbi.nlm.gov/cgi-bin/BLAST. In some embodiments, the identity of two nucleic acids to each other, or two polypeptides to each other are determined by a pairwise alignment according to EMBOSS Needle described in "The EMBL-EBI bioinformatics web and programmatic tools framework" (2015 Jul. 1) Nucleic acids research 43 (W1): W580-4). Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA.

Substantially complementary single stranded nucleic acids can hybridize to each other under certain conditions (e.g., hybridization conditions, amplification conditions), thereby forming a nucleic acid that is partially or fully double stranded. Amplification conditions often comprise hybridization conditions suitable for substantially complementary nucleic acids to hybridize to each other. The term "substantially complementary" means that the sequence of a first nucleic acid is substantially identical to the reverse complement sequence of a second nucleic acid and the first and second nucleic acids are therefore substantially complementary. All or a portion of an nucleic acid sequence may be substantially complementary to another nucleic acid sequence, in some embodiments. As referred to herein, "substantially complementary" also refers to nucleic acids that can hybridize with each other under suitable hybridization conditions. Hybridization conditions can be altered to tolerate varying amounts of sequence mismatch within complementary nucleic acids that are substantially complementary. Substantially complementary portions of nucleic acids that can hybridize to each other can be 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more or 99% or more complementary to each other. In some embodiments substantially complementary portions of nucleic acids that can hybridize to each other are 100% complementary.

Nucleic acids, or portions thereof, that are configured to hybridize to each other often comprise nucleic acid sequences that are substantially complementary to each other. The term "configured to" as used herein, with reference to a nucleic acid, is synonymous with the term "adapted to" and imparts a structural limitation to a nucleic, which structure is required for a nucleic acid to perform a specific defined function. A structural limitation of a nucleic acid is often defined, in part or entirely, by its nucleic acid sequence. Thus one of skill in the art would know how to make and use a primer configured to hybridize and/or amplify a target nucleic acid by producing a primer comprising a specific sequence that allows 1) hybridization of the primer to a portion of a target nucleic acid, in a predefined orientation, and 2) allows extension of the primer by a polymerase in a direction that results in a complimentary copy of the target nucleic acid, or a portion thereof. Likewise, one of skill in the art would know how to make and use an oligonucleotide primer pair configured to specifically hybridize to and/or amplify a target nucleic acid by producing two primers each comprising a specific sequence that allows 1) hybridization of each primer to a portion of a target nucleic acid, in a predefined orientation (e.g., opposite orientations) and at a predefined distance from each other, and 2) allows extension of the primers by a polymerase in a direction that results in a double stranded copy (e.g., an amplicon) of the target nucleic acid wherein the amplicon is of a predetermined length. A primer or primer pair may also have other structural limitations such a defined GC content and Tm (melting point), which one of skill in the art would incorporated into the design of a primer or primer pair configured to perform a specific function. In some embodiments an oligonucleotide primer pair comprises a first primer and second primer, both of which are configured to specifically hybridize to a portion of a target nucleic acid (e.g., under hybridization conditions). The first primer and second primer of an oligonucleotide primer pair which are configured to specifically hybridize to a portion of a target nucleic acid are often substantially complementary to opposite strands of a target nucleic acid regardless of whether the target nucleic acid is present in an amplification reaction in a single or double stranded form. In some embodiments a first primer and a second primer of an oligonucleotide primer pair which are configured to specifically hybridize to a portion of a target nucleic acid are often configured to hybridize to opposite strands of a target nucleic acid and in opposite orientation consistent with traditional amplification methods known in the art. In some embodiments an oligonucleotide primer pair is configured to produce an amplicon of a predetermined length and/or an amplicon of a predetermined nucleic acid sequence when an amplification reaction is performed. In some embodiments an oligonucleotide primer pair is configured to produce an amplicon of a predetermined length and/or sequence under amplification conditions. In certain embodiments an oligonucleotide primer pair configured to produce an amplicon of a predetermined length refers to a first and second primer of a primer pair which are designed to hybridize to opposite strands of a target nucleic acid and in opposite orientation consistent with traditional methods of primer design for nucleic acid amplification methods known in the art. An oligonucleotide primer pair configured to produce an amplicon of a predetermined length and/or sequence refers to an oligonucleotide pair designed to substantially hybridize to opposite strands of a template nucleic acid, in opposite orientation where the first and second primers of the pair are separated by a predetermined distance of at least 30, at least 40, at least 50, at least 75, at least 100, at least 150 or at least 200 contiguous nucleotides. In certain embodiments an oligonucleotide primer pair configured to produce an amplicon of a predetermined length is separated by a distance of 30 to 10,000, 30 to 5000, 30 to 2500, 30 to 1500, 50 to 1500 or 150 to 1500 contiguous nucleotides or bases pairs. In certain embodiments an oligonucleotide primer pair is configured to produce an amplicon of a predetermined length of 30 to 10,000, 30 to 5000, 50 to 5000, 30 to 2500, 30 to 1500, 50 to 1500 or 150 to 1500 contiguous bases or contiguous base pairs (e.g., for annealed double stranded amplicons). Amplicons can be single and/or double stranded nucleic acids.

Methods of designing oligonucleotide primer pairs and bioinformatics tools for designing oligonucleotide primer pairs (e.g., primer pairs configured to produce amplicons from a template nucleic acid under amplification conditions) are known in the art (e.g., see URL: http://www.ncbi.nlm-.nih.gov/tools/primer-blast/ entitled "Primer-BLAST: Finding primers specific to your PCR template (using Primer3 and BLAST)", published by NCBI (National Center for Biotechnology Information), accessed on Oct. 28, 2015).

As used herein, "specifically hybridizes" refers to preferential hybridization under hybridization and/or amplification conditions where two nucleic acids, or portions thereof, that are substantially complementary, hybridize to each other and not to other nucleic acids that are not substantially complementary to either of the two nucleic acid. In some embodiments nucleic acids, or portions thereof, that are configured to specifically hybridize are often about 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more or 100% complementary to each other over a contiguous portion of nucleic acid sequence. A specific hybridization discriminates over non-specific hybridization interactions (e.g., two nucleic acids that a not configured to specifically hybridize, e.g., two nucleic acids that are 80% or less, 70% or less, 60% or less or 50% or less complementary) by about 2-fold or more, often about 10-fold or more, and sometimes about 100-fold or more, 1000-fold or more, 10,000-fold or more, 100,000-fold or more, or 1,000,000-fold or more.

Hybridization of nucleic acids can be conducted under suitable conditions, which conditions can be modified and/or adjusted to select for different degrees of mismatch between complementary nucleic acids. Methods for optimizing and determining hybridization conditions are known in the art, and may be found in Current Protocols in Molecular Biology, John Wiley & Sons, N.Y., 6.3.1-6.3.6 (1989), which is incorporated herein by reference. Hybridization often comprise heating or cooling a sample comprising nucleic acid. Hybridization often comprises a denaturation step that precedes hybridization. Nucleic acid sequence content (e.g., GC content, degree of mismatch and/or length) of complementary nucleic acids are often consider when optimizing hybridization conditions. Hybridization conditions often comprise parameters that can be adjusted for optimal annealing of two or more substantially complementary nucleic acids of interest. Non-limiting examples of such adjustable parameters include temperature, time of denaturation and/or annealing, monovalent or divalent ion and/or cation concentration, buffer concentration, phosphate concentration, glycerol concentration, DMSO concentration, nucleic acid concentration, the like or combinations thereof.

Amplification

A nucleic acid can be amplified by a suitable method. The term "amplified" as used herein refers to subjecting a target nucleic acid (e.g., a template nucleic acid) to a amplification process (e.g., an amplification reaction) that selectively and linearly or exponentially generates amplicon nucleic adds (amplicons) each having the same (e.g., identical) or a substantially identical nucleotide sequence as the target nucleic acid, or a portion thereof. In some embodiments, a substantially identical nucleotide sequence refers to percent identity of a first and second nucleic acid sequence. In some embodiments substantially identical nucleic acids have at least 80% identity, at least 85% identity, at least 90% identity or at least 95% identity. In certain embodiments an amplicon can contain one or more additional and/or different nucleotides than the target template sequence, or portion thereof, from which the amplicon was generated (e.g., a primer can contain "extra" nucleotides). An amplification reaction refers to any amplification process wherein at least one specific target nucleic acid, or portion thereof, is amplified. In some embodiments an amplification reaction refers to a method that comprises a polymerase chain reaction (PCR). Any suitable PCR method or amplification reaction can be used for a method (e.g., an amplification reaction) described herein. An amplification reaction can be an isothermal or thermal amplification process. Non-limiting examples of amplification reactions that can be used for a method herein include Loop-mediated isothermal amplification (LAMP), Strand displacement amplification (SDA), Helicase-dependent amplification (HDA), Nicking enzyme amplification reaction (NEAR), standard FOR (i.e., thermal FOR using a thermal stable polymerase), Multiplex-PCR, Variable Number of Tandem Repeats (VNTR) PCR, Asymmetric PCR, Nested PCR, Quantitative PCR (qPCR), Touchdown PCR, Assembly PCR, RT-PCR, Ligation-mediated PCR, Methylation-specific PCR (MSP), COLD-FOR, the like or combinations or variations thereof.

In some embodiments a composition herein (e.g., a composition suitable for performing an amplification reaction, or an amplification product) comprises a suitable recombinant polymerase. Recombinant polymerases that are suitable for amplification reactions are known in the art and are commercially available. In certain embodiments an amplification reaction comprises a thermal stable polymerase. Thermal stable polymerases are stable at elevated temperature for extended periods of time, for example at temperature greater than 65° C.

In some embodiments, performing an amplification reaction comprises providing amplification conditions. Amplification conditions refer to conditions conducive to amplification of a target nucleic acid. Specific amplification conditions can be modified or adjusted according to the amplification method used. In some embodiments amplifications conditions comprise 1) a suitable recombinant polymerase, 2) nucleic acids comprising or suspected of comprising a nucleic acid template, 3) at least one suitable oligonucleotide primer, an oligonucleotide primer pair or set of primers configured to specifically hybridize to a portion of the nucleic acid template, 4) suitable nucleotides (e.g., dATP, dGTP, dCTP, dTTP and/or dUTP), and 5) a suitable buffer. In some embodiments amplifications conditions comprise modulating and/or maintaining temperature and incubations times of an amplification reaction mixture that are suitable for annealing, hybridization and/or extension of an oligonucleotide primer or primer pair. Performing an amplification reaction refers to providing the appropriate amplification conditions for generating a desired amplicon from a target nucleic acid.

In some embodiments a composition (e.g., a composition for performing an amplification reaction or an amplification product) comprises nucleic acids obtained from a mammal, an oligonucleotide primer pair configured to specifically hybridize to and amplify a target nucleic acid, and a recombinant polymerase. Nucleic acids obtained from a mammal can be obtained from a sample obtained from a mammal. A sample obtained from a mammal often comprise nucleic acid. Nucleic acids obtained from a mammal can be isolated, partially purified or purified. In some embodiments nucleic acids obtained from a mammal are not isolated, partially purified or purified. Nucleic acids obtained from a mammal can comprise mammalian derived nucleic acids and/or pathogen derived nucleic acids (e.g., nucleic acids derived from a fungus, e.g., a Mucorales species). In some embodiments nucleic acids obtained from a mammal comprise a target nucleic acid. A target nucleic acid often comprises a nucleic acid that encodes an H-toxin or S-toxin as described herein, or a portion thereof. Nucleic acids obtained from a mammal can comprise RNA or DNA derived from the mammal or a Mucorales species.

In some embodiments a composition comprises an oligonucleotide primer pair configured to specifically hybridize to a nucleic acid sequence selected from any one of SEQ ID NOS: 1, 2, 35, 36, 37, 38, 39, 47, 22, and/or 23. An oligonucleotide primer pair often comprises a first oligonucleotide primer and/or a second oligonucleotide primer. In some embodiments a first oligonucleotide primer of an oligonucleotide primer pair is selected from an oligonucleotide of Table 1. In some embodiments a second oligonucleotide primer of an oligonucleotide primer pair is selected from an oligonucleotide of Table 2. In some embodiments at least one oligonucleotide primer of an oligonucleotide primer pair comprises a distinguishing identifier. In some embodiments at least one oligonucleotide primer of an oligonucleotide primer pair comprises a label. In some embodiments at least one oligonucleotide primer of an oligonucleotide primer pair comprises an adapter. In some embodiment an adapter comprises a nucleic acid sequence configured to specifically hybridize to nucleic acid attached to a suitable substrate (e.g., a flow cell, a bead, a nanoparticle and the like).

In some embodiments a composition comprises an oligonucleotide primer pair that specifically hybridize to a nucleic acid sequence selected from any one of SEQ ID NOS: 1, 2, 35, 36, 37, 38, 39, 47, 22, and/or 23 under hybridization conditions. An oligonucleotide primer pair configured to specifically hybridize to and amplify a target nucleic acid is often configured to specifically hybridize to and amplify a nucleic acid having at least 80% identity to one or more of SEQ ID NOS: 1, 2, 35, 36, 37, 38, 39, 47, 22, and/or 23, or a portion thereof. In certain embodiments, a nucleic acid having at least 80% identity to one or more of SEQ ID NOS: 1, 2, 35, 36, 37, 38, 39, 47, 22, and/or 23 has between 80% and 100% identity to one or more of SEQ ID NOS: 1, 2, 35, 36, 37, 38, 39, 47, 22, and/or 23. In some embodiments a nucleic acid having at least 80% identity to one or more of SEQ ID NOS: 1, 2, 35, 36, 37, 38, 39, 47, 22, and/or 23 has between 80% and 100%, between 85% and 100%, between 90% and 100% or between 95% and 100% identity to a portion of one or more of SEQ ID NOS: 1, 2, 35, 36, 37, 38, 39, 47, 22, and/or 23. In some embodiments a nucleic acid having at least 80% identity to one or more of SEQ ID NOS: 1, 2, 35, 36, 37, 38, 39, 47, 22, and/or 23 has at least 85%, at least 90%, at least 95% or 100% identity to a portion of one or more of SEQ ID NOS: 1, 2, 35, 36, 37, 38, 39, 47, 22, and/or 23. A portion of a nucleic acid may comprise or consist of a nucleic acid that is 30 to 5000, 30 to 1500, or 30 to 500 nucleotides in length and may comprise non-protein coding regions of fungal genomic DNA or mRNA that flank one or more of SEQ ID NOS: 1, 2, 35, 36, 37, 38, 39, 47, 22, and/or 23.

In some embodiments a composition comprises nucleic acids obtained from a mammal, an oligonucleotide primer pair configured to specifically hybridize to and amplify a target nucleic acid, a recombinant polymerase and one or more amplicons. An amplicon is often of a predetermined length as determined by a specific oligonucleotide primer pair that is used for performing and amplification reaction. In certain embodiments an amplicon of a predetermined length is between about 25 and 5000, between about 25 and 2500, between about 25 and 1500, between about 25 and 1000, between about 50 and 2500, or between about 50 and 500 nucleotides in length. In certain embodiments an amplicon of a predetermined length is at least 25, at least 30, at least 40, at least 50, at least 75, at least 100, at least 150, at least 200 or at least 250 nucleotides in length. nucleic acids obtained from the mammal comprise mammalian RNA or DNA.

In some embodiments a composition comprises a recombinant polymerase. A polymerase can be an isolated and/or purified or partially purified recombinant polymerase. A recombinant polymerase is often derived by recombinant means using molecular biology techniques known in the art. In some embodiments a recombinant polymerase is a polypeptide comprising polymerase activity encoded by a cDNA and expressed using a suitable expression system. Non-limiting examples of expression systems include bacterial, yeast, baculovirus/insect, and mammalian expression systems. A recombinant polymerase is often expressed in a heterologous expression system. Therefore an recombinant polymerase is often expressed in a cell derived from a species that does not naturally produce the recombinant polymerase. Thus a recombinant polymerase is a polymerase produced by the hand of man. In some embodiments a recombinant polymerase is derived from a non-mammalian and/or non-fungal nucleic acid. In some embodiments a recombinant polymerase is not a mammalian polymerase. In some embodiments a recombinant polymerase is not a human polymerase. In certain embodiments, a recombinant polymerase is not a fungal polymerase. Thus a recombinant polymerase is not a polymerase found naturally occurring in a human. In some embodiments a recombinant polymerase is not a polymerase found naturally occurring in a Mucorales species. In certain embodiments a recombinant polymerase is a polymerase suitable for in vitro amplification of a target nucleic acid. In certain embodiments a recombinant polymerase is a polymerase suitable for a polymerase chain reaction (PCR). In certain embodiments a recombinant polymerase is a thermal stable polymerase. In certain embodiments a recombinant polymerase is a polymerase suitable for loop mediated isothermal amplification (LAMP).

In some embodiments an oligonucleotide primer pair comprises at least one modified nucleotide. A modified nucleotide can be a nucleotide analogue. Non-limiting examples of modified nucleotides include locked nucleic acids (LNAs, e.g., bicyclic nucleic acids), bridged nucleic acids (BNAs, e.g., constrained nucleic acids), C5-modified pyrimidine bases (for example, 5-methyl-dC, propynyl pyrimidines, among others) and alternate backbone chemistries, for example peptide nucleic acids (PNAs), morpholinos, the like or combinations thereof. In some embodiments, bridged nucleic acids are modified RNA nucleotides. Any suitable BNA can be used in a composition or method described herein. In certain embodiments BNA monomers can comprise a five-membered, six-membered or even a seven-membered bridged structure. Non-limiting examples of new generation BNA monomers include 2',4'-BNANC[NH], 2',4'-BNANC[NMe], and 2',4'-BNANC[NBn]. Non-base modifiers can also be incorporated into an oligonucleotide primer, for example to increase Tm (or binding affinity), non-limiting examples of which include a minor grove binder (MGB), spermine, G-clamp, a Uaq anthraquinone cap, the like or combinations thereof.

In some embodiments performing an amplification reaction results in an amplification product. An amplification product refers to a composition (e.g., an amplification reaction mixture) after an amplification reaction is performed. In some embodiments an amplification product comprises 1) a suitable recombinant polymerase, 2) nucleic acids comprising or suspected of comprising a nucleic acid template, 3) at least one suitable oligonucleotide primer, an oligonucleotide primer pair or set of primers configured to specifically hybridize to a portion of the nucleic acid template, 4) suitable nucleotides (e.g., dATP, dGTP, dCTP, dTTP and/or dUTP), and/or 5) a suitable buffer. In certain embodiments an amplification product comprises one or more amplicons. In some embodiments an amplification product comprises amplicons that are identical or substantially identical to a target nucleic acid. In certain embodiments an amplification product does not comprise an amplicon. For example, an amplification reaction can be performed using nucleic acids suspected of comprising a nucleic acid template, where the nucleic acid template is not present. Thus, In some embodiments an amplification reaction is performed in the absence of a nucleic acid template or target nucleic acid and the resulting reaction product does not contain a desired amplicon. In some embodiments an amplification product comprises non-specific nucleic acid products resulting from non-specific or non-desired polymerase activity. Therefore, an amplification product is often subjected to an analysis to determine the presence or absence of a desired amplicon. In some embodiments amplification of a target nucleic acid using an oligonucleotide primer pair configured to specifically hybridize to the target nucleic acid results in amplicons of a predetermined and/or expected length, sequence and/or molecular weight. In some embodiments analysis of an amplification product often comprises determining the presence or absence of amplicons of a predetermined and/or expected length, sequence and/or molecular weight in the amplification product. Analyzing an amplification product for the presence or absence of desired amplicons can be performed by any suitable method, non-limiting examples of which include polyacrylamide or agarose gel electrophoresis, nucleic acid sequencing, mass spectrometry, detection of a distinguishing identifier (e.g., by using labeled primers or labeled probes), digoxigenin (DIG)-PCR-enzyme-linked immunosorbent assay (ELISA)(Roche Molecular Biochemicals, Indianapolis, Ind.), PCR-immunoassay detection, the like or combinations thereof. In some embodiments analysis of an amplification product often comprises determining the presence or absence of amplicons of a predetermined and/or expected length, sequence and/or molecular weight in the amplification product.

In certain embodiments nucleic acids of an amplification product are analyzed by a process comprising nucleic acid sequencing. In some embodiments, nucleic acids may be sequenced. In some embodiments, a full or substantially full sequence is obtained and sometimes a partial sequence is obtained to determine the presence or absence of a desired amplicon. For example, in certain embodiments a primer may contain a nucleic acid barcode that can be detected and or sequence after incorporation into an amplicon. Any suitable method of sequencing nucleic acids can be used for analyzing an amplification product, non-limiting examples of which include Maxim & Gilbert, chain-termination methods, sequencing by synthesis, sequencing by ligation, sequencing by mass spectrometry, microscopy-based techniques, the like or combinations thereof. In some embodiments, a first generation technology, such as, for example, Sanger sequencing methods including automated Sanger sequencing methods, including microfluidic Sanger sequencing, can be used in a method provided herein. In some embodiments sequencing technologies that include the use of nucleic acid imaging technologies (e.g. transmission electron microscopy (TEM) and atomic force microscopy (AFM)), can be used. In some embodiments, a high-throughput sequencing method is used. High-throughput sequencing methods generally involve clonally amplified DNA templates or single DNA molecules that are sequenced in a massively parallel fashion, sometimes within a flow cell. Next generation (e.g., 2nd and 3rd generation) sequencing techniques capable of sequencing DNA in a massively parallel fashion can be used for methods described herein and are collectively referred to herein as "massively parallel sequencing" (MPS) or "massively parallel nucleic acid sequencing". In some embodiments MPS sequencing methods utilize a targeted approach, where sequence reads are generated from specific chromosomes, genes or regions of interest. Specific chromosomes, genes or regions of interest are sometimes referred to herein as targeted genomic regions. In certain embodiments a non-targeted approach is used where most or all nucleic acid fragments in a sample are sequenced, amplified and/or captured randomly.

Antibody Binding Agents

An antibody binding agent sometimes comprises or consists of a suitable antibody, an antibody fragment and/or an antigen binding portion thereof (e.g., a binding fragment). In some embodiments an antibody binding agent is an antibody or an antigen binding portion thereof. An antibody can refer to a natural antibody, polyclonal antibody, monoclonal antibody, recombinant antibody, a chimeric antibody, an antibody binding fragment (e.g., an antigen binding portion of an antibody), a CDR-grafted antibody, a humanized antibody, a human antibody, a synthetic polypeptide, aptamer or binding portions thereof. In some embodiments, an antibody is derived, obtained, isolated, or purified from a suitable animal non-limiting examples of which include rabbit, goat, horse, ruminant (e.g., goats, sheep, giraffes, yaks, deer, antelope, cows and the like), rodent (rat, mouse, hamster), pig, fish, shark (e.g., nurse shark), bird (e.g., chicken, e.g., bird eggs), llama, or the like. In some embodiments an antibody is derived, obtained, isolated, or purified from a suitable mammal. In certain embodiments a suitable mammal is a genetically altered mammal (e.g., a trans chromosomal or transgenic mammal) engineered to produce antibodies comprising human heavy chains and/or human light chains or portions thereof. In some embodiments, an antibody is derived, obtained, isolated, or purified from a rabbit, goat, horse, cow, rat, mouse, fish, bird, or llama, for example.

In some embodiments an antibody binding agent is configured to specifically bind to a fungal toxin, or portion thereof, as described herein (e.g., an H-toxin or S-toxin). In some embodiments, an antibody binding agent binds specifically to one or more antigens (e.g., one or more fungal toxin, or portions thereof). For example, an antibody binding agent that specifically binds a first fungal toxin can cross-react with and specifically bind to a second fungal toxin having at least 70%, 75%, 80%, 85%, 90% or at least 95% sequence identity with the amino acid sequence of the first fungal toxin, or a portion thereof. Antibody binding agents can specifically recognize and/or bind relatively small portions of a larger polypeptide where said smaller portions comprise or consist of 3 to 30 contiguous amino acids. In some embodiments an antibody binding agent specifically binds an amino acid sequence of 5, 6, 7, 8, 9, 10, 11, 12, 13, 14, 15, 16, 17, 18, 19 or 20 contiguous amino acids which can be an isolated oligonucleotide or located within a larger polypeptide. In some embodiments, an antibody binding agent that specifically binds a first polypeptide sequence comprising or consisting of 3 to 30 contiguous amino acids, specifically binds another polypeptide sequence (e.g., a second, third, fourth, or fifth polypeptide etc.) comprising or consisting of the a polypeptide having at least 70%, at least 75%, at least 80%, at least 85%, at least 90% at least 95%, at least 96%, at least 97%, at least 98%, at least 99% or 100% sequence identity with the first polypeptide sequence. In some embodiments, an antibody binding agent specifically binds a polypeptide sequence comprising or consisting of 3 to 30 contiguous amino acids of a polypeptide of SEQ ID NOs: 3-9 or 17-21.

An antibody binding agent is sometimes configured to specifically bind to an antigen or epitope (e.g., an H- or S-toxin or a portion thereof) and/or configured to specifically block toxin activity. The term, "toxin activity" as used herein refers to the ability of an H- or S-toxin to induce cell damage or cell death to a mammalian cell as assayed by a in vivo mouse models and in vitro methods described herein (e.g., see Example 1-5). The term "configured to" as used herein, with reference to an antibody binding agent, is synonymous with the term "adapted to" and imparts a structural limitation to an antibody binding agent, which structure is required for an antibody binding agent to perform a specific defined function (e.g., specific binding to an antigen and/or epitope, and/or blocking toxin activity). The structure of an antibody binding agent that is required for the antibody binding agent to perform a specific defined function is often defined, in part or entirely, by the amino acids sequences in the regions of on an antibody binding agent that bind to an antigen. For example, for mammalian antibodies, regions of an antibody that bind antigen are the variable regions that define the antibody paratope. The amino acids sequences in the regions of an antibody binding agent that bind to an antigen are sometimes known, can sometimes be determined and sometimes are not known. Nonetheless, the functional properties of an antibody binding agent are defined by these structures and one of skill in the art would know how to make and/or select for an antibody binding agent that possesses the structures necessary for the antibody binding agent to perform a specific defined function. Method of making antibodies that specifically bind an antigen or epitope sequences are described herein. Thus, from the instant specification, one of skill in the art would know how to make, select for and/or isolate an antibody binding agent that binds specifically to an H-toxin, S-toxin or a portion thereof. Also, as described herein, a portion of a toxin responsible for toxin activity can readily be identified by a method described herein (e.g., see Examples 3 and 5), and once identified, one of skill in the art would know from the instant specification how to make an antibody configured to specifically bind to an H- or S-toxin and block toxin activity.

Specific binding of an antibody binding agent to an antigen or epitope can be determined using a suitable method (e.g., an ELISA, FACs, etc.). In certain embodiments, specific binding is determined by measuring a binding affinity or dissociation constant (kd) of an antibody for an antigen or epitope. In some embodiments, an antibody that binds specifically to an antigen or epitope binds with a Kd on the order of $10^{-7}$ to $10^{-16}$, or higher. In some embodiments, an antibody that binds specifically to an antigen or epitope binds with a Kd of at least $10^{-7}$, $10^{-8}$, $10^{-8}$, $10^{-10}$, $10^{-11}$, or at least $10^{-12}$. Antibody binding agents disclosed herein are raised (e.g., by immunization of live animals), isolated, selected, configured and/or optimized to bind specifically to a Mucorales toxin described herein, or portion thereof.

In some embodiments an antibody binding agent (e.g., polyclonal or monoclonal) is obtained from screening a suitable expression library (e.g., phage display library, DARPin library, aptamer library, camelid library, and the like). In some embodiments and antibody binding agent comprises an aptamer, DARPin, or Camelid. In some embodiments an antibody binding agent comprises a camelid. Camelids are immunoglobulin single variable domain polypeptides that are derived from species including camel, llama, alpaca, dromedary, and guanaco, which produce heavy chain antibodies naturally devoid of light chains. Such VHH domains may be humanized by methods known in the art and described herein.

An antigen binding agents may be provided by screening arrangements (e.g., a library) of non-antibody protein scaffold domains using a suitable expression and screening system. In some embodiments a non-antibody scaffold domain comprises a scaffold domain of CTLA-4 (Evibody); lipocalin and anticalins; Protein A derived molecules such as Z-domain of Protein A (Affibody, SpA), A-domain (Avimer/Maxibody); heat shock proteins such as GroEl and GroES; transferrin (trans-body); ankyrin repeat protein (DARPin); peptide aptamer; C-type lectin domain (Tetranectin); human γ-crystallin and human ubiquitin (affilins); PDZ domains; scorpion toxin kunitz type domains of human protease inhibitors; and fibronectin (adnectin); which has been subjected to protein engineering in order to obtain binding to a ligand other than its natural ligand.

CTLA-4 (Cytotoxic T Lymphocyte-associated Antigen 4) is a CD28-family receptor expressed on mainly CD4+ T-cells. Its extracellular domain has a variable domain-like Ig fold. Loops corresponding to CDRs of antibodies can be substituted with heterologous sequence to confer different binding properties. CTLA-4 molecules engineered to have different binding specificities are also known as Evibodies. Methods of making Evibodies are known in the art and can be made as described in *Journal of Immunological Methods* 248 (1-2), 31-45 (2001) which is incorporated herein by reference.

Lipocalins are a family of extracellular proteins which transport small hydrophobic molecules such as steroids, bilins, retinoids and lipids. They have a rigid β-sheet secondary structure with a number of loops at the open end of the canonical structure which can be engineered to bind to different target antigens. Anticalins are between 160-180 amino acids in size, and are derived from lipocalins. Methods of making lipocalins and anticalins are known in the art and are described in *Biochim Biophys Acta* 1482: 337-350 (2000), U.S. Pat. No. 7,250,297B1 and US20070224633, which are incorporated herein by reference.

An affibody is a scaffold derived from Protein A of *Staphylococcus aureus* which can be engineered to bind to an antigen. The domain consists of a three-helical bundle of approximately 58 amino acids. Libraries have been generated by randomization of surface residues. Methods of making affibodies are known in the art and are described in Protein Eng. Des. Sel. 17, 455-462 (2004) and EP1641818A1, which are incorporated herein by reference.

Avimers are multidomain proteins derived from the A-domain scaffold family. The native domains of approximately 35 amino acids adopt a defined disulphide bonded structure. Diversity is generated by shuffling of the natural variation exhibited by the family of A-domains. Methods of making avimers are known in the art and are described in Nature Biotechnology 23(12), 1556-1561 (2005) and Expert Opinion on Investigational Drugs 16(6), 909-917 (June 2007), which are incorporated herein by reference.

A transferrin is a monomeric serum transport glycoprotein. Transferrins can be engineered to bind different target antigens by insertion of peptide sequences, such as one or more CDRs, in a permissive surface loop. Methods of making transferrins are known in the art and are described in J. Biol. Chem 274, 24066-24073 (1999), which is incorporated herein by reference.

Designed Ankyrin Repeat Proteins (DARPins) are derived from Ankyrin which is a family of proteins that mediate attachment of integral membrane proteins to the cytoskeleton. A single ankyrin repeat is a 33 residue motif consisting of two α-helices and a β-turn. They can be engineered to bind different target antigens by: randomizing residues in the first α-helix and a β-turn of each repeat; or insertion of peptide sequences, such as one or more CDRs. Their binding interface can be increased by increasing the number of modules (a method of affinity maturation). Methods of making DARPins are known in the art and are described in *J. Mol. Biol.* 332, 489-503 (2003), PNAS 100(4), 1700-1705 (2003) and *J. Mol. Biol.* 369, 1015-1028 (2007) and US Patent Publication No. 20040132028, which are incorporated herein by reference.

Fibronectin is a scaffold which can be engineered to bind to antigen. Adnectins consists of a backbone of the natural amino acid sequence of the 10th domain of the 15 repeating units of human fibronectin type III (FN3). Three loops at one end of the β-sandwich can be engineered to enable an Adnectin to specifically recognize a therapeutic target of interest. Methods of making adnectins are known in the art and are described in Protein Eng. Des. Sel. 18, 435-444 (2005), US Pat. Pub. No. 20080139791, WO2005056764 and U.S. Pat. No. 6,818,418, which are incorporated herein by reference.

Peptide aptamers are combinatorial recognition molecules that consist of a constant scaffold protein, typically thioredoxin (TrxA) which contains a constrained variable peptide loop inserted at the active site. Methods of making aptamers are known in the art and are described in Expert Opin. Biol. Ther. 5, 783-797 (2005), which is incorporated herein by reference.

Microbodies are derived from naturally occurring microproteins of 25-50 amino acids in length which contain 3-4 cysteine bridges; examples of microproteins include KalataBI and conotoxin and knottins. The microproteins have a loop which can be engineered to include up to 25 amino acids without affecting the overall fold of the microprotein. Methods of making microbodies are known in the art and are described in WO2008098796, for example, which is incorporated herein by reference.

In some embodiments antibody binding agents include proteins which have been used as a scaffold to engineer different target antigen binding properties include human γ-crystallin and human ubiquitin (affilins), kunitz type domains of human protease inhibitors, PDZ-domains of the Ras-binding protein AF-6, scorpion toxins (charybdotoxin), C-type lectin domain (tetranectins) which are reviewed in Chapter 7—*Non-Antibody Scaffolds from Handbook of Therapeutic Antibodies* (2007, edited by Stefan Dubel) and Protein Science 15:14-27 (2006).

Methods of selecting highly antigenic, exposed, and/or highly immunogenic portions of a polypeptide of known sequence for use as an antigen, or in a vaccine are known, and several algorithms are publically and commercially available for designing peptide antigens (e.g., see *Synthetic Peptides as Antigens*, CIBA Foundation Symposium, John Wiley & Sons, Apr. 30, 2008; and *Immunoinformatics: Predicting Immunogenicity In Silico*, Darren R. Flower, Springer Science & Business Media, Jun. 21, 2007; both of which are incorporated herein by reference). Methods of isolating, purifying and generating polypeptide antigens for use in generating antibodies, as well as methods of antibody generation are described in "Antibodies, A laboratory Manual" (1988) Cold Spring Harbor Laboratory Press, Col Spring Harbor, N.Y., by Ed Harlow and David Lane, which is incorporated herein by reference in its entirety. Method of generating antibody binding agents, screening libraries of binding agents, and selecting, purifying, cloning and producing high affinity binding agents (e.g., from a library of binding agents) is described in detail in "Antibody Engineering" (2001) Springer Science & Business, Springer lab manuals (Springer-Verlag Berline Heidelberg) by Dr. Roland Kontermann and Dr. Stefan Dubel; and "Antibody Engineering, Methods and Protocols" (2004), Methods in Molecular Biology, Vol 248; Humana Press Inc., New Jersey, by Benny K. C. Lo, which are incorporated herein by reference in their entirety.

In some embodiments, a monoclonal antibody or monoclonal binding agent is a substantially homogeneous population of antibody binding agents, or binding fragments thereof, where each individual binding agent in the population are substantially identical and/or bind the same epitope, with the except of possible variants that may arise during production of a monoclonal binding agent. In some embodiments, such variants generally are absent or may be present in minor amounts. In contrast to polyclonal antibody preparations which typically include different antibodies directed against different determinants (epitopes), each monoclonal antibody of a population often binds a single determinant on an antigen. Monoclonal antibodies are often uncontaminated by other immunoglobulins. The modifier "monoclonal" is not to be construed as requiring production of the antibody by any particular method. For example, in certain embodiments, a monoclonal antibody is made by the hybridoma method (e.g., as described by Kohler et al, Nature, 256:495 (1975)), or a variation thereof. In some embodiments a monoclonal binding agent is made by recombinant DNA method. For example, a monoclonal binding agent can be made by screening a recombinant library using a suitable expression system (e.g., a phage display expression system). In some embodiments, a monoclonal binding agent is isolated from a phage library of binding agents, for example by using a technique described in Clackson et al, Nature, 352:624-628 (1991) and/or Marks et al, J. Mol Biol, 222: 581-597 (1991), or a variation thereof.

In mammals an antibody can have two types of immunoglobulin light chains, lambda (Δ) and kappa (κ), which are often defined by the C-terminal constant regions of the light chain polypeptides (light chain constant regions). An antibody binding agent can have any suitable light chain constant region, or portion thereof. In some embodiments an antibody binding agent comprises a lambda light chain constant region or a portion thereof. In some embodiments an antibody binding agent comprises a kappa light chain constant region or a portion thereof. In some embodiments an antibody binding agent does not have a light chain constant region. In mammals, an antibody can have five types/classes of Ig heavy chains denoted as IgA, IgD, IgE, IgG, and IgM, which are determined by the presence of distinct heavy chain constant regions, or portion thereof (e.g., CH1, CL, CH2, CH3 domains). An antibody binding agent can have any suitable heavy chain constant region, or portion thereof. In some embodiments an antibody binding agent comprises a heavy chain constant region of an $IgG_1$, $IgG_2$, $IgG_3$ or $IgG_4$, or a portion thereof. In some embodiments an antibody binding agent comprises a heavy chain constant region of an IgM, IgD, IgA, or IgE isotype or a portion thereof. In some embodiments an antibody binding agent does not have a heavy chain constant region. Methods of modifying (e.g., adding, removing, modifying) heavy chain and light chain constant regions to modify the class and/or isotype of an antibody binding agent are well known in the art.

In certain embodiments, an antibody heavy chain, heavy chain variable region or antigen binding portion thereof, binds to an antigen in the absence of an antibody light chain, light chain variable region or antigen binding portion thereof. In certain embodiments, an antibody light chain, light chain variable region or antigen binding portion thereof, binds to an antigen in the absence of an antibody heavy chain, heavy chain variable region or antigen binding portion thereof. In certain embodiments, an antibody binding agent does not comprise an antibody light chain, or portion thereof. In certain embodiments, an antibody binding agent does not comprise an antibody heavy chain, or portion thereof. In certain embodiments, an antigen binding portion of an antibody variable region (e.g., a heavy chain or light chain variable region) specifically binds to an antigen in the absence of the other variable region.

In some embodiments an antibody binding agent comprises or consists of one or more suitable antigen binding portions of an antibody. In some embodiments an antibody binding agent comprises or consists of one or more variable regions of an antibody, or a portion thereof. In some embodiments an antibody binding agent comprises a Fab, Fab', F(ab')2, Fv fragment, single-chain Fv (scFv), diabody (Dab), synbody, the like and/or a combination or portion thereof. In some embodiments an antibody binding agent is a Fab, Fab', F(ab')2, Fv fragment, single-chain Fv (scFv), diabody (Dab), synbody, the like and/or a combination, or portion thereof (see, e.g., U.S. Pat. Nos. 6,099,842 and 5,990,296). In some embodiments, an antibody binding agent comprises a single-chain polypeptide comprising one or more antigen binding portions of an antibody. For example, a single-chain antibody binding agent can be constructed by joining a heavy chain variable region, or antigen binding portion thereof, with a light chain variable region, or antigen binding portion thereof, with a polypeptide linker (e.g., the linker is often attached at the C-terminus or N-terminus of each chain) using recombinant molecular biology processes. Such single chain antibody binding agents often exhibit specificities and affinities for an antigen similar to a parent two-chain monoclonal antibody. Antibody binding agents often comprise engineered regions such as CDR-grafted or humanized portions. In certain embodiments an antibody binding agent is an intact two-chain immunoglobulin, and in other embodiments an antibody binding agent is a Fab monomer or a Fab dimer. Methods for generating antibodies, recombinant antibodies and/or antigen binding portions thereof are known. The genes, or portions thereof, that encode a polypeptide of an antibody binding agent may be cloned, subcloned, rearranged or modified for recombinant expression by a suitable cloning procedure and subsequently expressed using a suitable expression system by a method known to those skilled in the art (e.g., see Maniatis et al., Molecular Cloning: A Laboratory Manual, Cold Spring Harbor Laboratory, 1982; Antibody Engineering: Methods and Protocols, Vol. 248 of Methods in molecular biology, edited by Benny K. C. Lo, Springer Science & Business Media, 2004; Antibody Engineering, Vol. 1, Roland E. Kontermann, Stefan Dübel, Edition 2, Publisher Springer Science & Business Media, 2010; Antibody Phage Display: Methods and Protocols, Biomed Protocols, Vol. 178 of Methods in molecular biology, Editors Philippa M. O'Brien, Robert Aitken, Springer Science & Business Media, 2004; which are hereby incorporated by reference in their entirety).

In mammals, the heavy chain variable region and light chain variable region of an antibody binding agent each contribute three CDRs (complementary determining regions, CDR1, CDR2 and CDR3) that are separated and/or flanked by framework regions (e.g., FR1, FR2, FR3 and FR4). In certain embodiments, definitive delineation of a CDR and identification of residues comprising the binding site of an antibody is accomplished by solving the structure of the antibody and/or solving the structure of the antibody-ligand complex. In certain embodiments, this can be accomplished by any of a variety of techniques known to those skilled in the art, such as X-ray crystallography and/or computer modeling. In certain embodiments, various methods of analysis can be employed to identify or approximate the CDR regions or an antibody. For example, the amino sequence and/or location of CDRs of an antibody can be identified using a suitable method, non-limiting examples of which include the Kabat system (e.g., see Kabat, E. A., et al., 1991; Sequences of Proteins of Immunological Interest, Fifth Edition, NIH Publication No. 91-3242, as well as Johnson, G. and Wu, T. T. 2000, Nucleic Acids Research), and/or the Chothia Numbering Scheme (e.g., Chothia & Lesk, (1987) J. Mol. Biol, 196:901-917; Chothia et al, Nature, (1989) 342:878-883; and A1-Lazikani et al., (1997) JMB 273, 927-948), all of which references are hereby incorporated by reference in their entirety. In some embodiments the amino sequence and/or location of CDRs of an antibody can be identified using the AbM method and/or contact method. The "AbM" definition uses an integrated suite of computer programs produced by Oxford Molecular Group that model antibody structure (see e.g., Martin et al, Proc. Natl. Acad. Sci. (USA), 86:9268-9272 (1989); "AbM™, A Computer Program for Modeling Variable Regions of Antibodies," Oxford, UK; Oxford Molecular, Ltd, all of which are hereby incorporated by reference in their entirety). The AbM definition models the tertiary structure of an antibody from primary sequence using a combination of knowledge databases and ab initio methods, such as those described by Samudrala et al., "Ab Initio Protein Structure Prediction Using a Combined Hierarchical Approach," in PROTEINS, Structure, Function and Genetics Suppl, 3:194-198 (1999), which is hereby incorporated by reference. In certain embodiments, a contact definition is based on an analysis of the available complex crystal structures (see e.g., MacCallum et ah, J. Mol. Biol, 5:732-45 (1996) which is hereby incorporated by reference).

In some embodiments, the CDR regions in a heavy chain are referred to as H1 (or alternatively CDR1, CDR1-HC, CDR-H1), H2 (or alternatively CDR2, CDR2-HC, CDR-H2), and H3 (or alternatively CDR3, CDR3-HC, CDR-H3) and are numbered sequentially in the direction from the amino terminus to the carboxy terminus. In certain embodiments the CDR regions in the light chain are referred to as L1 (or alternatively CDR1, CDR1-LC, CDR-L1), L2 (or alternatively CDR2, CDR2-LC, CDR-L2) and L3 (or alternatively CDR3, CDR3-LC, CDR-L3) and are numbered sequentially in the direction from the amino terminus to the carboxy terminus.

An antibody binding agent, whether natural or recombinant, can be polyclonal or monoclonal (e.g., a monoclonal antibody, or portion thereof). In some embodiments an antibody binding agent, or fragment thereof is chimeric, humanized or bispecific. Chimeric antibodies often comprise a mixture of portions of binding agents or antibodies derived from different species. In some embodiments chimeric antibodies comprise fully synthetic portions or sequences of amino acids not found in native antibody molecules. In some embodiments chimeric antibodies comprise amino acid substitutions derived from antibodies of other species or, in some embodiments chimeric antibodies comprise amino acid substitutions added in an attempt to increase binding affinity (e.g., by an in vitro process of affinity maturation) or alter antibody function (e.g., to increase or decrease complement mediated or cell mediated cell lysis).

In certain embodiments, modification of an antibody by methods known in the art is typically designed to achieve increased binding affinity for a target and/or to reduce immunogenicity of the antibody in the recipient. In certain embodiments, humanized antibodies are modified to eliminate glycosylation sites in order to increase affinity of the antibody for its cognate antigen. (See e.g., Co et al, Mol. Immunol, 30:1361-1367 (1993) which is hereby incorporated by reference). In certain embodiments, techniques such as "reshaping," "hyperchimerization," or "veneering/resurfacing" can be used to produce humanized antibodies. (See e.g., Vaswami et al, Annals of Allergy, Asthma, & Immunol. 81:105 (1998); Roguska et al, Prot. Engin., 9:895-904 (1996); and U.S. Pat. No. 6,072,035, which are hereby incorporated by reference). In certain such embodiments, these techniques typically reduce antibody immunogenicity by reducing the number of foreign residues, but do not prevent anti-idiotypic and anti-allotypic responses following repeated administration of the antibodies. Certain other methods for reducing immunogenicity are described (e.g., in Gilliland et al, J. Immunol, 62(6):3663-71 (1999) which is hereby incorporated by reference).

In some embodiments an antibody binding agent comprises a chimeric antibody, humanized antibody, human antibody, or a portion or fragment thereof. Methods for generating chimeric, grafted and/or humanized antibodies are known (see, e.g., U.S. Pat. Nos. 5,530,101, 5,707,622, 5,994,524 and 6,245,894, which are hereby incorporated by reference), which generally involve exchanging an antibody variable region, or portion thereof, from one species (e.g., mouse) into an antibody constant domain of another species (e.g., human). In some embodiments, an antibody can be humanized by exchanging one or more framework regions, or portions thereof (e.g., one or more individual amino acids), with one or more framework regions, or portions thereof (e.g., one or more individual amino acids), from a human antibody. Methods of humanizing an antibody by transferring one or more CDRs (e.g., 1, 2, 3, 4, 5 or all 6 CDRs) from a donor antibody binding agent (e.g., an antibody binding agent comprising framework regions of a mouse monoclonal antibody) to an acceptor antibody binding agent (e.g., an antibody binding agent comprising human framework regions) while retaining antigen binding are known (e.g., see Queen et al., (1988) PNAS 86:10029-10033; Riechmann et al., Nature (1988) 332:323-327; Antibody Engineering: Methods and Protocols, Vol. 248 of Methods in molecular biology, edited by Benny K. C. Lo, Springer Science & Business Media, (2004); Antibody Engineering, Vol. 1, Roland E. Kontermann, Stefan Dübel, Edition 2, Publisher Springer Science & Business Media, (2010), which are hereby incorporated by reference).

In certain embodiments the complementarity determining regions (CDRs) of the light and heavy chain variable regions of an antibody binding agent that binds specifically to a Mucorales toxin is grafted to framework regions from the same, or another, species. In certain embodiments, the CDRs of the light and heavy chain variable regions of an antibody binding agent that binds specifically to a Mucorales toxin can be grafted to consensus human framework regions. To create consensus human framework regions, in certain embodiments, framework regions from several human heavy chain or light chain amino acid sequences can be aligned to identify a consensus amino acid sequence. In certain embodiments, the heavy chain or light chain framework regions of an antibody that displays specific binding to a Mucorales toxin are replaced with the framework regions, or portions thereof, from a different heavy chain or light chain. In certain embodiments, grafted variable regions are part of a single chain Fv antibody. Additional examples of CDR grafting are described, e.g., in U.S. Pat. Nos. 6,180,370, 6,054,297, 5,693,762, 5,859,205, 5,693,761, 5,565,332, 5,585,089, and 5,530, 101, and in Jones et al, Nature, 321:522-525 (1986); Verhoeyen et al, Science, 239:1534-1536 (1988), and Winter, FEBS Letts., 430:92-94 (1998), which are hereby incorporated by reference.

In some embodiments an antibody binding agent is generated using a light chain, a light chain variable region, or a portion thereof, of known binding specificity and a library of heavy chain variable regions. Using such a method, the library of heavy chain variable regions can comprise a library of one or more heavy chain CDRs. For example, a library of heavy chain variable regions may comprise known framework regions, a known CDR1 and a known CDR2 and a library of different CDR3 regions. In some embodiments, the light chain, or portion thereof, of known binding specificity is co-expressed with a library of heavy chain variable regions, and the resulting light chain/heavy chain proteins are screened for binding to an antigen of interest (e.g., a Mucorales toxin) and/or for a specific function (e.g., blocking pathogenesis of a Mucorales infection; e.g., blocking toxin activity of a Mucorales toxin). Alternatively, in some embodiments an antibody binding agent is generated using a heavy chain, a heavy chain variable region, or a portion thereof, of known binding specificity and a library of light chain variable regions. Such methods of screening and optimizing antibody binding agents are known (e.g., see Portolano et al., (1993) Journal of Immunology 150:880-887; and Clarkson et al., (1991) Nature 352:624-628, which are hereby incorporated by reference in their entirety). Such references teach methods of producing antibodies that bind a specific antigen by using a specific known variable light chain, variable heavy chain, or a portion thereof (e.g., CDRs thereof) by screening a library of complementary variable domains.

In certain embodiments an antibody binding agent comprises one or more modifications. In some embodiments the number and/or type of glycosylation sites in an antibody binding agent is modified or altered compared to the amino acid sequence of a parent antibody binding agent. In certain embodiments, a modified antibody binding agent comprises a greater or a lesser number of N-linked glycosylation sites than the native protein. An N-linked glycosylation site is often characterized by the sequence Asn-X-Ser or Asn-X-Thr, where the amino acid residue designated as X can be any amino acid residue except proline. The substitution of amino acid residues to create this sequence provides a potential new site for the addition of an N-linked carbohydrate chain. Alternatively, substitutions which eliminate this sequence will remove an existing N-linked carbohydrate chain. Also provided in certain embodiments is a rearrangement of N-linked carbohydrate chains where one or more N-linked glycosylation sites (typically those that are naturally occurring) are eliminated and one or more new N-linked sites are created. In some embodiments an antibody binding agent is modified by deleting one or more cysteine residues or substituting one or more cysteine residues for another amino acid (e.g., serine) as compared to an unmodified antibody binding agent. In certain embodiments cysteine variants can be useful when antibodies must be refolded into a biologically active conformation such as after the isolation of insoluble inclusion bodies.

According to certain embodiments an antibody binding agent is modified to include certain amino acid additions, substitutions, or deletions designed to (1) reduce susceptibility of an antibody binding agent to proteolysis, (2) reduce susceptibility of an antibody binding agent to oxidation, (3) alter binding affinity to Fc receptors, (4) alter antigen binding affinity of an antibody binding agent, (4) increase serum half-life and/or (5) confer or modify other physicochemical, pharmacokinetic or functional properties of an antibody binding agent.

An antibody binding agent can be expressed, isolated from and/or purified from a suitable expression system non-limiting examples of which include a suitable bacteria, insect, plant or mammalian expression system. For example, a nucleic acid encoding an antibody binding agent can be introduced into a suitable mammalian cell line that expresses and secretes the antibody binding agent into the cell culture media.

The term "specifically binds" refers to an antibody binding agent that binds to a target polypeptide in preference to binding other molecules or other peptides as determined by, for example, a suitable in vitro assay (e.g., an Elisa, Immunoblot, Flow cytometry, and the like). A specific binding interaction discriminates over non-specific binding interactions by about 2-fold or more, often about 10-fold or more, and sometimes about 100-fold or more, 1000-fold or more, 10,000-fold or more, 100,000-fold or more, or 1,000,000-fold or more.

Distinguishable Identifiers

In some embodiments an antibody binding agent or nucleic acid described herein comprises one or more distinguishable identifiers. Any suitable distinguishable identifier and/or detectable identifier can be used for a composition or method described herein. In certain embodiments a distinguishable identifier can be directly or indirectly associated with (e.g., bound to) an antibody binding agent or a nucleic acid (e.g., a primer). For example a distinguishable identifier can be covalently or non-covalently bound to an antibody binding agent or a nucleic acid described herein. In some embodiments a distinguishable identifier is bound to, or associated with, an antibody binding agent and/or a member of binding pair that is covalently or non-covalently bound to an antibody binding agent. In some embodiments a distinguishable identifier is reversibly associated with an antibody binding agent or a nucleic acid. In certain embodiments a distinguishable identifier that is reversibly associated with an antibody binding agent or nucleic acid can be removed from an antibody binding agent or nucleic acid using a suitable method (e.g., by increasing salt concentration, denaturing, washing, adding a suitable solvent and/or salt, adding a suitable competitor, and/or by heating).

In some embodiments a distinguishable identifier is a label. As used herein, the terms "label" or "labeled" refers to incorporation of a detectable marker. In some embodiments an antibody binding agent or nucleic acid comprises a detectable label, non-limiting examples of which include a radiolabel (e.g., an isotope, radioisotopes or radionuclides (e.g., $^{3}H$, $^{14}C$, $^{15}N$, $^{35}S$, $^{90}Y$, $^{99}Tc$, $^{125}I$, $^{131}I$), a metallic label, a fluorescent label, a chromophore, a chemiluminescent label, an electrochemiluminescent label (e.g., Origen™), a phosphorescent label, a quencher (e.g., a fluorophore quencher), a fluorescence resonance energy transfer (FRET) pair (e.g., donor and acceptor), a dye, a protein (e.g., an enzyme (e.g., horseradish peroxidase, β-galactosidase, luciferase, alkaline phosphatase and the like)), an antibody, an antigen or part thereof, a linker, a member of a binding pair), an enzyme substrate, a small molecule (e.g., biotin, avidin), a mass tag, quantum dots, nanoparticles, the like or combinations thereof. Any suitable fluorophore or light emitting material can be used as a label. A light emitting label can be detected and/or quantitated by a variety of suitable techniques such as, for example, flow cytometry, gel electrophoresis, protein-chip analysis (e.g., any chip methodology), microarray, mass spectrometry, cytofluorimetric analysis, fluorescence microscopy, confocal laser scanning microscopy, laser scanning cytometry, the like and combinations thereof.

In some embodiments a composition or method described herein comprises one or more binding pairs. In some embodiments an antibody binding agent, polypeptide or nucleic acid described herein comprises one or more binding pairs. In certain embodiments one or more members of a binding pair comprises an antibody binding agent. In some embodiments a binding pair comprises at least two members (e.g., molecules) that bind non-covalently to (e.g., associate with) each other. Members of a binding pair often bind specifically to each other. Members of a binding pair often bind reversibly to each other, for example where the association of two members of a binding pair can be dissociated by a suitable method. Any suitable binding pair, or members thereof, can be utilized for a composition or method described herein. Non-limiting examples of a binding pair includes antibody/antigen, antibody/antibody, antibody/antibody fragment, antibody/antibody receptor, antibody/protein A or protein G, hapten/anti-hapten, sulfhydryl/maleimide, sulfhydryl/haloacetyl derivative, amine/isotriocyanate, amine/succinimidyl ester, amine/sulfonyl halides, biotin/avidin, biotin/streptavidin, folic acid/folate binding protein, receptor/ligand, vitamin B12/intrinsic factor, analogues thereof, derivatives thereof, binding portions thereof, the like or combinations thereof. Non-limiting examples of a binding pair member include an antibody, antibody fragment, reduced antibody, chemically modified antibody, antibody receptor, an antigen, hapten, anti-hapten, a peptide, protein, nucleic acid (e.g., double-stranded DNA (dsDNA), single-stranded DNA (ssDNA), or RNA), a nucleotide, a nucleotide analog or derivative (e.g., bromodeoxyuridine (BrdU)), an alkyl moiety (e.g., methyl moiety on methylated DNA or methylated histone), an alkanoyl moiety (e.g., an acetyl group of an acetylated protein (e.g., an acetylated histone)), an alkanoic acid or alkanoate moiety (e.g., a fatty acid), a glyceryl moiety (e.g., a lipid), a phosphoryl moiety, a glycosyl moiety, a ubiquitin moiety, lectin, aptamer, receptor, ligand, metal ion, avidin, neutravidin, biotin, B12, intrinsic factor, analogues thereof, derivatives thereof, binding portions thereof, the like or combinations thereof. In some embodiments, a member of a binding pair comprises a distinguishable identifier.

In some embodiments a distinguishing identifier, carrier, anti-fungal medication, toxin, isotope and/or a suitable polypeptide can be indirectly or directly associated with, or bound to (e.g., covalently bound to, or conjugated to) an antibody binding agent. In certain embodiments agents or molecules are sometimes conjugated to or bound to antibodies to alter or extend the in vivo half-life of an antibody binding agent or fragment thereof. In some embodiments, an antibody binding agent is fused or associated with one or more polypeptides (e.g., a toxin, ligand, receptor, cytokine, antibody, the like or combinations thereof). In certain embodiments, an antibody binding agent is linked to a half-life extending vehicle known in the art. Such vehicles include, but are not limited to, polyethylene glycol, glycogen (e.g., glycosylation of the antigen binding protein), and dextran. Such vehicles are described, e.g., in U.S. application Ser. No. 09/428,082, now U.S. Pat. No. 6,660,843 and published PCT Application No. WO 99/25044, hereby incorporated by reference.

In some embodiments carriers or anti-fungal medications are bound to an antibody binding agent by a linker. A linker can provide a mechanism for covalently attaching a carrier and/or an anti-fungal medications to an antibody binding agent. Any suitable linker can be used in a composition or method described herein. Non-limiting examples of suitable linkers include silanes, thiols, phosphoric acid, and polyethylene glycol (PEG). Methods of attaching two or more molecules using a linker are well known in the art and are sometimes referred to as "crosslinking". Non-limiting examples of crosslinking include an amine reacting with a N-Hydroxysuccinimide (NHS) ester, an imidoester, a pentafluorophenyl (PFP) ester, a hydroxymethyl phosphine, an oxirane or any other carbonyl compound; a carboxyl reacting with a carbodiimide; a sulfhydryl reacting with a maleimide, a haloacetyl, a pyridyldisulfide, and/or a vinyl sulfone; an aldehyde reacting with a hydrazine; any non-selective group reacting with diazirine and/or aryl azide; a hydroxyl reacting with isocyanate; a hydroxylamine reacting with a carbonyl compound; the like and combinations thereof.

Toxins

Novel hyphae-associated toxins (H-toxins) and secreted toxins (S-toxin) are provide herein.

In some embodiments an H-toxin comprises a polypeptide of any one of SEQ ID NOs: 3-9. In some embodiments an H-toxin comprises a portion of any one of SEQ ID NOs: 3-9. In certain embodiments an H-toxin is encoded by SEQ ID NOs: 1, 2, 35-39, or 47, or a portion thereof.

In some embodiments an S-toxin comprises a polypeptide of any one of SEQ ID NOs: 17-21. In some embodiments an S-toxin comprises a portion of any one of SEQ ID NOs: 17-21. In certain embodiments an S-toxin is encoded by SEQ ID NOs: 22 or 23.

An H- or S-toxin, or portion thereof can be made, expressed and/or purified using a suitable method. An H- or S-toxin can be generated by a recombinant method and expressed using an suitable expression system. For example, a nucleic acid encoding an S- or H-toxin, or a portion thereof, can be subcloned into a suitable vector, introduced into a suitable expression system (e.g., baculovirus, yeast (e.g., *S. cerevisiae*), mammalian or bacterial expression systems) and expressed with or without a suitable tag to facilitate detection, quantitation and/or purification. Non-limiting examples of suitable tags include poly-(His), Myc, Flag, V5, HA, Chitin binding protein (CBP), maltose binding protein (MBP), and glutathione-S-transferase (GST).

Anti-Fungal Agents

In some embodiments a method of treating a Mucorales infection comprises administration of an anti-fungal agent. In certain embodiments a composition comprises one or more anti-fungal agents. Non-limiting examples of anti-fungal agents include amphotericin B, candicidin, filipin, hamycin, natamycin, nystatin, rimocidin, imidazoles (e.g., bifonazole, butoconazole, clotrimazole, econazole, fenticonazoleisoconazole, ketoconazole, luliconazole, miconazole, omoconazole, oxiconazole, sertaconazole, sulconazole, tioconazole, and the like), triazoles (e.g., albaconazole, efinaconazole, epoxiconazole, fluconazole, isavuconazole, itraconazole, posaconazole, propiconazole, ravuconazole, terconazole, voriconazole, and the like), thiazoles, (e.g., abafungin), allylamines (e.g., amorolfin, butenafine, naftifine, and terbinafine), echinocandins (e.g., anidulafungin, caspofungin, micafungin), benzoic acid (e.g., combined with a keratolytic agent such as in whitfield's ointment), ciclopirox (ciclopirox olamine), flucytosine, 5-fluorocytosine, griseofulvin, haloprogin, tolnaftate, undecylenic acid, crystal violet, Balsam of Peru, the like or combinations thereof. Amphotericin B can be deoxy cholate formulation or a lipid formulations. In some embodiments Amphotericin B comprises liposomal Amphotericin B. In certain embodiments Amphotericin B comprises a lipid complex of Amphotericin B.

Pharmaceutical Compositions

In some embodiments, a composition comprises one or more toxin polypeptides (e.g., H- or S-toxin polypeptides), or portions thereof, and one or more adjuvants. In certain embodiments, a composition is an immunogenic composition. In some embodiments provided herein is a composition comprising one or more toxin polypeptides, or portions thereof, and one or more adjuvants for use as a vaccine. In some embodiments a composition comprises one or more polypeptides comprising 5 to 500, 5 to 400, 5 to 300, 5 to 200 or 5 to 100 consecutive amino acids selected from one or more of SEQ ID NOs: 3-9 or 17-21, and an adjuvant. In some embodiments a composition comprises one or more polypeptides comprising 5 or more, 10 or more, 15 or more, 16, or more, 17 or more, 18 or more, 19 or more, 20 or more, 25 or more or 30 or more consecutive amino acids selected from SEQ ID NOs: 3-9 or 17-21, and an adjuvant. In some embodiments a composition comprises one or more polypeptides each comprising 10, 11, 12, 13, 14, 15, 16, 17, 18, 19, 20, 21, 22, 23, 24 or 25 consecutive amino acids selected from SEQ ID NOs: 3-9 or 17-21, and an adjuvant. In certain embodiments, a composition comprising 5 to 500, 5 to 400, 5 to 300, 5 to 200 or 5 to 100 consecutive amino acids selected from SEQ ID NOs: 3-9 or 17-21, and an adjuvant is used as a vaccine to prevent a Mucorales infection in a subject. In certain embodiments a composition comprises a polypeptide comprising 5 to 500 consecutive amino acid having 80% identity or more, 85% identity or more, 90% identity or more, 95% identity or more, 96% identity or more, 98% identity or more, 99% identity or more, or 100% identity to 5 to 500 consecutive amino acids of any one of SEQ ID NOs: 3-9 or 17-21, and a suitable adjuvant. In certain embodiments a compositions comprises a polypeptide comprising the amino acid sequence NQLWRY(D/E)(D/N)GY.

In some embodiments a composition comprises a polypeptide comprising one or more immunogenic fragments of a polypeptide selected from SEQ ID NOs: 3-9 or 17-21. Methods of identifying highly immunogenic and or highly antigenic portions of a polypeptide for use in a vaccine, and methods of making effective vaccines using portions, or all, of a polypeptide of known sequence are known in the art (e.g., as described in "*Vaccinology: An Essential Guide*", by Gregg N. Milligan, and Alan D. T. Barrett, John Wiley & Sons, Dec. 4, 2014, which is incorporated herein by reference).

Any suitable adjuvant can be used for a composition or vaccine described herein. Adjuvants for use in immunogenic compositions and vaccines are known in the art and are described in, for example, Vaccine Adjuvants: Preparation Methods and Research Protocols, Derek T. O'Hagan, Springer Science & Business Media, Apr. 15, 2000; and Vaccinology: An Essential Guide, Gregg N. Milligan, Alan D. T. Barrett, John Wiley & Sons, Dec. 4, 2014, both of which are incorporated herein by reference. Non-limiting examples of adjuvants include, but are not limited to salts and amorphous materials (e.g., mineral salts), certain immunogenic serum peptides, immuno-stimulatory nucleic acids, immuno-stimulatory cytokines, plant components such as saponin-based compounds (e.g., natural and synthetic glycosidic triterpenoid compounds and pharmaceutically acceptable salts, derivatives, mimetics (e.g., isotucaresol and its derivatives) and/or biologically active fragments thereof, which possess adjuvant activity), bacterial and yeast antigens, and mammalian peptides.

Non-limiting examples of mineral salts include, but are not limited to, aluminum salts, aluminum phosphate, calcium phosphate, aluminum hydroxide (e.g., Alhydrogel), aluminum hydroxide in combination with gamma insulin (e.g., Algammulin), amorphous aluminum hydroxyphosphate (e.g., Adju-Phos), deoxycholic acid-aluminum hydroxide complex (e.g., DOC/Alum). In some embodiments an adjuvant comprises aluminium hydroxide, aluminum phosphate and/or hydrated potassium aluminum sulfate (e.g., potassium alum).

In certain embodiments an adjuvant comprises complement factor C3d, which is a 16 amino acid peptide (See, e.g., Fearon et al., 1998, Semin. Immunol. 10: 355-61; Nagar et al., 1998, Science; 280(5367):1277-81, Ross et al. 2000, Nature Immunol., Vol. 1(2), each of which is incorporated herein by reference in its entirety). C3d is also available commercially (e.g., Sigma Chemical Company Cat. C 1547). In one embodiment, the concentration of C3d in a composition of the invention is from about 0.01 μg/mL to about 200 μg/mL, preferably about 0.1 μg/mL to about 100 μg/mL, preferably about 1 μg/mL to about 50 μg/mL, more preferably about 5 μg/mL to about 20 μg/mL. It will be appreciated by one skilled in the art that the optimal C3d sequence will depend on the species to which the composition of the invention is administered.

Non-limiting examples of immuno-stimulatory nucleic acids include CpG, polyadenylic acid/poly uriddenlic acid, and Loxorbine (7-allyl-8-oxoguanosine). CpG sequences known in the art are described in U.S. Pat. No. 6,406,705, for example, which is incorporated herein by reference in its entirety. In certain embodiments, the concentration of CpG in a composition is from about 0.01 μg/mL to about 200 μg/mL, preferably about 0.1 μg/mL to about 100 μg/mL, preferably about 1 μg/mL to about 50 μg/mL, more preferably about 5 μg/mL to about 20 μg/mL.

Non-limiting examples of immuno-stimulatory cytokines include interferons (e.g., interferon-gamma), interleukins (e.g., interleukin-2 (IL-2), interleukin-4 (IL-4), interleukin-6 (IL-6), interleukin-7 (IL-7), interleukin-12 (IL-12), interleukin-15 (IL-15)), colony stimulating factors, e.g., macrophage colony stimulating factors (M-CSF); G-CSF, GM-CSF), tumor necrosis factor (TNF), IL-1 and MIP-3a.

Non-limiting examples of bacterial or yeast antigens include muramyl peptides such as, but not limited to, IMMTHER™, theramide (MDP derivative), DTP-N-GDP, GMDP (GERBU adjuvant), MPC-026, MTP-PE, murametide, murapalmitine; MPL derivatives such as, but not limited to, MPL-A, MPL-SE, 3D-MLA, and SBAS-2 (i.e., mix of QS-21 and MPL-A); and mannon. Other muramyl peptides that may be used in the compositions of the invention include, but are not limited to, N-acetyl-muramyl-L-threonyl-D-isoglutamine (thr-MDP), N-acteyl-normuramyl-L-alanyl-D-isogluatme (nor-MDP), N-acetylmuramyl-L-alanyl-D-isogluatminyl-L-alanine-2-(1'-2'-dipalmitoyl-s-n-glycero-3-huydroxyphosphoryloxy)-ethylamine (MTP-PE).

Non-limiting examples of mammalian peptides that may be used in the compositions of the invention include, but are not limited to, melanonin peptide 946, neutrophil chemoattractant peptide, and elastin repeating peptide. See, e.g., Senior et al., 1984, J Cell Bio 99 (Elastin); Needle et al., 1979, J. Biol. Chem. 254 (Neutrophil); and (Peptide 946) Cox et al. 1994, Science, 264), each of which is incorporated herein by reference in its entirety.

In some embodiments, the concentration of the adjuvant in an composition, immunogenic composition or vaccine described herein is at least 0.01% (w/v), at least 0.1% (w/v), at least 1% (w/v), at least 10% (w/v), at least 15% (w/v), at least 20% (w/v), at least 25% (w/v), or at least 30% (w/v). In some embodiments, the concentration of the adjuvant is greater than about 30% (w/v). In other embodiments, the concentration of the adjuvant compound is at least 0.1% (w/v), at least 0.5% (w/v), at least 1% (w/v), at least 5% (w/v), or at least 10% (w/v).

In some embodiments a composition (e.g., an immunogenic composition, a vaccine) comprises a suitable buffering agent and/or a suitable salts. In some embodiments a composition comprises a polypeptide, or immunogenic fragment thereof, an adjuvant and a pharmaceutically acceptable carrier. A composition is often aseptic and/or sterile.

In some embodiments a pharmaceutical composition comprises an antibody binding agent that binds specifically to an S-toxin or H-toxin as described herein. In some embodiments a pharmaceutical composition comprises an antibody binding agent that binds specifically to a Mucorales species.

In certain embodiments, acceptable pharmaceutical compositions are nontoxic to a recipient subject at the dosages and/or concentrations employed. A pharmaceutical composition can be formulated for a suitable route of administration. In some embodiments a pharmaceutical composition is formulated for subcutaneous (s.c.), intradermal, intramuscular, intraperitoneal and/or intravenous (i.v.) administration. In certain embodiments, a pharmaceutical composition can contain formulation materials for modifying, maintaining, or preserving, for example, the pH, osmolarity, viscosity, clarity, color, isotonicity, odor, sterility, stability, rate of dissolution or release, adsorption or penetration of the composition. In certain embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates (e.g., phosphate buffered saline) or suitable organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counter ions (such as sodium); solvents (such as glycerin, propylene glycol or polyethylene glycol); diluents; excipients and/or pharmaceutical adjuvants (Remington's Pharmaceutical Sciences, 18th Ed., A. R. Gennaro, ed., Mack Publishing Company (1995) which is hereby incorporated by reference).

In certain embodiments, a pharmaceutical composition comprises a suitable excipient, non-limiting example of which include anti-adherents (e.g., magnesium stearate), binders, fillers, monosaccharides, disaccharides, other carbohydrates (e.g., glucose, mannose or dextrins), sugar alcohols (e.g., mannitol or sorbitol), coatings (e.g., cellulose, hydroxypropyl methylcellulose (HPMC), microcrystalline cellulose, synthetic polymers, shellac, gelatin, corn protein zein, enterics or other polysaccharides), starch (e.g., potato, maize or wheat starch), silica, colors, disintegrants, flavors, lubricants, preservatives, sorbents, sweetners, vehicles, suspending agents, surfactants and/or wetting agents (such as pluronics, PEG, sorbitan esters, polysorbates such as polysorbate 20, polysorbate 80, triton, tromethamine, lecithin, cholesterol, tyloxapal), stability enhancing agents (such as sucrose or sorbitol), and tonicity enhancing agents (such as alkali metal halides, sodium or potassium chloride, mannitol, sorbitol), and/or any excipient disclosed in Remington's Pharmaceutical Sciences, 18th Ed., A. R. Gennaro, ed., Mack Publishing Company (1995).

In some embodiments a pharmaceutical composition comprises a suitable pharmaceutically acceptable additive and/or carrier. Non-limiting examples of suitable additives include a suitable pH adjuster, a soothing agent, a buffer, a sulfur-containing reducing agent, an antioxidant and the like. Non-limiting examples of a sulfur-containing reducing agents include those having a sulfhydryl group such as N-acetylcysteine, N-acetylhomocysteine, thioctic acid, thiodiglycol, thioethanolamine, thioglycerol, thiosorbitol, thioglycolic acid and a salt thereof, sodium thiosulfate, glutathione, and a C1-C7 thioalkanoic acid. Non-limiting examples of an antioxidant include erythorbic acid, dibutylhydroxytoluene, butylhydroxyanisole, alpha-tocopherol, tocopherol acetate, L-ascorbic acid and a salt thereof, L-ascorbyl palmitate, L-ascorbyl stearate, sodium bisulfite, sodium sulfite, triamyl gallate and propyl gallate, as well as chelating agents such as disodium ethylenediaminetetraacetate (EDTA), sodium pyrophosphate and sodium metaphosphate. Furthermore, diluents, additives and excipients may comprise other commonly used ingredients, for example, inorganic salts such as sodium chloride, potassium chloride, calcium chloride, sodium phosphate, potassium phosphate and sodium bicarbonate, as well as organic salts such as sodium citrate, potassium citrate and sodium acetate.

The pharmaceutical compositions used herein can be stable over an extended period of time, for example on the order of months or years. In some embodiments a pharmaceutical composition comprises one or more suitable preservatives. Non limiting examples of preservatives include benzalkonium chloride, benzoic acid, salicylic acid, thimerosal, phenethyl alcohol, methylparaben, propylparaben, chlorhexidine, sorbic acid, hydrogen peroxide, the like and/or combinations thereof. A preservative can comprise a quaternary ammonium compound, such as benzalkonium chloride, benzoxonium chloride, benzethonium chloride, cetrimide, sepazonium chloride, cetylpyridinium chloride, or domiphen bromide (BRADOSOL®). A preservative can comprise an alkyl-mercury salt of thiosalicylic acid, such as thimerosal, phenylmercuric nitrate, phenylmercuric acetate or phenylmercuric borate. A preservative can comprise a paraben, such as methylparaben or propylparaben. A preservative can comprise an alcohol, such as chlorobutanol, benzyl alcohol or phenyl ethyl alcohol. A preservative can comprise a biguanide derivative, such as chlorohexidine or polyhexamethylene biguanide. A preservative can comprise sodium perborate, imidazolidinyl urea, and/or sorbic acid. A preservative can comprise stabilized oxychloro complexes, such as known and commercially available under the trade name PURITE®. A preservative can comprise polyglycol-polyamine condensation resins, such as known and commercially available under the trade name POLYQUART® from Henkel KGaA. A preservative can comprise stabilized hydrogen peroxide. A preservative can be benzalkonium chloride. In some embodiments a pharmaceutical composition is free of preservatives.

In some embodiments a pharmaceutical composition is substantially free of blood components. For example, in certain embodiments, a pharmaceutical composition that comprises an antibody binding agent is substantially free of non-antibody proteins blood components (e.g., serum proteins, cells, lipids and the like). In certain embodiments where a pharmaceutical composition comprises a polyclonal antibody binding agent isolated or purified from an animal (e.g., a rabbit, sheep, goat, rodent, and the like), the composition is substantially free of non-antibody blood components derived from said animal, non-limiting examples of which include serum albumin, clotting factors, platelets, white blood cells, red blood cells, serum lipids, and the like. In some embodiments a pharmaceutical composition is sterile. In some embodiments a pharmaceutical composition is substantially free of endotoxin where the endotoxin component of the composition is less than 10, less than 1.0, less than 0.5, less than 0.1, less than 0.05 or less than 0.01 EU/ml. In some embodiments a pharmaceutical composition is lyophilized to a dry powder form, which is suitable for reconstitution with a suitable pharmaceutical solvent (e.g., water, saline, an isotonic buffer solution (e.g., PBS), and the like), which reconstituted form is suitable for parental administration (e.g., intravenous administration) to a mammal.

The pharmaceutical compositions described herein may be configured for administration to a subject in any suitable form and/or amount according to the therapy in which they are employed. For example, a pharmaceutical composition configured for parenteral administration (e.g., by injection or infusion), may take the form of a suspension, solution or emulsion in an oily or aqueous vehicle and it may contain formulation agents, excipients, additives and/or diluents such as aqueous or non-aqueous solvents, co-solvents, suspending solutions, preservatives, stabilizing agents and or dispersing agents. In some embodiments a pharmaceutical composition suitable for parental administration may contain, in addition to an antibody binding agent and/or one or more anti-fungal medications, one or more excipients.

In some embodiments a pharmaceutical compositions described herein may be configured for topical, rectal, or vaginal administration and may include one or more of a binding and/or lubricating agent, polymeric glycols, gelatins, cocoa-butter or other suitable waxes or fats. In some embodiments, a pharmaceutical composition described herein is incorporated into a topical formulation containing a topical carrier that is generally suited to topical drug administration and comprising any suitable material known in the art. A topical carrier may be selected so as to provide the composition in the desired form, e.g., as a solution or suspension, an ointment, a lotion, a cream, a salve, an emulsion or microemulsion, a gel, an oil, a powder, or the like. It may be comprised of naturally occurring or synthetic materials, or both. A carrier for the active ingredient may also be in a spray form. It is preferable that the selected carrier not adversely affect the active agent or other components of the topical formulation. Non-limiting examples of suitable topical carriers for use herein can be soluble, semi-solid or solid and include water, alcohols and other nontoxic organic solvents, glycerin, mineral oil, silicone, petroleum jelly, lanolin, fatty acids, vegetable oils, parabens, waxes, and the like. Semisolid carriers preferably have a dynamic viscosity greater than that of water. Other suitable vehicles include ointment bases, conventional creams such as HEB cream; gels; as well as petroleum jelly and the like. If desired, and depending on the carrier, the compositions may be sterilized or mixed with auxiliary agents, e.g., preservatives, stabilizers, wetting agents, buffers, or salts for influencing osmotic pressure and the like. Formulations may be colorless, odorless ointments, lotions, creams, microemulsions and gels.

Ointments can be semisolid preparations which are typically based on petrolatum or other petroleum derivatives. The specific ointment base to be used, as will be appreciated by those skilled in the art, is one that will provide for optimum delivery of the active agent, and, preferably, will provide for other desired characteristics as well, e.g., emolliency or the like. As with other carriers or vehicles, an ointment base should be inert, stable, nonirritating and nonsensitizing. Ointment bases can be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (OAV) emulsions, and include, for example, cetyl alcohol, glyceryl monostearate, lanolin and stearic acid. Exemplary water-soluble ointment bases are prepared from polyethylene glycols (PEGs) of varying molecular weight, e.g., polyethylene glycol-1000 (PEG-1000). Oils of animal or plant origin such as peanut oil, mineral oil, soybean oil, or sesame oil, corn oil, or synthetic oils may be added.

Antibody binding agents and/or peptides may be incorporated into lotions, which generally are preparations to be applied to the skin surface without friction, and are typically liquid or semiliquid preparations in which solid particles, including the active agent, are present in a water or alcohol base. Lotions can be suspensions of solids, and may comprise a liquid oily emulsion of the oil-in-water type. In certain embodiments, lotions are preferred formulations for treating large body areas, because of the ease of applying a more fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethylcellulose, or the like. In some embodiments a lotion formulation for use in conjunction with the present method contains propylene glycol mixed with a hydrophilic petrolatum.

In some embodiments pharmaceutical compositions are formulated as creams, which generally are viscous liquid or semisolid emulsions, either oil-in-water or water-in-oil. Cream bases are water-washable, and contain an oil phase, an emulsifier and an aqueous phase. The oil phase is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation can be a nonionic, anionic, cationic or amphoteric surfactant.

Pharmaceutical compositions can be formulated as microemulsions, which generally are thermodynamically stable, isotropic clear dispersions of two immiscible liquids, such as oil and water, stabilized by an interfacial film of surfactant molecules (Encyclopedia of Pharmaceutical Technology (New York: Marcel Dekker, 1992), volume 9). For the preparation of microemulsions, surfactant (emulsifier), co-surfactant (co-emulsifier), an oil phase and a water phase are necessary. Suitable surfactants include any surfactants that are useful in the preparation of emulsions, e.g., emulsifiers that are typically used in the preparation of creams. The co-surfactant (or "co-emulsifier") is generally selected from the group of polyglycerol derivatives, glycerol derivatives and fatty alcohols. In some embodiments emulsifier/co-emulsifier combinations are selected from the group consisting of: glyceryl monostearate and polyoxyethylene stearate; polyethylene glycol and ethylene glycol palmitostearate; and caprylic and capric triglycerides and oleoyl macrogolglycerides. In certain embodiments a water phase includes not only water, but also, typically, buffers, glucose, propylene glycol, polyethylene glycols, for example lower molecular weight polyethylene glycols (e.g., PEG 300 and PEG 400), and/or glycerol, and the like, while the oil phase will generally comprise, for example, fatty acid esters, modified vegetable oils, silicone oils, mixtures of mono- di- and triglycerides, mono- and di-esters of PEG, etc.

In certain embodiments, the primary vehicle or carrier in a pharmaceutical composition can be either aqueous or non-aqueous in nature. For example, in certain embodiments, a suitable vehicle or carrier can be water for injection, physiological saline solution or artificial cerebrospinal fluid, possibly supplemented with other materials common in compositions for parenteral administration. In some embodiments, the saline comprises isotonic phosphate-buffered saline. In certain embodiments, neutral buffered saline or saline mixed with serum albumin are further exemplary vehicles. In certain embodiments, pharmaceutical compositions comprise Tris buffer of about pH 7.0-8.5, or acetate buffer of about pH 4.0-5.5, which can further include sorbitol or a suitable substitute therefore. In certain embodiments, a composition comprising an antibody binding agent, with or without at least one additional therapeutic agents, can be prepared for storage by mixing the selected composition having the desired degree of purity with optional formulation agents (Remington's Pharmaceutical Sciences, supra) in the form of a lyophilized cake or an aqueous solution. Further, in certain embodiments, a composition comprising an antibody binding agent, with or without at least one additional therapeutic agents, can be formulated as a lyophilized form (e.g., a lyophilized powder or crystalline form, a freeze dried form) using appropriate excipients such as sucrose.

In some embodiments a carrier facilitates the incorporation of a compound into cells or tissues. For example dimethyl sulfoxide (DMSO) is a commonly utilized carrier as it facilitates the uptake of many organic compounds into the cells or tissues of an organism. In some embodiments, a pharmaceutical carrier for a composition described herein can be selected from castor oil, ethylene glycol, monobutyl ether, diethylene glycol monoethyl ether, corn oil, dimethyl sulfoxide, ethylene glycol, isopropanol, soybean oil, glycerin, zinc oxide, titanium dioxide, glycerin, butylene glycol, cetyl alcohol, and sodium hyaluronate.

The compounds and compositions used herein can include any suitable buffers, such as for example, sodium citrate buffer and/or sequestering agents, such as an EDTA sequestering agent. Ingredients, such as meglumine, may be added to adjust the pH of a composition or antibody binding agent described herein. Antibody binding agents and compositions described herein may comprise sodium and/or iodine, such as organically bound iodine. Compositions and compounds used herein may be provided in a container in which the air is replaced by another substance, such as nitrogen.

In certain embodiments, the optimal pharmaceutical composition will be determined by one skilled in the art depending upon, for example, the intended route of administration, delivery format and desired dosage (see e.g., Remington's Pharmaceutical Sciences, supra). In certain embodiments, such compositions may influence the physical state, stability, rate of in vivo release and rate of in vivo clearance of the antibodies of the invention.

Administration and Formulation

In some embodiments, compositions described herein (e.g., compositions comprising a mAb that binds to An S-toxin or H-toxin) are used to prevent and/or block a Mucorales infection. In certain embodiments a composition is administered to a subject at risk of acquiring a Mucorales infection. A composition that is used to prevent a Mucorales infection is often administered to a subject at risk of acquiring a Mucorales infection. In certain embodiments a method of preventing a Mucorales infection comprises administering a composition described herein prior to detection or diagnosis of a Mucorales infection. Any suitable method of administering a pharmaceutical composition to a subject can be used to administer an antibody binding agent described herein.

The exact formulation and route of administration for a composition for use according to the methods of the invention described herein can be chosen by the individual physician in view of the patient's condition. See, e.g., Fingl et al. 1975, in "The Pharmacological Basis of Therapeutics," Ch. 1, p. 1; which is incorporated herein by reference in its entirety. Any suitable route of administration can be used for administration of a pharmaceutical composition or antibody binding agent described herein. Non-limiting examples of routes of administration include topical or local (e.g., transdermally or cutaneously, (e.g., on the skin or epidermus), in or on the eye, intranasally, transmucosally, in the ear, inside the ear (e.g., behind the ear drum)), enteral (e.g., delivered through the gastrointestinal tract, e.g., orally (e.g., as a tablet, capsule, granule, liquid, emulsification, lozenge, or combination thereof), sublingual, by gastric feeding tube, rectally, and the like), by parenteral administration (e.g., parenterally, e.g., intravenously, intra-arterially, intramuscularly, intraperitoneally, intradermally, subcutaneously, intracavity, intracranially, intra-articular, into a joint space, intracardiac (into the heart), intracavernous injection, intralesional (into a skin lesion), intraosseous infusion (into the bone marrow), intrathecal (into the spinal canal), intrauterine, intravaginal, intravesical infusion, intravitreal), the like or combinations thereof.

In some embodiments a composition herein is provided to a subject. A composition that is provided to a subject is often provided to a subject for self-administration or for administration to a subject by another (e.g., a non-medical professional). For example a composition described herein can be provided as an instruction written by a medical practitioner that authorizes a patient to be provided a composition or treatment described herein (e.g., a prescription). In another example, a composition can be provided to a subject where the subject self-administers a composition orally, intravenously or by way of an inhaler, for example.

Pharmaceutical composition or antibody binding agents herein can be formulated to be compatible with a particular route of administration or use. Compositions for parenteral, intradermal, or subcutaneous administration can include a sterile diluent, such as water, saline solution, fixed oils, polyethylene glycols, glycerin, propylene glycol or other synthetic solvents. The preparation may contain one or more preservatives to prevent microorganism growth (e.g., antibacterial agents such as benzyl alcohol or methyl parabens; antioxidants such as ascorbic acid or sodium bisulfite; chelating agents such as EDTA; buffers such as acetates, citrates or phosphates and agents for the adjustment of tonicity such as sodium chloride or dextrose). In certain embodiments, a composition herein is substantially free of a chelator (e.g., a zinc chelator, e.g., EDTA or EGTA).

Compositions for injection include sterile aqueous solutions (where water soluble) or dispersions and sterile powders (e.g., sterile lyophilized preparations) for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). The carrier can be a solvent or dispersion medium containing, for example, water, ethanol, polyol (e.g., glycerol, propylene glycol, and polyethylene glycol), and suitable mixtures thereof. Fluidity can be maintained, for example, by the use of a coating such as lecithin, or by the use of surfactants. Antibacterial and anti-bacterial agents include, for example, parabens, chlorobutanol, phenol, ascorbic acid and thimerosal. Including an agent that delays absorption, for example, aluminum monostearate and gelatin can prolonged absorption of injectable compositions. Polysorbate 20 and polysorbate 80 can be added into the formulation mixture, for example, up to 1%. Other non-limiting additives include histidine HCl, α,α-trehalose dehydrate.

Alternately, one can administer compositions for use according to the methods of the invention in a local rather than systemic manner, for example, via direct application to the skin, mucous membrane or region of interest for treating, including using a depot or sustained release formulation.

In some embodiments, a pharmaceutical composition comprising an antibody binding agent can be administered alone. In other embodiments, a pharmaceutical composition comprising an antibody binding agent can be administered in combination with one or more additional materials, for example, as two separate compositions or as a single composition where the additional material(s) is (are) mixed or formulated together with the pharmaceutical composition. For example, without being limited thereto, the pharmaceutical composition can be formulated with additional excipients, additional active ingredients, other pharmaceutical compositions, anti-bacterial medications, anti-fungal medications, or other antibody binding agents.

The pharmaceutical compositions can be manufactured by any suitable manner, including, e.g., by means of conventional mixing, dissolving, granulating, dragee-making, levigating, emulsifying, encapsulating, entrapping or tableting processes.

Pharmaceutical compositions for use in accordance with the invention thus can be formulated in any suitable manner using one or more physiologically acceptable carriers comprising excipients and auxiliaries, which facilitate processing of the active compounds into preparations which can be used pharmaceutically. Proper formulation can depend upon the route of administration chosen. In particular, any suitable formulation, ingredient, excipient, the like or combinations thereof as listed in "Remington's Pharmaceutical Sciences," Mack Publishing Co., Easton, Pa., 18th edition, 1990. can be used with a composition described herein. The various antibody binding agents and compositions described herein, alone or in combination, can be incorporated into or used with the materials described in Remington's. Any suitable techniques, carriers, and excipients can be used, including those understood in the art; e.g., in Remington's Pharmaceutical Sciences, above, all pages of which are incorporated herein by reference in their entirety, including without limitation for all of the types of formulations, methods of making, etc.

In some embodiments, the composition may be formulated, for example, as a topical formulation. The topical formulation may include, for example, a formulation such as a gel, a cream, a lotion, a paste, an ointment, an oil, and a foam. The composition further may include, for example, an absorption emollient.

In some embodiments, at least part of the affected area of the mammal is contacted with the composition on a daily basis, on an as-needed basis, or on a regular interval such as twice daily, three times daily, every other day, etc. The composition can be administered for a period of time ranging from a single as needed administration to administration for 1 day to multiple years, or any value there between, (e.g., 1-90 days, 1-60 days, 1-30 days, etc.). The dosages described herein can be daily dosages or the dosage of an individual administration, for example, even if multiple administrations occur (e.g., 2 sprays into a nostril).

Some embodiments relate to methods of treating or preventing a Mucorales infection through administration of compositions described herein to the upper respiratory track/bronchi in a mammal in need thereof, for example, by contacting at least part of the upper respiratory tract/bronchi of a mammal with a therapeutically effective amount of a composition as described above or elsewhere herein. The composition can be, for example, formulated as an aerosol formulation, including formulated for use in a nebulizer or an inhaler. The composition further may include other pharmaceutically acceptable components such as a preservative.

In certain embodiments, the amount of an antibody binding agent can be any sufficient amount to prevent, treat, reduce the severity of, delay the onset of or alleviate a symptom of a Mucorales infection as contemplated herein or a specific indication as described herein.

Compositions for use according to the methods of the invention can be, in some embodiments, aerosolized compositions. The aerosolized composition can be formulated such that the composition has increased solubility and/or diffusivity. The composition can comprise a carrier. A carrier can improve the absorption of the composition, change the viscosity of a composition, improve the solubility of the composition, or improve the diffusivity of a composition compared to a pharmaceutical composition that does not comprise a carrier.

Liquid pharmaceutically administrable compositions can, for example, be prepared by dissolving, dispersing, etc. an antibody binding agent as defined above and optional pharmaceutical adjuvants in a carrier (e.g., water, saline, aqueous dextrose, glycerol, glycols, ethanol or the like) to form a solution or suspension. Solutions to be aerosolized can be prepared in any suitable form, for example, either as liquid solutions or suspensions, as emulsions, or in solid forms suitable for dissolution or suspension in liquid prior to aerosol production and inhalation.

For administration by inhalation, the compositions described herein can conveniently be delivered in the form of an aerosol (e.g., through liquid nebulization, dry powder dispersion or meter-dose administration). The aerosol can be delivered from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

For aqueous and other non-pressurized liquid systems, a variety of nebulizers (including small volume nebulizers) can be used to aerosolize the formulations. Compressor-driven nebulizers can utilize jet technology and can use compressed air to generate the liquid aerosol. Such devices are commercially available from, for example, Healthdyne Technologies, Inc.; Invacare, Inc.; Mountain Medical Equipment, Inc.; Pari Respiratory, Inc.; Mada Medical, Inc.; Puritan-Bennet; Schuco, Inc., DeVilbiss Health Care, Inc.; and Hospitak, Inc. Ultrasonic nebulizers generally rely on mechanical energy in the form of vibration of a piezoelectric crystal to generate respirable liquid droplets and are commercially available from, for example, Omron Healthcare, Inc. and DeVilbiss Health Care, Inc. Vibrating mesh nebulizers rely upon either piezoelectric or mechanical pulses to generate respirable liquid droplets. Commercial examples of nebulizers that could be used in certain embodiments include RESPIRGARD II®, AERONEB®, AERONEB® PRO, and AERONEB® GO produced by Aerogen; AERX® and AERX ESSENCE™ produced by Aradigm; PORTA-NEB®, FREEWAY FREEDOM™, Sidestream, Ventstream and 1-neb produced by Respironics, Inc.; and PARI LC-PLUS®, PARI LC-STAR®, and e-Flow7m produced by PARI, GmbH. By further non-limiting example, U.S. Pat. No. 6,196,219, is hereby incorporated by reference in its entirety.

In some embodiments, the drug solution can be formed prior to use of the nebulizer by a patient. In other embodiments, the drug can be stored in the nebulizer in solid form. In this case, the solution can be mixed upon activation of the nebulizer, such as described in U.S. Pat. No. 6,427,682 and PCT Publication No. WO 03/035030, both of which are hereby incorporated by reference in their entirety. In these nebulizers, the drug, optionally combined with excipients to form a solid composition, can be stored in a separate compartment from a liquid solvent.

Dosages and Products

Certain embodiments provide pharmaceutical compositions suitable for use in the technology, which include compositions where the active ingredients are contained in an amount effective to achieve its intended purpose. A "therapeutically effective amount" means an amount sufficient to prevent, treat, reduce the severity of, delay the onset of or inhibit a symptom of a Mucorales infection. The symptom can be a symptom already occurring or expected to occur. Determination of a therapeutically effective amount is well within the capability of those skilled in the art, especially in light of the detailed disclosure provided herein.

The term "an amount sufficient" as used herein refers to the amount or quantity of an active agent (e.g., an antibody binding agent, anti-fungal medication, and/or a combination of these active agents) present in a pharmaceutical composition that is determined high enough to prevent, treat, reduce the severity of, delay the onset of, or inhibit a symptom of a Mucorales infection and low enough to minimize unwanted adverse reactions. The exact amount of active agents or combination of active agents required will vary from subject to subject, depending on age, general condition of the subject, the severity of the condition being treated, and the particular combination of drugs administered. Thus, it is not always possible to specify an exact universal amount sufficient to prevent or treat a Mucorales infection for a diverse group of subjects. As is well known, the specific dosage for a given patient under specific conditions and for a specific disease will routinely vary, but determination of the optimum amount in each case can readily be accomplished by simple routine procedures. Thus, an appropriate "an amount sufficient" to prevent or treat a Mucorales infection in any individual case may be determined by one of ordinary skill in the art using routine experimentation.

In other embodiments, a therapeutically effective amount can describe the amount necessary for a significant quantity of the composition to contact the desired region or tissue where prevention or treatment of a Mucorales infection is desired.

The antibody binding agents and compositions comprising antibody binding agents as described herein can be administered at a suitable dose, e.g., at a suitable volume and concentration depending on the route of administration. Within certain embodiments of the invention, dosages of administered antibody binding agents can be from 0.01 mg/kg (e.g., per kg body weight of a subject) to 500 mg/kg, 0.1 mg/kg to 500 mg/kg, 0.1 mg/kg to 400 mg/kg, 0.1 mg/kg to 300 mg/kg, 0.1 mg/kg to 200 mg/kg, 0.1 mg/kg to 150 mg/kg, 0.1 mg/kg to 100 mg/kg, 0.1 mg/kg to 75 mg/kg, 0.1 mg/kg to 50 mg/kg, 0.1 mg/kg to 25 mg/kg, 0.1 mg/kg to 10 mg/kg, 0.1 mg/kg to 5 mg/kg or 0.1 mg/kg to 1 mg/kg. In some aspects the amount of an antibody binding agent can be about 10 mg/kg, 9 mg/kg, 8 mg/kg, 7 mg/kg, 6 mg/kg, 5 mg/kg, 4 mg/kg, 3 mg/kg, 2 mg/kg, 1 mg/kg, 0.9 mg/kg, 0.8 mg/kg, 0.7 mg/kg, 0.6 mg/kg, 0.5 mg/kg, 0.4 mg/kg, 0.3 mg/kg, 0.2 mg/kg, or 0.1 mg/kg. In some embodiments a therapeutically effective amount of an antibody binding agent is between about 0.1 mg/kg to 500 mg/kg, or between about 1 mg/kg and about 300 mg/kg. Volumes suitable for intravenous administration are well known.

In some embodiments an antibody binding agent or a pharmaceutical composition comprising an antibody binding agent that is formulated for topical or external delivery can include higher amounts of an antibody binding agent. For example pharmaceutical composition comprising an antibody binding agent that is formulated for topical administration may comprise at least 0.1 mg/ml, at least 1 mg/ml, at least 10 mg/ml, at least 100 mg/ml or at least 500 mg/ml of an antibody binding agent.

The compositions can, if desired, be presented in a pack or dispenser device, which can contain one or more unit dosage forms containing the active ingredient. The pack can for example comprise metal or plastic foil, such as a blister pack. The pack or dispenser device can be accompanied by instructions for administration. The pack or dispenser can also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert. Compositions comprising a compound of the invention formulated in a compatible pharmaceutical carrier can also be prepared, placed in an appropriate container, and labeled for treatment of an indicated condition.

Detecting Mucorales

In some embodiments, compositions described herein (e.g., compositions comprising a mAb that binds An S- or H-toxin) are used detect and/or diagnose a Mucorales infection. In some embodiments, provided herein, is a method of diagnosis of a Mucorales infection in a subject. In some embodiments, presented herein, is a method of detecting an S- or H-toxin, or a nucleic acid encoding an S- or H-toxin, in a sample or subject. A method of detecting Mucorales in a subject or sample often comprises determined the presence, absence or an amount of an S- or H-toxin in a sample obtained from a subject. In certain embodiments, detecting and/or determining the presence of an S- or H-toxin in a sample obtained from a subject indicates the subject has a Mucorales infection. In certain embodiments, determining the absence of an S- or H-toxin in a sample obtained from a subject indicates a subject does not have a Mucorales infection. In some embodiments, a method of detecting an S- or H-toxin in a subject comprises monitoring a Mucorales infection in a subject, often to determine if a patient having a Mucorales infection is responding to, or not responding to, an anti-fungal treatment (e.g., an antibody binding agent and/or an anti-fungal medication or treatment). Thus in certain embodiments is a method of diagnosing a Mucorales infection in a subject, which method comprises measuring the level of an S- or H-toxin in a sample obtained from said subject.

In some aspects, a method of detecting an S- or H-toxin in a sample comprises obtaining a sample from a subject suspected of having or suspected of having a Mucorales infection. In some embodiments, a sample is suspected of comprising Mucorales, or a portion thereof (e.g., a protein or nucleic acid). Often a sample suspected of comprising Mucorales, or a portion thereof, is obtained from a subject at risk of having, or suspected of having, a Mucorales infection. In some aspects, a method of detecting Mucorales in a sample comprises contacting a sample with an antibody binding agent described herein, for example, an antibody binding agent that specifically binds to an S- or H-toxin. In certain embodiments, an antibody binding agent that specifically binds to an S- or H-toxin can specifically bind the cell surface of Mucorales or to a polypeptide, carbohydrate, lipid or complex thereof that is exposed on the cell surface of Mucorales. An antibody binding agent that specifically binds to Mucorales can often form a bound complex with Mucorales, or with a portion thereof, which complex can be detected in vitro or ex vivo by a suitable method, non-limiting examples of which include ELISA, immunoblotting, flow cytometry, gel electrophoresis, protein-chip analysis (e.g., any suitable chip methodology), microarray, mass spectrometry, cytofluorimetric analysis, fluorescence microscopy, confocal laser scanning microscopy, laser scanning cytometry, the like and combinations thereof.

A method of detecting a bound complex comprising an antibody binding agent and Mucorales, or a portion thereof, can be a direct and indirect detection method. Direct detection methods often comprise detection of a distinguishable identifier that is covalently bound directly to an antibody binding agent (e.g., a primary antibody binding agent that binds directly to Mucorales or a portion thereof). In certain embodiments, indirect methods of detection comprise detecting a distinguishable identifier that is indirectly bound (e.g., non covalently bound) or indirectly associated with a primary antibody binding agent (e.g., a primary antibody binding agent that binds directly to Mucorales or a portion thereof). Any suitable method can be used to detect and/or quantitate the presence, absence and/or amount of an antibody binding agent specifically bound to Mucorales, or a portion thereof, non-limiting examples of which can be found in Immunology, Werner Luttmann; Academic Press, 2006 and/or Medical Detection and Quantification of Antibodies to Biopharmaceuticals: Practical and Applied Considerations, Michael G. Tovey; John Wiley & Sons, Jul. 12, 2011, which are incorporated by reference herein in their entirety. Additional non-limiting examples of methods that can be used to detect and/or quantitate the presence, absence and/or amount of an antibody binding agent specifically bound to Mucorales, or a portion thereof include use of a competitive immunoassay, a non-competitive immuno assay, western blots, a radioimmunoassay, an ELISA (enzyme (inked immunosorbent assay), a competition or sandwich ELISA, a sandwich immunoassay, an immunoprecipitation assay, an immunoradiometric assay, a fluorescent immunoassay, a protein A immunoassay, a precipitin reaction, a gel diffusion precipitin reaction, an immunodiffusion assay, an agglutination assay, a complement fixation assay, an immunohistochemical assay, a Western blot assay, an immunohistological assay, an immunocytochemical assay, a dot blot assay, a fluorescence polarization assay, a scintillation proximity assay, a homogeneous time resolved fluorescence assay, a IAsys analysis, a BIAcore analysis, the like or a combination thereof.

In certain embodiments, a determination of the presence or absence of Mucorales, or a Mucorales infection in a subject or sample, can be determined by comparing the levels of Mucorales present in a subject sample with control samples comprising a known amount of Mucorales, or portions thereof. In certain embodiments, a control sample may not contain Mucorales, or a portion thereof. In some embodiments, a median level of Mucorales detected in a group of control samples (for example, samples from healthy individuals) is used to set a zero standard (e.g., a level of detection that indicated the absence of Mucorales. In certain embodiments, sample containing known amounts of Mucorales, or portions thereof, are used to generate a standard curve from which the presence, absence or amount of Mucorales is a sample is determined. In certain embodiments, a kit (e.g., a diagnostic kit) is provided herein that comprises one or more control samples or samples that can be used to generate a standard curve. In some embodiments the determination of the incidence of Mucorales infection may comprise deriving a likelihood ratio using a multivariate analysis based on distribution parameters from a set of reference data derived from analysis of the levels of Mucorales in subjects in which a Mucorales infection is absent, present or in remission.

Thus provided herein, in certain embodiments, is diagnostic methods capable of measuring levels of Mucorales and/or comparing said levels to known levels that are indicative of the disease state in a subject.

Kits

In some embodiments the antibody binding agents, nucleic acids, oligonucleotide primers and/or primer pairs, compositions, polymerases, adjuvants, polypeptides, formulations, combination products and materials described herein can be included as part of kits, which kits can include one or more of pharmaceutical compositions, antibody binding agents, nucleic acids, polypeptides and formulations of the same, combination drugs and products and other materials described herein. In certain embodiments a kit is a diagnostic kit comprising one or more antibody binding agents described herein. In certain embodiments a kit is a diagnostic kit comprising one or more nucleic acids as described herein. In certain embodiments a kit is a diagnostic kit comprising one or more nucleic acids as described herein. In some embodiments a kit is a diagnostic kit comprising an oligonucleotide primer pair configured to specifically hybridize to a portion a nucleic acid encoding an S-toxin or H-toxin as described herein. In some embodiments a kit is a diagnostic kit comprising an oligonucleotide primer pair configured to specifically hybridize to a portion a nucleic acid encoding an S-toxin or H-toxin and produce an amplicon of a predetermined length that is at least 30, at least 50, at least 100 or at least 150 nucleotides in length. In some embodiments a kit is a diagnostic kit comprising an oligonucleotide primer pair that specifically hybridizes to a portion a nucleic acid encoding an S-toxin or H-toxin and configured to produce an amplicon of a predetermined length, a recombinant polymerase, and instructions for generating an amplicon from a sample obtained from a mammal. In some embodiments a kit comprises one or more deoxyribonucleotide triphosphates. In some embodiments a kit comprises a cell lysis buffer. A lysis buffer can be any suitable buffer used to lyse mammalian and/or fugal cells. In some embodiments a lysis buffer comprises a suitable detergent. In some embodiments a lysis buffer comprises a hypotonic solution.

In some embodiments a kit comprises one or more compositions of the invention packaged into a suitable packaging material. A kit optionally includes a printed label or packaging insert that includes a description of the components and/or instructions for use in vitro, in vivo, or ex vivo, of the components therein. Exemplary instructions include instructions for a diagnostic method, treatment protocol or therapeutic regimen.

A kit can contain a collection of such components, e.g., two or more conjugates alone, or in combination with another therapeutically useful composition (e.g., an anti-proliferative or immune-enhancing drug). The term "packaging material" refers to a physical structure housing the components of the kit. The packaging material can maintain the components sterilely, and can be made of material commonly used for such purposes (e.g., paper, corrugated fiber, glass, plastic, foil, ampules, vials, tubes, etc.).

Kits can include printed labels or inserts. Printed labels or inserts include "printed matter," e.g., paper or cardboard, or separate or affixed to a component, a kit or packing material (e.g., a box), or attached to an ampule, tube or vial containing a kit component. Inserts can additionally include a computer readable medium, optical disk such as CD- or DVD-ROM/RAM, DVD, MP3, magnetic tape, or an electrical storage media such as RAM and ROM or hybrids of these such as magnetic/optical storage media, FLASH media or memory type cards.

Printed labels and/or inserts can include identifying information of one or more components therein, dose amounts, clinical pharmacology of the active ingredient(s) including mechanism of action, pharmacokinetics (PK) and pharmacodynamics (PD). Printed labels and/or inserts can include information identifying manufacturer information, lot numbers, manufacturer location and date.

Printed labels and/or inserts can include information on a condition, disorder, disease or symptom for which a kit component may be used. Printed labels and/or inserts can include instructions for the clinician or for a subject for using one or more of the kit components in a method, treatment protocol or therapeutic regimen. Instructions can include dosage amounts, frequency or duration, and instructions for practicing any of the methods, treatment protocols or therapeutic regimes set forth herein. Kits of the invention therefore can additionally include printed labels or instructions for practicing any of the methods and uses of the invention described herein.

Printed labels and/or inserts can include information on any benefit that a component may provide, such as a prophylactic or therapeutic benefit. Printed labels and/or inserts can include information on potential adverse side effects, such as warnings to the subject or clinician regarding situations where it would not be appropriate to use a particular composition. Adverse side effects could also occur when the subject has, will be or is currently taking one or more other medications that may be incompatible with the composition, or the subject has, will be or is currently undergoing another treatment protocol or therapeutic regimen which would be incompatible with the composition and, therefore, instructions could include information regarding such incompatibilities.

Kits can additionally include other components. Each component of the kit can be enclosed within an individual container and all of the various containers can be within a single package. Invention kits can be designed for cold storage. Invention kits can further be designed to contain host cells expressing antibody binding agents, or that contain nucleic acids encoding antibody binding agents. The cells in the kit can be maintained under appropriate storage conditions until the cells are ready to be used. For example, a kit including one or more cells can contain appropriate cell storage medium so that the cells can be thawed and grown.

Such diagnostic methods and kits can take any suitable form. For example, a kit can comprise or consist of a stick test, including necessary reagents to perform the method of the invention and to produce, for example, a colorimetric result which can be compared against a color chart or standard curve. Such kits can also comprise, e.g., a buffering agent, a preservative, or a protein stabilizing agent. The kit can also comprise components necessary for detecting an antibody binding agent (e.g., an antibody that specifically binds a primary antibody binding agent, a distinguishable identifier, enzyme and/or substrate). A kit can also contain a control sample and/or a series of control samples (e.g., controls containing known amounts of Mucorales, e.g., a standard curve, known amounts of nucleic acid of Mucorales and/or a target nucleic acid) which can be assayed and compared to a sample obtained. In some embodiments, each component of the kit is usually enclosed within an individual container, and all of the various containers are within a single package, along with instructions for determining whether the subject from which the sample is derived is suffering from or is at risk of developing a Mucorales infection.

EXAMPLES

The examples set forth below illustrate certain embodiments and do not limit the technology.

Example 1: Toxin-Like Substances are Pathogenicity Factors of Mucormycosis

*R. oryzae* injures HUVEC (Human Umbilical Vein Endothelial Cells) via a process that involves endocytosis of the fungus by the host cells (i.e., invasion). This process is mediated by the interaction of a fungal CotH3 protein with the host GRP78 protein, which results in a relatively rapid damage that causes ~60% injury to the HUVEC in 8 hours as assayed by a chromium release assay. By 8 hours almost all the fungal cells have invaded HUVEC.

The "fast occurring damage" (i.e., damage occurring with 3-6 hours) of HUVEC by *R. oryzae* was completely abrogated by the use of cytochalasin D which prevents invasion of the host cells, or by membrane barriers that prevent cell-cell interaction, when the damage was measured at 3-6 hours. However, after 12 hours, cell damage was observed even though there was no cell-cell contact. Also, inhibition of CotH3 binding by use of a blocking antibody decreased *R. oryzae*-mediated damage at early incubation periods (3-6 hours), due to inability of the fungus to invade HUVEC. However, at later time points (>12 hours) considerable HUVEC injury was observed (data not shown). Based on these results, cell injury occurring after 12 hours and/or in the absence of cell-cell contact (e.g., in the absence of CotH3-Grp78 binding) was presumed to be caused by secretion of a cell damaging substance originating from the fungal hyphae.

Late damage (e.g., cell damage observed after 12 hours) was also observed with alveolar epithelial cells when membrane barriers were used. For example, ~52% cell damage was observed in the presence of a membrane barrier (FIG. 1, No Heat). Intriguingly, heat-killed *R. oryzae* hyphae (heating at 60° C.) cause equivalent partial damage to host cells in the absence of a membrane barrier (FIG. 1, ~51% cell damage). This phenomenon was also observed with other Mucorales species (data not shown for *C. bertholletiae, M. circinelloides*, and *L. corymbifera*). In contrast, the inclusion of membrane barriers with heat-killed *R. oryzae* totally abrogated the ability to cause damage to host cells (FIG. 1). Collectively, these data demonstrate the presence of secreted and hyphae-associated toxin-like substances that induce host cell damage. They are CotH independent.

Figure 2A:
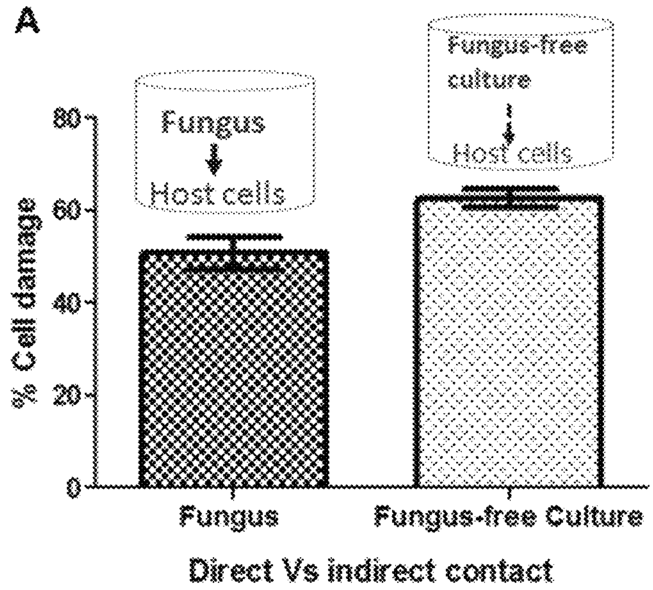
FIG. 2A shows a comparison between the effect of live cells and overnight fungus-free culture on epithelial cells.

A fungus-free supernatant taken from an overnight *R. oryzae* growth culture was lyophilized, and then reconstituted in fresh cell-free culture media. When placed in contact with host cells, (epithelial or endothelial cells) the re-constituted solution resulted in considerable damage to the host cells (FIG. 2A, see Fungus-free Culture; epithelial cells are shown as an example). The secreted (S) toxin-like substance responsible for this activity is referred to herein as "S-Toxin".

Figure 2B:
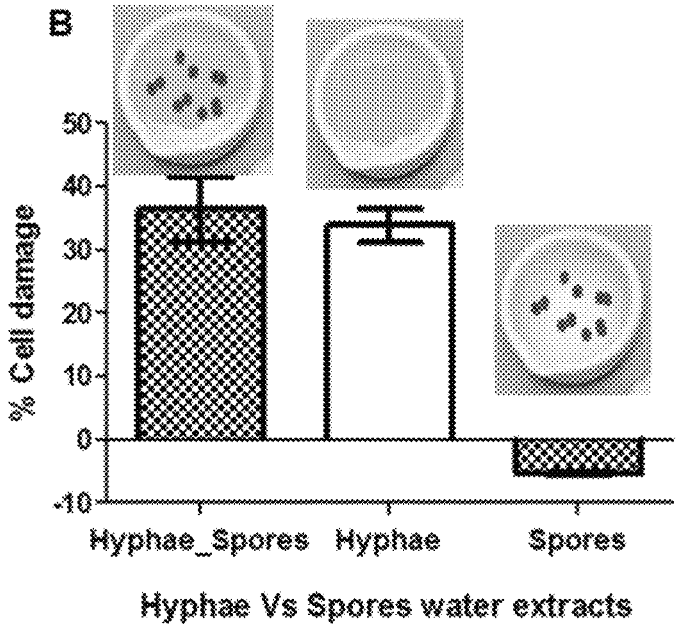
FIG. 2B shows a comparison between the effect of hyphae, sporulated hyphae and spore extract on epithelial cells damage.

An extract from filtrated hyphae (FIG. 2B, "Hyphae"), spores (FIG. 2B, "Spores"), or both hyphae and spores (FIG. 2B, "Hyphae_Spores") of *R. oryzae* was prepared by grinding dead hyphae and/or spores in liquid nitrogen followed by extracting with either water or host cell medium. The extract was filtered through a 0.45 μm membrane prior to use. The prepared extract prepared from hyphae and spores, and the extract prepared from hyphae alone induced extensive damage to host cells (FIG. 2B). In contrast, the extract prepared from *R. oryzae* spores (i.e., free of hyphae) collected from plates, ground similarly in liquid nitrogen, and then extracted in host cell medium caused no damage to mammalian cells (FIG. 2B). These data show that the hyphae (H), but not the spores, contain a toxin. The hyphae-associated toxin(s) responsible for this activity is referred to herein as "H-Toxin".

Figure 3A:
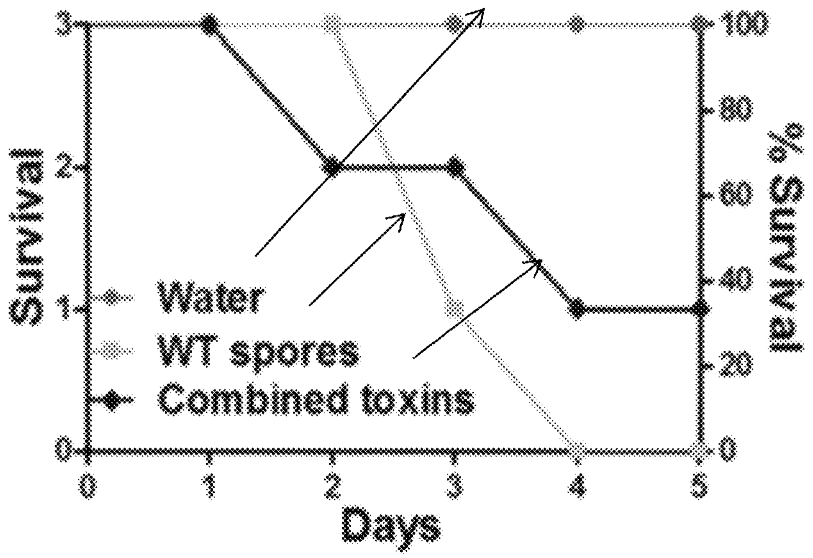
FIG. 3A shows % survival of neutropenic mice injected i.v. with control (Water), live spores of *R. oryzae* (WT spores) or concentrated toxin extracts (Combined toxins).
Figure 3B:
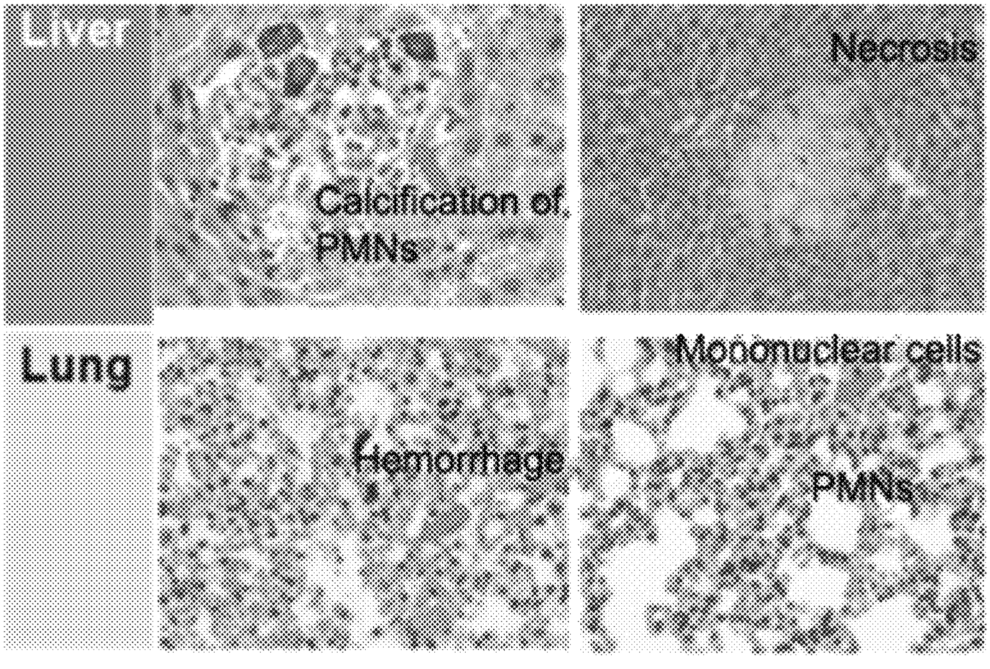
FIG. 3B shows histopathology images of Liver (top two panels) and Lung (bottom two panels) after death induced by injection of concentrated toxin extract.

Extracts comprising the S-toxin and H-toxin were combined, suspended in water and filter sterilization. The combined mixture of S- and H-toxins was injected intravenously into neutropenic mice at an interval of every other day for a total of 3 total injections. Injection of the combined mixture of S- and H-toxins resulted in behavior highly suggestive of sudden circulatory shock after about 30 minutes of a first injection, while mice injected with water or *R. oryzae* spores behaved normally (video data not shown). Further, mice injected with the combined mixture of S- and H-toxins lost weight progressively (~30% drop in body weight in 5 days compared to water injected mice) and ultimately required euthanasia, similar to mice injected intravenously with live spores (FIG. 3A). Finally, histopathological examination of organs from mice injected with the combined mixture of S- and H-toxins demonstrated necrosis, hemorrhage, clusters of mononuclear cells and the presence of megakaryocytes in the organs. Also, neutrophil infiltration and tissue calcification indicating uncontrolled inflammation was observed (FIG. 3B). Collectively, this data implicated involvement of the S- and/or H-Toxins in the pathogenesis of mucormycosis.

Purification and Identification of S-Toxin

Figure 4A:
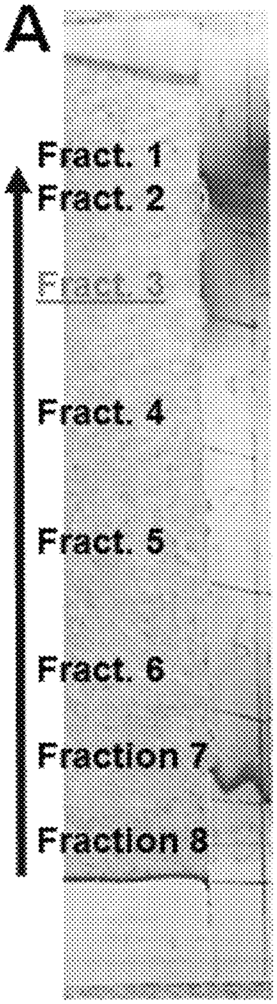
FIG. 4A shows the results of silica gel TLC showing the separation of a concentrated extract obtained from conditioned culture media obtained from fungal spore cultures which were allowed to grow into hyphae. The concentrated extract was confirmed to retain toxin activity prior to separation. Fraction 3 (Fract. 3) stained blue with P-anisaldehyde.

Fungal spores were grown into hyphae at 37° C. for 2-4 days in culture media. The conditioned culture media was separated from the fungal mats. The conditioned media was extracted with ethyl acetate, dehydrated with sodium sulfate anhydrous, and completely evaporated before reconstituting in host cell media followed by filter sterilization. The reconstituted and concentrated extract showed ~90% damage to host cells within 3 hours of incubation with host cells (data not shown). Un-inoculated culture medium, processed in an identical fashion, was included as a negative control and caused no damage to host cells. The reconstituted extract was dissolved in methanol and run on a preparative silica thin layer chromatography (TLC), followed by fractionation into 8 fractions (FIG. 4A). Each fraction was scraped from the plate (leaving a 1 cm layer of each fraction for later visualization to confirm separation of the crude extract) and suspended in host cell medium.

Figure 4B:
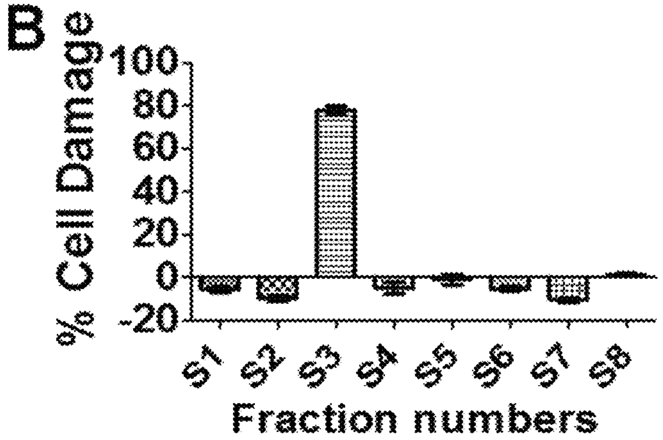
FIG. 4B shows a damage assay conducted for each fraction collected from the preparative TLC shown in FIG. 4A. Fractions 1-8 (Fract. 1-8) of FIG. 4A are in FIG. 4B as S1-S8 respectively.
Figure 4C:
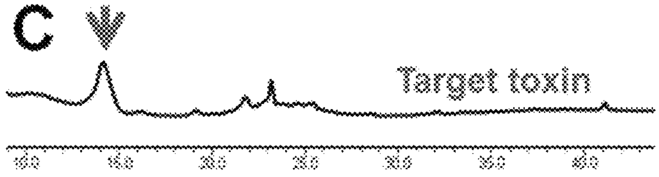
FIG. 4C shows LC-UV-MS analysis of combined Fractions 1-4 that were isolated from TLC.

The silica was separated from the liquid and the filtrate was filter sterilized prior to application to host cells. Only fraction #3, which visualized as a single blue substance upon staining with Para (P)-anisaldehyde, was shown to cause cell damage to host cells (FIG. 4B). Purified fraction #3 showed an "out of detection" range when injected into small molecule LC-MS, indicating the possibility that the substance is protein in nature (FIG. 4C). Therefore, fraction #3 was trypsinized prior to sequencing with micro-LC-MS. The retrieved data revealed an S-toxin peptide of SEQ ID NO: 17 with similarity to a type 6 bacterial toxin secretion system protein.

Figure 4D:
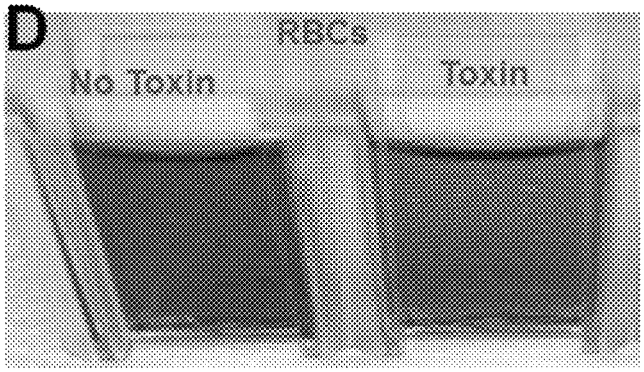
FIG. 4D shows red blood cells (RBCs) treated with the secreted toxin (right panel, "Toxin") or treated with a control (left panel, "No toxin").

The type 6 bacterial toxin secretion system (T6SS) represents a one-step pathogenic mechanism used by bacteria for injecting an effector toxin from a bacteria into a host cell. This S-toxin secretion system is novel to human pathogenic fungi. Bioinformatics analysis indicated that the S-toxin is extracellular with a hemolysin domain-like structure similar to Hcp, Diphtheria, and *Vibrio cholera* toxins. Addition of the S-toxin to mouse erythrocytes causes complete lysis of the red blood cells (FIG. 4D). Also, an ADP-rhibosylation domain required for the action of these toxins was found in *Rhizopus* polypeptide of SEQ ID NO: 33.

Purification and Identification of H-Toxin.

Figure 5:
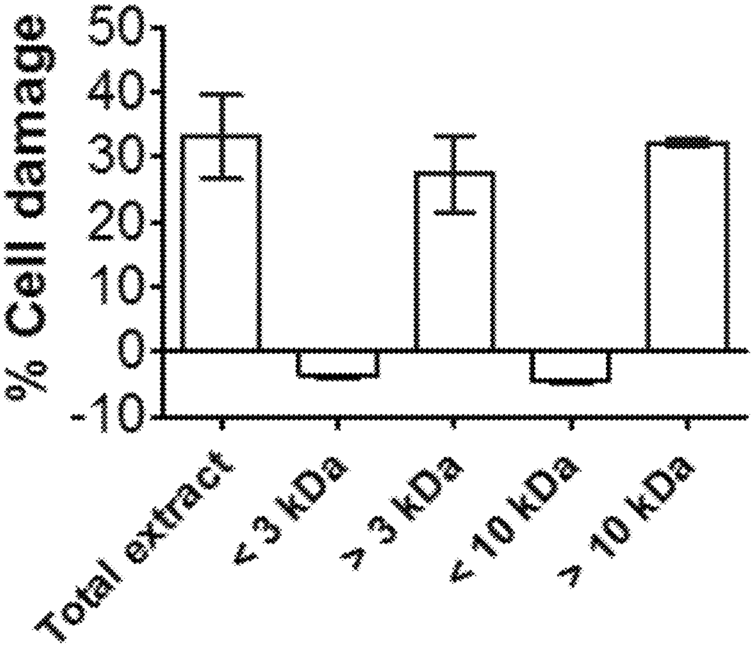
FIG. 5 shows size exclusion of hyphae water extract indicating that fractions with a molecular weight of greater than 10 kDa retain toxin activity.
Figure 6A:
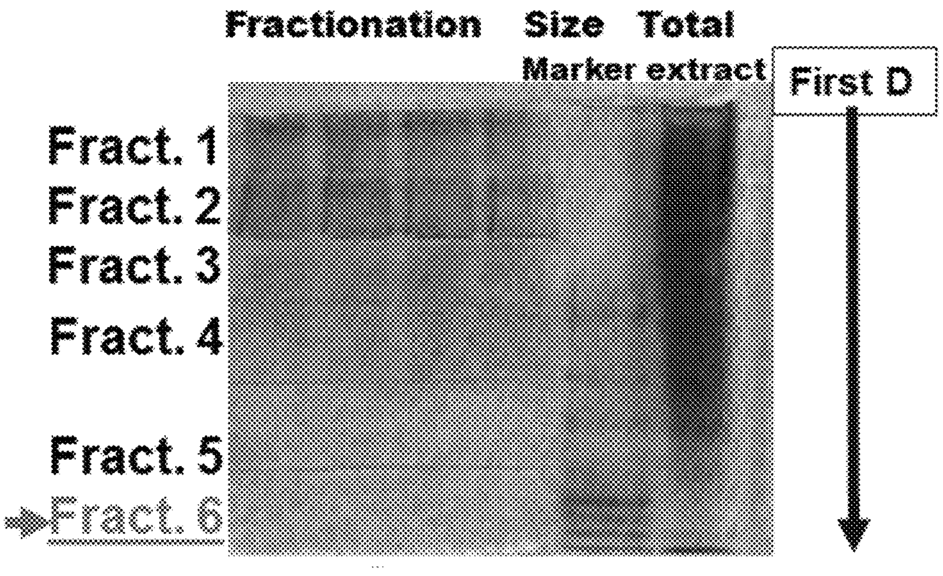
FIG. 6A shows the first dimension of a 3D chromatography separation of hyphae extract illustrating the positions of fractions 1-6 (FIG. 6A, Fract. 1-6) that were tested for toxin activity by a cell damage assay as shown in FIG. 6B. These results indicate that fraction 6 (FIG. 6, Fract. 6) of the first separation retained toxin activity.
Figure 6B:
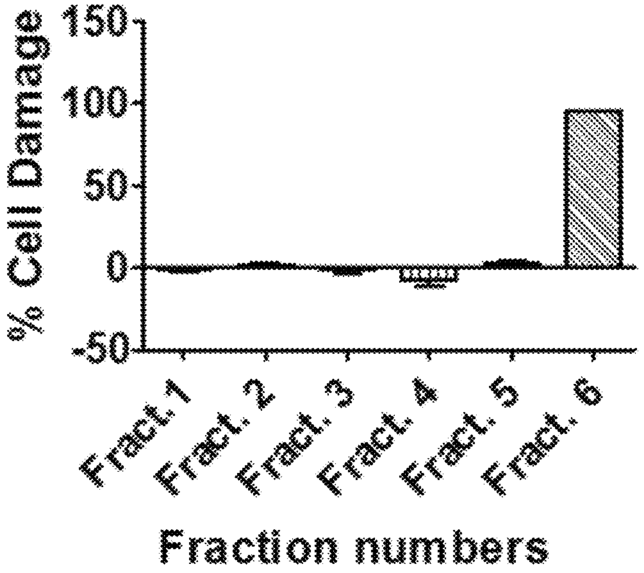

For purification of H-toxin (hyphae associated toxin), fungal spores were grown into hyphae at 37° C. for 2-4 days in culture media. Conditioned culture media was separated from the fungal mat and the separated fungal mat was ground in liquid nitrogen and extracted with sterile water, concentrated and analyzed by size exclusion chromatography. A host cell damage assay showed that fractions containing molecules with a molecular weight greater than 10 kDa retained H-Toxin activity (FIG. 5). The concentrated water extract was then subjected to 3D chromatographic separations (FIG. 6-8). For the first dimension, the extract was subjected to electrophoresis on a native polyacrylamide (FIG. 6A). After electrophoretic separation, the gel was cut into 6 fractions (FIG. 6A, Fract. 1-6) that were eluted separately in non-denaturing buffer, and each fraction was tested for toxin activity by a cell damage assay. Only fraction #6 (FIG. 6, Fract. 6), corresponding to 15-20 kDa, showed toxin activity (FIG. 6B).

Figure 7A:
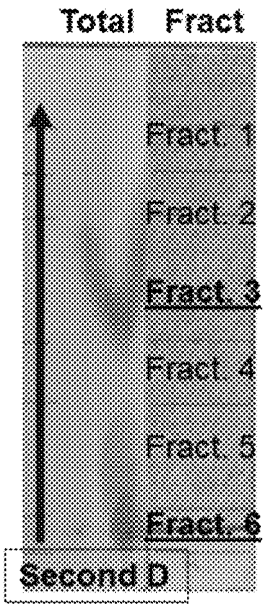
FIG. 7A shows the second dimension of the 3D chromatography analysis of hyphae extract where fraction 6 of FIG. 6 (FIG. 6, Fract. 6) was subjected to separation on a cellulose plate by capillary action (i.e., thin layer chromatography (TLC)) resulting in fractions 1-6 (FIG. 7A, Fract. 1-6) corresponding to TLC 1H-6H of FIG. 7B.
Figure 7B:
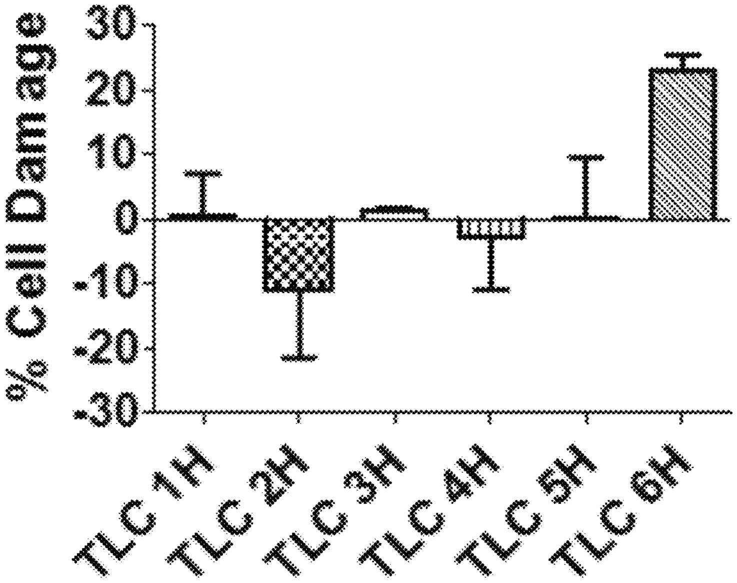
FIG. 7B shows the results of a cell damage assay conducted on fractions TLC 1H-6H. The results of FIG. 7B indicate that fraction TLC 6H retained toxin activity.

Fraction 6 of FIG. 6 was subsequently subjected to separation by TLC using cellulose plates into another 6 fractions (FIG. 7A). Each fraction was scraped from the cellulose plate, filter sterilized and incubated with host cells to test for toxin activity by a cell damage assay (FIG. 7B). Fraction 6 of FIG. 7 (FIG. 7B, TLC 6H) showed toxin activity.

Figure 8A:
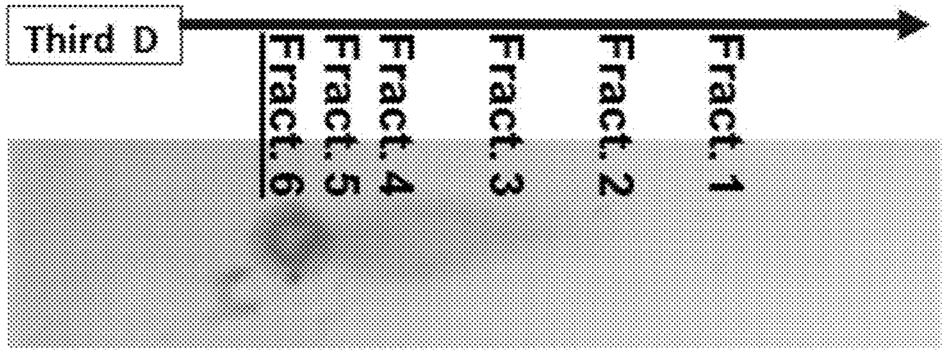
FIG. 8A shows the third dimension of the 3D chromatography analysis of hyphae extract where fraction TLC 6H of FIG. 7B was subjected to separation on a cellulose plate by capillary action (i.e., TLC) resulting in new fractions 1-6 (FIG. 8A, Fract. 1-6) corresponding to fraction numbers 1-6 of FIG. 8B.
Figure 8B:
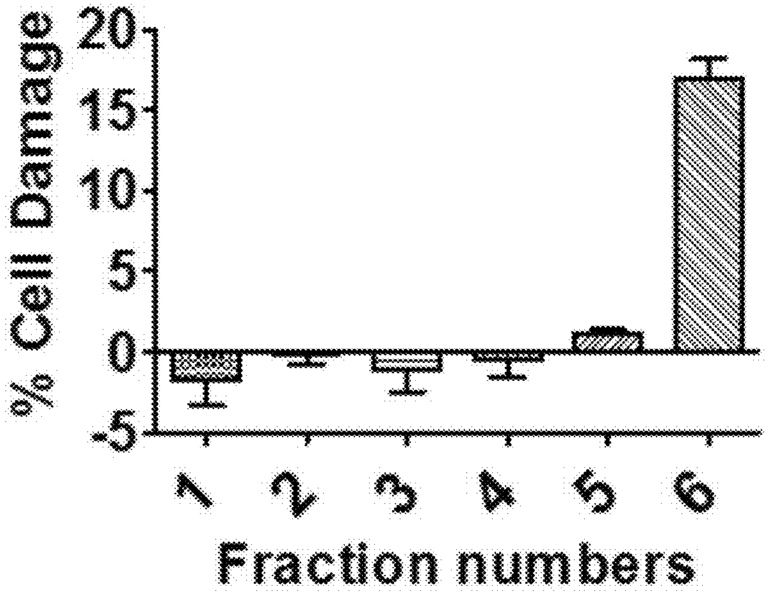
FIG. 8B shows the results of a cell damage assay conducted on fractions 1-6 of FIG. 8A. The results of FIG. 8B indicate that fraction number 6 retained toxin activity.

Fraction 6 of FIG. 7 (FIG. 7B, TLC 6H) was subsequently subjected to a third dimensional separation by TLC and separated into another 6 fractions (FIG. 8A), each of which were further tested for toxin activity on host cells by a cell damage assay. Only fraction number 6 of FIG. 8 (FIG. 8A, Fract. 6) demonstrated cell damaging activity (FIG. 8B, Fraction number 6). Fraction 6 of FIG. 8 was determined to be water-soluble, about 17 kDa in size and stained red with ninhydrin, indicating a protein substance (FIG. 8A).

Fraction 6 of FIG. 8 was subsequently trypsinized and micro-sequenced by MS identifying a peptide (SEQ ID NO: 3) encoded by the cDNA shown in SEQ ID NO: 2 of *R. oryzae*. SEQ ID NO: 3 has a domain structure similar to a highly toxic ricin polypeptide isolated from castor beans (~30% identity).

Forty one different isolates of Mucorales were sequenced. Nucleic acids and polypeptides having high identity to SEQ ID NOs: 1-3 were identified by bioinformatics and by functional assays of extracts from representatives of these isolates (e.g., see SEQ ID NOs 4-9).

Figures 9A, 9B, 9C, 9D:
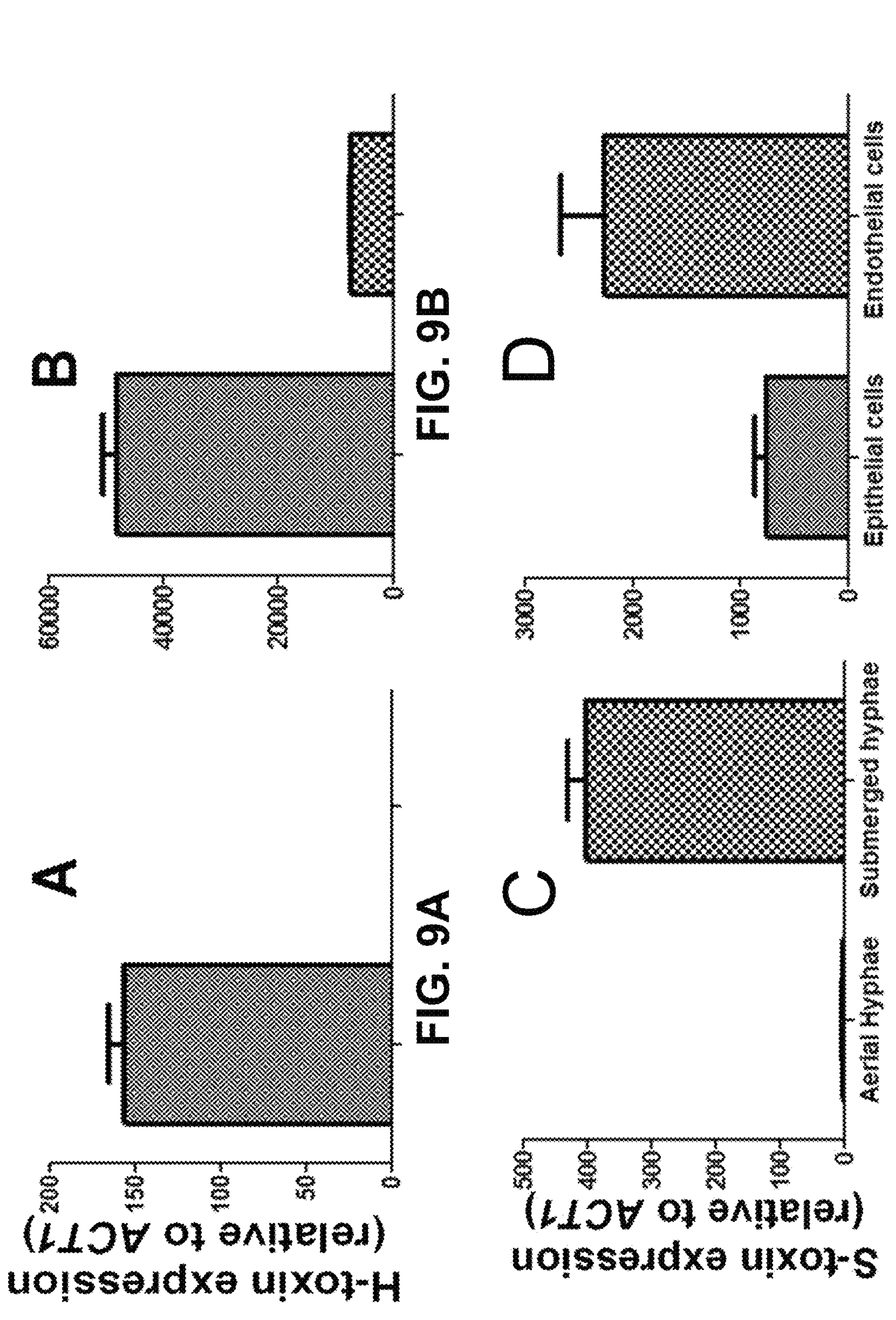
FIG. 9 shows analysis of gene expression of hyphae toxin (H-Toxin, Panels A and B) and secreted toxin (S-Toxin, Panels C and D) by qRT-PCR of fungus grown in aerated vs. submerged (Panes A and C) culture conditions, or on epithelial versus endothelial cells (Panes B and D) relative to actin gene expression.

S- and H-toxins are differently expressed in response to host cell type. We found that S-toxin gene expression only occurs when *R. oryzae* is grown in submerged medium (FIG. 9C), while the H-toxin is expressed in aerated hyphae (FIG. 9A). Our data indicate that these two toxins might act in the host at different niches of infection with the H-toxin operating in more aerated environments (initiation of infection in the sinus or lungs), while S-toxin being more important in hypoxic conditions (hematogenous dissemination). Consistent with these results, and by using qRT-PCR the H-toxin gene had a five fold increase in its expression on epithelial cells compared to the S-toxin gene (FIG. 9A), while the S-toxin gene was expressed more on endothelial cells (three fold increase compared to H-toxin) (FIG. 9D). The S-toxin is also capable of lysing erythrocytes (FIG. 4D), which suggests a primary role of this toxin in the vasculature.

Based on our preliminary data, and without being limited to theory, a model of pathogenesis is proposed founded on host cell type and patient predisposing conditions. Infection is often initiated when fungal spores are inhaled, and in the absence of phagocytes (or presence of dysfunctional phagocytes), fungal spores can bind to their respective host cell receptors and either seed the sinus (DKA patients via GRP78/CotH3 binding) or the lungs (neutropenic host via integrin/neuroplins and unidentified fungal ligand binding). After adhesion, spores can germinate and then invade epithelium (phagocytosis). This invasion is possibly mediated by H-toxin release (due to its putative phospholipase activity predicted from sequence homology) and limited secretion of S-toxin where sufficient air is present in the sinus and lungs.

Figure 10:
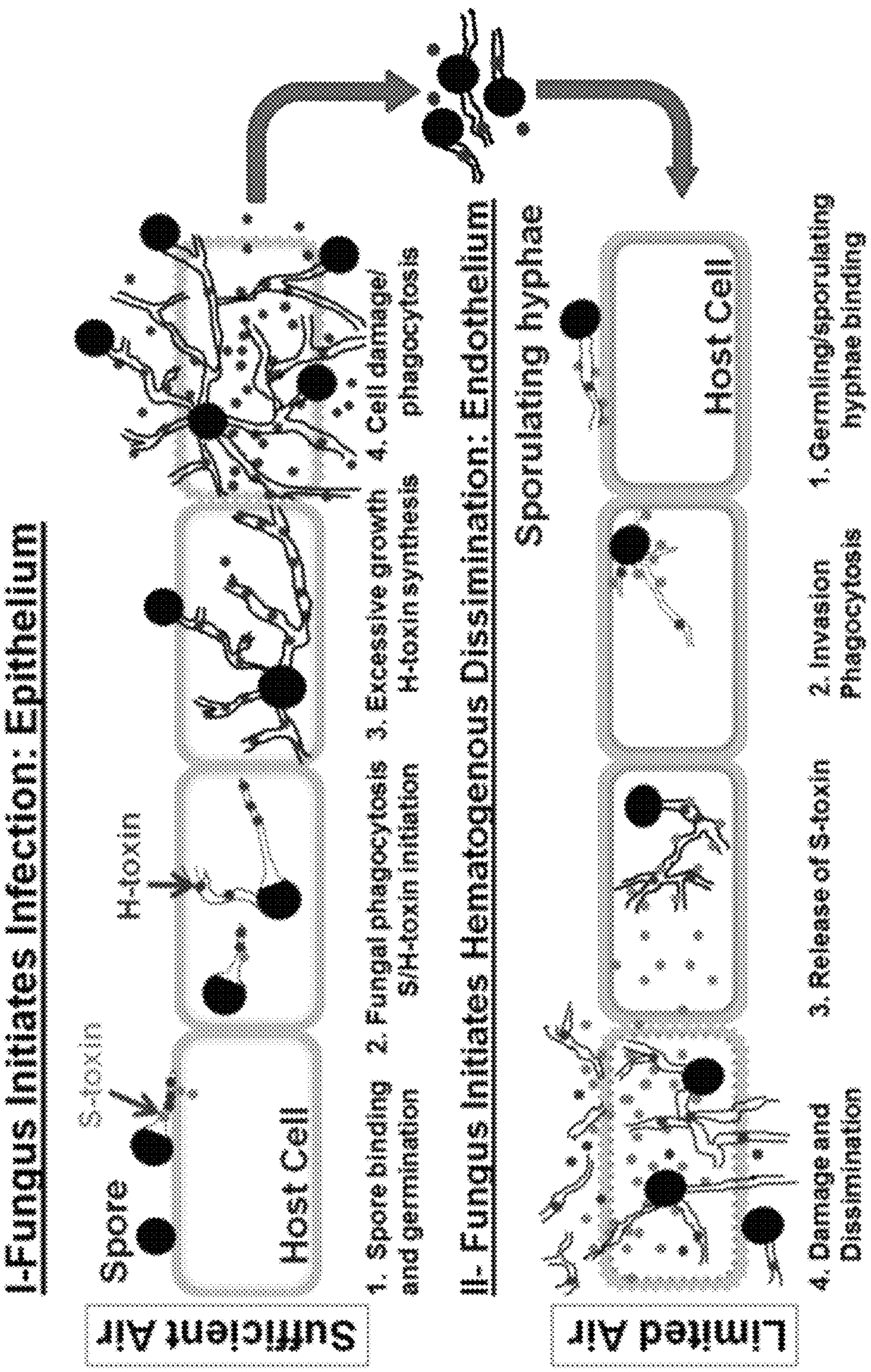
FIG. 10 shows a model of cell-based fungal/toxin pathogenesis.
Figure 11:
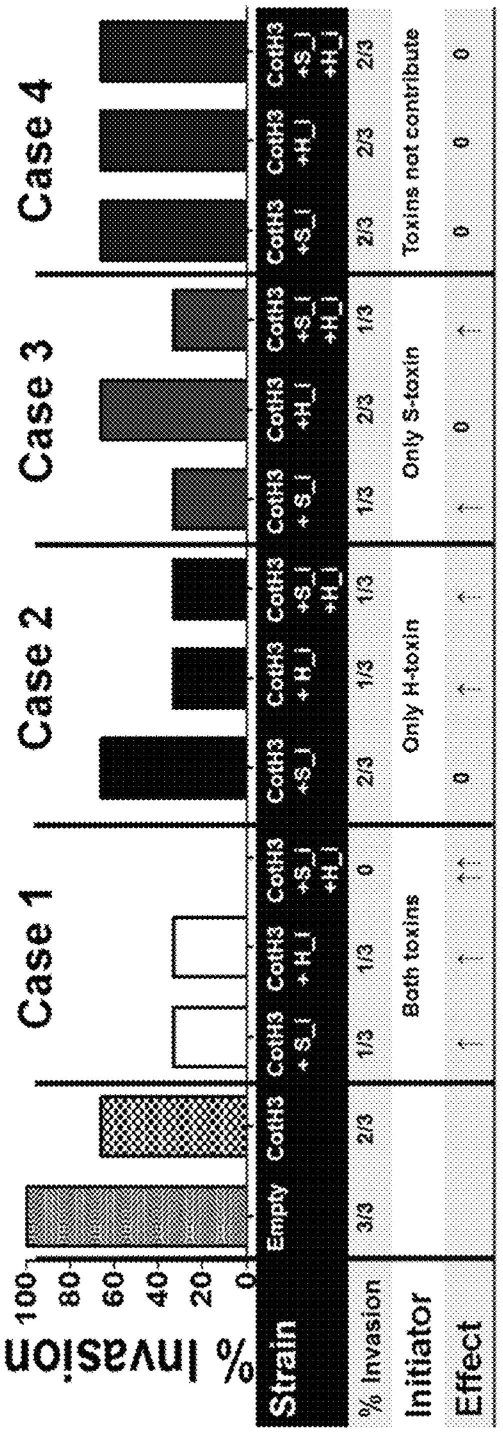
FIG. 11 shows the possible outcomes and interpretations thereof, of an invasion assay conducted in the presence of RNAi nucleic acids that target and block expression of S-toxin (FIG. 11, "+S_i") and/or H-toxin (FIG. 11, "+H_i") and the role of the two toxins in relation to CotH3.

The invasion process is followed by excessive fungal hyphenation, which is presumably accompanied by synthesis of the H-toxin. The H-toxin may exert a delayed lethal effect via signal transduction by binding to a lectin on the host cell and by exerting a damaging effect via inactivating ribosomes. In theory, cell damage to the epithelium may result in more fungal penetration which advances into invading blood vessels as sporulating hyphae (FIG. 10). During hematogenous dissemination where more hypoxic conditions are prevalent, germlings/sporulating hyphae can bind to GRP78 via CotH3 and the process of invasion may be hastened by the upregulation of S-toxin. During infection, the S-toxin may also cause hemolysis of erythrocytes, which results in further thrombosis and tissue necrosis. It is possible that the H-toxin is operative in the vasculature because of its presence in the invading hyphae (despite it's down regulation in hypoxic conditions) (FIG. 10).

Example 2: Characterizing the Role of Toxins in the Pathogenesis of Mucormycosis As described herein, Mucorales possess S- and H-toxins which cause damage to host cells in vitro and the crude toxin extracts cause mice morbidity necessitating euthanasia. It was also determined that the two toxins are differentially expressed on host cells with H-toxin being more expressed on epithelial cells and in aerated conditions, while S-toxin is more expressed on HUVEC and during hypoxia (FIG. 9) suggesting a role in initiation and dissemination of the infection, respectively (FIG. 10). Consistent with this hypothesis is the ability of the S-toxin to lyse erythrocytes (FIG. 4D). Finally, both toxins are likely to play a role in facilitating invasion of host cells since.

To define the role of each toxin in the pathogenesis mechanism, the function of the S- and/or H-toxins is blocked using RNAi technology[1] where sequence-specific RNAi nucleic acids target and inhibit expression of the S- and/or H-toxins. Six different *R. oryzae* strains will be generated with attenuated expression of 1) S-toxin; 2) H-toxin; 3) S/H toxin; 4) S/CotH3; 5) H/CotH3 (note: strains with reduced expression of CotH3 were already generated); or 6) T/S/CotH3. Other mutants of identified epithelial cells ligands will also be generated. Pathogenesis of host cells is observed in the presence and absence of antibodies that specifically block CotH3-mediated host cell endocytosis of fungal spores and cell invasion. These experiments will determine if invasion of *R. oryzae* cells is required for toxin activity or vice versa (e.g., invasion of host cells precedes damage). The generated strains will be compared to control strains in their ability to cause adherence to, invasion of and damage to HUVEC, nasal and alveolar epithelial cells as well as in IT[2] (initiation model) and i.v.[3,4,5] (dissemination model) infected mice. Recombinantly produced H-toxin and S-toxins toxins will also be investigated in their damaging effect to host cells and in establishing a biomarker of toxin detection in vivo. Blocking strategies using antibodies will be utilized to complement our gene disruption studies. Finally, studies will be conducted to investigate the mechanism by which these toxins exert their lethal effect on host cells.

Dual gene silencing strategies will use a single plasmid harboring the pyrF[6]. For triple RNAi mutants, another plasmid pRNAi-pdc which utilizes His3 as a selection marker, will be used to inhibit the third gene. Once the genes of interests are ligated, the dual inhibition plasmid is digested with a unique enzyme that cuts within the truncated pyrF downstream of the point mutation present in *R. oryzae* pyrf null (strain M16).[7] The pRNAi-pdc plasmid with the His3 is linearized in upstream sequence of the His3 that is homologous to upstream chromosomal sequence of the His3. Both constructs are sequentially transformed into pyrF his3 *R. oryzae* mutant using the biolistic technique.[8,9] Transformants are confirmed by using Southern blotting, gene expression,[1] chromatographic analysis of toxin production and activity of the fungal extracts on host cells. All strains are compared to *R. oryzae* M16 transformed with an integrated empty plasmid in their ability to adhere to, invade and damage host cells.[10,11]

Figure 12A:
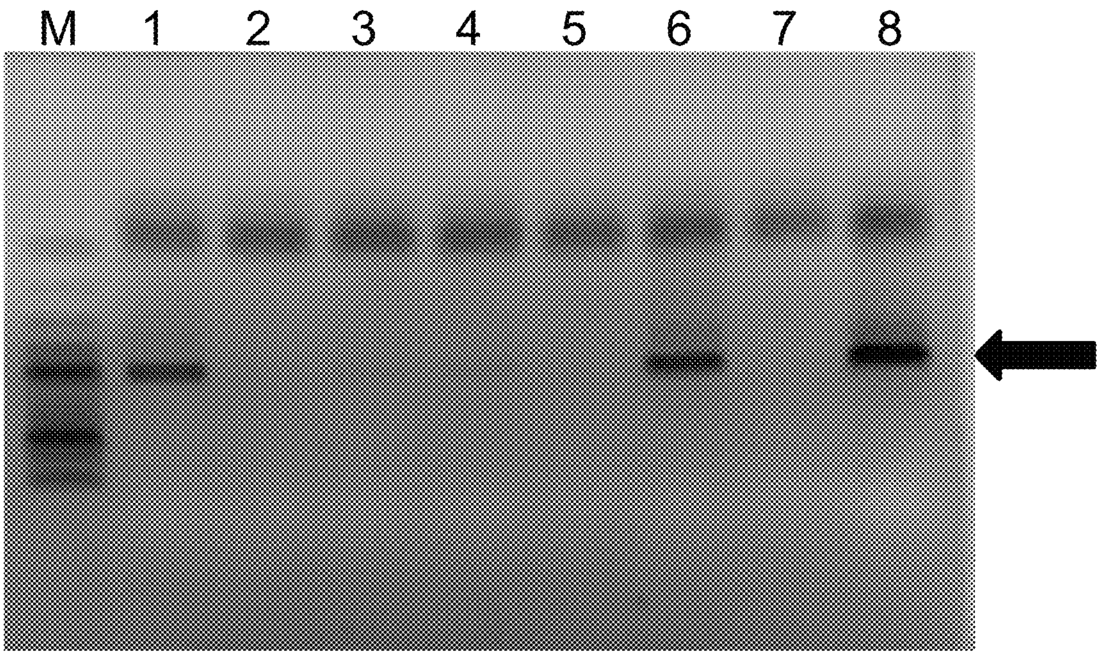
FIGS. 12A and 12B show detection of H-toxin specific amplicons by gel electrophoresis. Amplicons were generated by a polymerase chain reaction (PCR) using an oligonucleotide primer pair of SEQ ID NO: 10 and SEQ ID NO: 14. The arrow to the right of each gel indicates the expected position of the H-toxin specific amplicons. The "M" at the top of a lane indicates a DNA molecular weight marker.

It is expected that attenuation of each of the toxins results in compromised (but not complete) ability to damage endothelial and epithelial cells in vitro, because of our preliminary data showing that each toxin contributes equally to host cell injury (FIG. 1). It is also expected that attenuation of the dual toxins is likely to show complete abrogation of injury to host cells. It is also possible that S-toxin might enhance invasion in addition to its role in damage. It is possible the H-toxin binds to host cells which could influence invasion. These effects might be amplified in the background of an attenuated CotH3 strain. Possible scenarios and their interpretations are provided in FIG. 12 (other scenarios are also possible). It is also possible that the two toxins do not promote invasion but actually invasion is required for the maximal lethal effect of the toxins. This result can be easily determined by comparing damage caused by either toxins in the background of CotH3i to damage induced by CotH3i alone.

Example 3: Generation of Antibodies that Specifically Bind S- or H-Toxins

Nucleic acids encoding S- or H-toxins, or a portion thereof, are subcloned into a suitable yeast expression vector (e.g., pXW55), transformed into *S. cerevisiae* and expressed with a poly-(His) tag (e.g., 6×-His tag) to facilitate detection, quantitation and/or purification. The produced toxins are purified on Ni-agarose column as described.[12] Alternatively, antigenic epitopes of the S- or H-toxin are identified using a suitable algorithm and peptides representing the identified antigen epitopes are synthesized, purified and used as antigen. Alternatively, S-toxin and H-toxin are purified from *R. oryzae* (*R. delemar* 99-880) conditioned media or from *R. oryzae* fungal mats using a scaled up and/or modified version of the methods described herein (e.g., see FIGS. 4-8). The presence of pure S-toxin can be confirmed by LC-MS. Endotoxin can be reduced to levels below 0.01 ng per mg with Detoxi-Gel (Pierce), with confirmation of the endotoxin level by limulus amoebocyte assay.

Polyclonal antibodies are generated commercially, using standard protocols by immunization of one or more rabbits with purified antigen (e.g., recombinant toxin or synthesized peptide). High-titer polyclonal antibody is detected using standard ELISA-based assays where rabbit polyclonal antiserum bound to plate coated antigen is detected by HRP-conjugated goat anti-rabbit antibodies. Polyclonal rabbit antibodies that specifically bind the toxin antigens with high affinity are purified from rabbit serum using standard protein-A or protein-G affinity chromatography. The purified polyclonal antibodies are used to develop an ELISA for detection and/or quantitation of Mucorales species that express the S- and/or H-toxins. The ability of polyclonal antibodies to block toxin activity is assessed in a host cell damage assay (Cr release assay) as described herein. Briefly, purified toxin is used to induce cell damage of endothelial or epithelial cells in culture in the absence or presence of purified polyclonal antibody. Polyclonal antibody that shows toxin blocking activity (i.e., blocking antibodies) are tested in vivo to identify blocking antibodies that can be used to prevent and/or treat a Mucorales infection. Briefly, mice are administered a control vehicle (e.g., an isotype control) or increasing amounts of purified an anti-toxin antibody at a single dose of 30 ug, 100 ug or 300 ug) prior to, during or after administering a lethal dose of live fungal spores by i.v. injection. The ability of an anti-H-Toxin or anti-S-toxin antibody to prevent or treat a Mucorales infection is determined by assessing survival as a primary endpoint. A delay in the time of death, or absence of death, induced by the presence of purified anti-toxin antibody indicates that the antibody can prevent and/or protect a mammal from fungal infection. Multiple strains and species of pathogenic fungi, including a plurality Mucorales strains, are tested using this in vivo model to determine which species the blocking antibodies are effective against. Anti-H-toxin and anti-S-toxin antibodies can be tested alone or in combination. The ability of a toxin antibody to prevent and/or treat a fungal infection is determined by administering blocking antibodies prior to or during administration of a lethal dose of fungal spores (i.e., prevention) or after administration of a lethal dose of fungal spores (i.e., treatment).

Monoclonal antibodies that specifically bind and/or block toxin activity are generated by immunizing one or more mice with purified toxin antigen (e.g., recombinant toxin or synthesized peptide). Mice expressing high-titer antibodies with blocking activity are identified using mouse polyclonal anti-serum and standard ELISA-based assays, cell damage assays and in vivo infection models as described above. Once a mouse is identified having a desired anti-serum activity (e.g., toxin blocking activity), hybridomas are generated using a suitable method. Briefly, the spleen of a high-titer mouse is removed, splenocytes are isolated and fused with a myeloma fusion partner (e.g., NS1, or any suitable myeloma fusion partner) in the presence of PEG. Fused cells are plated in selection media (e.g., HAT media) and conditioned media is tested for toxin binding activity. Hybridomas showing high titer binding to purified toxin are cloned and expanded. Monoclonal antibodies having toxin binding and/or blocking activity are identified by screening conditioned media or purified antibody obtained from clonal hybridoma cultures using in vitro ELISA assays or cell damage assays as described above. Monoclonal antibodies that can be used to prevent or treat a Mucorales infection are identified by administering a lethal dose of Mucorales spores to mice, in the presence or absence of anti-toxin monoclonal antibody, and assessing survival (e.g., as described above for identifying polyclonal antibodies to treat or prevent Mucorales infection).

Example 4: Vaccine Generation

Recombinant H-toxin, S-toxin and/or synthesized H- and S-peptides are formulated alone or in combination to generate protective vaccine compositions. Briefly, different combination of recombinant toxins and purified peptide are combined with a suitable adjuvant (e.g., alum) and administered by subcutaneous or intramuscular injection to one or more mice every two weeks for a total of 3 doses. Recombinant proteins are administered at about 20-100 ug (~0.5 to 2.5 mg/kg) of protein per dose, and purified peptides (~10-20 amino acids in length) are administered at about 1-20 ug per dose (~0.025 to 0.5 mg/kg). To determine the protective ability of a vaccine, a lethal dose of live *R. oryzae* spores are administered to each vaccinated mouse two weeks after the final vaccine composition is administered and time to death and/or survival is observed. A composition that protects more than 60%, and preferably more than 80% of mice from fungal induced death is identified as a protective vaccine composition.

Example 5: Generation of Mutant Toxins

Genes encoding the H-toxin and S-toxin of *R. oryzae* (*R. delemar* 99-880) are cloned into yeast or fungal expression vectors, and expressed with a tag (e.g., a His tag or other suitable tag) for easy purification and isolation. Mutations are systematically introduced into the coding region thereby providing expression vectors encoding mutant H- and S-toxins, each comprising at least one amino acid substitution along the entire length of the encoded toxin polypeptide. Expression vectors are introduced into a suitable yeast or fungal expression system. Wild type and mutant toxins are isolated from conditioned media (e.g., for S-toxins) or cell extracts (H-toxins) and purified by affinity chromatography using the incorporated tags. Wild type and mutant toxins are also expressed in mammalian cell expression systems to assess toxin activity. Expression of a wild-type toxins in a mammalian system are expected to be lethal to the mammalian cells for which they are expressed in. Thus, mutants having abrogated toxin activity would be expressed in a mammalian cell, thus selecting for mutants that lack toxin activity. By this method, regions of an H-toxin or S-toxin that are responsible for toxin activity can be identified. Small peptides (10-30 amino acids in length) are generate representing wild-type regions of an H- or S-toxin which are responsible for toxin activity, the peptides are conjugated to an antigenic carrier (e.g., HSA or KLH) and injected into mice with adjuvant to produce antibodies that block toxin activity.

Data described herein suggests that H-toxin is expressed more on epithelial cells and in aerated hyphae, while S-toxin is more expressed on endothelial cells and in submerged hypoxic conditions (FIG. 9). Therefore, the virulence of the purified wild-type and mutant toxins are evaluated in DKA and neutropenic mice by i.v. injection (e.g., as a model for hypoxic hematogenously disseminated disease), and IT (e.g., as an aerated and initiation of infection) infected models.[3,2,13,14] Toxin activity recombinant mutants are also assessed by evaluating cell damage in vitro and by assessing survival of mice as a primary endpoint as described herein.

As a secondary endpoint the tissue fungal burden of target organs (e.g., brains, lungs and Kidneys) is assessed in the i.v. and IT models of mice infected with each mutant toxin strain at selected time intervals (decided from the survival curve which will represent early, mid, and late stages of infection).[15,3] Blood is collected by exsanguination using cardiac puncture under anesthesia and serum is separated. The organs are divided into thirds. One third is processed for histopathological analysis and immuno-histochemistry (to localize the toxin production in relation to infections and its targets either by anti-toxin antibodies or immunogold labelling).[16,17,18,19] Another portion is processed for detecting the expression of the genes under investigation.[1] The final third is processed for tissue fungal burden by qPCR[13,20] and determination of the contribution of each toxin to the inflammatory immune response (see toxin mechanism below). The amount of toxin in each organ and in serum is determined by capture ELISA assay using antibodies that bind specifically to each toxin. Mutant toxins are identified as lacking toxin activity in one of the experimental models or test described herein thereby identifying amino acid regions of the H- and S-toxins that are important to and/or required for toxin activity. Short peptides representing portions of the wild type toxins that are important to and/or required for toxin activity are generated. Peptides (15-35 amino acids in length) are generated using standard chemical peptide synthesis methods. These peptides are used as antigens (e.g., conjugated to an antigenic carrier) and are injected into mice with adjuvant to generate polyclonal and/or monoclonal antibodies as described above. Antibodies that specifically bind to wild type toxin (e.g, as determined by ELISA and Western blots) with the ability to block and/or inhibit wild type toxin activity (referred to as "blocking antibodies") are tested and identified using i.v. and IT mouse models and in vitro cell damage assays using wild-type toxins.

Blocking antibodies (i.e., antibodies that block toxin activity) are further evaluated and selected for use in treating or preventing Mucorales infection (e.g., mucormycosis) in mice as previously described.[10,1] Blocking antibodies to H- and S-toxins are evaluated alone or in combination using the described mouse models of mucormycosis. Briefly, mice are infected IT, then given different doses of the antibodies (30 μg, 100 μg, and 300 μg) 24 h after infection (established infection) to identify blocking antibodies with efficacy for treating mucormycosis in a mammal. Mice are given different doses of the antibodies (30 μg, 100 μg, and 300 μg) 12 and/or 2 hours prior to infection (i.e., prior to a first administration of a lethal dose of fungal spores) to identify blocking antibodies with efficacy for preventing mucormycosis in a mammal. Survival, tissue fungal burden and histopathological examination are be performed as described above. The methods proposed and techniques used herein are described in greater details in the following references.[1,6,10,14,19,20,21]

Example 6: Sample Isolation

Blood samples (~100-500 μl) were obtained from mice, clotted at room temperature for 30 minutes and centrifugation at 1000×g for 30 minutes to separate serum from clotted material. Serum samples were isolated from the top layer. Urine and bronchoalveolar lavage samples were obtained using suitable methods known in the art.

Samples were collected and used directly fresh or sometimes were frozen for later use. Prior to use, samples were sonicated for 30 seconds at 40%, or vortexed with beads for one minute. Samples were sometimes filtered and/or concentrated using a 3 kDa cutoff column to remove proteins and nucleases for further analysis. Nucleic acids were isolated from filtered samples using silica membrane column. Nucleic acids were eluted with 15-20 μl elution buffer containing Tris/EDTA. Isolated nucleic acids were frozen or used directly for PCR analysis.

Example 7: Amplification and Detection

PCR was conducted using a suitable thermocycler to detect the presence of absence of nucleic acids encoding H-toxin. Briefly, samples (spores, serum, urine or bronchoalveolar lavage) was mixed with a primer pair, dNTPs, a suitable thermostable polymerase and a buffer. For PCR, reaction mixtures were typically subjected to 35 cycles comprising denaturation at 95° C. for 30 seconds, annealing at 60° C. for 30 seconds and extension at 72° C. for 1 minute, which conditions are often optimized for individual primer sets.

Figure 12B:
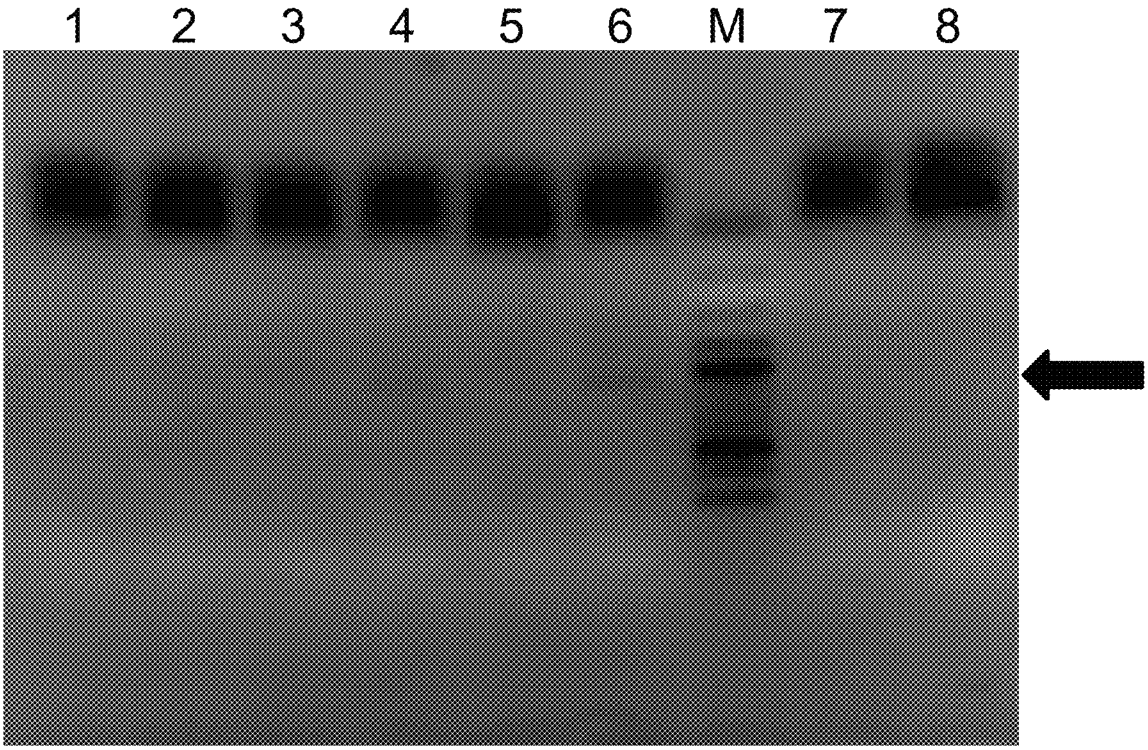
Figure 13A:
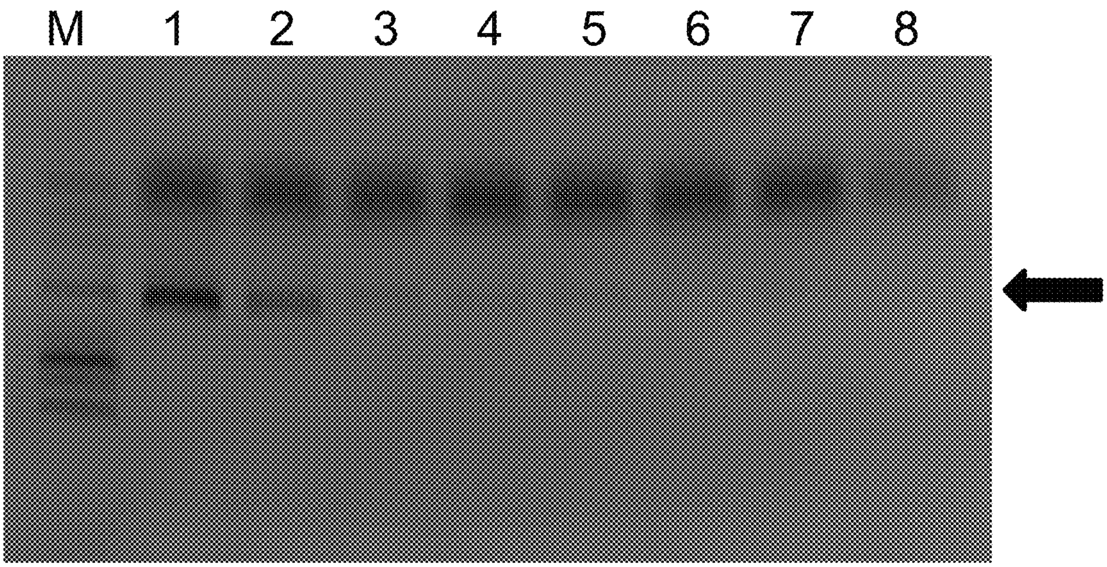
FIGS. 13A and 13B show detection of H-toxin specific amplicons by gel electrophoresis. Amplicons were generated by a polymerase chain reaction (PCR) using an oligonucleotide primer pair of SEQ ID NO: 10 and SEQ ID NO: 14. The arrow to the right of each gel indicates the expected position of the H-toxin specific amplicons. The "M" at the top of a lane indicates a DNA molecular weight marker.
Figure 13B:
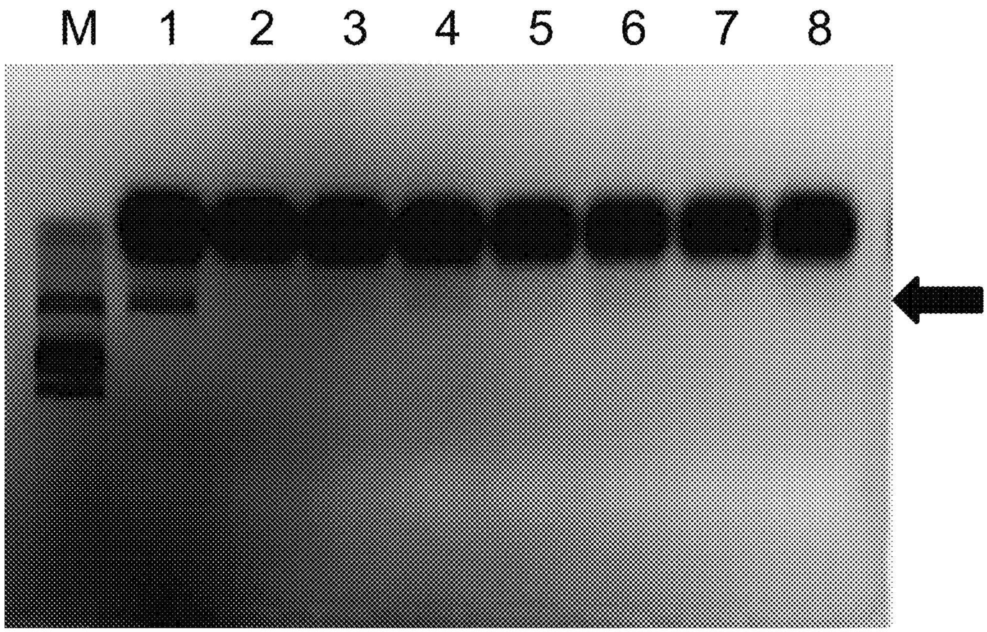
Figure 14A:
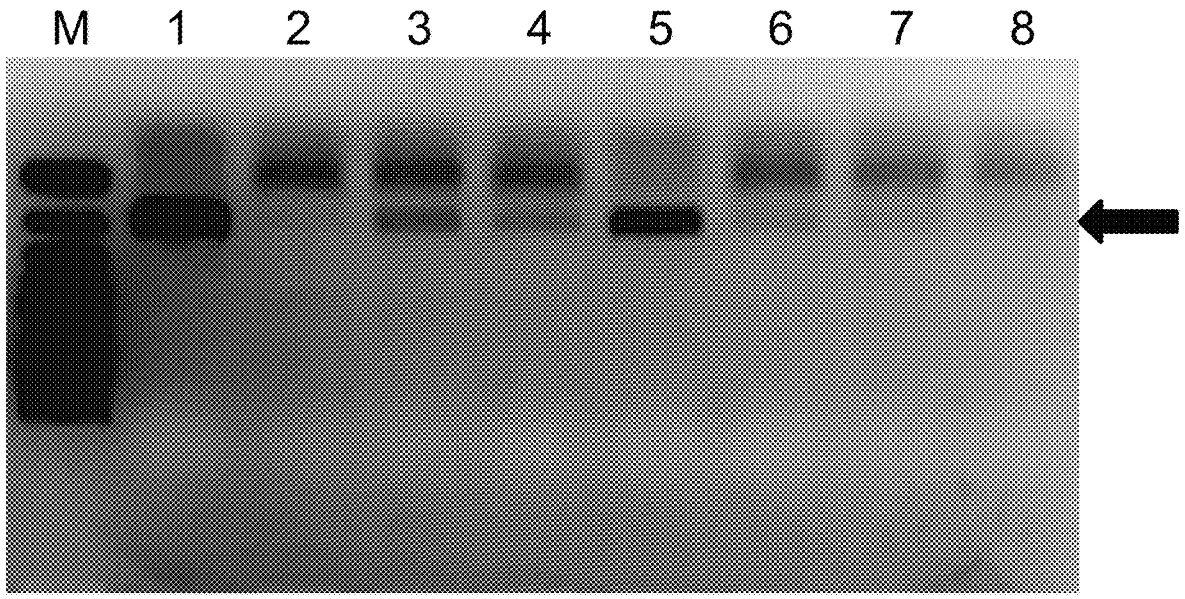
FIGS. 14A and 14B show detection of H-toxin specific amplicons by gel electrophoresis. Amplicons were generated by a polymerase chain reaction (PCR) using an oligonucleotide primer pair of SEQ ID NO: 10 and SEQ ID NO: 14. The arrow to the right of each gel indicates the expected position of the H-toxin specific amplicons. The "M" at the top of a lane indicates a DNA molecular weight marker.
Figure 14B:
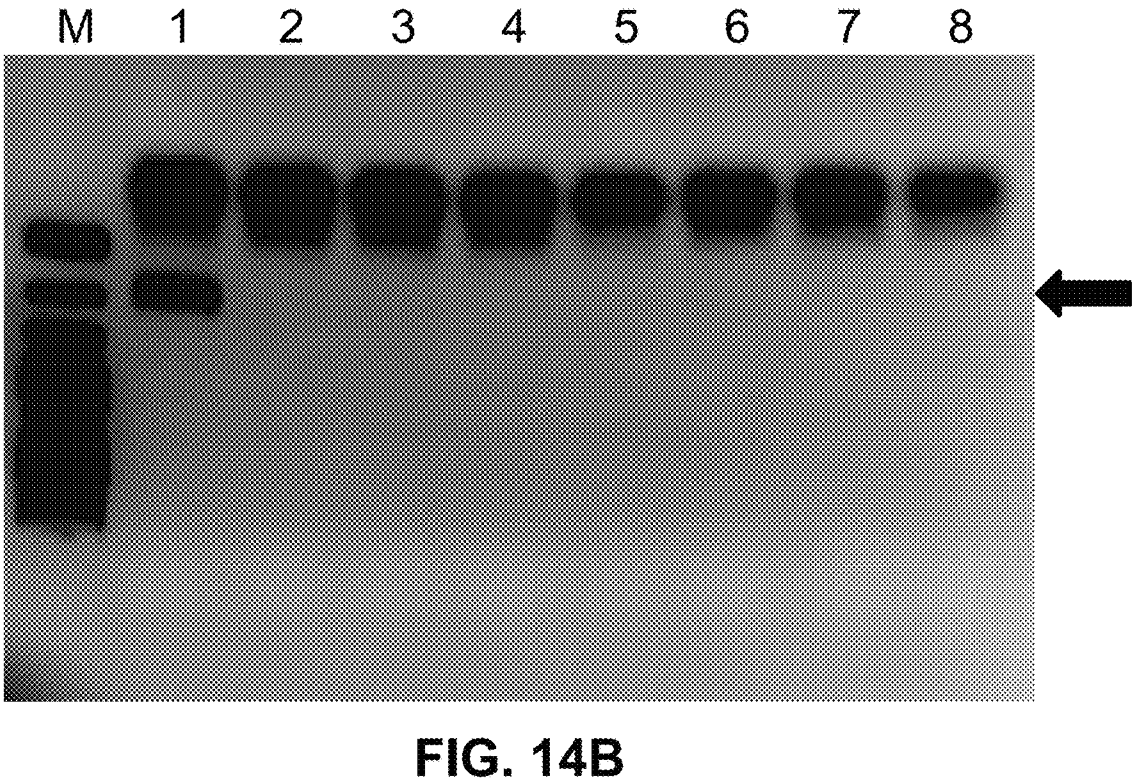
Figure 16:
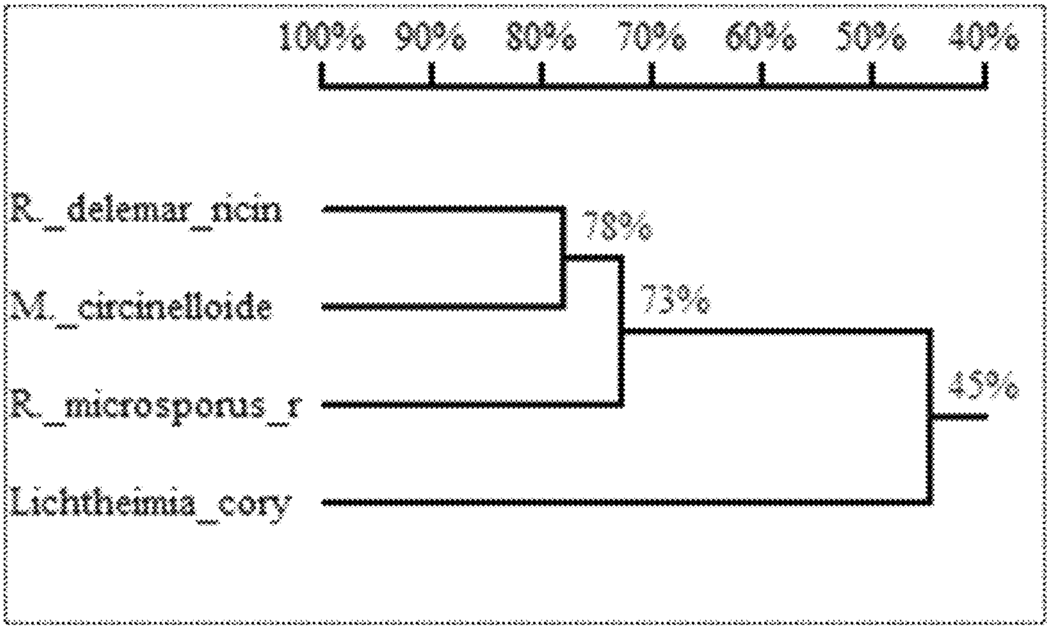
FIG. 16 shows a homology tree of H-toxins in different Mucorales species.

H-toxin specific amplicons were generated by a polymerase chain reaction (PCR) using an oligonucleotide primer pair of SEQ ID NO: 10 and SEQ ID NO: 14 and visualized by gel electrophoresis. H-toxin specific amplicons were detected in genomic DNA isolated from fungal spores of *R. oryzae* (*R. delemar* 99-880) and *Mucor circinelloides* (FIG. 12A), and in serum isolated from human patients having mucormycosis (FIGS. 12B and 13B). H-toxin specific amplicons were also detected in bronchoalveolar lavage fluids and serum of mice having mucormycosis (FIGS. 12B, 13A and 14A). H-toxin specific amplicons were not detected in spores of *Aspergillus fumigatus* (FIG. 12A) or in mice infected with *Aspergillus fumigatus* (FIG. 14B). H-toxin specific amplicons were detected in serum samples obtained from mice infected with Mucorales of the genus *Cunninghamella* (FIG. 14A, lanes 2 & 3), *Lichtheimia* (FIG. 14A, lanes 4 & 5) and *Mucor* (FIG. 14A, lanes 6, 7, & 8). Similar results were obtained from urine samples obtained from Mucorales infected mice (data not shown).

Example 8: Polypeptides and Nucleic Acids

H-Toxin Sequences (H-Toxin; *R.oryzae* (R. delemar 99-880); Genomic DNA)

SEQ ID NO: 1

ATGTATTTCGAAGAAGGCCGCTTATTTTTTATCAAAAGTCAATTTAACGGACGTGTCCTTGATG

TTGAGGATGGTTCTACTGAGGTAAGAATTATTGGGTTGTTTATGCTTGCTAAATCTAACTTTGT

ATAAAGGATGATGCCAATATCATTGTTTACACACAAAAGTATGAAGATTGCTTGAACCAACTCT

GGCGTTACGAAAATGGTTATTTCATCAACGCAAAGTCTGCCAAGGTCTTGGATATCCGTGGAG

GTGAAATGCAACCTGAGTCTCAAATCATTCAATATGCTCAAAAGATGGTCGAAGAAGCTGCCA

ACCAAAGATGGGCTATAGATGAGGATGGCTATATCTTTTGTGAAGCCCGTCCTGATTTAGTTTT

AGATATCCAAGGCGCTGAAGATGAAGACTGTGTACCTGTGATTTTATACGAAAGACGTGAAGG

TGAAGTTTCAGCCAACCAACGCTGGGAATTAGTGCCATTTGAAGGATAA (H-Toxin; *R.oryzae* (R. delemar 99-880); cDNA)

SEQ ID NO: 2

ATGTATTTCGAAGAAGGCCGCTTATTTTTTATCAAAAGTCAATTTAACGGACGTGTCCTTGATG

TTGAGGATGGTTCTACTGAGGATGATGCCAATATCATTGTTTACACACAAAAGTATGAAGATTG

CTTGAACCAACTCTGGCGTTACGAAAATGGTTATTTCATCAACGCAAAGTCTGCCAAGGTCTT

GGATATCCGTGGAGGTGAAATGCAACCTGAGTCTCAAATCATTCAATATGCTCAAAAGATGGT

CGAAGAAGCTGCCAACCAAAGATGGGCTATAGATGAGGATGGCTATATCTTTTGTGAAGCCC

GTCCTGATTTAGTTTTAGATATCCAAGGCGCTGAAGATGAAGACTGTGTACCTGTGATTTTATA

CGAAAGACGTGAAGGTGAAGTTTCAGCCAACCAACGCTGGGAATTAGTGCCATTTGAAGGAT

AA

-continued (H-Toxin; *Rhizopus oryzae*)

SEQ ID NO: 3

MYFEEGRLFFIKSQFNGRVLDVEDGSTEDDANIIVYTQKYEDCLNQLWRYENGYFINAKSAKVLDI

RGGEMQPESQIIQYAQKMVEEAANQRWAIDEDGYIFCEARPDLVLDIQGAEDEDCVPVILYERRE

GEVSANQRWELVPFEG (H-Toxin; *Rhizopus microspores*)

SEQ ID NO: 4

MSYLAGRTFYIKSQFNGRVLDVEGASTEDDAPVIVYTQKYDDNLNQLWRYENGYFVNVNSAKVLD

IRGGQMDPESEIIQYSQKVYEEAVNQRWNIDEEGYIYIEARPDLVLDIQGAEDEDGVPVILYNRREG

EVSSNQRWVLEPVD (H-Toxin; *Mucor circinelloides*)

SEQ ID NO: 5

MTGTMFFIKSQMNGRVLDVSEGSTEDEAPIIVYSQKGEDCLNQLWRYEDGYFINAKSAKVLDISGG

EMQPESPIIQYAQKMSEEAANQKWEIDEDGYIFCSARPDLVLDIQGREDEDGAVVILYEKRDGEIAS

NQRWFLEEYSG (H-Toxin; *Mucor ambiguous*)

SEQ ID NO: 6

MTGTMYFIKSQMNGRVLDVSEGSTEDEAPIIVYSQKGEHCLNQLWRYEDGYLINANSAKVLDISGG

EMQPESAIIQYAQKMSEEAANQKWElDGEGYICCSARPDLVLDIAERNDEDGAAVILYEKREGEIAS

NQRWFLEEFSG (H-Toxin; *Absidia idahoensis*)

SEQ ID NO: 7

MSNFPSGWFFIQSKCPHKMVLDVAMDSHKDTAKIVVWPRKEQDFDNQLWMYDNGYIINKSSGLV

LDVIGGVLENDKQIIQYRRKMVEDAQNQRWYYREDGFIYPQVNPNLVLDIRGNWTKPGTVVLLYD

RKFSDNENQLWDLIPHDPQGSNTPKDDDASDIDKDYSFSTASYAL (H-Toxin; *Lichtheimia corymbifera*)

SEQ ID NO: 8

MVLDVAWDSLKANAKIIVWPRKKQDYDNQLWMYDHGYLINKNSGLVLDVAGGILETDKQMIQYRR

KMLEDAHNQRWYYREDGFIYPQVDPNLVLDIRGNWTKPGTVVLLYERKYSDNENQLWDLIPDTSD

DESSASILLREEEDGDDDYSFSTSSYAL (H-Toxin; *Mortierella verticillata*)

SEQ ID NO: 9

MAGSPSTSARSSRVLSFPKGQFYIQSPIADLVLDIESGFLKDPLKANARVELVHKKSPKHNAESSLI

QQEQQQWREEEGYIINTRTGHVLDIQGGVIRSGTRVIQNVRKTGKDAAGQHWLNDDGVLTLASNP

KFVVTIDGDATKDGTRITIQEKKPYYEKQKWLYLNGFDARPVSPSPSRAESLSIRPDNFPTSWFYIK

SAASGLVVDIEHGYFTDPMKAGARAEMNHQKIDNGDGRHSLLELQLWRYEAGFLINRRTGFVLDI

QGGTLKLAARVVQWQRKSGKEAQNQHWFYENGFIANVYNSRLVLDIDGDGSKDGAKIAIGERKA

VSNADQKWLLEEVRFQWLAAPTSASASISSNVTEEITVVERGISSPKVATPPTTVTALPTSGWFYIK

SQSSGLVVDVEQDADPLAPNVLVSMNTQITSVTEENQAKVESQLWTYQNGQIINRRSQLVLDCKQ

GVVRYGARLMQGIPKEGKESHHQRWESSNGTLVVQGKPLYAIDIEGDGTKSGSRLSLQRPKVQN

NSDQQWSFQIATYEWLKVQRSVIRTFTETTTSSSKVVNIEKNDWFFIKSGATGLVMDLEAGWITQ

PTDVGAYISMKKQRSLEESDRALLERQLWRYEDGYLINRRTNYVVDIYGRSAVVGVKLIQQYKATT

EVCGK

Additional examples of toxin sequences are shown in Table A.

TABLE A

| Description | Max Score | Total score | Query cover | E value | Ident | Accession |
|---|---|---|---|---|---|---|
| hypothetical protein RO3G 06568 (*Rhizopus delemar* RA 99-880) | 245 | 305 | 89% | 1e−79 | 99% | EIE81863.1 |
| hypothetical protein RMCBS344292 16175 (*Rhizopus microsporus*) | 196 | 239 | 90% | 1e−60 | 77% | CEJ02162.1 |
| hypothetical protein HMPREF1544 09339 (*Mucor circinelloides f. circinelloides* 1006PhL) | 195 | 236 | 88% | 4e−60 | 77% | EPB83885.1 |
| hypothetical protein RMATCC62417 04130 (*Rhizopus microsporus*) | 194 | 237 | 90% | 1e−59 | 76% | CEG67744.1 |
| hypothetical protein RMATCC62417 10102 (*Rhizopus microsporus*) | 194 | 238 | 90% | 1e−59 | 76% | CEG74984.1 |
| hypothetical protein (*Parasitella parasitica*) | 186 | 186 | 72% | 1e−54 | 74% | CEP13132.1 |
| hypothetical protein MAM1 0129d06072 (*Mucor ambiguus*) | 177 | 218 | 86% | 3e−53 | 73% | GAN06585.1 |
| hypothetical protein RMATCC62417 01384 (*Rhizopus microsporus*) | 131 | 131 | 72% | 3e−35 | 48% | CEG64405.1 |
| hypothetical protein RMCBS344292 13428 (*Rhizopus microsporus*) | 130 | 130 | 72% | 6e−35 | 48% | CEI99338.1 |
| hypothetical protein RMATCC62417 13512 (*Rhizopus microsporus*) | 130 | 130 | 72% | 1e−34 | 48% | CEG78967.1 |
| hypothetical protein RO3G 11215 (*Rhizopus delemar* RA 99-880) | 129 | 129 | 69% | 3e−34 | 50% | EIE86504.1 |
| hypothetical protein (*Parasitella parasitica*) | 122 | 122 | 71% | 1e−31 | 51% | CEP15518.1 |
| hypothetical protein HMPREF1544 10991 (*Mucor circinelloides f. circinelloides* 1006PhL) | 120 | 120 | 71% | 4e−31 | 52% | EPB82270.1 |
| hypothetical protein MAM1 0011c01155 (*Mucor ambiguus*) | 120 | 120 | 71% | 4e−31 | 52% | GAN01720.1 |
| hypothetical protein RMATCC62417 11260 (*Rhizopus microsporus*) | 120 | 120 | 73% | 2e−30 | 47% | CEG76355.1 |
| hypothetical protein RMATCC62417 04772 (*Rhizopus microsporus*) | 120 | 120 | 73% | 2e−30 | 47% | CEG68525.1 |
| hypothetical protein (*Parasitella parasitica*) | 119 | 119 | 73% | 2e−30 | 50% | CEP16308.1 |
| hypothetical protein LRAMOSA09131 (*Absidia idahoensis* var. *thermophila*) | 116 | 116 | 72% | 4e−29 | 48% | COS06603.1 |
| hypothetical protein LRAMOSA01149 (*Absidia idahoensis* var. *thermophila*) | 113 | 159 | 73% | 2e−28 | 45% | COS03748.1 |
| hypothetical protein RO3G 02323 (*Lichtheimia corymbifera* JMRCFSU9682) | 114 | 114 | 72% | 3e−28 | 46% | COH49546.1 |
| hypothetical protein HMPREF1544 01913 (*Mucor circinelloides f. circinelloides* 1006PhL) | 113 | 113 | 72% | 4e−28 | 48% | EPB91208.1 |
| hypothetical protein RMATCC62417 04772 (*Rhizopus microsporus*) | 112 | 112 | 73% | 3e−27 | 42% | CEG68524.1 |
| hypothetical protein HMPREF1544 08616 (*Mucor circinelloides f. circinelloides* 1006PhL) | 114 | 161 | 70% | 3e−27 | 49% | EPB84599.1 |
| hypothetical protein RMATCC62417 11260 (*Rhizopus microsporus*) | 111 | 111 | 70% | 4e−27 | 43% | CEG76356.1 |
| hypothetical protein RMCBS344292 17022 (*Rhizopus microsporus*) | 111 | 111 | 70% | 5e−27 | 43% | CEJ03031.1 |

TABLE 1

H-Toxin Forward Primers

| Forward Primer | Primer Sequence | SEQ ID NO: |
|---|---|---|
| 10 | 5'-CTGGCGTTACGAAAATGGTT-3' | 10 |
| 11 | 5'-ACGGACGTGTCCTTGATGTT-3' | 11 |
| 12 | 5'-AACGGACGTGTCCTTGATGT-3' | 12 |
| 13 | 5'-TAACGGACGTGTCCTTGATG-3' | 13 |
| 40 | 5'-ATCATTCAATATGCTCAAAAG-3' | 40 |
| 41 | 5'-GAAGAAGCTGCCAACCAAAGATGGGCT-3' | 41 |
| 44 | 5'-TCTGGCGTTACGAAAATGGT-3' | 44 |
| 46 | 5'-GGACGTGTCCTTGATGTTGA-3' | 46 |

TABLE 2

H-Toxin Reverse Primers

| Forward Primer | Primer Sequence | SEQ ID NO: |
|---|---|---|
| 14 | 5'-TAAATCAGGACGGGCTTCAC-3' | 14 |
| 15 | 5'-CTAAATCAGGACGGGCTTCA-3' | 15 |
| 16 | 5'-AGGTTGCATTTCACCTCCAC-3' | 16 |
| 42 | 5'-TCAGCGCCTTGGATATCTAAAACTAAAT CAG-3' | 42 |
| 43 | 5'-TGGTTGGCTGAAACTTCACCTTCACGT-3' | 43 |
| 45 | 5'-TCCAAGACCTTGGCAGACTT-3' | 45 |

Exemplary, non-limiting primer pairs for amplification of an H-toxin nucleic acid, or portion thereof, include primer pairs 10 and 14, 10 and 15, 10 and 16, 10 and 42, 10 and 43, 11 and 43, 11 and 15, 11 and 16, 13 and 16, 12 and 16, 40 and 42, 40 and 43, 41 and 42, 44 and 14, 11 and 45, 12 and 45, 13 and 45, 46 and 16, and 41 and 43.

S-Toxin Sequences

>S-Toxin *Rhizopus oryzae* (*R. delemar* 99-880)

SEQ ID NO: 17

MIMNHHNKRKAFSLLSLNSNSRFKVSNPTSQKHLIRYIRSKSPTFVALQEIDNSGGTGIHLQTLHQQ

FCSQQSLWAQYCGLLCFDPQYSLQRIPLPEDSRCILAKVTHVNEQMAPFHILWPHFHQYRFQNVM

TDLFLRNHHL

-continued

>S-Toxin *Rhizopus microspores*

SEQ ID NO: 18

MFVTLQEVDNSDNSSSHFDLWHQQFVCHQSLWIQYCGLACFDPSFSTTCIPIPEDARCLLAQVTHI

NDFIEPFFILVIYVSANVTRERREFFEQLLQFHQLDPYDDRSCADRLIIAGDCNFTIQSSQASSSYRN

WIQLLNSHFHNLMSELRDLCILTFRRSAVTRSTINYLFLSTILSANHIDATVDFADPEWSDHAIISVEL

KLDLADSHGPGAWRANPVYLDHRDFLDVLLTC

>S-Toxin *Mucor circinelloides*

SEQ ID NO: 19

MSLLDPIISNIEIIDSSYSTVNYSQTSLNPPDTSFVKLNIGSLNCRGPTKIAATSTRSQFIRYLRTRSLD

LLALQETHASSTSLQDMFHSQFQAKSSIWSPHCGLVSFSSDISFSNSIVSICGRIISTTISHSSDAFE

PFSITVVYLPAFRSERFHFLSSILTDFRSVFSSSPSRSTFLGDFNYTYSNASSSRNRQAPRSWLQY

YIDDYFLDGVTPTGKASSVTFQRGISHSCIDYIMFSNDLASSVAFFDHCNTSYIQPAWWSDHLLISS

SKLRLHPAPDASVEYIHCDLYSVHSSSSYHILI

>S-Toxin *Lichtheimia corymbifera*

SEQ ID NO: 20

MISRNNHITFLSLNCNGLAKLRRPSARSSLIRFLRQQSAHIITLQETHASTPTLKDTFHKQFCAHQSF

WTPHCGIVLLSSDLHMNEISLDFTTRAQLVHVQHNDQAFHDFYVLNIYAPAHSTRERFQFFNSLYQ

HLAPLLDNQINIDRLFIMGDFNYDLQRSGLHLNAPSTWLTWLDSHFVNCTRDDVHFAGIPTYRHSN

YLSTIDYIYAPSHFSSSIHNKDISFVNNDWTDHALLSATFIMGPPKLGKGLWRGNPLLFKQPSFRRQ

LNDALTQHYQQLHDMPSPQSQWESIKGIITQHLKTYSRQQAEWRKKQLSALQSKRNRFLRSKPPA

AIRAWRLPIMERQIATLQQELVDIQALRAGQRWRERGETSAGYLKRTIHDRQVKRSIATLQHPHTG

AMCSTTDDMHSAVQCFYQDLYSPDPISTTDMNTLLDQLPSHLRLDHTDQEHLVRAFSIDDLQSAA

SRTPHHSSPGPDGLPYQAWRLVFTHPLYTTLVMRVYEDALQHGIFPSSWNDTCMCLLPKKGDLS

NLANWRPISLINCDAKIFTRLLNARIIDAATSLVTPYQRGFMPGRFIGVNGLLTRITMEQASEQASTEI

GLLLDQEKAYDRVHPNYLSAVLHRFGFPSSIIQAICTLFFSTSIRINVNGHISQPIQQLRGLRQGDPL

SPILFNLALEPFLRSIIDDANFQGFQPWHSGATSPLPPIKVLAYADDVMVFLKDPMDFERLLAHVAC

YQKASNARFNRQKTQAISLSGATHDTWCQVLLSNAMSTPHDRRCPTAVTYLGYPLTSSKHQLELF

LDQLLQDLTSACNQHSQRTLSIRGRATVANSLILSRIWHVLRLTPTTIVFLNQLKSVIGKFLMRNIFP

RVAFTTLCRSRSHGGIGILDPVTQQSALQTRWIQELLSFSTDEWSPHTHVLYHHLLRDCRFASGTI

HTLLRCPGARKPRTNEVSISTLIYRTMDLIPTSWDTIQPSPATCLILPLNAIWYASAESTSFRQPGFK

NLLVGDLFVLEENENYSLRLRTSADGCHYPILLSRFRSYLAQNQLQLHPYFARLCDHTHVTHIHTHT

SPRLQDTSPLLSSFVQVMDGKMWRSKAYRKFIAPDTPSDNSSVSWTTFWHTPMHHTARNVWFR

LLHGRIPTSSRVHHYAPDFVTSPLCRICSTTSDDDFHFLMGCPKKRRSLDSSLETHSFCGS

>S-Toxin *Mucor ambiguous*

SEQ ID NO: 21

MRNNIKNKITDLQIGSINCRSLSKSSNIPRSQSFSRHLTTQHLDIICLQETQEAHSDTIQQRLDMQLK

AQQSIWSSHCGIVSLNPQVHITSLYVSSDDRVILCKVSHPNNVFPSFTIMNIYASATNFQRYAFYAT

LLQLVYFQSILTNMNTGNPLPSQHPDIVVGDFNYNFTQFPAHSITDYSPPALEFLSSSYASQVLTET

SLDPDSHFVMPQLDQHTTPPVCSQWIWHGLLLHHYSEVSHKLNTDPTTPTFRREFTSTTIDYIFISP

DLAPFVTKSDIQFISSTWTDHALLRFDLRFTSTTHGTGIWKANLYLVQNEYFITQLHTALDEFHSNLA

SFTVPPPVQISWDEIKILTINIVKKISRHKACWCTRHLILLQKKRNKLIKSYQGQAYIATQILKVERLIN

NLQEELVEVATLRSGLRWREKGEKSAGLMKRLITQRTIRRSIETLQHTDTNVICTQPSDLQSAARR

YYEILYTPTPVDPSNVTYFTNQTPQSDRLSDSSHGPLCAPFSPEDLIDGASRSPNKNSPGMDSLPY

EVLALLFQHPASLKLALQVFDKALSTGAFPATWQETCLILLPKKGDLSQLKNWRPISVINTDAKIFTR

-continued

VINHRLMIQLGTKLCTNQMGFMPQRFIGEQGMIVQCMQEIATKTGSPAIALLLDQEKAYDQVHLDY

LRACMAAFNIPSTLITAVTPYSHPQLVQ

>Toxin genomic DNA *R.oryzae* (*R. delemar* 99-880)

SEQ ID NO: 22

ATGATTATGAATCATCATAACAAACGAAAGGCATTTTCTTTACTTTCCTTGAATAGCAACAGTCG

CTTCAAGGTTAGTAATCCAACTTCACAAAAACATTTAATCCGGTACATTCGCTCCAAATCTCCC

ACTTTTGTCGCTCTTCAAGAAATTGATAATAGTGGTGGTACTGGTATTCATTTACAGACTTTACA

TCAACAGTTTTGTAGTCAACAATCCCTGTGGGCTCAATACTGTGGTCTTCTCTGTTTTGATCCT

CAATACTCTTTACAGCGTATTCCTCTTCCAGAAGATTCACGTTGTATTTTAGCCAAAGTTACGC

ATGTCAATGAGCAAATGGCTCCTTTCCATATTTTGGTAATCTATGCCCGGCTTCATCAAATTGA

GCTCGTCATGAATTTTTTAACCCATTGTTGACTTTCCGTCAATTATCACCGTACCATCCTATCTC

TTGTGTGGATCGCATGGTTATTGCCGGAGATTTTAATTACTCACTGCAATCCTCTTCAATGGCG

CATCGATCTATTCCATATCCTCAGTGGCCACATTTTCACCAATATCGCTTCCAAAACGTGATGA

CCGACCTGTTCCTTAGAAACCACCACCTTTAG

>Toxin cDNA *R.oryzae* (*R. delemar* 99-880)

SEQ ID NO: 23

ATGATTATGAATCATCATAACAAACGAAAGGCATTTTCTTTACTTTCCTTGAATAGCAACAGTCG

CTTCAAGGTTAGTAATCCAACTTCACAAAAACATTTAATCCGGTACATTCGCTCCAAATCTCCC

ACTTTTGTCGCTCTTCAAGAAATTGATAATAGTGGTGGTACTGGTATTCATTTACAGACTTTACA

TCAACAGTTTTGTAGTCAACAATCCCTGTGGGCTCAATACTGTGGTCTTCTCTGTTTTGATCCT

CAATACTCTTTACAGCGTATTCCTCTTCCAGAAGATTCACGTTGTATTTTAGCCAAAGTTACGC

ATGTCAATGAGCAAATGGCTCCTTTCCATATTTTGTGGCCACATTTTCACCAATATCGCTTCCA

AAACGTGATGACCGACCTGTTCCTTAGAAACCACCACCTTTAG

TABLE 3

| S-Toxin Forward Primers | | |
|---|---|---|
| Forward Primer | Primer Sequence | SEQ ID NO: |
| 24 | 5'-GCAAATGGCTCCTTTCCATA-3' | 24 |
| 25 | 5'-CCCTGTGGGCTCAATACTGT-3' | 25 |
| 26 | 5'-GTAATCTATGCCCGGCTTCA-3' | 26 |
| 27 | 5'-TCTCCCACTTTTGTCGCTCT-3' | 27 |
| 28 | 5'-CCCTGTGGGCTCAATACTGT-3' | 28 |

TABLE 4

| S-Toxin Reverse Primers | | |
|---|---|---|
| Forward Primer | Primer Sequence | SEQ ID NO: |
| 29 | 5'-GAATAGATCGATGCGCCATT-3' | 29 |
| 30 | 5'-TGAAGCCGGGCATAGATTAC-3' | 30 |
| 31 | 5'-CCATTTGCTCATTGACATGC-3' | 31 |
| 32 | 5'-CCGGGCATAGATTACCAAAA-3' | 32 |

Exemplary, non-limiting primer pairs for amplification of an S-toxin nucleic acid, or portion thereof, include primer pairs 24 and 29, 24 and 30, 24 and 31, 24 and 32, 25 and 29, 25 and 30, 25 and 31, 25 and 32, 26 and 29, 26 and 20, 26 and 31, 26 and 32, 27 and 29, 27 and 30, 27 and 31, 27 and 32, 28 and 29, 28 and 30, 28 and 31, and 28 and 32.

Other Sequences

-ADP-rhibosylation domain containing protein of *Rhizopus*.

SEQ ID NO: 33

VLAVPRNESTMTAEELAEREQEAKMTKLENSELMMQQHDVTEDTNKNDTFANQLVTRILNNLQFS

IQTIHIRYEDNVSTEHRFAAGITLNELSAITTDEEWTPNTLGEAANTIYKLATLESLSIYWDTNIQSIAD

EDNEHEAFKALIATKQHVPKEHQYILKPVSGSGRVKFNKHFGDKVPKFEASLLFDELSFTVDNEQY

RDTILMIDLFHSYLKKQKYRECHPPSHMTPKSHPLEYFRFAGQAILSEIHERNQRWTWDRLKKRRD

DRKAYIHCYVNYKLDRATPEELEQLEGLERALSFEDLRFYRSLAKPKLRSEKARLAAIEKRRKEEET

-continued

AKKAKQGWGISSWWYGSGKLSEDSENEAEEIVITEEQKQEFYDVIDYDADKAAIAASIDLPKDTTLL

SLNMTLNRGSFNVRKNPHKQPVDLLSLVFDNFSMSLTKYVESFTATAALGDMSLYDGQRPESPYY

KLMGAKGKDVSHRKSITLDSQLKNFSNPMKDPFFTATFEYKPLDERADNAAALYMRNIDIVYNPQV

IYEIVEFFTPSETSADSINALIEVAGDTLEGFKKQTRASLKYALEQHTTLDLKVDMDAPPENAIVID

AGHINVESNLLPPETRAQLKSRSGAEMTAEDDTNLHSLMFDRFTVQLTQTKILVGDSLDTCLVQVR

RPRPELDYLHLVDRIDMTFLLELCIIRKSFDMPRLKVSGHLPLLKVNFSDTKYKAIMQLPHLIEASGL

LGDKKTEVDLNEYPVQNQADQSWFNLMGNPLWNKPEEEDDMFLLSDSESSDLYTDSLADTVDTE

VTKATTVKSVKSSKETVNVEERLFELDFKVDRVLANILRAQKGHRSDSDGLSPEHLLCEVDLKSLK

LNYNMRPMDMTVGLSLKSLDVTDRMKHGNEFKYLVTSDQHILQPDASNDSGLKELVNVEYVQCD

KQNPEYMTRYKGVGQTVHVTLSTLNFIVTRSSVLTLHSFVMDTFVDSEINSNQKTAAITPSLAHTIP

ATQASKPSSNTTDNNIYVRLLLDSVNFVLNNDGVRLATGELSLGDLSTVVSDGQVNVAAKFANFTL

TDDLSPRKAADTQTWPHQLLTIQGEELIDLKYTSFVDDGRQDYPGYDHAVYLRMGSAQFRFLEEP

VHQLLQFLSKFAEMKLAYDMARAAALESAQQLSQAATKMHFDVVIKTPVVLFPEFHQHPSDCVVA

HLGEIWASNTFVTDEDGCINTIQAGLRAINLTSKFHFARPEILLQTLPIVDDIDVTFAIDIPEQGSSERP

MVDIKGKVSDISMRLTERQYIFLMEAIHMFSRIFTDTDEDEANLQALSNKRSSTVQHRSSQASIQPA

AATEKTRSPQIQMAIDAKMIKLEIYMGTGPDLQSPPSLASFALHNSQVNFRMQRDNTMDVFLVIPS

LTVDDTRPGINSGFKNIMPVVKDKNQFELQLDLKAPNPIRSGI

>H-toxin Common Epitope 1

SEQ ID NO: 34

Asn Gln Leu Trp Arg Tyr Xaa Asx Gly Tyr; where Xaa is Asp or Glu.

>H-Toxin, nucleic acid, *R. microspores*.

SEQ ID NO: 35

ATGAGTTACTTAGCAGGACGTACATTCTATATCAAGAGTCAATTCAATGGACGCGTGCTCGAT

GTTGAAGGCGCTTCCACCGAAGATGATGCCCCCGTGATTGTTTATACCCAAAAATATGATGAC

AACTTGAATCAACTCTGGCGTTATGAAAATGGTTACTTTGTCAACGTCAACTCTGCCAAGGTTT

TGGATATCCGCGGTGGCCAAATGGACCCTGAATCTGAAATTATTCAATACTCTCAAAAGGTAT

ACGAAGAAGCTGTGAACCAAAGATGGAACATTGATGGGGAAGGCTATATCTATATTGAAGCTC

GTCCTGACTTAGTCTTGGACATTCAAGGTGCCGAGGATGAGGATGGTGTTCCCGTCATCTTGT

ACAATAGACGTGAGGGTGAAGTCTCTTCTAACCAACGTTGGGTGTTGGAACCAGTTGATTAA

>H-Toxin, nucleic acid, *M. circinelloides*.

SEQ ID NO: 36

ATGACTGGTACCATGTTCTTTATCAAAAGCCAAATGAACGGCCGTGTTCTCGATGTGAGCGAA

GGCTCTACTGAGGATGAAGCCCCTATCATTGTCTACTCTCAAAAGGGCGAAGATTGCTTGAAC

CAATTGTGGCGCTACGAAGACGGTTATTTCATCAATGCCAAGTCTGCCAAGGTTCTCGATATT

AGCGGTGGTGAAATGCAACCCGAGTCTCCTATCATTCAATATGCTCAAAAGATGTCTGAGGAA

GCTGCTAATCAAAAGTGGGAAATCGATGAAGATGGTTATATCTTCTGTTCTGCTCGCCCTGATT

TAGTCTTGGACATTCAAGGTCGTGAAGACGAGGATGGCGCTGTTGTCATTTTGTACGAAAAGC

GTGATGGTGAAATTGCTTCTAACCAACGCTGGTTCTTGGAAGAGTACTCTGGTTAA

>H-Toxin, nucleic acid, *M. ambiguus*.

SEQ ID NO: 37

ATGACTGGTACCATGTATTTTATCAAAAGCCAAATGAACGGCCGTGTTCTTGATGTGAGTGAA

GGCTCTACCGAGGACGAGGCCCCTATCATTGTCTACTCTCAAAAGGGCGAACATTGCTTGAA

CCAATTGTGGCGTTATGAAGATGGATACCTCATCAATGCTAACTCTGCCAAGGTGCTCGATAT

CAGTGGTGGAGAAATGCAACCCGAATCTGCTATCATTCAATATGCTCAAAAGATGTCTGAGGA

-continued

GGCCGCTAATCAGAAATGGGAAATCGATGGTGAAGGCTATATCTGTTGTTCTGCTCGCCCTGA

TTTAGTCTTGGACATTGCAGAGCGCAATGACGAGGATGGTGCTGCTGTCATCTTGTATGAGAA

GCGCGAGGGTGAGATTGCCTCTAACCAACGTTGGTTCTTGGAAGAGTTCTCTGGTTAA

>H-Toxin, nucleic acid, *L. corymbifera*.

SEQ ID NO: 38

ATGATCCAATATCGTCGAAAGATGCTCGAAGATGCGCACAATCAACGCTGGTATTATCGTGAG

GATGGTTTCATTTACCCTCAAGTCGATCCTAATTTGGTTCTTGATATTCGCGGCAATTGGACCA

AGCCTGGAACGGTGGTACTTCTTTACGAGCGAAAATACAGCGATAACGAGAATCAGCTATGG

GATCTTATTCCAGATACCAGCGACGACGAGTCATCAGCATCGATATTATTACGAGAAGAGGAG

GATGGTGATGATGATTACTCCTTCAGCACTTCAAGCTATGCACTCTAG

>H-Toxin, nucleic acid, *Mortierella verticillata*.

SEQ ID NO: 39

ATGGCAGGCTCCCCTTCAACTTCTGCCCGATCCAGTCGTGTGCTGTCCTTCCCCAAGGGCCA

GTTCTACATCCAGTCGCCCATTGCTGACCTGGTTCTCGACATTGAGTCCGGGTTCCTGAAGGA

CCCCCTCAAGGCCAACGCGCGTGTCGAGCTCGTACACAAGAAGTCACCCAAACACAACGCCG

AGTCCTCGCTGATCCAGCAGGAGCAGCAGCAGTGGCGCGAGGAGGAGGGTTACATCATCAA

CACTCGTACTGGCCACGTCTTGGATATCCAAGGAGGGGCCCCATTGGACAACGGGCATTGGT

ATTGGGCAGTGGGCGGCATCCATGGTATCATTGCCATCAATATGACTAACCGTCCATCTCTCC

ACATCACCTTTCTTCACACACACACAGGTGTCATCCGTTCCGGTACTCGCGTTATCCAAAACG

TGCGCAAGACTGGAAAGGATGCTGCTGGCCAGCACTGGTTGAACGATGACGGTGTCCTGACC

TTGGCCAGCAACCCCAAGTTCGTCGTCACCATCGATGGAGATGCCACCAAAGATGGAACCCG

CATCACTATCCAAGAAAAGAAGCCATACTACGAGAAGCAAAAATGGTTGTATCTGAACGGCTT

CGATGCTCGCCCTGTGTCGCCTTCTCCTTCCAGAGCAGAGTCACTCTCCATCCGCCCTGACA

ACTTCCCCACCAGCTGGTTCTACATCAAGTCCGCTGCCTCGGGCTTGGTCGTCGACATTGAG

CACGGCTACTTCACAGACCCCATGAAGGCCGGTGCCCGCGCCGAAATGAACCACCAAAAGAT

CGACAACGGTGACGGCCGCCACTCCTTGCTTGAGCTCCAGCTTTGGCGCTACGAGGCTGGTT

TCCTTATCAACCGTCGCACCGGTTTCGTTCTGGACATTCAAGGAGGCACTCTCAAACTCGCCG

CCAGAGTCGTCCAGTGGCAGCGCAAGTCTGGAAAGGAGGCCCAGAACCAGCACTGGTTCTA

CGAGAACGGCTTCATTGCCAACGTCTACAACTCGAGGCTGGTTCTGGACATTGATGGCGATG

GTTCCAAGGACGGAGCCAAGATCGCCATCGGTGAGCGCAAGGCTGTCAGCAACGCTGATCA

GAAGTGGCTGTTGGAGGAGGTTCGCTTCCAATGGTTGGCTGCTCCTACCTCAGCCTCGGCCT

CCATCTCCTCCAATGTCACCGAGGAGATTACCGTCGTCGAGAGAGGCATCTCGTCCCCCAAG

GTCGCCACTCCCCCCACCACCGTCACCGCTCTGCCCACCAGCGGCTGGTTCTACATCAAGTC

CCAGTCCTCTGGTCTCGTTGTCGACGTTGAGCAGGATGCCGATCCTTTGGCCCCTAACGTCC

TCGTCAGCATGAACACCCAGATCACCTCTGTCACTGAGGAGAACCAGGCCAAGGTCGAGTCA

CAGCTCTGGACATACCAGAATGGTCAGATCATCAACAGGAGATCTCAGCTCGTCCTCGACTG

CAAACAGGGTGTCGTCCGCTATGGCGCCAGACTGATGCAGGGAATTCCCAAGGAGGGCAAA

GAGAGCCACCACCAGCGTTGGGAGTCATCCAACGGCACCCTCGTCGTCCAGGGCAAGCCTC

TCTACGCTATCGACATTGAGGGTGATGGCACCAAGTCCGGTTCCCGCCTCTCGCTCCAGCGC

CCCAAGGTCCAGAACAACTCGGATCAGCAGTGGTCCTTCCAGATCGCCACTTACGAGTGGCT

CAAGGTCCAGCGTTCTGTCACCCGCACCTTCACCGAGACCACCACCTCTTCGTCTAAGGTTGT

TAACATCGAGAAGAACGACTGGTTCTTCATCAAGTCCGGAGCCACCGGCTTGGTCATGGATCT

CGAGGCTGGCTGGATTACTCAGCCCACCGATGTTGGTGCCTACATTTCCATGAAGAAGCAGC

-continued

GCTCGCTCGAGGAGTCTGATCGTGCCCTTTTGGAGAGACAGTTGTGGCGCTATGAGGACGGC

TACCTCATCAACCGCAGAACCAACTACGTCGTTGACATCTATGGTCGCTCCGCCGTTGTTGGC

GTCAAGTTGATCCAGCAGTACAAGGCTACCACCGAGGTCTATGATGCTGTCCTCACCGAGAA

GCACACTGGTGTTACCTACGTGACCCAGCTGTTGTTCGACACCCAGACCAATGCCTACTACGT

CTACGTCCGCTGGGGCGAGACCGAGTACAGATTGGATGGGCCCCACGAGACCATTGAGTCC

GCCAAGGCCGCTTTCTTGATCACCTACCACGATCAGTTTGGTGTTGAATGGCAAACTCGCGAG

ACCACCGTCAGCGAACAATGGACCTACGAAGTCAAGACCTATGAGACTTTCGAGGAGATCGA

GTACGTTGAGGAGGTCGTTGAGGAGACTGAGGCAGTCACCATCATTGAGCAGCAGCGCGAG

ATCGTTGTCCAGGAACAGTCCGAGCATGTTGAAGTTACCGAGGGCGAGGAGATCATCAAGGT

TGTCACCACCGTCAAGGAGACTGGTGTCGTTGCCGAGCCCGCCGTGTCCAAGGGCACTTCCT

GGTTCCGCCGCCTGGCCTCCGGAGCTGGCGCCGTCGCATCGGGCGCTTTGACTGAGGTCGA

TGGCGTCTGGAAGCGCACTGTCCAGGTCCTCACCACCCGCAAGGCTCACGTCGACAAGGTT

GCCCCTATTGCCGAGACCTCGTATGTGTACTATGATGAGGAGGTCTACGATTCCGTCCTTGTT

GAGAAGTCGACTGGCATCACCTATGTCACCCAGCTTCTGTTCGACACCAAGGTCCAGAAGTA

CTACGTCTACGTCCGCTGGGGCGAGACTGACTACAAGTTGGATGGACCCCACGACACTATCG

AGGCTGCCAAGGCCGCTTTCCAGATCACCTACAAGGAGAGATTCGGTTTGGAGTGGGCTACC

CGCGAGACCACCGTCAGCGAACGCTGGACCTATGAGGTTCGCACCTACGAGACCTTCGAGG

AGACTGAGGAGATCGAGGAGATCGTGGAGGATTACGAGGTCAAGGAGATTGTTGCCCGTGA

GCAGCAGGTCATTGTCGAGGGCAAGGTCATTTCGACCGAGCAGTCCGTGTCGTCGTCCCATG

ACGACACTGTTGTCCGCACCGTGAGCGAGCAGGTTGTGTCCAAGGATGGCTCTGCCTCTGGA

TCTTCGTCCAGCCGCGGTGGCGCCTTTGGCTTTGGTGGCTCGTCGTCTTACGAGTACACCCA

GACCCAGTCTGAGGAGAGCAAGAAGTCCACTTTCTTGGCCAACCTCCCCACCTTGAACGCTG

GCATCAACGCCGATACCGGTGCCGCCATTGGCGTGATCGATCTGACCTCTGGCACCGCCGA

GAACCTTCGCGAGTTGCCCGCCCACTTGCGCCCCCGTGCCTGGGTCTCGCTCCACGTTGGA

GGCTGGCAGAACGCCCCCCACGAGCTTGAAGGATTTATGCGCCTCGATGACCAGTCGGGCC

AGCGTCTGATGGAGACTGCCCGCGATGAGTCCCTTGGCAAGGCCCAGGAGTCGACCCCTATT

GACAACCTGAGCTTGCCCGAGATTGTGGGATTGTTTGCCCAGAAGTTGTACGGACACTTTGG

CGAGGAGCTGCCCAAGGAGCTGGAGATGGAGAAGCTGAGGGATCTGGCCCGCGGATTCCCT

GGTCGTCACTAA

>H-Toxin, nucleic acid, *Puccinia graminis f.* sp. *tritici.*

SEQ ID NO: 47

ATGGCCGACTTCCCTACCGCTTGGTTTTACATCAAGTCGGTTTGCTCAAAGAAAGTCATCCAA

CCACTCGGTGGAAGTTTCGAACCAACCCGACTAGTCGTTGTCGATCAAAAATTCGGTCAGGAA

TCAGCAGCCCAACTCTGGAAACATGAGAACGGTTACTTGGTCAACAAGCTGACTAACCTCTGT

CTGGATTACGAACATGGCAACTATAAGCGCTTAGGTGATATTCACGTTTGCCAGTGGCATCAA

AAAGTCGGCAAGGATGCTCATAACCAAAAATGGCTATACAGGACAAGCAACTTGATTGCATCG

AATGACGACATCAACCGAGTATTAGACATCAAGGGAGGATCGATTCATCCGGGGGCAGAAGT

TTTACTCAAGAAACTCGAGACGATCAAAGGCGCCCATCCGGCCCACCAACGATGGCTGCTAG

AAGTGATTGACCAGGACGGCTTACCAGACTCATTATCAACCTACCAGGAAGACCAAATCGCTG

GCAGCTATGCTGCCCCCGTGGAACACGTCAATCCTTGGGCTACTCTCGAGCCTTCGACGGAT

GATGAACCAGGCGAAGCTCAAACCACATATTACTAA

Example 9: Production of Recombinant H-Toxin & Anti-H-Toxin Antibody

Figure 18A:
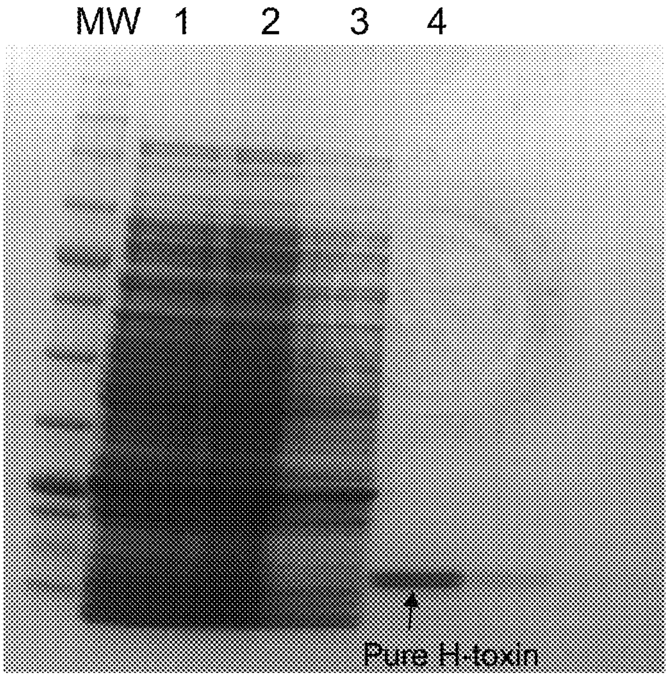
FIG. 18A shows an image of a stained polyacrylamide gel showing the expression of and purification of a recombinant hyphal-associated toxin (toxin H) produced in *E. coli*. MW indicates a molecular weight marker. Purified H-toxin in shown in lane 4.

The entire coding sequence of H-toxin from *R. delemar* was cloned into a pGex_2T vector and expressed in *Escherichia coli* BL21 (DE3) pLys. The vector promoted expression of the protein fused with GST. Sepharose 4B beads were used to purify the H-toxin; elution of the toxin from the beads was obtained using a thrombin cleavage site in between the GST-tag and the protein. Purified toxin is shown in FIG. 18A.

Figure 18B:
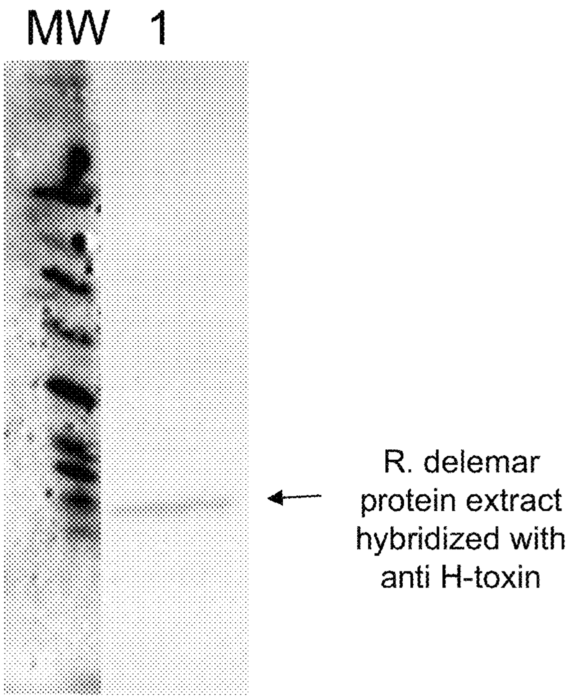
FIG. 18B shows detection of native H-toxin in a fungal extract of *R. delemar* by Western blot using a rabbit polyclonal antibody raised to recombinant H-toxin.

Purified H-toxin was concentrated, quantified and injected into rabbits to produce polyclonal anti-H-toxin antibody. Polyclonal anti-H-toxin antibody (also referred as anti-ricin antibody) was purified from serum and determined to be free of endotoxin. The antibody has been tested for its ability to specifically bind to H-toxin of *R. delemar* by western blot. Briefly, fungal extracts of *R. delemar* were ran on a polyacrylamide gel (SDS-page), transferred to blotting membrane and blocked. Membranes were probed with anti-H-toxin antibody, followed by visualization with labeled anti-rabbit antibody secondary (FIG. 18B, lane 1). Lane "MW" shows a molecular weight marker.

Figure 19:
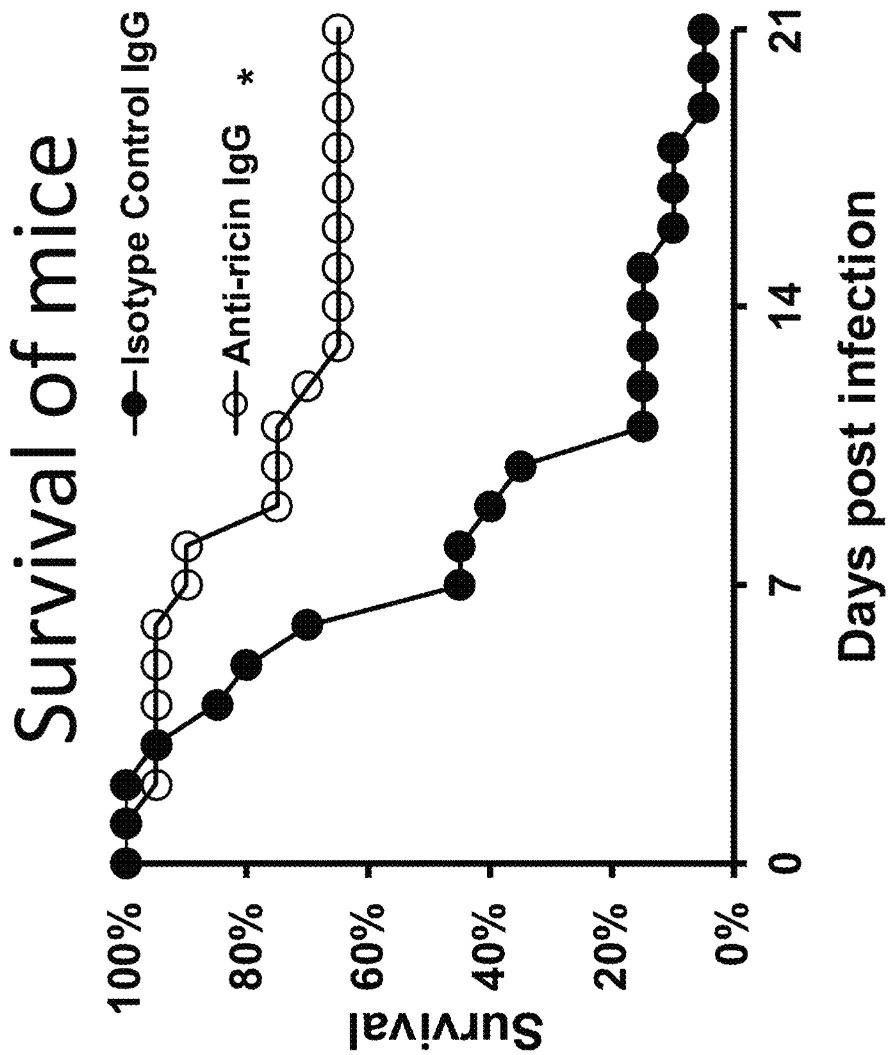
FIG. 19 shows a survival graph of mice infected with a lethal dose of *R. delemar* and treated with rabbit anti-H-toxin antibody (open circles, "anti-ricin IgG") or control IgG antibody (solid circles).

Example 10: Treatment of *R. delemar* Infected Mice with Anti-H-Toxin Antibody CD-1 male mice were made diabetic with streptozotocin (210 mg/kg body weight) given 10 days prior to infection. Mice we also given cortisone acetate (250 mg/kg on days −2, +3 and +8 relative to infection. Baytril antibiotic (50 ug/mL) was added into the drinking water on Day-2 to Day 0. On Day 0 (infection day), mice were infected with $2.5\times10^5$ spores of *R. delemar* 99-880 via intratraceal instillation. Ceftazidime (5 mg/mouse) was started on Day 0 and was continued until day +13 post infection (given SQ). This treatment replaced Baytril. Antibody treatment (either IgG isotype as control, or anti-H antibody of Example 9) was administered 4 hours post infection in a single dose at 30 μg. Survival of mice was monitored for 21 days. The results are shown in FIG. 19. All control antibody treated mice died by day 21 post infection. Anti-H-toxin antibody (anti-ricin) treated mice showed significant survival (>60% survival) over untreated mice.

Example 11: References

The following references are hereby incorporated by reference in their entirety.

1. Ibrahim A S, Gebremariam T, Lin L, et al. The high affinity iron permease is a key virulence factor required for *Rhizopus oryzae* pathogenesis. Mol Microbiol; 77:587-604.
2. Luo G, Gebremariam T, Lee H, et al. Efficacy of liposomal amphotericin B and posaconazole in intratracheal models of murine mucormycosis. Antimicrob Agents Chemother; 57:3340-7.
3. Ibrahim A S, Gebermariam T, Fu Y, et al. The iron chelator deferasirox protects mice from mucormycosis through iron starvation. J Clin Invest 2007; 117:2649-57.
4. Ibrahim A S, Edwards J E, Jr., Fu Y, Spellberg B. Deferiprone iron chelation as a novel therapy for experimental mucormycosis. J Antimicrob Chemother 2006; 58:1070-3.
5. Ibrahim A S, Avanessian V, Spellberg B, Edwards J E, Jr. Liposomal amphotericin B, and not amphotericin B deoxycholate, improves survival of diabetic mice infected with *Rhizopus oryzae*. Antimicrob Agents Chemother 2003; 47:3343-4.
6. Liu M, Lin L, Gebremariam T, et al. Fob1 and Fob2 Proteins Are Virulence Determinants of *Rhizopus oryzae* via Facilitating Iron Uptake from Ferrioxamine. PLoS Pathog 2015; 11:e1004842.
7. Skory C D, Ibrahim A S. Native and modified lactate dehydrogenase expression in a fumaric acid producing isolate *Rhizopus oryzae* 99-880. Curr Genet 2007; 52:23-33.
8. Skory C D. Inhibition of Non-Homologous End Joining and integration of DNA upon transformation of *Rhizopus oryzae*. Mol Genet Genomics 2005; 274:373-83.
9. Skory C D. Homologous recombination and double-strand break repair in the transformation of *Rhizopus oryzae*. Mol Genet Genomics 2002; 268:397-406.
10. Gebremariam T, Liu M, Luo G, et al. CotH3 mediates fungal invasion of host cells during mucormycosis. J Clin Invest; 124:237-50.
11. Liu M, Spellberg B, Phan Q T, et al. The endothelial cell receptor GRP78 is required for mucormycosis pathogenesis in diabetic mice. J Clin Invest; 120:1914-24.
12. Fu Y, Ibrahim A S, Sheppard D C, et al. *Candida albicans* Als1p: an adhesin that is a downstream effector of the EFG1 filamentation pathway. Mol Microbiol 2002; 44:61-72.
13. Ibrahim A S, Bowman J C, Avanessian V, et al. Caspofungin inhibits *Rhizopus oryzae* 1,3-beta-D-glucan synthase, lowers burden in brain measured by quantitative PCR, and improves survival at a low but not a high dose during murine disseminated zygomycosis. Antimicrob Agents Chemother 2005; 49:721-7.
14. Ibrahim A S, Gebremariam T, Fu Y, Edwards J E, Jr., Spellberg B. Combination echinocandin-polyene treatment of murine mucormycosis. Antimicrob Agents Chemother 2008; 52:1556-8.
15. Ibrahim A S, Spellberg B, Avanessian V, Fu Y, Edwards J E, Jr. *Rhizopus oryzae* adheres to, is phagocytosed by, and damages endothelial cells in vitro. Infect Immun 2005; 73:778-83.
16. Cannom R R, French S W, Johnston D, Edwards Jr J E, Filler S G. *Candida albicans* stimulates local expression of leukocyte adhesion molecules and cytokines in vivo. J Infect Dis 2002; 186:389-96.
17. Waldorf A R, Halde C, Vedros N A. Murine model of pulmonary mucormycosis in cortisone-treated mice. Sabouraudia 1982; 20:217-24.
18. Ibrahim A S, Luo G, Gebremariam T, et al. NDV-3 protects mice from vulvovaginal candidiasis through T- and B-cell immune response. Vaccine; 31:5549-56.
19. Fu Y, Filler S G, Spellberg B J, et al. Cloning and Characterization of CAD1/AAF1, a Gene from *Candida albicans* That Induces Adherence to Endothelial Cells after Expression in *Saccharomyces cerevisiae*. Infection and Immunity 1998; 66:2078-84.
20. Spellberg B, Fu Y, Edwards J E, Jr., Ibrahim A S. Combination therapy with amphotericin B lipid complex and caspofungin acetate of disseminated zygomycosis in diabetic ketoacidotic mice. Antimicrob Agents Chemother 2005; 49:830-2.
21. Ibrahim A, Bowman J, Avanessian V, Douglas C, Edwards J J. Efficacy of Caspofungin Acetate (CAS) in a Diabetic Murine Model of Induced Mucormycosis. Interscience conference on antimicrobial agents and chemotherapy; 2003; Chicago, Ill.: American Society for Microbiology. p. M-371.

Example 12: Embodiments

A1. A method of detecting the presence of Mucorales in a sample comprising:
a) contacting a sample comprising nucleic acids obtained from a mammal with an oligonucleotide primer pair thereby providing a mixture, wherein the oligonucleotide primer pair is configured to specifically hybridize to and amplify one or more nucleic acids having at least 80% identity to SEQ ID NO:1, SEQ ID NO: 2, SEQ ID NOs: 35-39, SEQ ID NO: 47, SEQ ID NO: 22, and/or SEQ ID NO: 23, or a portion thereof;
b) performing an amplification reaction with the mixture, thereby providing an amplification product; and
c) analyzing the amplification product for the presence of an amplicon of a predetermined length, wherein the presence of the amplicon indicates the presence of Mucorales in the sample.

A2. A method of detecting the presence of Mucorales in a sample comprising:
a) contacting a sample comprising nucleic acids obtained from a mammal with an oligonucleotide primer pair thereby providing a mixture, wherein the oligonucleotide primer pair is configured to produce an amplicon under amplification conditions, wherein the amplicon comprises at least 80% identity to SEQ ID NO:1, SEQ ID NO: 2, SEQ ID NOs: 35-39, SEQ ID NO: 47, SEQ ID NO: 22, and/or SEQ ID NO: 23, or a portion thereof;
b) performing an amplification reaction with the mixture, thereby providing an amplification product; and
c) analyzing the amplification product for the presence of the amplicon, wherein the presence of the amplicon indicates the presence of a Mucorales species in the sample.

A3. The method of any one of embodiments A1 to A2, wherein the mammal has, or is suspected of having a Mucorales infection.

A4. The method of embodiment A1 or A2, wherein the amplicon comprises the oligonucleotide pair.

A5. The method of any one of embodiments A1 to A4, wherein the amplicon is at least 50 nucleotides in length.

A6. The method of any one of embodiments A1 to A5, wherein the amplicon comprises a portion of SEQ ID NOs: 1, 2, 35, 36, 37, 38, 39, and/or 47.

A7. The method of any one of embodiments A1 to A5, wherein the amplicon comprises a portion of SEQ ID NO:22 or SEQ ID NO:23.

A8. The method of any one of embodiments A1 to A5, wherein the oligonucleotide primer pair is configured to specifically hybridize to one or more nucleic acid sequences selected from SEQ ID NOs: 1, 2, 35, 36, 37, 38, 39, 47, 22, and/or 23.

A9. The method of any one of embodiments A1 to A8, wherein the oligonucleotide primer pair is configured to specifically hybridize to the nucleic acid sequence of SEQ ID NOs: 1, 2, 35, 36, 37, 38, 39, and 47.

A10. The method of any one of embodiments A1 to A8, wherein the oligonucleotide primer pair is configured to specifically hybridize to the nucleic acid sequence of SEQ ID NO:22 and/or SEQ ID NO:23.

A11. The method of any one of embodiments A1 to A10, wherein the oligonucleotide primer pair comprises a first oligonucleotide and a second oligonucleotide, wherein the first oligonucleotide is selected from an oligonucleotide of Table 1 and the second oligonucleotide is selected from Table 2.

A12. The method of any one of embodiments A1 to A10, wherein the oligonucleotide primer pair comprises a first oligonucleotide and a second oligonucleotide, wherein the first oligonucleotide is selected from an oligonucleotide of Table 3 and the second oligonucleotide is selected from Table 4.

A13. The method of any one of embodiments A1 to A12, wherein the method comprises administering an anti-fungal agent to the mammal when the presence of the amplicon is detected.

A14. The method of embodiment A13, wherein the anti-fungal agent is selected from one or more of amphotericin B, candicidin, filipin, hamycin, natamycin, nystatin, rimocidin, bifonazole, butoconazole, clotrimazole, econazole, fenticonazoleisoconazole, ketoconazole, luliconazole, miconazole, omoconazole, oxiconazole, sertaconazole, sulconazole, tioconazole, albaconazole, efinaconazole, epoxiconazole, fluconazole, isavuconazole, itraconazole, posaconazole, propiconazole, ravuconazole, terconazole, voriconazole, abafungin, amorolfin, butenafine, naftifine, terbinafine, anidulafungin, caspofungin, micafungin, benzoic acid, ciclopirox, flucytosine, 5-fluorocytosine, griseofulvin, haloprogin, tolnaftate, undecylenic acid, crystal violet, and Balsam of Peru.

A15. The method of embodiment A14, wherein the anti-fungal agent is selected from one or more of amphotericin B, isavuconazole and posaconazole.

A16. The method any one of embodiments A1 to A15, wherein the amplification reaction comprises a polymerase chain reaction.

A17. The method any one of embodiments A1 to A16, wherein the sample comprises urine, blood, serum, or a bronchoalevolar lavage obtained from the mammal.

A18. The method any one of embodiments A1 to A17, wherein analyzing the amplification product for the presence of the amplicon in (c) comprises gel electrophoresis.

A19. The method any one of embodiments A1 to A17, wherein analyzing the amplification product for the presence of the amplicon in (c) comprises nucleic acid sequencing.

A20. The method any one of embodiments A1 to A17, wherein analyzing the amplification product for the presence of the amplicon in (c) comprises mass spectrometry.

B1. A composition comprising:
a) nucleic acids obtained from a mammal;
b) an oligonucleotide primer pair configured to specifically hybridize to and amplify a nucleic acid having at least 80% identity to one or more of SEQ ID NOs: 1, 2, 35, 36, 37, 38, 39, 47, 22, and/or 23, or a portion thereof; and
c) a recombinant polymerase.

B2. A composition comprising:
a) nucleic acids obtained from a mammal;
b) an oligonucleotide primer pair configured to produce an amplicon under amplification conditions, wherein the amplicon comprises at least 80% identity to one or more of SEQ ID NOs: 1, 2, 35, 36, 37, 38, 39, 47, 22, and/or 23, or a portion thereof; and
c) a recombinant polymerase.

B3. The composition of embodiment B1, further comprising an amplicon of a predetermined length that is at least 50 nucleotides in length, wherein the amplicon comprises the oligonucleotide pair and a nucleic acid having at least 80% identity to one or more of SEQ ID NOs: 1, 2, 35, 36, 37, 38, 39, 47, 22, and/or 23, or a portion thereof.

B4. The composition of embodiment B2, further comprising the amplicon, wherein the amplicon is at least 50 nucleotides in length.

B5. The composition of any one of embodiments B1 to B4, wherein the oligonucleotide primer pair is configured to specifically hybridize to one or more of SEQ ID NOs: 1, 2, 35, 36, 37, 38, 39, and 47.

B6. The composition of any one of embodiments B1 to B4, wherein the oligonucleotide primer pair is configured to specifically hybridize to SEQ ID NO: 22 and/or SEQ ID NO: 23.

B7. The composition of any one of embodiments B1 to B6, wherein the nucleic acids obtained from the mammal comprise mammalian RNA or DNA.

B8. The composition of any one of embodiments B1 to B7, wherein the nucleic acids obtained from the mammal comprise fungal RNA or DNA.

B9. The composition of any one of embodiments B1 to B8, comprising nucleic acids obtained from a Mucorales species.

B10. The composition of any one of embodiments B1 to B9, wherein the oligonucleotide primer pair comprises a first oligonucleotide selected from an oligonucleotide of Table 1 and a second oligonucleotide selected from an oligonucleotide of Table 2.

B11. The composition of any one of embodiments B1 to B9, wherein the oligonucleotide primer pair comprises a first oligonucleotide selected from an oligonucleotide of Table 3 and a second oligonucleotide selected from an oligonucleotide of Table 4.

B12. The composition of any one of embodiments B1 to B11, wherein the polymerase is an isolated recombinant polymerase.

B13. The composition of any one of embodiments B1 to B12, wherein at least one of the oligonucleotides of the primer pair comprise a distinguishing identifier.

B14. The composition of any one of embodiments B1 to B3, wherein at least one of the oligonucleotides of the primer pair comprises an adapter.

B15. The composition of any one of embodiments B1 to B14, wherein the composition comprises a buffer or buffer solution.

B16. The composition of any one of embodiments B1 to B15, wherein the mammal is a human.

B17. The composition of any one of embodiments B1 to B16, wherein the oligonucleotide primer pair comprises at least one modified nucleotide.

B18. A kit comprising:

a) an oligonucleotide primer pair configured to (i) specifically hybridize to a portion of one or more of SEQ ID NOs: 1, 2, 35, 36, 37, 38, 39, 47, 22, and/or 23, and (ii) produce an amplicon of a predetermined length that is at least 50 nucleotides in length;
b) a recombinant polymerase, and
c) instructions for generating an amplicon from a sample obtained from a mammal.

B19. The kit of embodiment B18, wherein the amplicon comprises a nucleic acid at least 80% identical to one or more of SEQ ID NOs: 1, 2, 35, 36, 37, 38, 39, 47, 22, and/or 23.

B20. The kit of embodiment B18 or B19, comprising one or more deoxyribonucleotide triphosphates.

B21. The kit of any one of embodiments B18 to B20, comprising a cell lysis buffer.

B22. The kit of any one of embodiments B18 to B21, comprising one or more printed labels or one or more inserts.

C1. An antibody binding agent that specifically binds to a polypeptide comprising an amino acid sequence having at least 80% identity to any one of SEQ ID NOs: 3-9 or SEQ ID NOs: 17-21.

C2. An antibody binding agent that specifically binds to a polypeptide comprising 16 or more consecutive amino acids having 80% or more identity to SEQ ID NOs: 3-9, SEQ ID NOs: 17-21, or a portion thereof.

C3. The antibody of embodiment C2, wherein the 16 or more consecutive amino acids have 80% or more identity to a portion of any one of SEQ ID NOs: 3-9 or SEQ ID NOs: 17-21, and wherein the 16 or more consecutive amino acids and the portion consists of the same number of consecutive amino acids.

C4. The antibody of embodiment C2, wherein the antibody binding agent specifically binds to a polypeptide comprising 16 or more consecutive amino acids of any one of SEQ ID NOs: 3-9 or SEQ ID NOs: 17-21.

C5. The antibody binding agent of any one of embodiments C1 to C4, and a pharmaceutically acceptable carrier.

C6. The antibody binding agent of any one of embodiments C1 to C5, wherein the antibody binding agent comprises a distinguishable identifier.

C7. The antibody binding agent of any one of embodiments C1 to C6, wherein the antibody binding agent is a polyclonal binding agent.

C8. The antibody binding agent of any one of embodiments C1 to C7, wherein the antibody binding agent is a monoclonal binding agent.

C9. The antibody binding agent of any one of embodiments C1 to C8, wherein the antibody binding agent comprises an antibody or binding portion thereof.

C10. The antibody binding agent of any one of embodiments C1 to C9, wherein the antibody binding agent specifically binds to one or more polypeptides selected from SEQ ID NOs: 3, 4, 5, 6, 7, 8, 9, 17, 18, 19, 20 and 21.

C11. The antibody binding agent of any one of embodiments C1 to 010, wherein the antibody binding agent blocks H-toxin activity.

C12. The antibody binding agent of any one of embodiments C1 to 010, wherein the antibody binding agent blocks S-toxin activity.

C13. The antibody binding agent of any one of embodiments 01 to C12, wherein the antibody binding agent is a monoclonal antibody.

C14. The antibody binding agent of embodiment C13, wherein the monoclonal antibody is a human or humanized antibody, or binding fragment thereof.

D1. A method comprising:

a) providing an antibody binding agent that specifically binds to a polypeptide comprising an amino acid sequence having at least 80% identity to any one of SEQ ID NOs: 3-9 or SEQ ID NOs: 17-21; and
b) contacting the antibody binding agent with the polypeptide, wherein the antibody binding agent specifically binds to the polypeptide.

D1.1 The method of D1, further comprising:

c) detecting the presence, absence or amount of the antibody that is specifically bound to the polypeptide.

D2. A method comprising:

a) providing an antibody binding agent that specifically binds to a polypeptide comprising 16 or more consecutive amino acids having 80% or more identity to SEQ ID NOs: 3-9, SEQ ID NOs: 17-21, or a portion thereof; and b) contacting the antibody binding agent with the polypeptide, wherein the antibody binding agent specifically binds to the polypeptide.

D3. A method of embodiment D2, wherein the 16 or more consecutive amino acids have 80% or more identity to a portion of any one of SEQ ID NOs: 3-9 or SEQ ID NOs: 17-21, and wherein the 16 or more consecutive amino acids and the portion consists of the same number of consecutive amino acids.

D4. A method comprising:

a) providing an antibody binding agent that specifically binds to a polypeptide comprising 16 or more consecutive amino acids of any one of SEQ ID NOs: 3-9 or SEQ ID NOs: 17-21; and, b) contacting the antibody binding agent with the polypeptide, wherein the antibody binding agent specifically binds to the polypeptide.

D5. The method of any one of embodiments D1 to D4, wherein the specific binding of (b) comprises forming a bound complex comprising the antibody binding agent and the polypeptide.

D6. The method of any one of embodiments D1 to D5, wherein the polypeptide comprises an H-toxin or S-toxin activity.

D7. The method of embodiment D6, wherein the specific binding of the antibody binding agent to the polypeptide inhibits and/or blocks the H-toxin or S-toxin activity.

D8. The method of embodiment D7, wherein the specific binding of the antibody binding agent to the polypeptide inhibits and/or blocks at least 50% of the H-toxin or S-toxin activity.

D9. The method of any one of embodiments D1 to D8, wherein the contacting of (b) comprises administering the antibody binding agent to a mammal, wherein the mammal has, or is suspected of having a Mucorales infection.

D10. The method of any one of embodiments D1 to D9, wherein the antibody binding agent comprises a distinguishable identifier.

D11. The method of embodiment D10, wherein the distinguishable identifier is a label.

D12. The method of any one of embodiments D5 to D11, comprising detecting the presence or absence of the bound complex.

E1. A method of detecting the presence of Mucorales in a sample comprising:

a) contacting an antibody binding agent with a sample suspected of comprising a Mucorales species, or portion thereof, wherein the antibody binding agent is configured to specifically bind to a polypeptide comprising an amino acid sequence having at least 80% identity to any one of SEQ ID NOs: 3-9 or SEQ ID NOs: 17-21, or a portion thereof; and b) detecting the presence or absence of a bound complex in the sample, wherein the bound complex comprises the antibody binding agent and the polypeptide, and the presence of the bound complex indicates the presence of a Mucorales species, or portion thereof, in the sample.

E2. A method comprising:

a) contacting an antibody binding agent with a sample suspected of comprising a Mucorales species, or portion thereof, wherein the antibody binding agent is configured to specifically bind to a polypeptide comprising 16 or more consecutive amino acids having 80% or more identity to SEQ ID NOs: 3-9, SEQ ID NOs: 17-21, or a portion thereof; and b) detecting the presence or absence of a bound complex in the sample, wherein the bound complex comprises the antibody binding agent and the polypeptide, and the presence of the bound complex indicates the presence of a Mucorales species, or portion thereof, in the sample.

E3. A method of embodiment E2, wherein the 16 or more consecutive amino acids have 80% or more identity to a portion of any one of SEQ ID NOs: 3-9 or SEQ ID NOs: 17-21, and wherein the 16 or more consecutive amino acids and the portion consists of the same number of consecutive amino acids.

E4. A method of detecting the presence of Mucorales in a sample comprising:

a) contacting an antibody binding agent with a sample suspected of comprising a Mucorales species, or portion thereof, wherein the antibody binding agent is configured to specifically bind to a polypeptide comprising 16 or more consecutive amino acids of any one of SEQ ID NOs: 3-9 or SEQ ID NOs: 17-21; and b) detecting the presence or absence of a bound complex in the sample, wherein the bound complex comprises the antibody binding agent and the polypeptide, and the presence of the bound complex indicates the presence of a Mucorales species, or portion thereof, in the sample.

E5. The method of any one of embodiments E1 to E4, wherein the antibody binding agent comprises a distinguishable identifier.

E6. The method of embodiments E5, wherein the distinguishable identifier is a label.

E7. The method of any one of embodiments E1 to E6, wherein the detecting in (b) comprises detecting the presence of a distinguishable identifier.

E8. The method of any one of embodiments E1 to E7, wherein the sample is obtained from a mammal.

E9. The method of any one of embodiments E1 to E7, wherein the sample comprises urine, blood, serum, or a bronchoalevolar lavage obtained from a mammal.

E10. The method of any one of embodiments E1 to E9, comprising detecting the presence of the bound complex.

E11. The method of any one of embodiments E1 to E10, wherein the antibody binding agent is a polyclonal binding agent.

E12. The method of any one of embodiments E1 to E11, wherein the antibody binding agent is a monoclonal binding agent.

E13. The method of any one of embodiments E1 to E12, wherein the antibody binding agent is an antibody.

E14. The method of any one of embodiments E1 to E13, wherein the antibody binding agent is a monoclonal antibody, or binding portion thereof.

E15. The antibody binding agent of embodiment E14, wherein the monoclonal antibody is a human or humanized antibody, or binding portion thereof.

F1. A composition comprising a polypeptide comprising an amino acid sequence having at least 80% identity to any one of SEQ ID NOs: 3-9 or SEQ ID NOs: 17-21, or a portion thereof, and an adjuvant.

F2. A composition comprising a polypeptide comprising 16 or more consecutive amino acids having 80% or more identity to SEQ ID NOs: 3-9, SEQ ID NOs: 17-21, or a portion thereof, and an adjuvant.

F3. The composition of embodiment F2, wherein the 16 or more consecutive amino acids have 80% or more identity to a portion of any one of SEQ ID NOs: 3-9 or SEQ ID NOs:

17-21, and wherein the 16 or more consecutive amino acids and the portion consists of the same number of consecutive amino acids.

F4. A composition comprising a polypeptide comprising 16 or more consecutive amino acids of any one of SEQ ID NOs: 3-9 or SEQ ID NOs: 17-21, and an adjuvant.

F5. The composition of any one of embodiments F1 to F4, wherein the polypeptide comprises 16 or more consecutive amino acids of SEQ ID NO: 3.

F6. The composition of any one of embodiments F1 to F5, wherein the polypeptide comprises SEQ ID NO: 34.

F7. The composition of any one of embodiments F1 to F6, wherein the polypeptide is immunogenic.

F8. The composition of any one of embodiments F1 to F7, wherein the composition comprises a pharmaceutically acceptable carrier.

F9. The composition of any one of embodiments F1 to F8, wherein the adjuvant comprises an aluminum salt.

F10. The composition of embodiment F9, wherein the aluminum salt comprises aluminum phosphate.

F11. The composition of any one of embodiments F1 to F10, wherein the composition comprises a pH buffering agent.

G1. A method comprising:

a) providing a polypeptide comprising at least 90% identity to an amino acid sequence selected from SEQ ID NOs: 3-9, SEQ ID NOs: 17-21, or a portion thereof, wherein the polypeptide comprises a toxin activity; and b) administering the polypeptide to a mammal having or suspected of having a cancer, wherein the polypeptide contacts a cancer cell in the mammal.

G2. The method of embodiment G1, wherein upon contacting the cancer cell in (b), the polypeptide induces cell-damage to the cancer cell.

G3. The method of embodiment G1 or G2, wherein the polypeptide comprises a cancer cell binding molecule.

G4. The method of any one of embodiments G1 to G3, wherein the cancer cell binding molecule comprises a mammalian growth factor or an antibody binding agent, or binding portion thereof.

G5. The method of embodiment G4, wherein the antibody binding agent, or binding portion thereof, specifically binds to human CD22, CD25, CD123, CD44, EpCAM, Her2 or CD133.

G6. The method of any one of embodiments G1 to G5, wherein the polypeptide comprises an H-toxin, an S-toxin or portion thereof.

G7. The method of any one of embodiments G4 to G6, wherein the polypeptide is fused to the mammalian growth factor or antibody binding agent, or binding portion thereof, thereby providing a fusion protein.

H1. A binding agent that specifically binds to a polypeptide comprising an amino acid sequence selected from SEQ ID NOs: 3-9, SEQ ID NOs: 17-23, and portions thereof.

H1.1. The binding agent of embodiment H1, wherein the binding agent specifically binds to a polypeptide comprising an amino acid sequence selected from SEQ ID NOs: 3-9.

H1.2. The binding agent of embodiment H1, wherein the binding agent specifically binds to a polypeptide comprising an amino acid sequence selected from SEQ ID NOs: 17-23.

H1.3. The binding agent of embodiment H1, wherein the binding agent specifically binds to a polypeptide comprising or consisting of an amino acid sequence of SEQ ID NO: 3.

H2. The binding agent of any one of embodiments H1 to H1.3, wherein the binding agent comprises an antibody, or a binding fragment thereof.

H3. The binding agent of embodiment H2, wherein the antibody is a polyclonal antibody, or binding fragment thereof.

H4. The binding agent of embodiment H2, wherein the antibody is a monoclonal antibody, or binding fragment thereof.

H5. The binding agent of any one of embodiments H2 to H4, wherein the antibody or monoclonal antibody comprises an IgG1, IgA or IgM isotype.

H6. The binding agent of embodiment H4 or H5, wherein the monoclonal antibody is a chimeric antibody.

H7. The binding agent of any one of embodiments H4 to H6, wherein the monoclonal antibody is a humanized monoclonal antibody.

H8. The binding agent of any one of embodiments H1 to H1.3, wherein the binding agent comprises an aptamer, camelid, DARPin, or an affibody.

H9. The binding agent of any one of embodiments H2 to H8, wherein the binding fragment comprises a Fab, Fab', F(ab')2, Fv or scFV fragment of an antibody.

H10. The binding agent of any one of embodiments H2 to H9, wherein the binding agent is comprised of a single chain polypeptide.

H11. The binding agent of any one of embodiments H1 to H3, wherein the binding agent is a rabbit polyclonal antibody.

I1. A pharmaceutical composition comprising the binding agent of any one of embodiments H1 to H11, and a pharmaceutical acceptable excipient, diluent, additive or carrier.

I2. The pharmaceutical composition of embodiment I1, wherein the pharmaceutical composition comprises one or more antifungal medications configured for administration to a mammal.

I3. The pharmaceutical composition of embodiment I2, wherein the antifungal medication comprises a polyene antimycotic.

I4. The pharmaceutical composition of embodiment I3, wherein the polyene antimycotic is selected from amphotericin B, candicidin, filipin, hamycin, natamycin, nystatin, rimocidin and derivatives or analogues thereof.

I5. The pharmaceutical composition of embodiment I2, wherein the antifungal medication comprises an imidazole antifungal medication.

I6. The pharmaceutical composition of embodiment I5, wherein the imidazole antifungal medication is selected from bifonazole, butoconazole, clotrimazole, econazole, fenticonazole, isoconazole, ketoconazole, luliconazole, miconazole, omoconazole, oxiconazole, sertaconazole, sulconazole, tioconazole and derivatives or analogues thereof.

I7. The pharmaceutical composition of embodiment I2, wherein the antifungal medication comprises an triazole antifungal medication.

I8. The pharmaceutical composition of embodiment I7, wherein the triazole antifungal medication is selected from albaconazole, efinaconazole, fluconazole, isavuconazole, itraconazole, posaconazole, ravuconazole, terconazole, voriconazole, and derivatives or analogues thereof.

I9. The pharmaceutical composition of embodiment I2, wherein the antifungal medication comprises abafungin.

I10. The pharmaceutical composition of embodiment I2, wherein the antifungal medication comprises an allylamine antifungal medication.

I11. The pharmaceutical composition of embodiment I10, wherein the allylamine antifungal medication is selected from amorolfin, butenafine, naftifine, terbinafine and derivatives or analogues thereof.

I12. The pharmaceutical composition of embodiment I2, wherein the antifungal medication comprises an echinocandin antifungal medication.

I13. The pharmaceutical composition of embodiment I12, wherein the echinocandin antifungal medication is selected from anidulafungin, caspofungin, micafungin, and derivatives or analogues thereof.

I14. The pharmaceutical composition of embodiment I2, wherein the antifungal medication is selected from one or more of benzoic acid, a keratolytic agent, ciclopirox olamine, flucytosine, 5-fluorocytosine, griseofulvin, haloprogin, tolnaftate, undecylenic acid, crystal violet, tolnaftate, and derivatives or analogues thereof.

I15. The pharmaceutical composition of embodiment I2, wherein the antifungal medication is selected from one or more of amphotericin B, anidulafungin, caspofungin, fluconazole, flucytosine, micafungin, posaconazole, and voriconazole.

I16. The pharmaceutical composition of any one of embodiments I1 to I15, wherein the excipient comprises a preservative.

I17. The pharmaceutical composition of any one of embodiments I1 to I16, wherein the pharmaceutical composition is free of serum proteins.

I18. The pharmaceutical composition of any one of embodiments I1 to I17, wherein the pharmaceutical composition is sterile.

I19. The pharmaceutical composition of any one of embodiments I1 to I18, wherein the pharmaceutical composition comprises a sterile, lyophilized powder suitable for intravenous administration to a mammal.

J1. A method of treating a subject having or suspected of having a mucorales infection comprising:

a) providing a subject having, or suspected of having, a mucorales infection; and b) administering a therapeutically effective amount of the binding agent or composition of any one of embodiments C1 to I19 to the subject.

J2. The method of embodiment J1, wherein the subject has, or is suspected of having a murcorales infection caused by the presence of a mucorales species selected from the group consisting of *A. idahoensis, A. corymbifera, Apophysomyces elegans, Actinomucor elegans, A. rouxii, B. circina, B. multispora, C. brefeldii, C. angarensis, C. recurvatus, D. fulva, E. anomalus, H. elegans, H. assamensis, K. cordensis, Lichtheimia corymbifera, Lichtheimia ramosa, M. ambiguus, Mucor amphibiorum, Mucor circinelloides, M. verticillata, P. parasitica, P. agaricine, P. anomala, P. circinans, S. umbellata, S. megalocarpus, T. elegans, T indicaeseudaticae, Z. californiensis, Rhizomucor endophyticus, Rhizopus javensis, R. azygosporus, Rhizopus caespitosus, Rhizopus homothallicus, Rhizopus oryzae Rhizopus delemari, Rhizopus delemar* (*R. delemar* 99-880)), *Rhizopus stolonifer, Rhizopus reflexus, Rhizopus microsporus, Rhizopus microsporus* (e.g., var. *rhizopodiformis*), and *Rhizopus schipperae.*

J3. The method of embodiment J1, wherein the subject has, or is suspected of having a murcorales infection caused by the presence of *Rhizopus oryzae* or *Rhizopus delemar.*

J4. The method of embodiment J1, wherein the subject has, or is suspected of having a murcorales infection caused by the presence of *Rhizopus delemar* 99-880.

J5. The method of any one of embodiments J1 to J4, wherein the binding agent is selected from a binding agent of any one of embodiments C1 to C14.

J6. The method of any one of embodiments J1 to J4, wherein the binding agent is selected from a binding agent of any one of embodiments H1 to H11.

J7. The method of any one of embodiments J1 to J4, wherein the composition is selected from a composition of any one of embodiments F1 to F11.

J8. The method of any one of embodiments J1 to J4, wherein the composition is a pharmaceutical composition selected from any one of embodiments I1 to I19.

J9. The method of any one of embodiments J1 to J8, wherein the subject is a mammal.

J10. The method of any one of embodiments J1 to J8, wherein the subject is a human.

J13. The method of any one of embodiments J1 to J10, further comprising administering an antifungal medication to the subject.

K1. A binding agent of any one of embodiments C1 to C14 and H1 to H11 for use in the treatment of a mucorales infection.

L1. A composition of any one of embodiments F1 to F11, for use in the treatment of a mucorales infection.

M1. A pharmaceutical composition of any one of embodiments I1 to I19, for use in the treatment of a mucorales infection.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

Certain embodiments of the technology are set forth in the claim(s) that follow(s).

What is claimed is:

1. A method of treating a subject having or suspected of having a mucorales infection comprising: a) providing a subject having, or suspected of having, a mucorales infection; and b) administering a therapeutically effective amount of a binding agent that specifically binds to at least 5 contiguous amino acids of a polypeptide comprising an amino acid sequence of SEQ ID NO: 3, wherein the murcorales infection is caused by the presence of *Rhizopus oryzae*.

2. The method of claim 1, wherein the binding agent specifically binds to a polypeptide comprising the amino acid sequence of SEQ ID NO: 3.

3. The method of claim 1, wherein the binding agent specifically binds to a polypeptide consisting of the amino acid sequence of SEQ ID NO:3.

4. The method of claim 1, wherein the binding agent comprises an antibody.

5. The method of claim 4, wherein the binding agent comprises a monoclonal antibody.

6. The method of claim 1, wherein the binding agent blocks H-toxin activity.

7. The method of claim 1, wherein the binding agent blocks S-toxin activity.

8. The method of claim 1, wherein the murcorales infection is caused by the presence of *Rhizopus oryzae*.

9. The method of claim 1, wherein the subject is a human.

10. A method of treating a human subject having or suspected of having a mucorales infection caused by the presence of *Rhizopus oryzae* comprising: administering a therapeutically effective amount of an antibody to the subject wherein the antibody specifically binds to at least 5 contiguous amino acids of a polypeptide comprising the amino acid sequence of SEQ ID NO: 3.

11. The method of claim 10, wherein the antibody specifically binds to a polypeptide consisting of the amino acid sequence of SEQ ID NO:3.

12. The method of claim 10, wherein the antibody comprises a monoclonal antibody.

13. The method of claim 11, wherein the antibody comprises a monoclonal antibody.

* * * * *